US012580040B2

(12) United States Patent
Ingraham et al.

(10) Patent No.: US 12,580,040 B2
(45) Date of Patent: Mar. 17, 2026

(54) DIFFUSION MODEL FOR GENERATIVE PROTEIN DESIGN

(71) Applicant: Generate Biomedicines, Inc., Somerville, MA (US)

(72) Inventors: John Ingraham, Cambridge, MA (US); Ahmed Ismail, Somerville, MA (US); Fritz Heinrich Obermeyer, Bellingham, WA (US); Maxim Baranov, Golden, CO (US); Wujie Wang, Toronto (CA); Zachary Kohl Costello, Cambridge, MA (US); Gevorg Grigoryan, Arlington, MA (US)

(73) Assignee: Generate Biomedicines, Inc., Somerville, MA (US)

(*) Notice: Subject to any disclaimer, the term of this patent is extended or adjusted under 35 U.S.C. 154(b) by 0 days.

(21) Appl. No.: 19/003,490

(22) Filed: Dec. 27, 2024

(65) Prior Publication Data

US 2025/0218530 A1 Jul. 3, 2025

Related U.S. Application Data

(63) Continuation of application No. PCT/US2023/037034, filed on Nov. 8, 2023.

(Continued)

(51) Int. Cl.

*G16B 15/20* (2019.01)
*G16B 40/00* (2019.01)

(52) U.S. Cl.

CPC ............. *G16B 15/20* (2019.02); *G16B 40/00* (2019.02)

(58) Field of Classification Search

None

See application file for complete search history.

(56) References Cited

U.S. PATENT DOCUMENTS

| | | | |
|---|---|---|---|
| 2022/0189579 | A1 | 6/2022 | Si et al. |
| 2022/0270711 | A1 | 8/2022 | Feala et al. |

(Continued)

OTHER PUBLICATIONS

Avery C, Patterson J, Grear T, Frater T, Jacobs DJ. Protein function analysis through machine learning. Biomolecules. Sep. 6, 2022; 12(9):1246. (Year: 2022).*

(Continued)

*Primary Examiner* — Vincent Gonzales

(74) *Attorney, Agent, or Firm* — Wolf, Greenfield & Sacks, P.C.

(57) ABSTRACT

A system is disclosed for de novo protein generation. The system receives a set of design condition(s) that specify target characteristics of a synthetic protein. The system defines a modular energy function as a composition of a diffusion energy component and one or more conditioner energy components. The system applies a diffusion model to determine a denoised protein backbone. In applying the diffusion model, in each sampling step: the system transforms one prior sampled state of the synthetic protein from unconstrained space into constrained space based on the one or more design conditions, denoises the prior sampled state in the constrained space, and samples a subsequent sampled stated by applying a gradient of the modular energy function to the denoised prior sampled state in the constrained space. The final sampled state is a denoised protein backbone for the synthetic protein that satisfies the set of design condition(s).

11 Claims, 83 Drawing Sheets

Related U.S. Application Data

(60) Provisional application No. 63/578,763, filed on Aug. 25, 2023, provisional application No. 63/522,538, filed on Jun. 22, 2023, provisional application No. 63/470,672, filed on Jun. 2, 2023, provisional application No. 63/469,822, filed on May 30, 2023, provisional application No. 63/499,963, filed on May 3, 2023, provisional application No. 63/385,619, filed on Nov. 30, 2022, provisional application No. 63/385,020, filed on Nov. 26, 2022, provisional application No. 63/384,076, filed on Nov. 16, 2022, provisional application No. 63/383,242, filed on Nov. 10, 2022, provisional application No. 63/424,044, filed on Nov. 9, 2022, provisional application No. 63/383,074, filed on Nov. 9, 2022, provisional application No. 63/423,775, filed on Nov. 8, 2022.

(56) References Cited

U.S. PATENT DOCUMENTS

2024/0161864 A1 5/2024 Ingraham
2024/0404123 A1 12/2024 Wang et al.

OTHER PUBLICATIONS

Kayser O, Warzecha H, editors. Pharmaceutical biotechnology: drug discovery and clinical applications. John Wiley & Sons; May 21, 2012. (Year: 2012).*
Ingraham, John, Vikas Garg, Regina Barzilay, and Tommi Jaakkola. "Generative models for graph-based protein design." Advances in neural information processing systems 32 (2019). (Year: 2019).*
S. Russell and P. Norvig, Artificial Intelligence: A Modern Approach, 2nd Ed., 2003, chapt. 2-6, pp. 59-193. (Year: 2003).*
International Search Report and Written Opinion for International Application No. PCT/US2023/037034 mailed Mar. 5, 2024.
Invitation to Pay Additional Fees for International Application No. PCT/US2023/037034 mailed Jan. 5, 2024.
International Search Report and Written Opinion for International Application No. PCT/US2024/028426 mailed Aug. 22, 2024.
Anand et al., Generative Modeling for Protein Structures. 32nd Conference on Neural Information Processing Systems (NeurlPS 2018). 2018: 12 pages.
Anand et al., Protein sequence design with a learned potential. Nature communications. Feb. 8, 2022;13(1):746.
Anand et al., Protein Structure and Sequence Generation with Equivariant Denoising Diffusion Probabilistic Models. arXiv Preprint arXiv:2205.15019v1. May 26, 2022. 18 pages.
Barnes et al., A hierarchical O (N log N) force-calculation algorithm. nature. Dec. 4, 1986;324(6096):446-9.
Battaglia et al., Relational Inductive Biases, Deep Learning, and Graph Networks. arXiv:1806.01261 v3. Oct. 17, 2018. 40 pages.
Bittracher et al., A Weak Characterization of Slow Variables in Stochastic Dynamical Systems. arXiv:2005.01631 v1. May 4, 2020. 20 pages.
Cao et al., Design of protein-binding proteins from the target structure alone. Nature. May 19, 2022;605(7910):551-60.
Castro et al., Transformer-based protein generation with regularized latent space optimization. Nature Machine Intelligence. Oct. 2022;4(10):840-51.
Corso, Modeling Molecular Structures with Intrinsic Diffusion Models. arXiv preprint arXiv:2302.12255. Feb. 23, 2023. 6 pages.
Dauparas et al., Robust deep learning-based protein sequence design using ProteinMPNN. Science. Oct. 7, 2022;378(6615):49-56.
Eguchi et al., Ig-VAE: Generative modeling of protein structure by direct 3D coordinate generation. PLoS computational biology. Jun. 27, 2022;18(6):e1010271.
Ferruz et al., A deep unsupervised language model for protein design. BioRxiv. Mar. 12, 2022. 14 pages.
Gao et al., Deep learning in protein structural modeling and design. Patterns. Dec. 11, 2020;1(9). 23 pages.
Gilmer et al., Neural message passing for Quantum chemistry. Proceedings of the 34th International Conference on Machine Learning—vol. 70 Aug. 6, 2017. 10 pages.
Gong et al., Diffuseq: Sequence to sequence text generation with diffusion models. arXiv preprint arXiv:2210.08933. Feb. 14, 2023. 20 pages.
Greener et al., Design of metalloproteins and novel protein folds using variational autoencoders. Scientific reports. Nov. 1, 2018;8(1):16189.
Huang et al., The coming of age of de novo protein design. Nature. Sep. 15, 2016;537(7620):320-7.
Ingraham et al., Generative models for graph-based protein design. Proceedings of the 33rd International Conference on Neural Information Processing Systems. 2019;32. 12 pages.
Joh et al., De novo design of a transmembrane Zn2+-transporting four-helix bundle. Science. Dec. 19, 2014;346(6216):1520-4.
Jumper et al., Highly accurate protein structure prediction with AlphaFold. nature. Aug. 2021;596(7873):583-9.
Koga et al., Principles for designing ideal protein structures. Nature. Nov. 8, 2012;491(7423):222-7.
Kries et al., De novo enzymes by computational design. Current opinion in chemical biology. Apr. 1, 2013;17(2):221-8.
Kuhlman et al., Advances in protein structure prediction and design. Nature reviews molecular cell biology. Nov. 2019;20(11):681-97.
Lee et al., ProteinSGM: Score-based generative modeling for de novo protein design. bioRxiv. Jul. 13, 2022. 20 pages.
Lin et al., Deep generative models create new and diverse protein structures. InMachine Learning for Structural Biology Workshop, NeurIPS 2021. 17 pages.
Luo et al., Antigen-Specific Antibody Design and Optimization with Diffusion-Based Generative Models. bioRxiv Preprint. Jul. 11, 2022. 13 pages.
Madani et al., ProGen: Language Modeling for Protein Generation. arXiv:2004.03497v1. Mar. 8, 2020. 17 pages.
Notin et al., Tranception: Protein Fitness Prediction with Autoregressive Transformers and Inference-time Retrieval. Proceedings of the 39th International Conference on Machine Learning. Jul. 2022. 28 pages.
Ramesh et al., Hierarchical Text-Conditional Image Generation with CLIP Latents. arXiv:2204.06125v1. Apr. 13, 2022. 27 pages.
Ramesh et al., Zero-shot text-to-image generation. Proceedings of the 37th International Conference on Machine Learning. 2020. 11 pages.
Riesselman et al., Deep Generative Models of Genetic Variation Capture the Effects of Mutations. Nat Methods. Author Manuscript: available in PMC Aug. 14, 2019. Published in final edited form as: Nat Methods. Oct. 2018;15(1):816-822.
Rives et al., Biological structure and function emerge from scaling unsupervised learning to 250 million protein sequences. Proceedings of the National Academy of Sciences. Apr. 13, 2021;118(15):e2016239118.
Saharia et al., Photorealistic text-to-image diffusion models with deep language understanding. Proceedings of the 36th International Conference on Neural Information Processing Systems. Nov. 28, 2022. 16 pages.
Smith, Natural Selection and the Concept of a Protein Space. Nature, vol. 225, No. 5232, Feb. 7, 1970, pp. 563-564.
Sohl-Dickstein et al., Deep unsupervised learning using nonequilibrium thermodynamics. Proceedings of the 32nd International Conference on International Conference on Machine Learning. Jul. 6, 2015:37. 10 pages.
Song et al., Score-Based Generative Modeling through Stochastic Differential Equations. International Conference on Learning Representations. 2021. 36 pages.
Strokach et al., Deep generative modeling for protein design. Current opinion in structural biology. Feb. 1, 2022;72:226-36.
Trippe et al., Diffusion probabilistic modeling of protein backbones in 3d for the motif-scaffolding problem. arXiv:2206.04119. Jun. 8, 2022. 27 pages.

(56) References Cited

OTHER PUBLICATIONS

Trippe et al., Diffusion Probabilistic Modeling of Protein Backbones in 3D for the motif-scaffolding problem. The Eleventh International Conference on Learning Representations. 30 pages.
Watson et al., De novo design of protein structure and function with RFdiffusion. Nature. Aug. 31, 2023;620(7976):1089-100.
Wu et al., EBM-Fold: fully-differentiable protein folding powered by energy-based models. arXiv:2105.04771. May 31, 2021. 18 pages.
Wu et al., Protein Structure Generation via Folding Diffusion. arXiv:2209.15611v2. Nov. 24, 2022. 27 pages.
Yue et al., Inverse protein folding problem: designing polymer sequences. Proceedings of the National Academy of Sciences. May 1, 1992;89(9):4163-7.
Zhang et al., Cross-Modal Contrastive Learning for Text-to-Image Generation. arXiv preprint arXiv:2101.04702. Apr. 14, 2022. 19 pages.
Zhang et al., Text-to-image diffusion models in generative AI: A survey. arXiv preprint arXiv:2303.07909. Apr. 2, 2023. 13 pages.

* cited by examiner

Protein Generation
900

Receive a set of one or more design conditions that specify target
characteristics of a synthetic protein
910

Define a modular energy function as a composition of a diffusion energy
component and one or more conditioner energy components
920

Rescale the modular energy function based on a time-dependent
temperature and/or a time-dependent Langevin dynamics equilibration rate
930

Apply a diffusion model to generate a denoised protein backbone
940

Transform prior sampled state from unconstrained space into
constrained space
950

Denoise the prior sampled state in the constrained space
960

Sample a subsequent sampled state in unconstrained space
by applying a gradient of the modular energy function to the
denoised prior sampled state in the constrained space
970

Repeat sampling

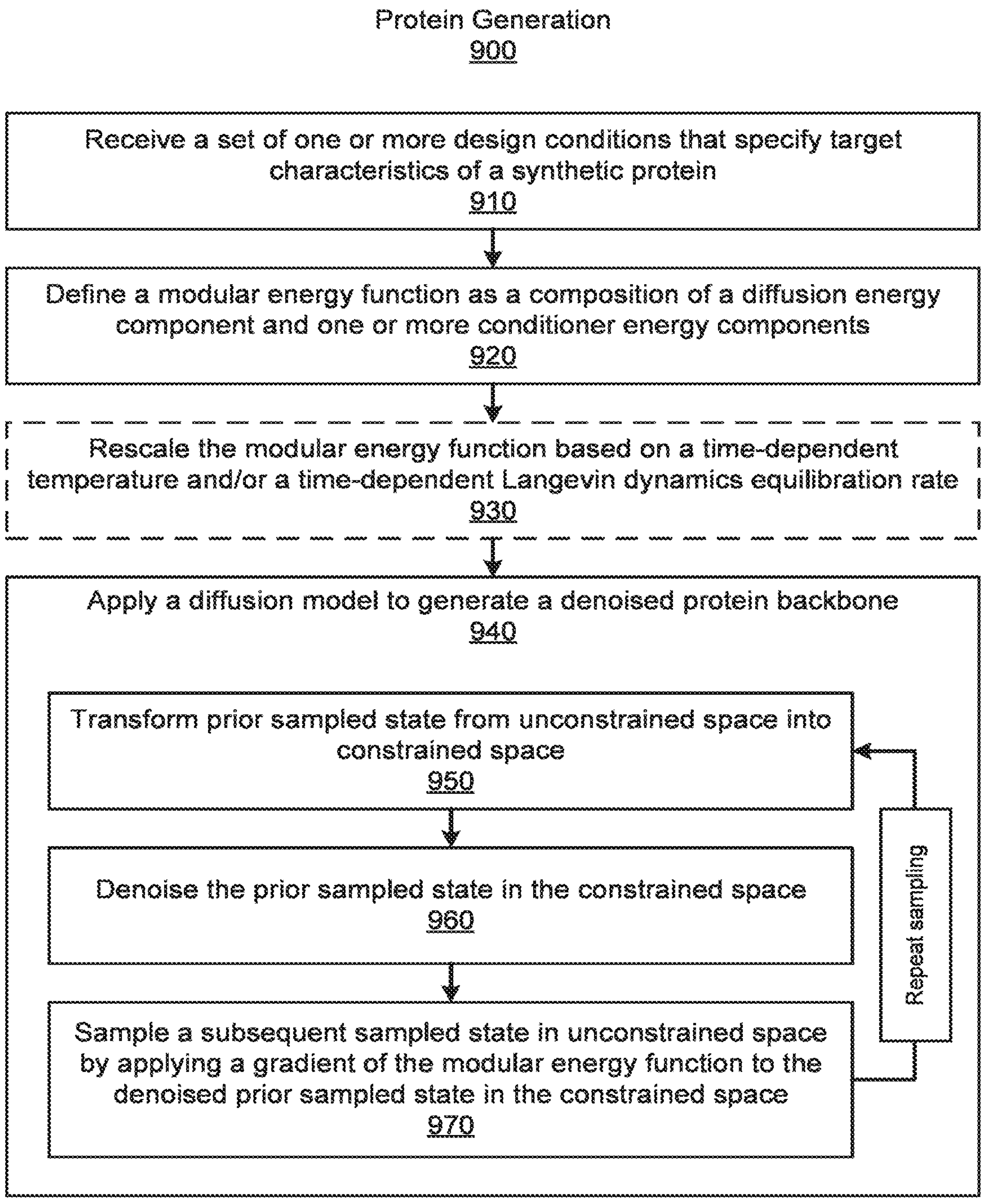

FROM
FIG. 15B-1
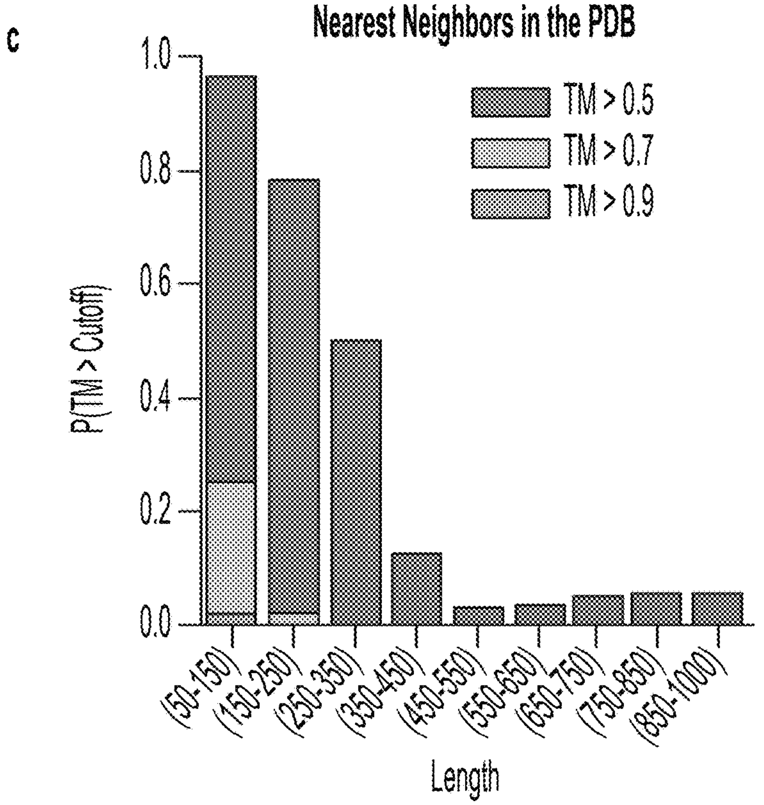
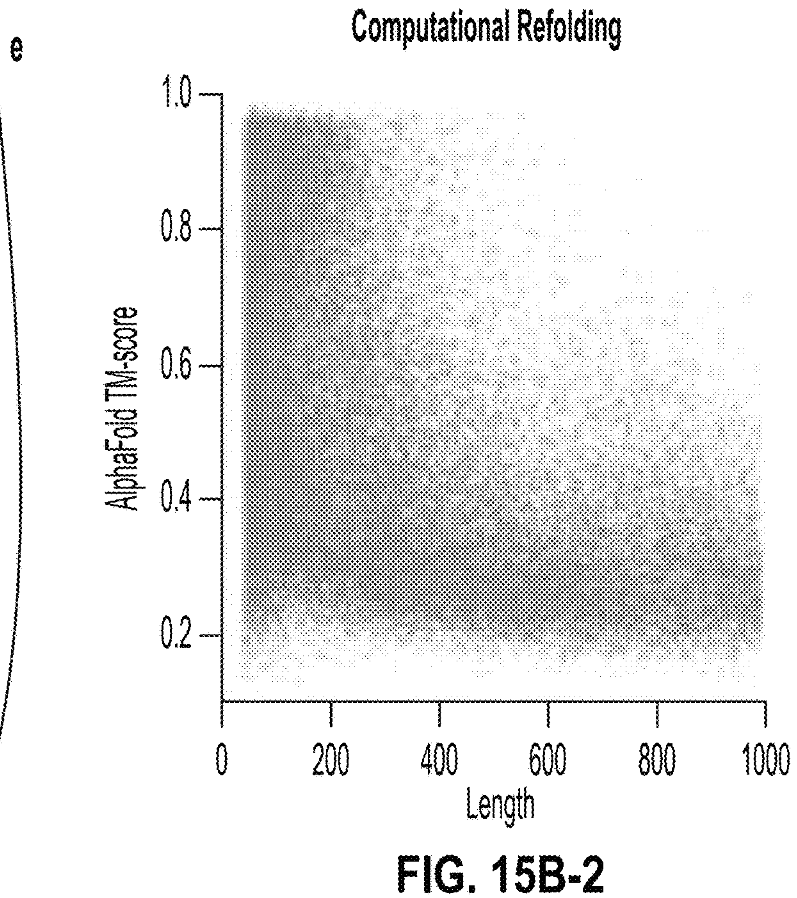
FIG. 15B-2

TO

FROM

TO

FROM

FROM FIG. 22A (a) (b) (c)

Western blots: Streptactin-HRP

*Top 20 proteins from split-GFP screen*

12% Bis Tris SDS-PAGE run in MES
Streptactin-HRP western blot

12% Bis Tris SDS-PAGE run in MES
Streptactin-HRP western blot

| Lane | PRO ID | MW (kDa) | Observed |
|---|---|---|---|
| 1 | UNC_113 | 15.6 | Yes |
| 2 | UNC_163 | 17.5 | Yes |
| 3 | UNC_102 | 17.7 | Yes |
| 4 | UNC_083 | 14.1 | Yes |
| 5 | UNC_159 | 24.2 | Yes |
| 6 | UNC_096 | 14.9 | Yes |
| 7 | UNC_077 | 18.4 | No |
| 8 | UNC_017 | 22.5 | Yes |
| 9 | UNC_153 | 17.2 | Yes |
| 10 | UNC_092 | 33.4 | Yes |
| 11 | UNC_002 | 23.3 | Yes |
| 12 | UNC_121 | 27.1 | Yes |
| 13 | UNC_079 | 17.9 | Yes |
| 14 | UNC_154 | 25.0 | Yes |
| 15 | UNC_086 | 31.0 | No |
| 16 | UNC_073 | 17.0 | Yes |
| 17 | UNC_018 | 18.7 | Yes |
| 18 | UNC_146 | 34.4 | No |
| 19 | UNC_028 | 20.5 | No |
| 20 | UNC_119 | 16.1 | Yes |

Top 20

TO FIG. 54B

FROM FIG. 54A

| | | | |
|---|---|---|---|
| 21 | UNC_138 | 31.7 | No |
| 22 | UNC_051 | 34.9 | No |
| 23 | UNC_037 | 44.5 | No |
| 24 | UNC_166 | 32.7 | No |
| 25 | UNC_045 | 52.2 | No |
| 26 | UNC_097 | 31.0 | No |
| 27 | UNC_057 | 36.5 | No |
| 28 | UNC_087 | 45.5 | No |
| 29 | UNC_114 | 38.0 | No |
| 30 | UNC_033 | 42.0 | No |
| 31 | UNC_112 | 49.5 | No |
| 32 | UNC_050 | 33.1 | No |
| 33 | UNC_063 | 41.9 | No |
| 34 | UNC_098 | 27.0 | No |
| 35 | UNC_103 | 22.7 | No |
| 36 | UNC_066 | 44.4 | No |
| 37 | UNC_107 | 17.6 | No |
| 38 | UNC_030 | 25.2 | No |
| 39 | UNC_019 | 40.4 | No |
| 40 | UNC_061 | 32.9 | No |

Bottom 20

TO FIG. 54C

FROM FIG 54B

Western blots: Anti-Strep-tag-HRP

*Top 20 proteins from split-GFP screen*

| Lane | PRO ID | MW (kDa) | Observed |
|---|---|---|---|
| 1 | UNC_113 | 15.6 | Yes |
| 2 | UNC_163 | 17.5 | Yes |
| 3 | UNC_102 | 17.7 | Yes |
| 4 | UNC_083 | 14.1 | Yes |
| 5 | UNC_159 | 24.2 | Yes |
| 6 | UNC_096 | 14.9 | Yes |
| 7 | UNC_077 | 18.4 | No |
| 8 | UNC_017 | 22.5 | Yes |
| 9 | UNC_153 | 17.2 | Yes |
| 10 | UNC_092 | 33.4 | No |
| 11 | UNC_002 | 23.3 | No |
| 12 | UNC_121 | 27.1 | Yes |
| 13 | UNC_079 | 17.9 | Yes |
| 14 | UNC_154 | 25.0 | Yes |
| 15 | UNC_086 | 31.0 | Yes |
| 16 | UNC_073 | 17.0 | Yes |
| 17 | UNC_018 | 18.7 | Yes |
| 18 | UNC_146 | 34.4 | Yes |
| 19 | UNC_028 | 20.5 | Yes |
| 20 | UNC_119 | 16.1 | Yes |

Top 20

TO FIG. 54D

FROM FIG. 54C

| | | | | |
|---|---|---|---|---|
| 21 | UNC_138 | 31.7 | No | Bottom 20 |
| 22 | UNC_051 | 34.9 | No | |
| 23 | UNC_037 | 44.5 | No | |
| 24 | UNC_166 | 32.7 | No | |
| 25 | UNC_045 | 52.2 | No | |
| 26 | UNC_097 | 31.0 | No | |
| 27 | UNC_057 | 36.5 | No | |
| 28 | UNC_087 | 45.5 | No | |
| 29 | UNC_114 | 38.0 | No | |
| 30 | UNC_033 | 42.0 | No | |
| 31 | UNC_112 | 49.5 | No | |
| 32 | UNC_050 | 33.1 | No | |
| 33 | UNC_063 | 41.9 | No | |
| 34 | UNC_098 | 27.0 | No | |
| 35 | UNC_103 | 22.7 | No | |
| 36 | UNC_066 | 44.4 | No | |
| 37 | UNC_107 | 17.6 | No | |
| 38 | UNC_030 | 25.2 | No | |
| 39 | UNC_019 | 40.4 | No | |
| 40 | UNC_061 | 32.9 | No | |

Western blot: Anti-Strep-tag-HRP

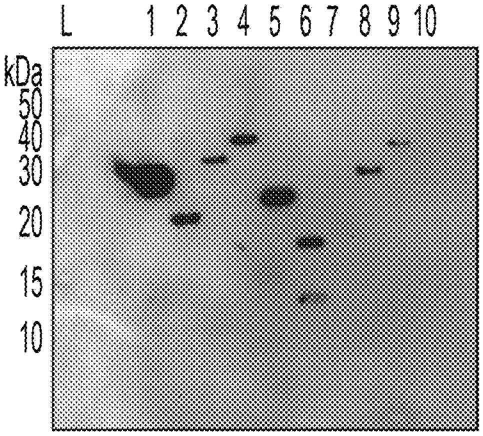

12% Bis Tris SDS-PAGE run in MES
Anti-Strep-HRP western blot

| Lane | PRO-ID | MW (kDa) | Observed |
|---|---|---|---|
| 1 | UNC_239 | 32.6 | Yes |
| 2 | UNC_174 | 21.2 | Yes |
| 3 | UNC_264 | 33.6 | Yes |
| 4 | UNC_258 | 41.7 | Yes |
| 5 | UNC_194 | 25.5 | Yes |
| 6 | UNC_227 | 17.2 | Yes |
| 7 | UNC_244 | 34.6 | Yes |
| 8 | UNC_262 | 25.1 | Yes |
| 9 | UNC_267 | 35.0 | Yes |
| 10 | UNC_185 | 20.3 | No |

Western blot: Streptactin-HRP

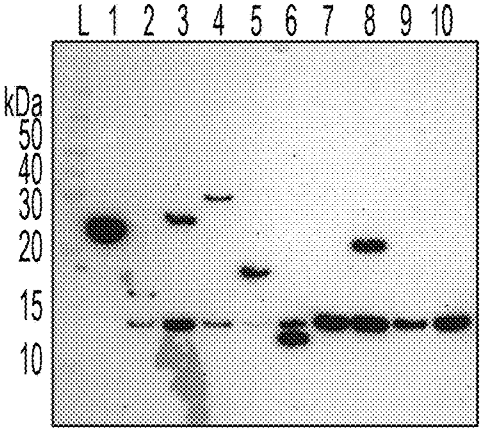

12% Bis Tris SDS-PAGE run in MES
Streptactin-HRP western blot

| Lane | PRO-ID | MW (kDa) | Observed |
|---|---|---|---|
| 1 | UNC_239 | 32.6 | Yes |
| 2 | UNC_174 | 21.2 | Yes |
| 3 | UNC_264 | 33.6 | Yes |
| 4 | UNC_258 | 41.7 | Yes |
| 5 | UNC_194 | 25.5 | Yes |
| 6 | UNC_227 | 17.2 | Yes |
| 7 | UNC_244 | 34.6 | No |
| 8 | UNC_262 | 25.1 | Yes |
| 9 | UNC_267 | 35.0 | No |
| 10 | UNC_185 | 20.3 | No |

FIG. 55D

DIFFUSION MODEL FOR GENERATIVE PROTEIN DESIGN

CROSS-REFERENCE TO RELATED APPLICATIONS

The present application claims the benefit under 35 U.S.C. § 365(c) and § 120 and is a continuation of International Patent Application Serial No. PCT/US2023/037034, filed Nov. 8, 2023, titled "DIFFUSION MODEL FOR GENERATIVE PROTEIN DESIGN", which claims the benefit of and priority to U.S. Provisional Application No. 63/423,775 filed on Nov. 8, 2022, U.S. Provisional Application No. 63/424,044 filed on Nov. 9, 2022, U.S. Provisional Application No. 63/383,074 filed on Nov. 9, 2022, U.S. Provisional Application No. 63/383,242 filed on Nov. 10, 2022, U.S. Provisional Application No. 63/384,076 filed on Nov. 16, 2022, U.S. Provisional Application No. 63/385,020 filed on Nov. 26, 2022, U.S. Provisional Application No. 63/385,619 filed on Nov. 30, 2022, U.S. Provisional Application No. 63/499,963 filed on May 3, 2023, U.S. Provisional Application No. 63/469,822 filed on May 30, 2022, U.S. Provisional Application No. 63/470,672 filed on Jun. 2, 2023, U.S. Provisional Application No. 63/522,538 filed on Jun. 22, 2023, and U.S. Provisional Application No. 63/578,763 filed on Aug. 25, 2023, all of which are incorporated by reference in their entirety.

BACKGROUND

Challenges arise when trying to design protein as protein space is vast. Because of this vast space, modeling the relationship between amino acid sequences, protein structure, and function is extremely difficult. Some computational techniques to iteratively sample and explore the protein space have been implemented, but such techniques are ill-equipped with traversing the vast protein space as computations remain combinatorially large. Moreover, attempting to discover de novo protein sequences that satisfy particular design conditions often lead to models pigeonholing into a small subset of the protein space, typically around prior known protein sequences.

SUMMARY

An analytics system implements a diffusion model for generative protein design. The analytics system receives a set of one or more design conditions for generating a de novo protein. The diffusion model is guided by the set of design conditions to conditionally sample the protein space in generating the de novo protein. In one or more embodiments, the analytics system generates a modular energy function that drives the conditional sampling of the protein space. The modular energy function thereby constrains the sampling process to satisfy the design conditions. Design conditions are effectively target characteristics of the desired protein to be designed. During deployment, the diffusion model is configured to denoise from an initial random state in the protein space to determine the de novo protein. In some embodiments, the analytics system may also determine the protein residue sequence, the protein folding structure, or some combination thereof.

To train the diffusion model, the analytics system leverages known proteins from a protein database. The analytics system injects Gaussian noise to the proteins to generate noised states of the proteins. The analytics system applies the diffusion model to the noised states to predict the denoised states of the proteins. The analytics system then trains the diffusion model to minimize a loss determined by comparing the predicted denoised states to the initial states of the proteins. When training, the analytics system may directly predict the denoised state of the training sample, thereby scaling subquadratically.

In some embodiments, the analytics system implements low-temperature sampling to target high likelihood regions in the multidimensional protein space. The low-temperature sampling algorithm implements low temperature rescaling and hybrid Langevin dynamics to better guide the diffusion process towards the high-likelihood distributions, i.e., optima in the protein space. The low-temperature rescaling aims to exploit high likelihood states, whereas the equilibration rate of the Langevin dynamics operates as a counterbalance to promote exploration of the protein space.

With the novel synthetic protein design, the analytics system may provide the design to a protein manufacturing system to manufacture the synthetic protein. In general, the protein manufacturing system uses synthesized DNA molecules coded for the expression of the amino acid sequence of the synthetic protein. The manufacturing system transfects a cell line with the synthetically generated DNA molecules. Example cell lines include bacteria, yeast, and mammalian cells. The transfected cell lines are cultivated to express the protein through the cell's natural functions. Following protein expression, the manufacturing system may perform protein extraction and purification to yield a high-quality and functional protein product. The end result is the extracted and purified synthetic protein. Thus, the disclosure includes a synthetic protein that is generated by a process that includes the steps presented below. However, in some embodiments, the system provides or designs a data representation of a synthetic protein. Thus, the disclosure includes a synthetic protein representation or a synthetic protein design that is generated by or designed by a process includes the steps presented below. The synthetic protein can be a novel or de novo protein that does currently exist or has not previously existed in nature or that is not currently known to exist in nature, or that has not previously been discovered or not known to have been discovered in nature.

Clause 1. A computer-implemented method comprising: receiving a set of one or more design conditions that specify target characteristics of a synthetic protein; defining a modular energy function as a composition of a diffusion energy component and one or more conditioner energy components, wherein the diffusion energy component determines an energy value based on a sampled state of the synthetic protein and a time step of the sampled state and each conditioner energy component determines an energy value based on the sample state of the synthetic protein and the target characteristic of each design condition; and applying a diffusion model to determine a denoised protein backbone, wherein applying the diffusion model comprises, in each sampling step of a plurality of sampling steps: transforming one prior sampled state of the synthetic protein from unconstrained space into constrained space based on the one or more design conditions, denoising the prior sampled state in the constrained space, and sampling a subsequent sampled state in the unconstrained space by applying a gradient of the modular energy function to the denoised prior sampled state in the constrained space; wherein the final sampled state is a denoised protein backbone for the synthetic protein that satisfies the set of one or more design conditions.

Clause 2. The computer-implemented method of clause 1, wherein each design condition is either: a restraint that reweights the modular energy function to bias for a target characteristic of the synthetic protein; or a constraint that limits multidimensional protein space that defines possible states of the synthetic protein.

Clause 3. The computer-implemented method of any of clauses 1-2, wherein the set of one or more design conditions one or more of: a symmetry constraint that requires symmetry in the denoised protein backbone; a substructure infilling restraint that biases towards particular substructures; a shape constraint that requires a particular shape of the denoised protein backbone; a distance constraint that requires a particular distance between at least two residues; a substructure root mean squared deviation (RMSD) constraint that requires a structural motif to have a low RMSD; a text caption restraint derived from a text input including one or more design conditions; a sequence constraint that requires the denoised protein backbone to include a particular amino acid sequence; a domain classifier constraint that inputs a target structure and outputs a functional characteristic required of the denoised protein backbone; and a secondary structure constraint that requires a particular secondary structure to be present in the denoised protein backbone.

Clause 4. The computer-implemented method of any of clauses 1-3, further comprising: applying a sequence generation model to the denoised protein backbone to determine an amino acid sequence that folds into the denoised protein backbone.

Clause 5. The computer-implemented method of any of clauses 1-4, wherein the diffusion model is further configured to output an amino acid sequence that is configured to structurally create the denoised protein backbone.

Clause 6. The computer-implemented method of any of clauses 1-5, wherein an initial state is a base protein backbone to be modified by the diffusion model and is input with the set of one or more design conditions.

Clause 7. The computer-implemented method of any of clauses 1-5, wherein an initial state is randomly sampled in multidimensional protein space.

Clause 8. The computer-implemented method of any of clauses 1-7, wherein the plurality of sampling steps are discretized timesteps.

Clause 9. The computer-implemented method of clause 8, wherein the plurality of sampling steps includes 100 or more sampling steps.

Clause 10. The computer-implemented method of any of clauses 1-9, wherein the set of one or more design conditions are derived from applying a natural language processing model to an input text query.

Clause 11. The computer-implemented method of any of clauses 1-10, wherein, in each sampling step, sampling another sampled state comprises rescaling the modular energy function based on a time-dependent temperature.

Clause 12. The computer-implemented method of clause 11, wherein, in each sampling step, sampling another sampled state comprises applying a time-dependent Langevin dynamics equilibration rate.

Clause 13. The computer-implemented method of any of clauses 1-12, further comprising: initializing a first seed state and a second seed state that is different than the first seed state; wherein applying the diffusion model comprises applying the diffusion model to the first seed state to determine a first denoised protein backbone and applying the diffusion model to the second seed state to determine a second denoised protein backbone.

Clause 14. The computer-implemented method of any of clauses 1-13, further comprising: receiving a second set of one or more design conditions that specify one or more modifications to the denoised protein backbone of the synthetic protein; modifying the modular energy function to further comprise one or more conditioner energy components based on the second set of one or more design conditions; and applying the diffusion model to modify the denoised protein backbone to satisfy the one or more modifications to the denoised protein backbone.

Clause 15. A non-transitory computer-readable storage medium storing instructions that, when executed by a computer processor, cause the computer processor to perform the computer-implemented method of any of clauses 1-14.

Clause 16. A system comprising: a computer processor; and the non-transitory computer-readable storage medium of clause 15.

Clause 17. A non-transitory computer-readable storage medium storing a synthetic protein design that is generated by the computer-implemented method of any of clauses 1-14.

Clause 18. A synthetic protein that is generated by a process comprising steps of: determining a synthetic protein design that is generated by the computer-implemented method of any of clauses 1-14; and manufacturing the synthetic protein via cell expression.

Clause 19. A computer-implemented method for training a diffusion model, comprising: accessing from a protein database a set of protein backbones; generating a noised state for each protein backbone by transforming an initial state of the protein backbone with noise; applying the diffusion model to the noised state for each protein backbone to predict a denoised state of the protein backbone; determining a loss for each protein backbone as a difference between the denoised state and the initial state of the protein backbone; and training the diffusion model as a neural network by adjusting one or more parameters of the diffusion model based on the losses.

Clause 20. The computer-implemented method of clause 19, wherein a protein backbone comprises three-dimensional coordinates for each heavy atom of amino acid residues in the protein backbone.

Clause 21. The computer-implemented method of any of clauses 19-20, wherein generating the noised state for each protein backbone comprises, for each protein backbone: selecting a random time step on a time continuum, wherein the initial state is at time step zero; and adding an amount of Gaussian noise based on the random time step to the initial state of the protein backbone to generate the noised state.

Clause 22. The computer-implemented method of clause 21, wherein applying the diffusion model to the noised state for each protein backbone comprises: predicting the amount of Gaussian noise added to generate the noised state based on the initial state and the random time step; and removing the predicted amount of Gaussian noise from the noised state to generate the denoised state.

Clause 23. The computer-implemented method of any of clauses 21-22, further comprising: generating a second noised state for each protein backbone by: selecting a second random time step on the time continuum, and adding an amount of Gaussian noise based on the second random time step to the initial state of the protein backbone to generate the second noised state; and applying the diffusion model to the second noised state for each protein backbone to predict a second denoised state of the protein backbone; determining a second loss for each protein backbone as a difference between the second denoised state and the initial state of the protein backbone; and wherein training the diffusion model is further based on the second losses.

Clause 24. The computer-implemented method of any of clauses 19-23, wherein the loss for each protein backbone is based on a difference between coordinates of each heavy atom of amino acid residues in the denoised state and coordinates of each heavy atom of amino acid residues in the initial state.

Clause 25. The computer-implemented method of any of clauses 19-24, further comprising: filtering the protein database to deduplicate similar protein backbones.

Clause 26. The computer-implemented method of clause 25, wherein filtering the protein database to deduplicate similar protein backbones comprises: determining a similarity score between a first protein backbone and a second protein backbone as a distance between coordinates of the first protein backbone and coordinates of the second protein backbone; and removing the second protein backbone based on the similarity score being below a threshold.

Clause 27. The computer-implemented method of any of clauses 19-26, further comprising: filtering the protein database to obtain a high percentage of protein backbones of one type of protein.

Clause 28. A computer program product comprising: a non-transitory computer-readable storage medium storing a diffusion model generated by the computer-implemented method of any of clauses 19-27.

Clause 29. A non-transitory computer-readable storage medium storing a diffusion model generated by the computer-implemented method of any of clauses 19-27.

Clause 30. A system comprising: a computer processor; and the non-transitory computer-readable storage medium of clause 29.

Clause 31. A computer-implemented method comprising: receiving an input with an inverse temperature and an equilibration rate; generating an energy function comprising a diffusion energy component which determines an energy value based on a state of a synthetic protein; modifying a reverse-time dynamics function with a first scaling factor based on the inverse temperature, wherein the reverse-time dynamics function comprises a gradient of the energy function; modifying a Langevin dynamics function with a second scaling factor based on the equilibration rate, wherein the Langevin dynamics function comprises the gradient of the energy function; generating an aggregate dynamics function by combining the modified reverse-time dynamics function and the modified Langevin dynamics function; initializing an initial state of a protein backbone comprising coordinates of heavy atoms of amino acids of a synthetic protein; applying a diffusion model to the initial state to determine a denoised protein backbone, wherein applying the diffusion model comprises, in each sampling step of a plurality of sampling steps: denoising one prior sampled state, and sampling a subsequent sampled stated by applying the aggregate dynamics function to the denoised prior sampled state; wherein the final sampled state is the denoised protein backbone for the synthetic protein.

Clause 32. The computer-implemented method of clause 31, wherein the inverse temperature is configured to drive the sampling towards high-likelihood regions of multidimensional protein space.

Clause 33. The computer-implemented method of any of clauses 31-32, wherein the equilibration rate is a ratio of Langevin dynamics to conventional dynamics.

Clause 34. The computer-implemented method of any of clauses 31-33, wherein the initial state is randomly sampled in multidimensional protein space.

Clause 35. The computer-implemented method of any of clauses 31-34, wherein the plurality of sampling steps are discretized timesteps of a time continuum.

Clause 36. The computer-implemented method of clause 35, wherein the plurality of sampling steps includes 100 or more sampling steps.

Clause 37. The computer-implemented method of any of clauses 31-36, further comprising: applying a sequence generation model to the denoised protein backbone to determine an amino acid sequence that folds into the denoised protein backbone.

Clause 38. The computer-implemented method of any of clauses 31-37, wherein the diffusion model is further configured to output an amino acid sequence that is configured to structurally create the denoised protein backbone.

Clause 39. The computer-implemented method of any of clauses 31-38, wherein an initial sampled state is a base protein backbone to be modified by the diffusion model and is input with the inverse temperature and the equilibration rate.

Clause 40. The computer-implemented method of any of clauses 31-38, wherein an initial sampled state is randomly sampled in multidimensional protein space.

Clause 41. A non-transitory computer-readable storage medium storing instructions that, when executed by a computer processor, cause the computer processor to perform the computer-implemented method of any of clauses 31-40.

Clause 42. A system comprising: a computer processor; and the non-transitory computer-readable storage medium of clause 41.

Clause 43. A non-transitory computer-readable storage medium storing a synthetic protein design that is generated by the computer-implemented method of any of clauses 31-40.

Clause 44. A synthetic protein that is generated by a process comprising steps of: determining a synthetic protein design that is generated by the computer-implemented method of any of clauses 31-40; and manufacturing the synthetic protein via cell expression.

BRIEF DESCRIPTION OF THE DRAWINGS

FIG. 9 illustrates a flowchart describing de novo protein generation through deployment of a diffusion model, according to one or more embodiments.

FIGS. 15B-1-15B-2 show that analysis of unconditional samples reveals diverse geometries that exhibit novel higher-order structure that refold in silica.

FIGS. 15C-1-15C-2 show that symmetry, substructure, and shape conditioning enable geometric molecular programming.

FIG. 15E-1-15E-3 show experimental validation of Chroma-designed proteins.

FIGS. 55A-55D show evaluation of additional set of unconditional protein designs.

DETAILED DESCRIPTION

Overview

Figure 1:
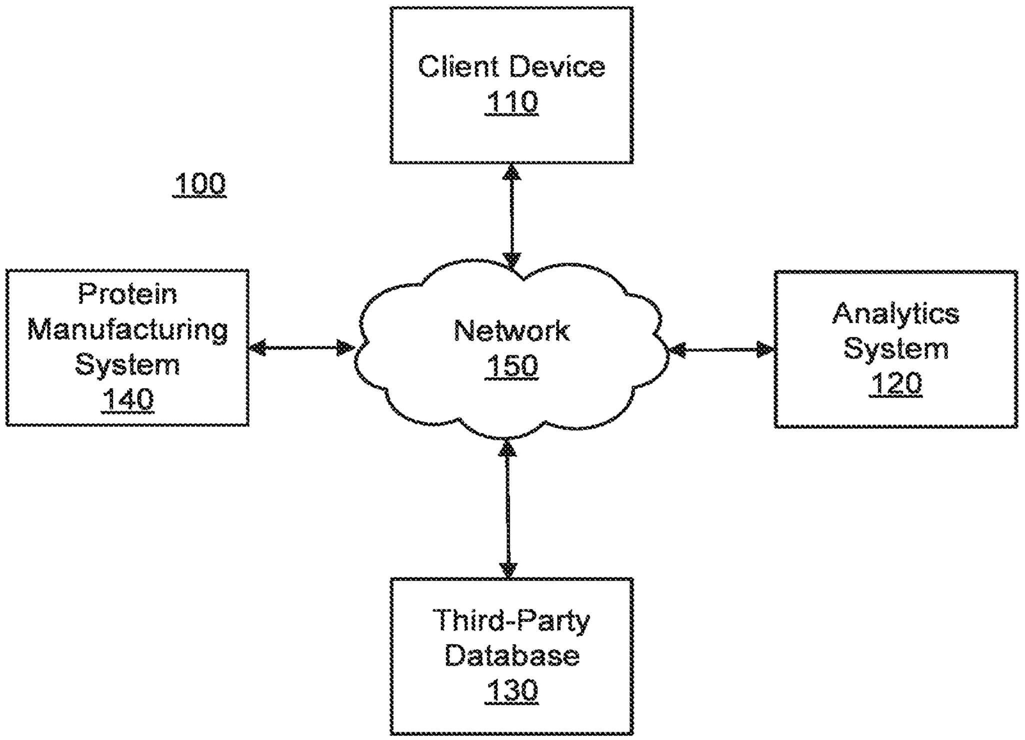
FIG. 1 is a system environment of an analytics system implementing a diffusion model for generative protein design, according to one or more embodiments.

One of the cornerstone technical challenges in novel protein design is exploring the vast multidimensional protein space. Past approaches have been limited in their success in exploring the protein space. Reasons for this include 1) modeling the relationship between sequence, structure, and function is difficult, and 2) most computational design methods rely on iterative search and sampling processes which must navigate a rugged fitness landscape incrementally. Due to the vastness of the protein space, these iterative search and sampling processes may be limited to exploring already known designs. Determining how to efficiently explore the space of designable protein structures remains an open challenge.

Here, an analytics system implements a diffusion model that accelerates the exploration of the protein space through a learned reverse diffusion process. The learned diffusion process is trained efficiently by learning the instantaneous reverse-time diffusion process with training samples. The training thereby provides an improvement to the technical field of computation protein design. During deployment, the diffusion model may be conditioned through one or more design conditions to generate novel protein designs that satisfy target characteristics specified by the design conditions. Such provides flexibility in the protein design process to utilize the same learned diffusion process to generate distinct, diverse, yet novel protein designs. A user may further modify protein designs based on the conditioner framework, allowing for tailored designs. Further, in some embodiments, the system implements a low-temperature sampling algorithm that modifies the dynamics to guide the diffusion process towards high-likelihood distributions, also amounting to a technical improvement. All the above amount to technical improvements and practical applications in the field.

With the novel synthetic protein design, the analytics system may provide the design to a protein manufacturing system to manufacture the synthetic protein. In general, the protein manufacturing system uses synthesized DNA molecules coded for the expression of the amino acid sequence of the synthetic protein. The manufacturing system transfects a cell line with the synthetically generated DNA molecules. Example cell lines include bacteria, yeast, and mammalian cells. The transfected cell lines are cultivated to express the protein through the cell's natural functions. Following protein expression, the manufacturing system may perform protein extraction and purification to yield a high-quality and functional protein product. The end result is the extracted and purified synthetic protein. Accordingly, the diffusion model may be applied to create real-world physical synthetic proteins, e.g., not previously found in nature. Such is a practical application.

The training of the machine-learned models described herein (such as the diffusion models, neural networks, and other models referenced herein) include the performance of one or more non-mathematical operations or implementation of non-mathematical functions at least in part by a machine or computing system, examples of which include but are not limited to data loading operations, data storage operations, data toggling or modification operations, non-transitory computer-readable storage medium modification operations, metadata removal or data cleansing operations, data compression operations, protein structure modification operations, image modification operations, noise application operations, noise removal operations, and the like. Accordingly, the training of the machine-learned models described herein may be based on or may involve mathematical concepts, but is not simply limited to the performance of a mathematical calculation, a mathematical operation, or an act of calculating a variable or number using mathematical methods.

Likewise, it should be noted that the training of the models describes herein cannot be practically performed in the human mind alone. The models are innately complex including vast amounts of weights and parameters associated through one or more complex functions. Training and/or deployment of such models involve so great a number of operations that it is not feasibly performable by the human mind alone, nor with the assistance of pen and paper. In such embodiments, the operations may number in the hundreds, thousands, tens of thousands, hundreds of thousands, millions, billions, or trillions. Moreover, the training data may include hundreds, thousands, tens of thousands, hundreds of thousands, millions, or billions of protein backbones (or derivatives thereof), each protein backbone may further include hundreds, thousands, tens of thousands, hundreds of thousands, or millions of three-dimensional coordinates of heavy atoms in the peptide sequence. Accordingly, such models are necessarily rooted in computer-technology for their implementation and use.

System Environment

FIG. 1 illustrates an example system environment for an analytics system 130, in accordance with one or more embodiments. The system environment illustrated in FIG. 1A includes a client device 110, an analytics system 120, a third-party database 130, a protein manufacturing system 140, and a network 150. Alternative embodiments may include more, fewer, or different components from those illustrated in FIG. 1, and the functionality of each component may be divided between the components differently from the description below. Additionally, each component may perform their respective functionalities in response to a request from a human, or automatically without human intervention.

A client device 110 may be operated by a user in designing proteins. The client device 110 is configured to receive inputs and to display results of analyses by the analytics system, including synthetic protein designs. Accordingly, the client device 110 is a computing device that interacts with other components in the system environment 100 via the network 140. In one or more embodiments, a user may provide to the client device 110 an input including a set of one or more design conditions, optionally with any other instructions, for generating one or more synthetic proteins. The client device 110 may relay the input to the analytics system 120 via the network 140 to generate the one or more synthetic proteins. After generation of the synthetic proteins, the analytics system 120 may relay the generated synthetic proteins to the client device 110 for display to the user. The user may provide additional inputs to the client device 110 to modify the generated protein designs or to regenerate protein designs.

In one or more embodiments, the client device 110 may present a design interface for protein design. The design interface may accept input in various forms. For example, the design interface may include a set of togglable menus. Each togglable menu may include target characteristics for the target protein. In one example, a first togglable menu may include all types of symmetry. Another togglable menu may include different structural motifs to include. A third togglable menu may include various protein types (e.g., antibodies, contractile proteins, enzymes, hormonal proteins, structural proteins, storage proteins, and transport proteins). Other types of input options in the design interface may include range inputs, text input, sequence input, picture input, etc. For example, the design interface may include a single text input for inputting a text string.

The analytics system 120 performs one or more computational analyses. The analytics system 120 is configured to receive inputs from the client device 110 to guide protein design. The analytics system 120 generally applies a diffusion model in conjunction with a sampling algorithm to generate a de novo protein design. The de novo protein design may be provided to a manufacturing system for manufacturing of the protein. The analytics system 120 may also provide the de novo protein design to the client device 110, e.g., for display in the design interface. The client device 110 may provide further inputs for modification of the protein design.

In one or more embodiments, the analytics system 120 generates protein design with a set of one or more design conditions that constrain the protein design. The inputs from the client device 110 may include the set of one or more design conditions including target characteristics of a protein to be generated. The analytics system 120 utilizes the design conditions to constrain application of the diffusion model. The analytics system defines a modular energy function based on the one or more design conditions. The analytics system also transforms coordinates of the sampled state from unconstrained space into constrained space based on the one or more design conditions. The analytics system traverses the protein space from an initial sampled state. At each sampling step, the analytics system utilizes the diffusion model to determine a subsequent sampled state based on the modular energy function and the one or more design conditions. The final sampled state is a protein backbone, e.g., defined by three-dimensional coordinates of residue heavy atoms in the protein chain.

In one or more embodiments, the analytics system 120 may generate a full amino acid sequence configured to structurally create the protein backbone. In one or more embodiments, the diffusion model may be trained to further output the full amino acid sequence. In other embodiments, the analytics system 120 deploys a sequence generation model to determine the full amino acid sequence. The sequence generation model inputs the protein backbone and outputs the full amino acid sequence.

Prior to deployment of the diffusion model, the analytics system 120 may train the diffusion model. The analytics system 120 retrieves protein backbones for use as training samples, e.g., from a database. With each protein backbone, the analytics system transforms an initial state of the protein backbone into a noised state by injecting noise. The amount of noise injected is based on random sampling of a time step on a time continuum. At training time, the analytics system 120 applies the diffusion model to the noised states of the training samples to predict a denoised state from the noised state. The denoised state is predicted based on a gradient of an energy function as applied to the noised state. The analytics system 120 may determine a loss for each training sample based on the initial state and the denoised state. The analytics system 120 trains the diffusion model, e.g., by adjusting parameters (also referred to as weights) of the diffusion model, to minimize the losses.

In one or more embodiments, the analytics system 120 leverages low-temperature sampling during deployment of the diffusion model to drive the sampling towards high-likelihood and confident regions. The low-temperature sampling algorithm implements low temperature rescaling and hybrid Langevin dynamics to better guide the diffusion process towards high-likelihood distributions, i.e., optima in the protein space. The low temperature rescaling may include a combination of a temperature-adjusted reverse time stochastic differential equation (SDE) and a temperature-adjusted probability flow ordinary differential equation (ODE). The hybrid Langevin dynamics may include a combination of an annealed Langevin dynamics SDE and a Langevin reverse-time SDE.

The third-party database 130 is an online database that stores data, e.g., that may be retrieved and used by the analytics system 120. In one or more embodiments, the third-party database 130 stores data on past protein designs. Each protein design may be described by a nucleic acid sequence coded for expression of the protein, an amino acid sequence of the protein (and variants thereof), information on protein folding structure, protein function, chemical properties, physical properties, thermodynamic properties, etc.

The protein manufacturing system 140 is a platform for manufacturing protein. In some embodiments, the protein manufacturing system 140 may be a human-operated laboratory environment. In other embodiments, the protein manufacturing system 140 may be an automated platform with one or more devices for manufacturing protein. For example, the protein manufacturing system 140 may include a DNA synthesis device for manufacturing DNA molecules for coding a target protein. The DNA synthesis device may implement chemical synthesis to create the DNA molecules. Chemical synthesis is a solid-phase phosphoramidite chemical process. In chemical synthesis, the desired DNA sequence is built step-by-step by adding one nucleotide at a time. The process occurs on a solid support, usually a controlled pore glass bead, where the first nucleotide is attached. The synthesis proceeds using a series of reactions to add each subsequent nucleotide successively. This method can produce DNA molecules, e.g., up to 200 base pairs long. These synthesized DNA molecules can be assembled into larger constructs. The protein manufacturing system 140 may also include another protein synthesis device for protein expression with the synthetically generated DNA molecules coded for expression of the target protein. The protein synthesis device may be configured to transfect a cell line with the synthetically generated DNA molecules. Example cell lines include bacteria, yeast, and mammalian cells. The choice of host cell system depends on factors such as scalability, cost, and compatibility with the protein's structure and function. The transfected cell lines are maintained to produce the protein through the cell's natural functions. Following protein expression, the protein manufacturing system 140 may perform protein extraction and purification to yield a high-quality and functional protein product. Common purification methods include affinity chromatography, ion exchange chromatography, size exclusion chromatography, and precipitation. The end result is the extracted and purified target protein.

In some embodiments, the protein manufacturing system 140 may also perform one or more wet lab analyses on the protein manufactured. Wet lab analyses aim to characterize or to validate the manufactured protein. For example, the protein manufacturing system 140 may sequence the manufactured protein to determine whether the manufactured protein matches to the intended target protein. In other examples, the protein manufacturing system 140 may characterize the structure of the manufactured protein, e.g., through x-ray crystallography. The protein manufacturing system 140 may further run experiments with the manufactured protein while measuring characteristics, e.g., denaturing the manufacture protein to determine refolding structure, etc.

The client device 110, the analytics system 120, the third-party database 130, and the protein manufacturing system 140 can communicate with each other via the network 150. The network 150 is a collection of computing devices that communicate via wired or wireless connections. The network 150 may include one or more local area networks (LANs) or one or more wide area networks (WANs). The network 150, as referred to herein, is an inclusive term that may refer to any or all of standard layers used to describe a physical or virtual network, such as the physical layer, the data link layer, the network layer, the transport layer, the session layer, the presentation layer, and the application layer. The network 150 may include physical media for communicating data from one computing device to another computing device, such as multiprotocol label switching (MPLS) lines, fiber optic cables, cellular connections (e.g., 3G, 4G, or 5G spectra), or satellites. The network 150 also may use networking protocols, such as TCP/IP, HTTP, SSH, SMS, or FTP, to transmit data between computing devices. In some embodiments, the network 150 may include Bluetooth or near-field communication (NFC) technologies or protocols for local communications between computing devices. The network 150 may transmit encrypted or unencrypted data.

Analytics System

Figure 2:
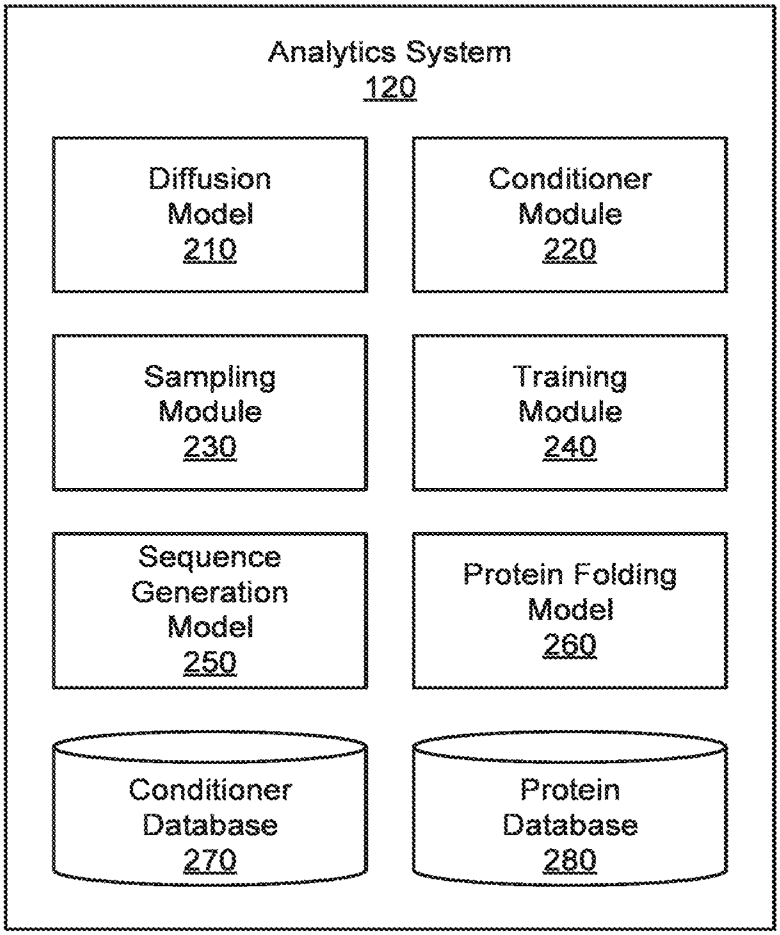
FIG. 2 is a block diagram of the analytics system implementing the diffusion model, according to one or more embodiments.

FIG. 2 is a block diagram of the analytics system 120 implementing a diffusion model for de novo protein generation, according to one or more embodiments. The analytics system 120 includes the diffusion model 210, a conditioner module 220, a training module 230, and a sampling module 240, a sequence generation model 250, a protein folding model 260, a conditioner database 270, and a protein database 280. In other embodiments, the analytics system 120 may have additional, fewer, or different components than those listed in FIG. 2.

The diffusion model 210 is configured to transform one state of a protein backbone into another state of the protein backbone through removal of noise. The diffusion model 210 is a computation, machine-learning generative model. The diffusion model 210 simulates the forward and reverse diffusion of a protein backbone on a time continuum, i.e., where $t \in [0, 1]$. The denoised state is at time step $t=0$, whereas time step $t=1$ represents complete diffusion and thereby loss of any signal. When training the diffusion model 210, the diffusion model 210 learns to predict the reverse flow of time, from a noised state (at some time step in the time continuum) to the denoised state at time step $t=0$. At run-time, the diffusion model 210 is configured to predict small steps of reverse diffusion that is guided by a sampling algorithm employed by the sampling module 230. The diffusion model 210 inputs one state and outputs another state based on the input state and an energy function. In one or more embodiments, the energy function is a modular energy function defined by a diffusion energy component and one or more conditioner energy components. The diffusion energy component is a baseline energy component, whereas the conditioner energy components further modify the energy function to satisfy the one or more design conditions. Further details relating to the diffusion model 210 are described below in conjunction with FIGS. 3-6.

The conditioner module 220 conditions deployment of the diffusion model 210 based on a set of one or more design conditions. Design conditions are target characteristics of a target protein. The design conditions may include one or more restraints and one or more constraints. The restraints are soft conditions that bias the diffusion model to achieve a target characteristic. The constraints are hard conditions that limit the multidimensional protein space to ensure target protein wholly satisfies the constraints. Example design conditions include, but are not limited to, a symmetry constraint, a substructure infilling restraint, a shape constraint, a distance constraint, a substructure root mean squared deviation (RMSD) constraint, a text caption restraint, a sequence constraint, a domain classifier constraint, a secondary structure constraint, etc. The symmetry constraint specifies a certain symmetry of the target protein. The substructure infilling restraint biases towards particular substructures. The shape constraint specifies a particular shape of the target protein. The distance constraint specifies a particular distance between at least two residues. The substructure RMSD constraint specifies a structural motif to have a low RMSD. The text caption restraint biases towards a text input including one or more design conditions. The sequence constraint specifies the target protein to include a particular amino acid sequence. The secondary structure constraint specifies a particular secondary structure to be present in the target protein. In one or more embodiments, the conditioner module 220 applies a natural language processing (NLP) model to parse a text query into the one or more design conditions. The NLP model may be machine-learning model.

In one or more embodiments, the conditioner module 220 generates the modular energy function based on the set of one or more design conditions. The conditioner module 220 may generate the modular energy function by selecting a baseline conditioner energy component for each design condition. The conditioner module 220 may further modify the conditioner energy component based on the design condition. For example, the conditioner energy component for the distance constraint may include a variable for the distance value specified. Accordingly, the conditioner module 220 fills in the variable of the baseline conditioner energy component with the specified distance value. In other examples, the symmetry constraint design condition may include different conditioner energy components for each type of possible symmetry. Further details relating to different design conditions are described below in the subsection entitled "Conditioner Examples."

The sampling module 230 implements a sampling algorithm to traverse the multidimensional protein space with the diffusion model 210 to generate a de novo protein. Initially, the sampling module 230 may determine the initial sampled state. The initial sampled state may be a random state in the multidimensional protein space. The sampling module 230 iteratively inputs one sampled state into the diffusion model 210 to generate another sampled state based on the modular energy function as applied to the first sampled stated. The sampling module 230 iterates over a plurality of sampling steps. In one or more embodiments, the number of sampling steps is based on a time increment. For example, if the sampling module initializes a random state at $t=0.850$ on the time continuum that ranges $t \in [0, 1]$, with $t_0=0$ as the time step of the initial state, then the number of sampling steps is 850 with a time increment $\Delta t=0.001$. The final sampled state where $t=0$ is the de novo protein backbone.

In some embodiments, the sampling module 230 may leverage a constrained space defined by the set of one or more design conditions. The sampling module 230 transforms an input sampled state in unconstrained space into constrained space based on the one or more design conditions. The sampling module 230 may denoise the input state in the constrained space. The sampling module 230 may transform the denoised input state from the constrained space back into the unconstrained space. Then the sampling module 230 may apply the gradient of the diffusion model's modular energy function to the input sampled state (e.g., after denoising in the constrained space, and transformed back into the unconstrained space) to determine an output sampled state.

In some embodiments, the sampling module 230 performs low-temperature sampling. The low-temperature sampling algorithm implements low temperature rescaling and hybrid Langevin dynamics to better guide the diffusion process towards high-likelihood distributions, i.e., optima in the protein space. The low temperature rescaling may include a combination of a temperature-adjusted reverse time stochastic differential equation (SDE) and a temperature-adjusted probability flow ordinary differential equation (ODE). The hybrid Langevin dynamics may include a combination of an annealed Langevin dynamics SDE and a Langevin reverse-time SDE. Further details relating to different design conditions are described below in the subsection entitled "Low-Temperature Sampling."

The training module 240 trains the diffusion model 210. The training module 240 may train the diffusion model to predict a reverse-time diffusion process of protein backbones. The training module 240 may obtain a set of known protein backbones to use as training samples for training the diffusion model 210. The known protein backbones may be accessed from the third-party database 130. For each known protein backbone's initial state, the training module 240 may inject an amount of noise based on a randomly sampled time step on the time continuum. For example, the time continuum ranges $t \in [0, 1]$, with $t_0=0$ as the time step of the initial state and $t_n$ is the randomly selected time step on the time continuum. At $t=1$, all signal is lost, and the protein backbone is completely noised. The greater the time step, the more noise is injected into the training sample. The training module 240 trains the diffusion model 210 to predict the initial state from the noised state. To accomplish the training, the training module 240 applies the diffusion model 210 to the noised state to predict the denoised state. The training module 240 calculates, for each training sample, a loss between the initial state and the predicted denoised state. The training module 240 tunes the diffusion model 210, i.e., by adjusting parameters of the diffusion model 210, to minimize the losses of the training samples. As the training module 240 trains the diffusion model 210 by directly predicting the initial state, the training scales O(N). Further details related to training of the diffusion model 210 are described in conjunction with FIG. 3.

The sequence generation model 250 generates a full amino acid sequence for a de novo protein backbone. The sampling module 230 provides the de novo protein backbone, i.e., which describes the 3D coordinates of the heavy atoms in each amino acid sequence. The sequence generation model 250 inputs the de novo protein backbone to output the full amino acid sequence that structurally creates the de novo protein backbone. In one or more embodiments, the sequence generation model 250 may further output the DNA sequence for coding the protein. The sequence generation model 250 may be trained as a machine-learning model based on known protein backbones with corresponding known amino acid sequences. In some embodiments, the training module 240 trains the sequence generation model 250 by applying the sequence generation model 250 to a known protein backbone to predict a full amino acid sequence for the known protein backbone. The training module 240 may calculate a loss for each known protein backbone based on a comparison (e.g., a difference) between the predicted full amino acid sequence and the corresponding known amino acid sequence.

The protein folding model 260 validates the full amino acid sequence generated by the sequence generation model 250. The protein folding model 260 inputs an amino acid sequence and determines a protein backbone based on the input amino acid sequence. The protein folding model 260 may be applied to the full amino acid sequence, e.g., generated by the sequence generation model 250, to validate whether the full amino acid sequence successfully folds into the de novo protein backbone. The protein folding model 260 may be retrieved from the third-party database 130. The protein folding model 260 may also be trained by the training module 240, e.g., with known protein backbones and corresponding known amino acid sequences.

The conditioner database 270 stores the one or more baseline conditioner energy components for use by the conditioner module 220. As described above, each type of design condition may be associated with one or more baseline conditioner energy components. The baseline conditioner energy component may include one or more variables to be filled in based on the design condition input by the client device 110. For example, with the symmetry constraint, the conditioner database 270 may store a conditioner energy component for each symmetry.

The protein database 280 stores information on proteins. For example, the protein database 280 stores known protein backbones and corresponding known amino acid sequences, e.g., for training of the various models. The protein database 280 may further store proteins generated by other modules of the analytics system 120. For example, the protein database 280 may store the generated protein backbones and/or the corresponding full amino acid sequences. The protein database 280 may further store results of validation experiments. For example, the analytics system 120 may provide a full amino acid sequence for a de novo protein design to the protein manufacturing system 140 to validate the synthetic protein. The protein manufacturing system 140 may manufacture the synthetic protein and conduct one or more validation experiments to assess characteristics of the manufactured synthetic protein.

Diffusion Model Training

Figure 3:
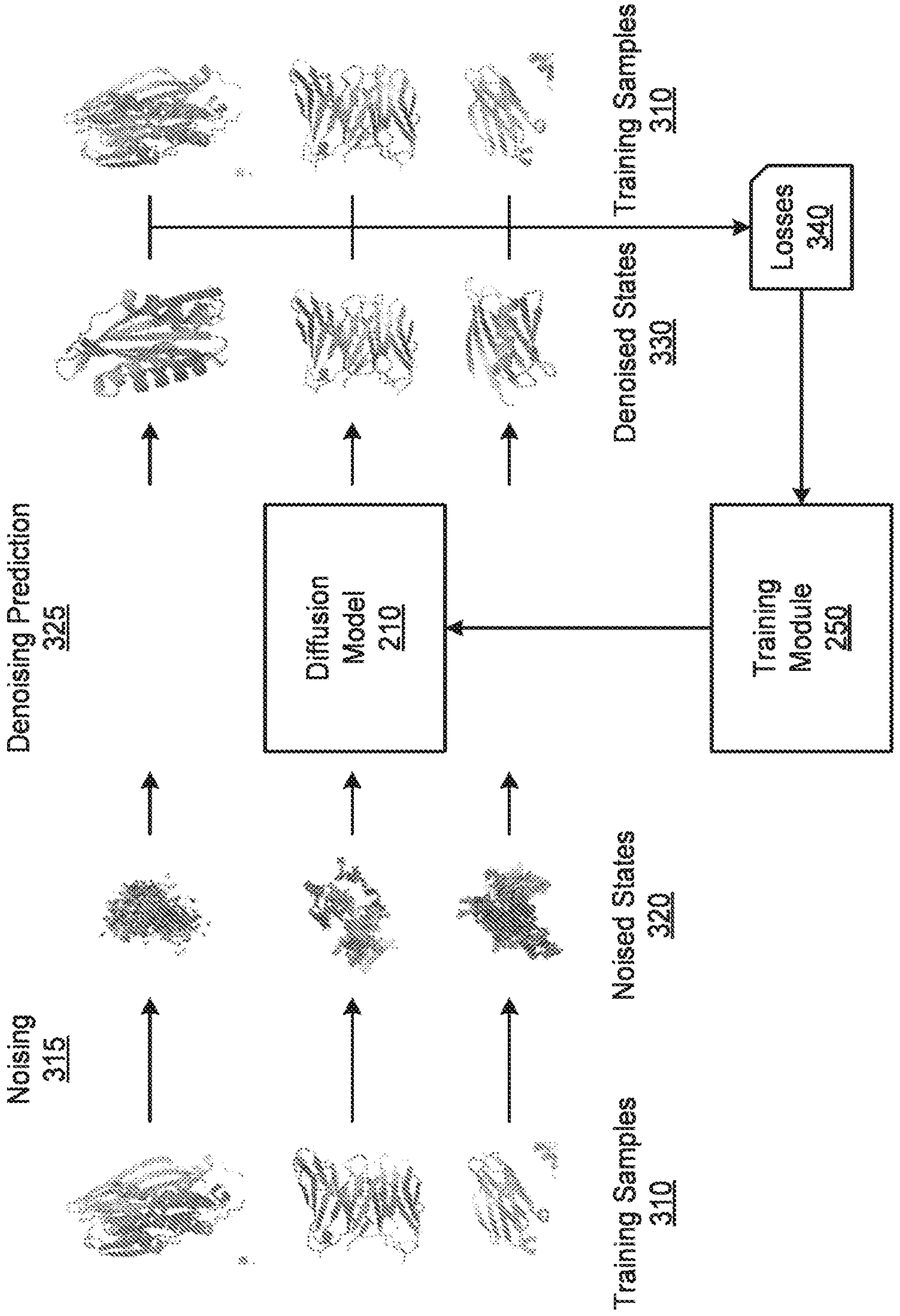
FIG. 3 illustrates a training process of the diffusion model, according to one or more embodiments.

FIG. 3 illustrates a training process of the diffusion model 210, according to one or more embodiments. The training process may be performed by the analytics system 120, or more specifically the training module 240. The training process is representatively illustrated as the use of three training samples 310, but any number of training samples may be used in the training process. Each reference numeral may be referenced in the singular when referring to individual units or in the plural when referring to the whole set.

To train the diffusion model 210, the analytics system 120 utilizes training samples 310. The training samples 310 may be known protein backbones, e.g., as retrieved from the third-party database 130. The analytics system 120 injects some noise into each known protein backbone to generate a noised state 320 for each known protein backbone. As noted above, the amount of noise may be based on the randomly sampled time step on the time continuum.

The analytics system 120 may filter the training samples 310 to refine the training of the diffusion model 210. For example, the analytics system 120 may deduplicate training samples 310 that are similar. To assess whether two training samples 310 are similar, the analytics system 120 may calculate a distance between the protein backbones of the two training samples 310. If the distance is below a threshold distance, then the analytics system 120 may retain one training sample, whilst excluding the second training sample as redundant. The analytics system 120 may also focus training of the diffusion model 210 to certain types of proteins, e.g., antibodies. In some embodiments, the analytics system 120 may apply a different threshold distance between different types of proteins to bias training of the diffusion model 210 towards particular types of proteins.

In some embodiments, the analytics system 120 may generate multiple training samples 310 from one known protein backbone. For example, the analytics system 120 may generate a first training sample 310 by injecting a first amount of noise to the known protein backbone and may generate a second training sample 310 by injecting a different amount of noise to the known protein backbone. The analytics system 120 may also generate synthetic protein backbones by introducing one or more modifications to the known protein backbones.

The analytics system 120 applies the diffusion model 210 to each noised state 320 to predict a denoised state 330 for each training sample 310. The analytics system 120 calculates a loss 340 for each training sample 310. The loss 340 may be calculated as a difference between the denoised states 330 and the initial states of the training samples 310. The training module 250, thereafter, trains the diffusion model 210 by adjusting parameters of the diffusion model 210 to minimize the losses 340.

Diffusion Model Deployment for De Novo Protein Generation

Figure 4:
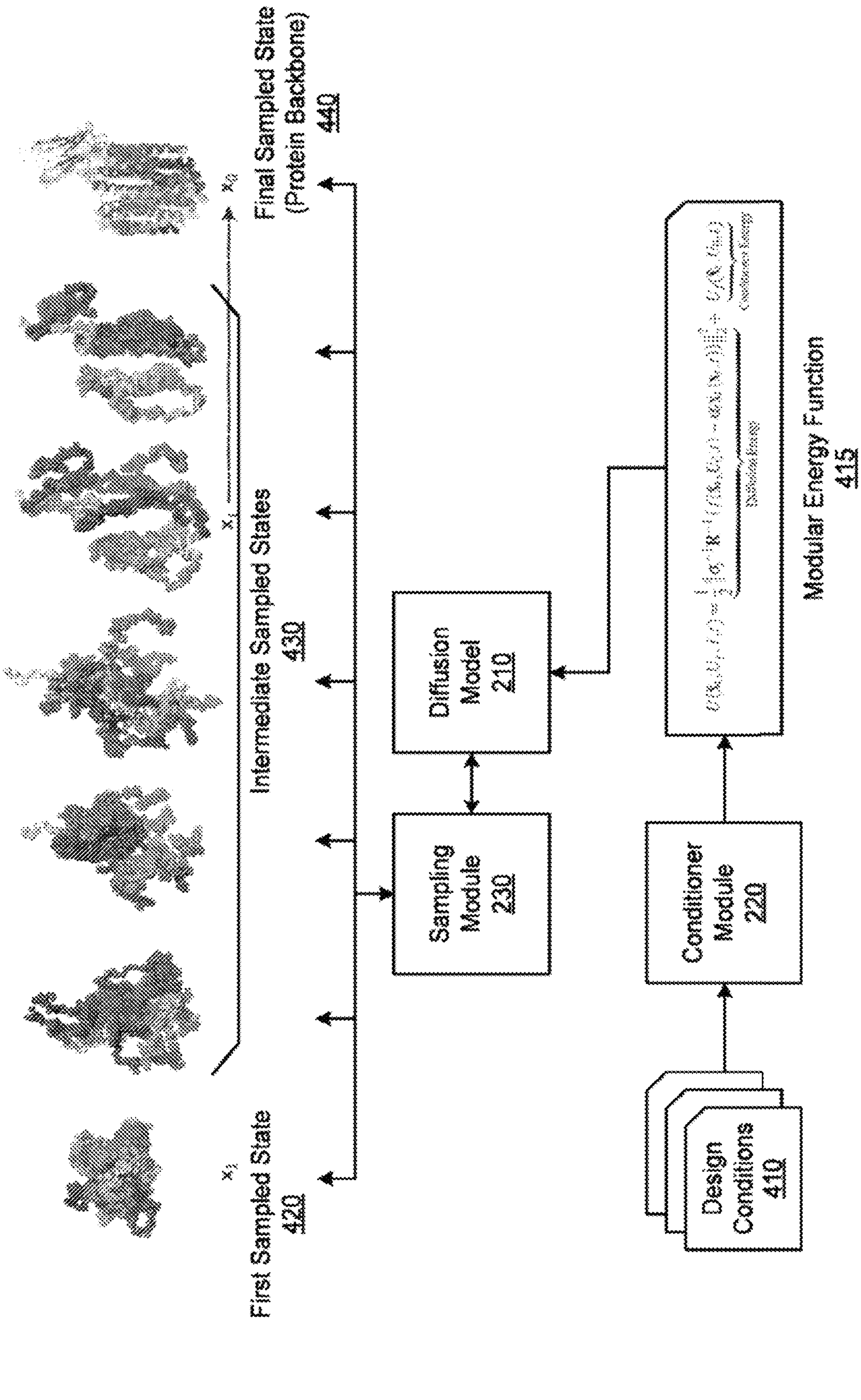
FIG. 4 illustrates deployment of the diffusion model to generate a protein backbone based on a set of one or more design conditions, according to one or more embodiments.

FIG. 4 illustrates deployment of the diffusion model 210 to generate a protein backbone based on a set of one or more design conditions, according to one or more embodiments. The deployment of the diffusion model 210 may be performed by the analytics system 120. The training process is representatively illustrated as performing seven sampling steps, but any number of sampling steps may be used in the deployment process. Each reference numeral may be referenced in the singular when referring to individual units or in the plural when referring to the whole set.

The analytics system 120 receives design conditions 410, e.g., from the client device 110. The design conditions 410 may include one or more restraints, one or more constraints, or some combination thereof. The design conditions 410 specify target characteristics of the protein to be generated. The conditioner module 220 generates a modular energy function 415 based on the design conditions 410. The modular energy function 415 includes a diffusion energy component and one or more conditioner energy components corresponding to the design conditions 410. The modular energy function 415 is utilized by the diffusion model 210 during the sampling process.

The sampling module 230 initializes the sampling process with a first sampled state 420. The first sampled state 420 may be a random state in the multidimensional protein space. In some embodiments, the client device 110 may provide an initial sampled state to serve as a launch point. In a first sampling step, the sampling module 230 inputs the first sampled state 420 into the diffusion model 210 to output a second sampled state (not shown in FIG. 4) based on a gradient of the modular energy function 415. In one or more embodiments, the sampling module 230 may also transform the first sampled state 420 from unconstrained space into constrained space based on the one or more design conditions (e.g., the constraints). The diffusion model 210 denoises in the constrained space. Then the sampling module 230 transforms back into unconstrained space, where the sampling module 230 applies the diffusion model 210 to output the second sampled state. In subsequent sampling steps, the sampling module 230 iteratively inputs a sampled state to output a subsequent sampled state making up the intermediate sampled states 430, e.g., with an incremented reverse time step, trending towards t=0. The final sampled state 440 at t=0 is the de novo protein backbone.

Diffusion Model Architecture

Figure 5:
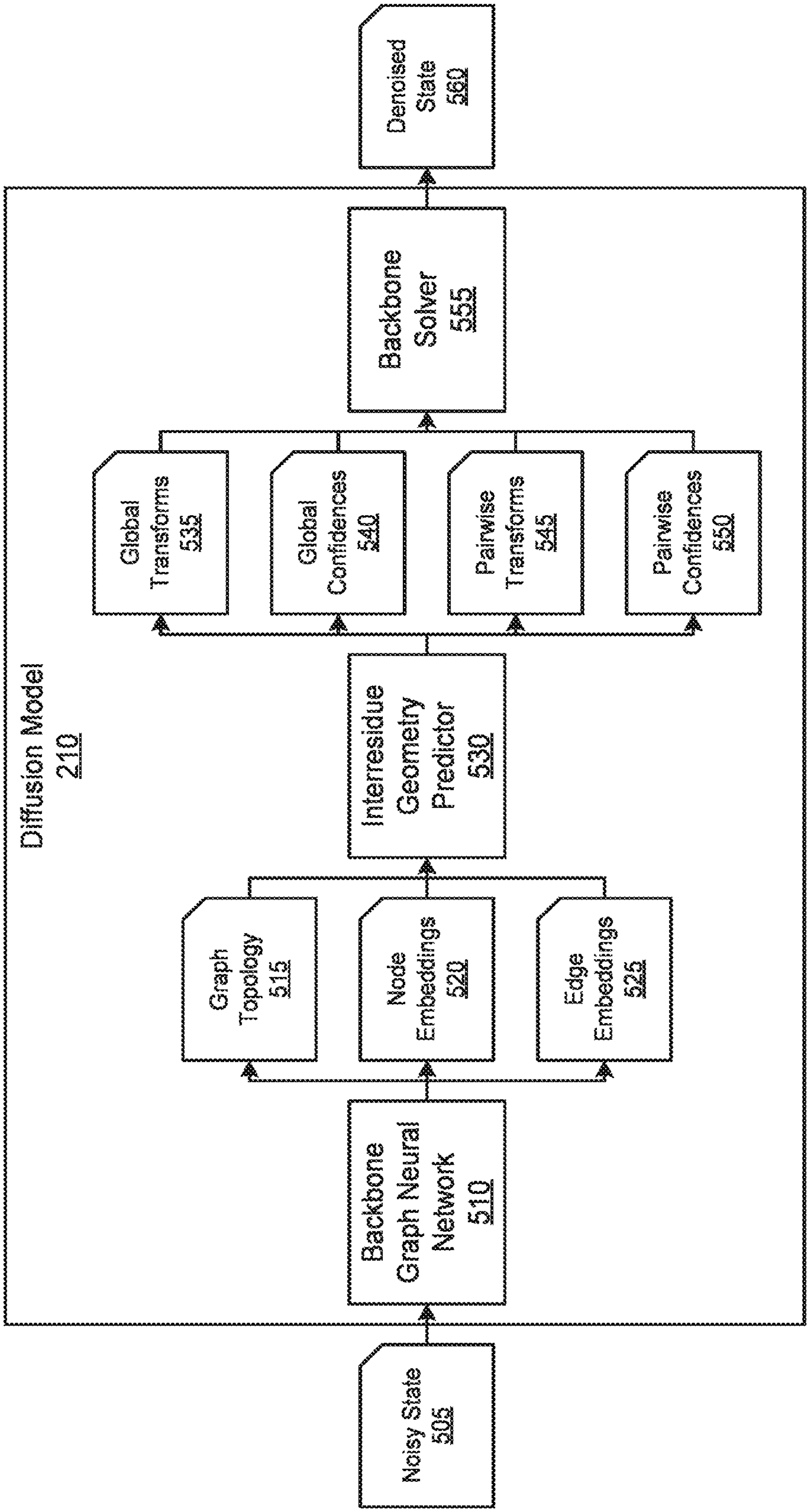
FIG. 5 is a block diagram exampling the architecture of a diffusion model, according to one or more embodiments.

FIG. 5 is a block diagram exampling the architecture of a diffusion model 210, according to one or more embodiments. In FIG. 5, the diffusion model 210 comprises a backbone graph neural network (GNN) 510, an interresidue geometry predictor 530, and a backbone solver 555. In other embodiments, the diffusion model 210 may comprise additional, fewer, or different components than those listed herein. Each reference numeral may be referenced in the singular when referring to individual units or in the plural when referring to the whole set.

The diffusion model 210 is configured to input one noisy state 505 of a protein backbone and to output a denoised state 560 of a protein backbone. The noisy state 505 may be a first sampled state at a time step in the time continuum further towards t=1, whereas the denoised state 560 may be a second sampled state at a time step in the time continuum further towards t=0.

The backbone GNN 510 inputs the noisy state 505 and outputs a graph topology 515, node embeddings 520, and edge embeddings 525. The graph topology 515 describes a graph architecture of the protein backbone. The graph architecture may describe positions of nodes in the graph relative to other nodes and edges between nodes. Each node may have a node embedding 520. Each edge may have an edge embedding 525. The embeddings (e.g., node embeddings 520 and/or edge embeddings 525) may be vector representations (e.g., respectively of nodes and edges in the graph). An edge includes weights that pass values between nodes based on the values of the nodes connected by the edge. The backbone graphical neural network 510 may, in one or more embodiments, a permutation equivariant layer that maps a representation of the graph into an updated representation of the same graph, a local pooling layer that coarsens the graph via downsampling, a global pooling layer that reduces the graph into vector form, or some combination thereof.

The interresidue geometry predictor 530 inputs the graph topology 515, the node embeddings 520, and the edge embeddings 525 to output global transforms 535, global confidences 540, pairwise transforms 545, and pairwise confidences 550. The global transforms 535 indicate a denoised position (e.g., coordinates) of each residue in the protein backbone, while each global transform 535 has an associated global confidence 540 specifying a confidence in the denoised position. The pairwise transforms 545 indicate a denoised relative distance between each pair of residues in the protein backbone, while each pairwise transform 545 has an associated pairwise confidence 550 specifying a confidence in the relative distance.

The backbone solver 555 combines the global transforms 535, the global confidences 540, the pairwise transforms 545, and the pairwise confidences 550 to output the denoised state 560. The backbone solver 555 identifies an optimal solution that attempts to fit all the transforms based on the corresponding confidences. In one or more embodiments, the backbone solver 555 may weight the pairwise transforms 545 more heavily than the global transforms 535. The optimal solution maximizes fitting to transforms with high confidences, e.g., while conversely opting to trade off fitting to transforms with low confidences. The output is the denoised state 560 of the protein backbone, e.g., incrementally denoised from the noisy state 505. In practice, the diffusion model 210 is, iteratively applied to incrementally denoise from a first sampled state through a plurality of intermediate sampled states to the final sampled state, i.e., the denoised protein backbone.

Figure 6:
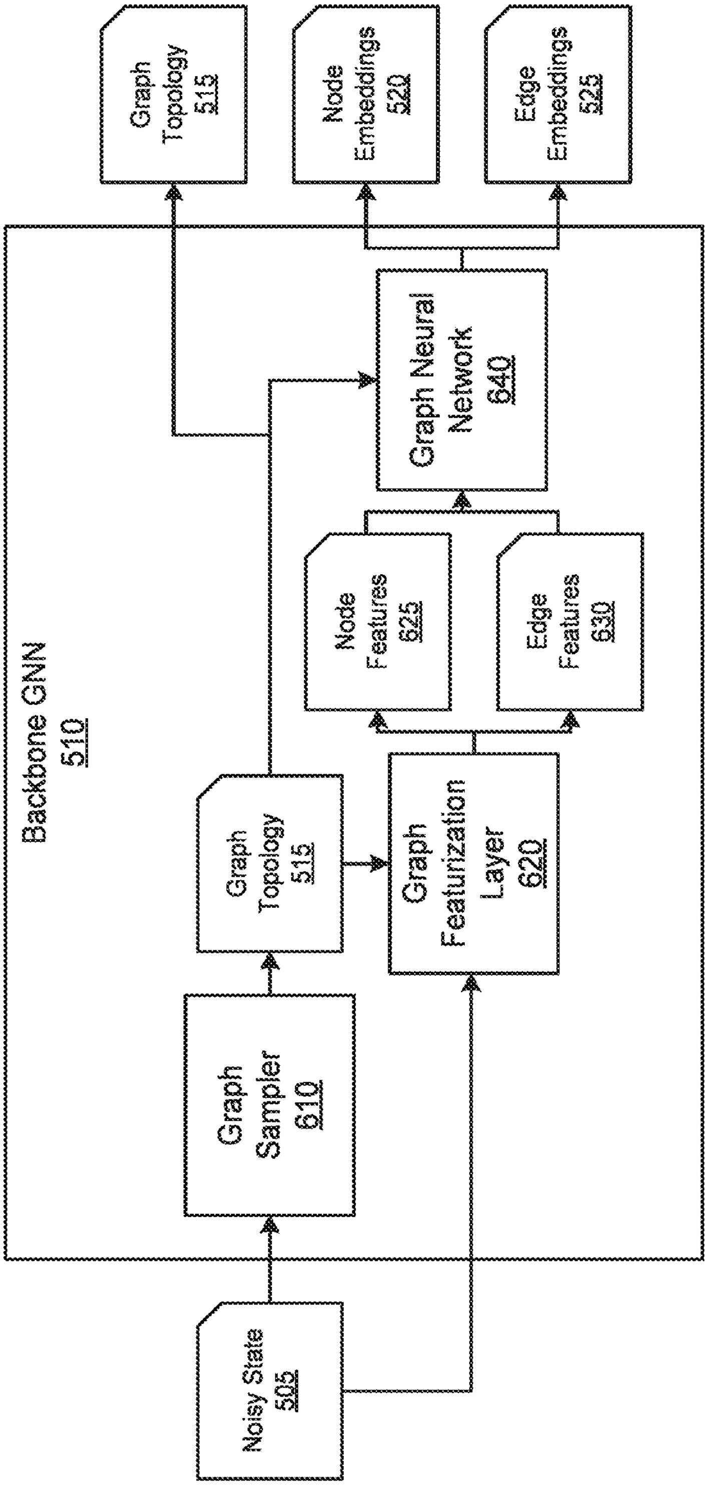
FIG. 6 is a block diagram exampling the architecture of a backbone graph neural network, according to one or more embodiments.

FIG. 6 is a block diagram exampling the architecture of a backbone graph neural network (GNN) 510, according to one or more embodiments. In FIG. 6, the backbone GNN 510 comprises a graph sampler 610, a graph featurization layer 620, and a graph neural network (GNN) 640. In other embodiments, the GNN 510 may comprise additional, fewer, or different components than those listed herein. Each reference numeral may be referenced in the singular when referring to individual units or in the plural when referring to the whole set.

The graph sampler 610 inputs the noisy state 505 to output the graph topology 515. The graph sampler 610 can build the graph topology 515 based on the coordinates of residues in the noisy state 505.

The graph featurization layer 620 inputs the graph topology 515 and the noisy state 505 to output node features 625 and edge features 630. The graph topology 515 defines the graph architecture including number of nodes, position of nodes, and edges connecting pairs of nodes. The node features 625 may encode local geometry, e.g., bond lengths and dihedral angles. The edge features 630 may encode inter-atomic distances, inter-atomic directions, chain distance indicating whether two residues are part of the same polymer chain or different polymer chains, transform features denoting a transform in coordinates of one frame corresponding to one residue to coordinates of the other frame corresponding to the other residue, or some combination thereof.

The GNN 640 inputs the graph topology 515, the node features 625, and the edge features 630 to output the node embeddings 520 and the edge embeddings 525. The GNN 640 is a graph neural network model that is trained to resolve messages passed between nodes according to the edges. The GNN 640 resolves concatenates all messages passed between nodes to generate the node embeddings 520 and the edge embeddings 525.

Sequence Generation Model Architecture

Figure 7:
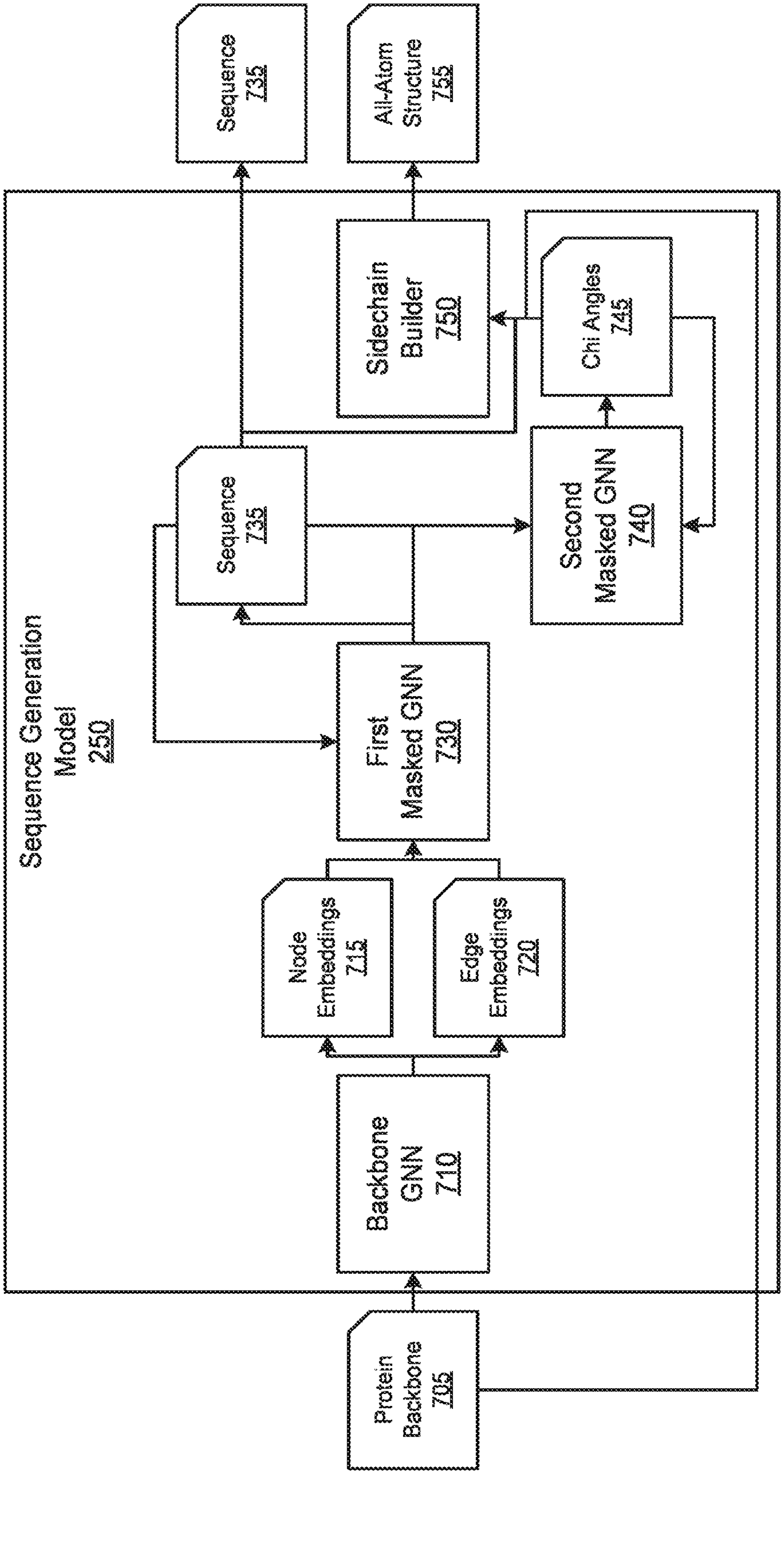
FIG. 7 is a block diagram exampling the architecture of a sequence generation model, according to one or more embodiments.

FIG. 7 is a block diagram exampling the architecture of a sequence generation model 250, according to one or more embodiments. The sequence generation model 250 includes a backbone GNN 710, a first masked GNN 730, a second masked GNN 740, and a sidechain builder 750. In other embodiments, the sequence generation model 250 may comprise additional, fewer, or different components than those listed herein. Each reference numeral may be referenced in the singular when referring to individual units or in the plural when referring to the whole set.

The backbone GNN 710 inputs the protein backbone 705 to output node embeddings 715 and edge embeddings 720. In one or more embodiments, the backbone GNN 710 is an embodiment of the backbone GNN 510. The backbone GNN 710 outputs the node embeddings and the edge embeddings which encode features of the nodes and the edges of the protein backbone 705.

The first masked GNN 730 inputs the node embeddings 715 and the edge embeddings 720 to output the sequence 735. The sequence 735 is an amino acid sequence indicating an order and particular amino acid residue in the peptide chain. The first masked GNN 730 may be trained using the known protein backbones and corresponding known amino acid sequences.

The second masked GNN 740 inputs the sequence 735 to determine chi angles 745 of each amino acid residue. Each amino acid is composed of a number of heavy atoms that, due to intermolecular and intramolecular forces, bend at varying angles relative to one another. The chi angles 745 describe the bends in an amino acid residue caused by the forces between the heavy atoms.

The sidechain builder 750 builds amino acid sidechains based on the chi angles 745 and the sequence 735. As noted, each amino acid residue may comprise a sidechain based on heavy atoms present in the amino acid residue. Accordingly, sidechain builder 750 generates the all-atom structure 755 based on the sequence 735 and the chi angles 745. The all-atom sequence 755 comprehensively describes the coordinates of each atom in the protein.

Methods

Figure 8:
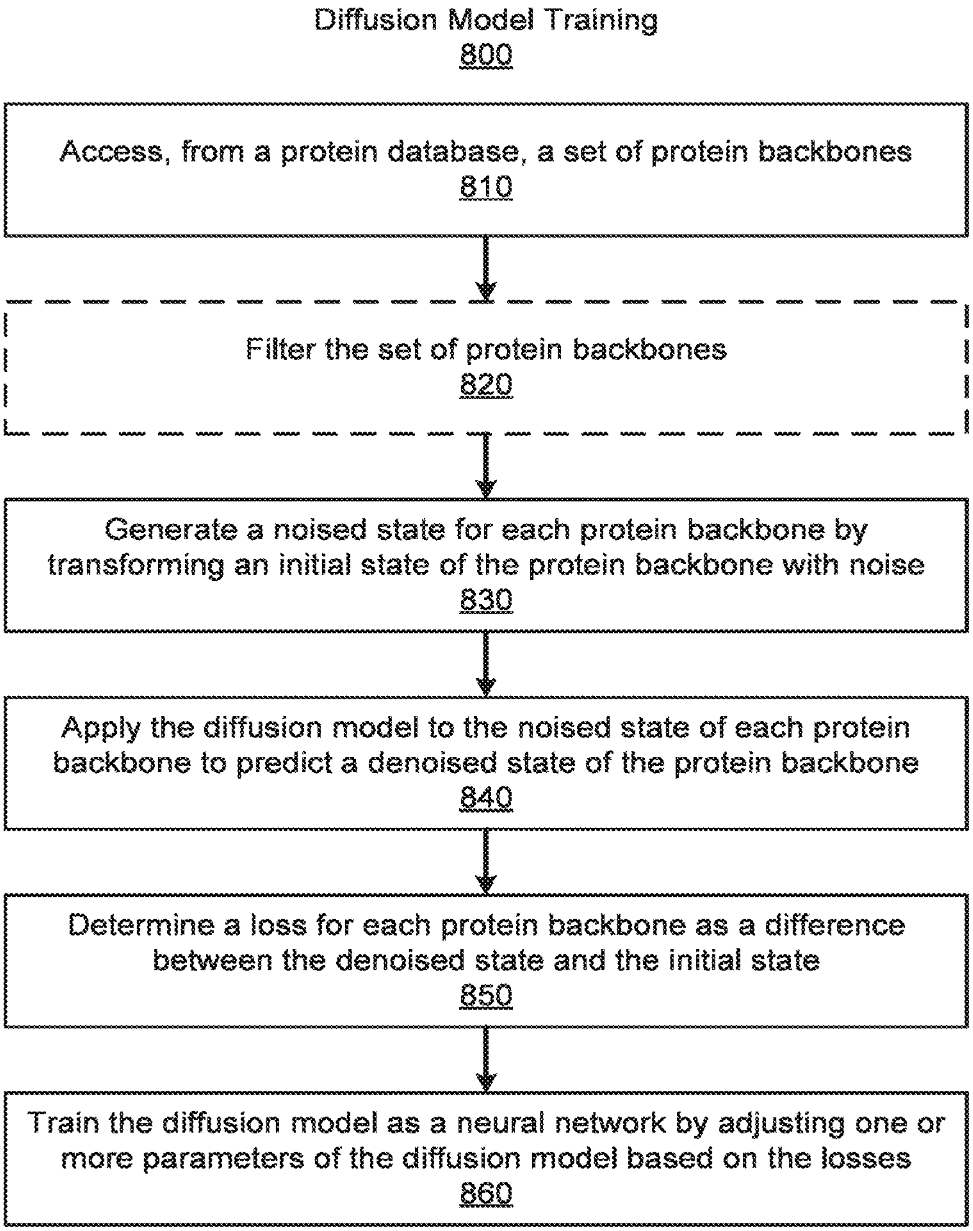
FIG. 8 illustrates a flowchart describing training of a diffusion model for protein design, according to one or more embodiments.

FIG. 8 illustrates a flowchart describing training 800 of a diffusion model for protein design, according to one or more embodiments. The training 800 is described as performed by an analytics system (e.g., the analytics system 120 of FIG. 1). In other embodiments, any step of the training 800 may be performed by another computing device in conjunction with the analytic system. In other embodiments, the training 800 may include additional, fewer, or different steps than those listed herein (as will also be described throughout FIG. 8 description).

The analytics system accesses 810, from a protein database, a set of known protein backbones. The protein database may be a third-party database 130. The protein database stores information relating to known proteins. In some embodiments, the analytics system retrieves the amino acid sequences of the known proteins and generates a protein backbone based on a protein folding model. Each protein backbone describes three-dimensional coordinates of each heavy atom of each amino acid residue in the protein's peptide chain. In other embodiments, the protein backbone may further describe the three-dimensional coordinates of atoms on a sidechain of each amino acid residue.

The analytics system may filter 820 the set of protein backbones to achieve a training set of protein backbones for use in training the diffusion model. In one or more embodiments, filtering includes deduplication of similar protein backbones. To determine if two protein backbones are similar, the analytics system may determine a similarity score as a distance between the coordinates of the two protein backbones. If the similarity score is below a threshold, then the two protein backbones may be deemed sufficiently similar. Accordingly, the analytics system may remove one of the two similar protein backbones. In other embodiments, filtering may include obtaining a high percentage of protein backbones of one or more particular types of protein.

The analytics system generates 830 a noised state for each protein backbone by transforming an initial state of the protein backbone with noise. As the diffusion model learns a reverse-time diffusion process, the analytics system may generate the training samples by simulating forward-time diffusion. The amount of noise added to the initial state may be based on a randomly selected time step on the time continuum. The noise may be Gaussian noise. In some embodiments, the analytics system may generate multiple training samples from one known protein backbone by adding differing amounts of noise to the initial state, thereby generating two distinct noised states.

The analytics system applies 840 the diffusion model to the noised state of each protein backbone to predict a denoised state of the protein backbone. The analytics system applies the diffusion model to predict the initial time step associated with the initial state of the protein backbone. The diffusion model may predict the denoised state based on a gradient of an energy function as applied to the noised state.

The analytics system determines 850 a loss of each protein backbone as a difference between the denoised state and the initial state of the protein backbone. In one or more embodiments, the difference may be a L1 norm, a L2 norm, some other distance calculation, or some combination thereof.

The analytics system trains 860 the diffusion model as a neural network by adjusting one or more parameters of the diffusion model based on the losses. The analytics system may backpropagate through the diffusion model to adjust parameters to minimize the losses between the predicted denoised states and the initial states. In some embodiments, the analytics system may perform batch training of the diffusion model, which generally entails adjusting parameters of the diffusion model to minimizes losses for a batch of training samples. In other embodiments, the analytics system may perform iterative training over epochs. An epoch of training is an instance parameter adjustment from a complete pass of the training set through the diffusion model. The diffusion model may be structured with the architectures described in FIGS. 5 & 6.

The trained diffusion model may be stored in a database of the analytics system, and/or the trained diffusion model may transmitted to one or more other computing devices. When fully trained, the analytics system may deploy the diffusion model in conjunction with a sampling algorithm to generate a de novo protein design.

FIG. 9 illustrates a flowchart describing de novo protein generation 900 through deployment of a diffusion model, according to one or more embodiments. The de novo protein generation 900 is described as performed by an analytics system (e.g., the analytics system 120 of FIG. 1). In other embodiments, any step of the de novo protein generation 900 may be performed by another computing device in conjunction with the analytic system. In other embodiments, the de novo protein generation 900 may include additional, fewer, or different steps than those listed herein (as will also be described throughout FIG. 8 description).

The analytics system receives 910 a set of one or more design conditions that specify target characteristics of a synthetic protein. The set of one or more design conditions may be parsed from a text query by a client device. For example, the text query may be "design an antibody with C5 symmetry with Beta hairpin motifs." The analytics system may parse the text query, e.g., with a NLP model, to determine the one or more design conditions. Following the above example, the analytics system may determine a symmetry constraint of "C5 symmetry," a text caption restraint of "antibody," and a secondary structure constraint of "Beta hairpin motif."

Other types of design conditions may include, but are not limited to, a symmetry constraint, a substructure infilling restraint, a shape constraint, a distance constraint, a substructure root mean squared deviation (RMSD) constraint, a text caption restraint, a sequence constraint, a domain classifier constraint, a secondary structure constraint, etc.

The analytics system defines 920 a modular energy function as a composition of a diffusion energy component and one or more conditioner energy components. The diffusion energy component determines an energy value based on a sampled state of the synthetic protein and a time step of the sampled state. Each conditioner energy component determines an energy value based on the sample state of the synthetic protein and the target characteristic of each design condition. The conditioner energy components may be pulled together based on the set of design conditions received, e.g., from the client device. As such, one design query having one set of design conditions yields a different modular energy function compared to another design query having a distinct set of design conditions. In some embodiments, the conditioner energy components include one or more variables that are filled in based on the received design conditions.

The analytics system may rescale 930 the modular energy function based on a time-dependent temperature and/or a time-dependent Langevin dynamics equilibration rate. The time-dependent temperature enables an adjustable temperature throughout the sampling process, such that the sampling can bias towards high likelihood regions in the multidimension protein space. The time-dependent Langevin dynamics equilibration rate sets the equilibration rate of the Langevin dynamics per unit time. The equilibration rate effectively operates to promote exploration as a counterbalance to low-temperature as a driver of exploitation. The high-likelihood states exhibit increased rates of backbone hydrogen bonding that underlie secondary structure.

The analytics system applies 940 the diffusion model to generate a denoised protein backbone. To generate the denoised protein backbone, the analytics system iteratively samples the multidimensional space with the diffusion model, e.g., trained according to the training 800 in FIG. 8. The initialize the sampling, the analytics system may randomly sample a noised state in the multidimensional protein space.

In one sampling step: the analytics system transforms 950 the prior sample state from unconstrained space into constrained space based on the one or more design conditions. For example, if one design condition is an amino acid sequence constraint, then the analytics system constrains the sampled state to substitute some portion of the sampled state of the protein backbone to include the specified amino acid sequence. In the same sampling step: the analytics system denoises 960 the prior sampled state in the constrained space. The analytic system denoises by determining an amount of noise in the sampled state and removing that amount of noise. In the same sampling step: the analytics system samples 970 a subsequent sampled state in the unconstrained space by applying a gradient of the modular energy function to the denoised prior sampled sate in the constrained space. The subsequent sampled state is one subsequent incremented time step, i.e., towards $t \rightarrow 0$. The analytics system iteratively performs sampling over a plurality of discrete sampling steps to incrementally progress from the first sampled state to the final sampled state, being the denoised protein backbone.

In further embodiments, the analytics system applies a sequence generation model to the denoised protein backbone to determine a full amino acid sequence for the synthetic protein. The sequence generation model inputs the denoised protein backbone and determines an amino acid sequence that can fold to structurally create the denoised protein backbone. The sequence generation model may further output the sidechain sequences, completing the all-atom structure.

In additional embodiments, the analytics system may perform parallel sampling of the multidimensional protein space with different seed sampled states. The analytics system may use each seed sampled state to generate a diverse set of de novo protein designs that satisfy the set of one or more design conditions. The analytics system may provide the diverse set of de novo protein designs for experimental validation, e.g., of protein folding, of function, etc.

Conditioner Framework

The previously described restraints and constraints for Langevin dynamics share a common form of implementation: they modify the system coordinates x and/or the total energy U. This suggests a natural building block for a protein programming framework: transformation functions which input and output system states (x, U).

The conditioner framework can be expressed as a function $\mathcal{F}: \mathbb{R}^N \times \mathbb{R} \rightarrow \Omega \subseteq \mathbb{R}^M \times \mathbb{R}$ which maps state-energy pairs in unconstrained input space $\mathbb{R}^N \times \mathbb{R}$ to potentially constrained state-energy pairs in $\Omega \subseteq \mathbb{R}^M \times \mathbb{R}$. For ease of notation, conditioners component-wise $\mathcal{F} = (f, U_f)$ in terms of a state update function $f: \mathbb{R}^N \times \mathbb{R} \rightarrow \Omega_f \subseteq \mathbb{R}^M$ and an energy update function $U_f: \mathbb{R}^N \times \mathbb{R} \rightarrow \Omega_U \subseteq \mathbb{R}$.

To sample from conditioner-biased diffusion problems, the system uses a gradient-based sampling algorithm, such as Langevin dynamics or Hamiltonian Monte Carlo, on the conditioner-transformed instance of the energy function:

$$U(\tilde{x}_t; U_f, f, t) = \frac{1}{2}\left\|\sigma_t^{-1} R^{-1}(f(\tilde{x}_t, U_0; t) - \alpha_t \hat{x}_t(x_t, t))\right\|_2^2 + U_f(\tilde{x}_t, U_0; t)$$

where the gradient $\nabla_{\tilde{x}} U(\tilde{x}_t; U_f, f, t)$ for sampling is computed with respect to the unconstrained coordinates $\tilde{x}_t$. These gradients and dynamics can be computed efficiently even for complex composed conditioners by leveraging modern automatic differentiation frameworks.

The Conditioner formulation satisfies the following objectives:

- Compositionality. Let $\mathcal{F}_1: \mathbb{R}^{N_1} \times \mathbb{R} \rightarrow \Omega \subseteq \mathbb{R}^{M_1} \times \mathbb{R}$ and $\mathcal{F}_2: \mathbb{R}^{N_2} \times \mathbb{R} \rightarrow \Omega \subseteq \mathbb{R}^{M_2} \times \mathbb{R}$ be Conditioners and assume $N_1 = M_2$[6]. Then $\mathcal{F}_3 = \mathcal{F}_1 \cdot \mathcal{F}_2$ is a Conditioner with $\mathcal{F}_3: \mathbb{R}^{N_2} \times \mathbb{R} \rightarrow \Omega_1 \subseteq \mathbb{R}^{M_1} \times \mathbb{R}$.
- Generalized restraints may be realized with state update $f(x, U) = x$ (Identity function) and energy update $U_f(U, \tilde{x}_t, t) = U - \log p(y|x, t)$.
- Constraints: Linear Transforms. Distribution-preserving linear transform constraints may be realized with state update $f(x, U) = Ax + b$ and energy update $U_f(U, \tilde{x}_t, t) = U$ (Identity function).
- Constraints: Non-Linear Transforms. Distribution-preserving nonlinear domain constraints may be realized with bijective and differentiable state update $f: \mathbb{R}^N \times \mathbb{R} \rightarrow \Omega f \subseteq \mathbb{R}^M$ and energy update $$U_f(U, \tilde{x}_t, t) = U + \log \det\left|\frac{\partial f}{\partial \tilde{x}}\right|$$

(Change of volume adjustment).

- Automated Sampling. Any gradient-based sampling algorithm may be used in concert with the Conditioner-adjusted energy and an annealing schedule on the diffusion time t.

In some embodiments, the modular energy function may condition for sequence and structure. The Conditioner framework is also straightforwardly applicable to joint sampling of sequence and structure, where the joint energy function is defined as:

$$U(x_t; y, t) = \frac{1}{2}\left\|\sigma_t^{-1} R^{-1}(f(\tilde{x}_t, U_0; t) - \alpha_t \hat{x}_t(x_t, t))\right\|_2^2 - \log p(f_s(\tilde{s}_t) \mid f_x(\tilde{x}_t), t) + U_f(\tilde{x}_t, \tilde{s}_t, U_0; t).$$

where gradient and dynamics are computed in unconstrained space $\tilde{x}_t$, $\tilde{s}_t$. Discrete Langevin sampling can be implemented in conjunction to sample from sequence space while leveraging gradients for building locally-informed proposals. Sequence and structure gradients can be computed in one pass via automatic differentiation frameworks. Thus, joint sequence and structure sampling can be conditioned on a target objective without needing to train a joint diffusion on sequence and structure at the same time. The valid joint posterior for sequence and structure conditioned on function which may be realized, for example, with a conditional language model for sequence given structure together with a diffusion model for the backbone structure joint marginal.

Substructure Conditioning

Many protein design tasks including imputation of missing structural data, redesign of an enzyme scaffold given an active site, and redesign of the CDRs of a known antibody framework require exact specification of the known structural coordinates. In this section, a method is disclosed that allows for such specification as a hard constraint on the reverse diffusion trajectories.

Substructural conditioning can bias sampling by adding a conditional score term $\nabla_x \log p_t(y|x)$ to the drift component in the reverse SDE. To enforce y in these regimes one must upweight the conditional score relative to the prior score function which can result in a reduction in the likelihood (or ELBO) of the samples drawn, or even in numerical instability.

The method presented below leverages an approach where the equilibrium states of a system are sampled by simulating the dynamics of an auxiliary system with a modified mass matrix. If the mass matrix is chosen appropriately, the original system's configuration space can be sampled more efficiently.

The method works by initializing $x_1$ in a way that enforces condition y, so that $p_1(y|x_1) = 1$, and then integrating a modified Annealed Langevin Dynamics SDE backwards in time to sample from $p_0(x|x_1)$, where the dynamics are modified to be y preserving by using a mass matrix that assigns higher mass to particles closer (in chain distance) to known coordinates and assigning infinite mass to known atoms. Samples drawn using this method satisfy y with probability 1.

Let S, M $\subset$ [1, . . . , N] denote the atoms comprising the unknown scaffold and known motif, respectively, throughout this section.

It is known that for $x \sim \mathcal{N}(\mu, \Sigma)$. The system can partition the coordinates as above into subsets M, S and write:

$$x = \begin{bmatrix} x^S \\ x^M \end{bmatrix} \text{ with } \mu = \begin{bmatrix} \mu^S \\ \mu^M \end{bmatrix} \text{ and } \sum = \begin{bmatrix} \sum_{SS} & \sum_{SM} \\ \sum_{MS} & \sum_{MM} \end{bmatrix}$$

that $(x^S|x^M=a)\sim\mathcal{N}(\bar{\mu},\bar{\Sigma})$ where:

$$\bar{\mu}=\mu^S+\sum_{SM}\sum_{MM}^{-1}(a-\mu^M)$$

and:

$$\bar{\Sigma}=\sum_{SS}-\sum_{SM}\sum_{MM}^{-1}\sum_{MS}$$

where inverse matrices are understood to denote pseudo-inverses. The system also computes the Cholesky factorization $\bar{R}\bar{R}^T=\bar{\Sigma}$.

To draw an approximate conditional sample from $p(x_0^S|x_0^M=a)$, the system proceeds as follows: first, the system samples $x_1^S\sim\mathcal{N}(\bar{\mu},\bar{\Sigma})$ from the conditional prior, set $x_0^M=a$, and integrate a modified Annealed Langevin Dynamics SDE:

$$dx=-\frac{\beta_t\Psi}{2}\lambda_0 RR^T\nabla_x\log p_t(x)\,dt+\sqrt{\beta_t\Psi}R\,d\bar{w}$$

backwards in time, where the matrices are $\bar{R}$, $\bar{R}^T$ are broadcast to the correct size with the conditioned on rows and columns filled by zeroes.

In additional embodiments, the system incorporates a reconstruction-guidance based score term. While this can introduce some instability to the sampling it can sometimes improve sample quality. To do so, in the energy block formulation the system defines:

$$U_f(\tilde{x}_t,U,t)=U+\left\|\hat{x}_\theta(x_t,t)^M-x_t^M\right\|_2^2$$

where $$x_t=f(\tilde{x}_t)=\bar{R}\bar{R}^{-1}\tilde{x}_t+\bar{\mu}.$$

Distance-Based Constraints

In one or more embodiments, a distance constraint specifies that one or more specific residue pairs be in spatial proximity (i.e., form a "contact"). Such a conditioner could be used, for example, in designing binders, to ensure that the desired binding site is being engaged. Or it could be used to insure some desired topological properties—i.e., the proximity of N- and C-termini (e.g., for ease of circular permutation).

To condition on a contact between atoms i and j, the system is seeking the probability that the distance between these two atoms in the fully denoised structure is below some desired cutoff c, $d_0^{ij}<c$, given a noised sample at time t and the corresponding distance $d_t^{ij}$.

In one or more embodiments, the system trains a time-dependent classifier $p_t(y|x(t))$ to classify noisy inputs. For the case of a contact classifier, the system can directly compute the desired probability analytically. By definition of the forward noise process, the i-th coordinate of the protein at time 0 and t are related to each other by:

$$x_0^{(i)}=\frac{x_t^{(i)}}{\alpha_t}-\sqrt{(1-\alpha_t^2)}\,[Rz]_i$$

Below are the derivations of the distribution $d_0^{ij}$ cases of Brownian and globular noise schedules.

Here:

$$[Rz]_i=\gamma\sum_k^i z_k-\frac{\gamma}{N}\sum_{j=1}^N\sum_{k=1}^j z_k+\delta z_1$$

and therefore:

$$x_0^{(j)}-x_0^{(i)}=\frac{x_t^{(j)}-x_t^{(i)}}{\alpha_t}-\gamma\sqrt{(1-\alpha_t^2)}\sum_{k=j}^i z_k$$

But as $\Sigma_{k=j}^i z_k\sim\mathcal{N}(0,|i-j|)$ by independence of $\{z_i\}$, the system has $$x_0^{(j)}-x_0^{(i)}\sim N\left(\frac{x_t^{(j)}-x_t^{(i)}}{\alpha_t},\gamma^2(1-\alpha_t^2)\cdot|1-j|\right),$$

so that:

$$\frac{(d_0^{ij})^2}{|i-j|(1-\alpha_t^2)\gamma^2}\sim NonCentralChiSquared\left[\frac{(d_t^{ij})^2}{|i-j|(1-\alpha_t^2)\alpha_t\gamma^2},k=3\right]$$

For a contact threshold c>1, the system has:

$$d_0^{ij}<c\Leftrightarrow(d_0^{ij})^2<c^2\Leftrightarrow\frac{(d_0^{ij})^2}{|i-j|(1-\alpha_t^2)\gamma^2}<\frac{c^2}{|i-j|(1-\alpha_t^2)\gamma^2}$$

and so $p_t(d_0^{ij}<c|X_T)$ is given exactly by the cumulative density function of the noncentral chi-squared distribution above, evaluated at $c^2[|i-j|(1-\alpha_t^2)\gamma^2]^{-1}$.

For the globular chain noise process, the system instead utilizes:

$$[Rz]_i=a\sum_{k=2}^i b^{i-k}z_k+a\frac{b^{i-1}}{\sqrt{1-b^2}}z_1$$

By substituting:

$$x_0^{(j)}-x_0^{(i)}=\frac{x_t^{(j)}-x_t^{(i)}}{\alpha_t}+\sqrt{1-\alpha_t^2}\,([Rz]_j-[Rz]_i).$$

So that $$x_0^{(j)}-x_0^{(i)}\sim N\left(\frac{x_t^{(j)}-x_t^{(i)}}{\alpha_t},(1-\alpha_t^2)\mathrm{Var}([Rz]_j-[Rz]_i)\right).$$

But assuming j>i:

$$\mathrm{Var}([Rz]_j - [Rz]_i) = \frac{2a^2(1-b^{j-i})}{1-b^2} =: \sigma_{j-i}^2.$$

It then follows that:

$$\frac{x_0^{(j)} - x_0^{(i)}}{\sqrt{1-\alpha_t^2}\,\sigma_{j-i}} \sim \mathcal{N}\left(\frac{x_t^{(j)} - x_t^{(i)}}{\sigma_{j-i}\alpha_t\sqrt{1-\alpha_t^2}}, I\right)$$

and finally:

$$\frac{(d_0^{ij})^2}{(1-\alpha_t^2)\sigma_{j-i}^2} \sim NonCentralChiSquared\left[\frac{(d_t^{ij})^2}{\sigma_{j-i}^2\alpha_t(1-\alpha_t^2)}, k=3\right].$$

Sub-Structure RMSD

In one or more embodiments, a design condition of sub-structure RMSD may specify a particular structural motif to include in the protein backbone. This motif can be an arbitrary substructure, composed of any number of disjoint backbone segments, that should be present in the final generated structure. In practice, such a motif could represent a functional (e.g., catalytic) constellation of residues or a metal/small-molecule binding site—this could be useful for designing enzymes or other functional proteins, by exploring ideas around a core functional mechanism. In another example, the motif could correspond to a scaffolding part of the molecule that may be important to preserve, e.g., the binding scaffold that can admit different loop conformations. Or the motif could represent a desired epitope that to present on the surface of a generated protein in the context of vaccine design.

The task of determining whether the pre-specified motif is present in a given structure S is simple, the system can, for example, find the substructure of S with the lowest optimal superposition root-mean-squared-deviation (RMSD) to the motif in question and ask whether this RMSD value is below a desired cutoff. But in the diffusion model, the system needs to determine the probability that the desired motif is expressed in a noisy structure at the current time point in the diffusion.

Specifically, if $x_t \in \mathbb{R}^{N\times 3}$ is the coordinate array and the forward diffusion process is represented by:

$$x_t = \alpha_t x_0 + \sqrt{1-\alpha_t^2}\,R\epsilon,\ \epsilon \sim N(0, I)$$

then the system aims to express $p_t(y|x_t)$ the probability that $x_0$ contains the motif given $x_t$, where y stands for the condition of motif presence (e.g., as defined by RMSD to a template motif below a desired cutoff). If the presence of a motif is defined in terms of optimal-alignment best-fit RMSD being below a cutoff, the system aims to understand how this RMSD behaves (in a probabilistic sense) as a function of noise. Further, as it is not given where within $x_t$ the motif may be (i.e., the system would not know a priori the matching between motif atoms and a sub-structure of the target structure), $p_t(y|x_t)$ needs to integrate information for the full structure $x_t$ to determine possible motif location(s). Achieving this analytically seems non-trivial. For this reason, here the system considers an empirical approach to expressing $p_t(y|x_t)$.

The goal is to observe the behavior of optimal-alignment best-fit RMSD in practice, as a function of $\alpha_t$, using a set of reasonable structures and diverse motifs, and find an analytical approximation for its probability distribution. Specifically, given a motif m and a structure represented by $x_t$, 1er$_t$t represent the RMSD of optimal alignment of m onto $x_t$ (i.e., the lowest RMSD between atoms of m and any sub-structure of $x_t$, and $r_0$ represents the RMSD induced by the same matching in the context of structure $x_0$, and $r_0$. The system seeks to approximate the cumulative distribution function $F(r_0 - r_t|x_t, \alpha_t)$.

With this, the system can calculate $p_t(y|x_t)$ as:

$$p_t(y \mid x_t) = p(r_0 < \sigma \mid x_t) = p(r_0 - r_t < \sigma - r_t \mid x_t) = F(\sigma - r_t \mid x_t, \alpha_t),$$

where σ is the desired RMSD cutoff for classifying the existence of the motif.

Clearly, the distribution of rt (and $\Delta r_t = r_0 - r_t$) should depend on $\alpha_t$. But these distributions should also depend on the size and complexity of the motif. For example, in the extreme case when the motif consists of a single atom, $r_t$ will always be zero. On the other hand, for large and complex motifs, the system may expect rt to increase rapidly with added noise.

The simplest surrogate for motif complexity is its size—i.e., the number of residues it involves. However, under the noise model, the atoms closer to each other in the protein chain will move in a more correlated manner than those that are farther apart. So it should matter whether the motif consists of multiple short disjoint segments matching to far-away (in sequence) portions of the target structure versus a motif consisting of one long contiguous segment. As a purely empirical measure to capture this notion, the system utilizes the following effective length definition:

$$L_e = -\log\left[\frac{2}{n(n-1)}\sum_{i=1}^{N-1}\sum_{j=i+1}^{N}\frac{1}{\sqrt{|i-j|}}C(i, j)\right]$$

where C(i, j) is an indicator function that is 1 if atoms i and j are part of the same chain and 0 otherwise. The motivation for the inverse square root of the index distance is from Brownian motion (displacement distance growing as the square root of time, here the number of atom hops). And the motivation for ignoring atom pairs from different chains is that these move independently under the noise model. In practice, $L_e$ appears to better explain variation of $r_t - r_0$ than just pure number of motif residues L, despite the fact that overall $L_e$ correlates somewhat closely with log (L).

The distribution of $r_0 - r_t$ depends on $\alpha_t$ and $L_e$. To get a sense of the general shape of this distribution and its dependence on $\alpha_t$, the system can take slices of the training data with $\alpha_t$ in different narrow ranges. Inspection and fitting of these $\alpha_t$-window histograms of $r_0$-$r_t$ suggested that the Gumbel family of distribution should work reasonably well for describing the observed variations.

The dependence on $L_e$ can be captured defining the parameters of the Gumbel distribution as functions of $L_e$. Towards defining a reasonable functional form, the system consider extremes. The Gumbel distribution has two parameters-location μ and scale β. The latter is solely responsible for the variance $$\left(\text{i.e., } \frac{\pi^2}{6}\beta^2\right)$$

and the mean is contributed to by both (μ+βγ), where γ is the Euler-Mascheroni constant, or approximately 0.577). For a motif that only has one atom, $\Delta r_t$ is a delta function at 0, meaning that both μ and β would be zero. And in general, for small (and simple) motifs the system would expect μ and β to be low, while for large (and complex) motifs the system would expect it to be high. Thus, both μ and β should be monotonically increasing functions of $L_e$ that pass through the origin. Experimentation with different curve families under these criteria, using the overall data likelihood as the objective metric (see below), the system arrived at the simple linear parameterization option as being best, i.e., where $\mu=\mu_s L_e$ and $\beta=\beta_s L_e$ with $\mu_s$ and $\beta_s$ being fitting parameters.

With the parameterization choices above, the fitting approach employs the following steps.

For 50 equally-spaced $\alpha_t$ windows, fit the observed $\Delta r_t=r_t-r_0$ to Gumbel distributions, whose location and scale parameters linearly depend on $L_e$ of each motif, using likelihood maximization. Specifically, the likelihood function being maximized was:

$$\log\mathcal{L} = \sum_{i=1}^{N_D} -\log(\beta_s L_e^i) - \frac{\Delta r_t^i - \mu_s L_e}{\beta_s L_e} - \exp\left(-\frac{\Delta r_t^i - \mu_s L_e}{\beta_s L_e}\right)$$

where $L_e^i$ and $\Delta r_t$ are the effective motif length and $\Delta r_t$ is the i-th data point, respectively, and $N_D$ is the number of data points. The result of this procedure then estimates $\mu_s$ and $\beta_s$ parameters specific for the current at window.

Next, the system fits the parameters $\mu_s$ and $\beta_s$ as functions of $\alpha_t$ analytically. The functional form chosen for both parameters was $k\cdot(1-\alpha_t^2)^n$, such that at $\alpha_t=1$ both parameters become zero (i.e., as the noise level reaches zero, the Δr distribution should approach a delta function).

Symmetry Constraint

Built from identical subunit proteins, many protein complexes are assembled symmetrically. Many symmetric complexes such as tube-shaped channel proteins and icosahedral viral capsids are biologically important. Incorporating symmetry in computational protein generation holds promise in designing large functionalized protein complexes. To fully explore the sampling of protein complexes subject to symmetry constraints, the system symmetrizes the underlying ODE/SDE sampling to satisfy any prescribed Euclidean symmetries. Incorporating group equivariance in machine learning has been an important topic in the machine learning community. Incorporating space group symmetries is critical in molecular simulations.

Let $G=[g]_{i=0}^N$ to be a collection of symmetry operations that form a group such as point groups and space groups. For point sets in $\mathbb{R}^3$, these symmetry operations can be represented as a set of orthogonal transformations (rotation/reflection) and translations. For synthesizing symmetric protein complexes, the system want to sample complexes $x_t\in\mathbb{R}^{N\times n\times 3}$ which are built from N=|G| identical single-chain proteins $x\in\mathbb{R}^{M\times 3}$ where M is the number of residues for each subunit. The SDE solving process produces final sample with:

$$x_0 = \text{sde\_solve}(x_T)$$

For sample generation to respect symmetries for an arbitrary group G, the SDE/ODE dynamics need to be G-invariant up to a permutation of subunits. Let • represent the symmetric operations (rotation, reflection, and translation) performed on point sets in R3, the system define the sampling procedure sde_solve: $\mathbb{R}^{|G|\times n\times 3}\to\mathbb{R}^{|G|\times n\times 3}$ with $x_0$=sde_solve ($x_T$) being the desired samples. The sampling procedure needs to follow the following invariance condition:

$$\text{sde\_solve}(x_T) = g\text{sde\_solve}(x_T) = \sigma(g)\text{sde\_solve}(x_T),$$

where $g_i$ indicates the i-th group element in G and the system impose an arbitrary order on G and the method is equivariant to the permutation of subunits. σ(g) is the induced permutation operation satisfying the relation: gG=σ(g)G, as computed from the group multiplication table (also called the Caley table).

The first equality is trivially satisfied if $f(\cdot)$ or the underlying gradient update is E(3) equivariant, as G consists of only orthogonal transformations and translations. However, the second equality is generally not satisfied. For molecular simulations where the Hamiltonian dynamics is used, the second equality can be satisfied if (i) the energy function is E(3) invariant, and (ii) the initial $x_T$ and $$\frac{dx_T}{dt}$$

are symmetric, i.e., $$g_i\cdot x_T = \sigma(g),\ g_i\cdot\frac{dx_T}{dt} = \sigma(g)\frac{dx_T}{dt}.$$

At each successive time step, $x_T$ automatically satisfies the prescribed G-symmetry. This approach confines both the position and momentum update to ensure the sampled configurations remain symmetric.

However, this is not the case with SDE/ODE sampling in the framework. There are, in some embodiments, three origins of symmetry-breaking error. (i) $f(x_T, t)$ uses distances as features and is automatically E(3) equivariant. However, because the protein feature graphs are generated probabilistically, $f(gx_T, t)\neq gf(x_T, t)$ with each subunit protein having different geometric graphs, although they are symmetric. (ii) The polymer structured noise is randomly sampled from $\mathcal{N}(x_T; \mu, \Sigma)$, so each subunit protein has different chain noises. (iii) The sampling procedure requires solving an ODE/SDE which is vulnerable to accumulated integration error. Integration error can induce unwanted geometric drifts such as rotation and translation, and be a substantial symmetry breaking force.

In one or more embodiments, the system employs the symmetric sampling approach as a constrained transformation formalism implemented as a conditioner block. Using the representations of G roto-translations of G, the system demonstrate the building of protein symmetric assemblies from an asymmetric unit (AU) chain $\tilde{x}$ through symmetrization. The system commences with the mathematical formulation of the transformation, subsequently elucidating the induced linear transformation on the intrinsic gradient dynamics. Representing G as N×n×3, a collection of rotation matrices G, the system define the constrained transformation as:

$$x_T = f(\tilde{x}_t, t) = \text{symmetrize}(\tilde{x}_t) = G\tilde{x}_t$$

with the equivalent indexed multiplication as:

$$[x_t]_{nim} = \sum_j G_{nij}[\tilde{x}_t x_t]_{mj}$$

where n is the index of group elements, m is the index for atoms in AU, and i, j are Euclidean indices. The associated diffusion energy transformation is:

$$\frac{1}{|G|}U_f(x_t) = \frac{1}{|G|}\left\|\sigma_t^{-1}R^{-1}(x_t - \alpha_t\tilde{x}_t)\right\|_2^2$$

The energy is averaged with |G| to account for the diffusion energy in individual AU with M atoms. the system can compute the Jacobian of the transformation $f$: $\mathbb{R}^{M\times3} \to \mathbb{R}^{N\times M\times 3}$:

$$\frac{df(x_t)}{d\tilde{x}_t} = G \to \left[\frac{d[f(x_t)]_{nim}}{d\tilde{x}_t}\right]_{jm} = G_{nij}$$

To derive the transformed dynamics, the system incorporates a one-solver step for the reverse Langevin dynamics (the analysis is the same for reverse diffusion):

$$\tilde{x}_{t+dt} = \tilde{x}_t - \frac{1}{2}RR^T\left[\frac{df(\tilde{x}_t)}{d\tilde{x}_t}\right]^T\left[\frac{dU(x_t)}{dx_t}\right]dt + Rd\overline{w}$$

The system analyzes the induced gradient transform with its associated indexed representation:

$$\frac{dU_f(x_t)}{d\tilde{x}_t} = \left|\frac{df(\tilde{x}_t)}{d\tilde{x}_t}\right|^T\left[\frac{dU_f(x_t)}{dx_t}\right] = G^T\frac{dU_f(x_t)}{dx_t}$$

$$\frac{dU_f(x_t)}{d[\tilde{x}_t]_{jm}} = \sum_n\sum_i G_{nij}\left[\frac{dU_f(x_t)}{dx_t}\right]_{nim}.$$

Observe that in the gradient transformation, summation occurs over indices i, contrasting with index j used in the forward transformation. This method inherently pulls gradients back to AU. The computation of the transformed gradient can be adeptly handled using auto-differentiation, specifically as vector-Jacobian products. Additionally, the gradient accumulated onto AU are also averaged by the number of chains in the tesselated domain by dividing the gradient with |G|.

The system next analyzes the transformed solver step with the pull-back gradient transform:

$$f(\tilde{x}_t + d\tilde{x}_t) = f\left(\tilde{x}_t - \frac{1}{2}RR^T\left[\frac{df(\tilde{x}_t)}{d\tilde{x}_t}\right]^T\frac{1}{|G|}\left[\frac{dU(x_t)}{dx_t}\right]dt + Rd\overline{w}\right) = G\left(\tilde{x}_t - \frac{1}{2}RR^TG^{-1}\frac{1}{|G|}\left[\frac{dU(x_t)}{dx_t}\right]dt + Rd\overline{w}\right)$$

where G is the symmetrize component and $$\left(\tilde{x}_t - \frac{1}{2}RR^TG^{-1}\frac{1}{|G|} - 1\left[\frac{dU(x_t)}{dx_t}\right]dt + Rd\overline{w}\right)$$

is the folding to AU component.

The constrained transformation has a nice interpretation, the solver step first folds the infinitesimal change back followed by symmetrization. Another option to pull the gradients is perform a “broadcasting” operation from a single AU (indexed with u) of x. This is also a valid gradient transformation that ensures G-invariance.

$$f(\tilde{x}_t + d\tilde{x}_t) = f\left(\tilde{x}_t - \frac{1}{2}RR^T[G]_u^{-1}\left[\frac{dU(x_t)}{dx_t}\right]_u dt + Rd\overline{w}\right).$$

For efficient memory sampling of large symmetric assemblies, the system may reduce the number of chains using chain subsampling techniques. This approach allows us to concentrate on updating a specific subset, denoted as $S \subset [1, \ldots, |G|]$, of subunits in $x_T$, thereby conserving both memory and computational time.

Given a designated subunit i, the subset S is derived by selecting the k-nearest neighbor (k-NN) subunits. This selection is determined by the distances between the geometric centers of the subunits, ensuring the incorporation of short-range interactions between them. Through this method, K subunits are chosen, where K represents the count of neighbors the denoiser interacts with during each integration phase.

This randomized selection not only ensures that the gradient update remains globally consistent, but also prevents potential structural clashes and suboptimal contact formations.

This procedure, at its core an index selection mechanism, can also be depicted as a linear transformation using a sparse matrix comprised of 0s and 1s. By harnessing inter-chain distances, the system are equipped to select K<|G| chains following an exhaustive symmetric tessellation. This method of subsampling aligns with established techniques in molecular simulations that employ periodic boundary conditions. To further understand the subsampling process, it is interesting to note that, much like the tessellation method, the subsampling can be described as:

$$x_t = f(\tilde{x}_t, t) = \tilde{x}_t^S = \text{subsample}(\tilde{x}_t) = S\tilde{x}_t$$

$$\frac{df(x_t)}{d\tilde{x}_t} = S \in [0,1]^{[G|N]\times M}$$

where S is the chain selection matrix of size (NK×M) where K<N is the number of chains selected for computation, and this can be efficient.

The conditioner block formalism provides the flexibility to seamlessly incorporate restraint energy during energy updates. To ensure optimal contact and packing, the system integrates an $R_g$ penalty through an inter-chain potential or flat-bottom potential. This serves to maintain both the inter-chain distance and the Asymmetric Unit (AU) Radius of Gyration as follows:

$$U_f(x_t, U, t) = U + U_{R_g}(x_t) = U + \|R_g(x_t, t) - \langle R_g \rangle\|_2^2$$

The proposed samplers can also be combined with other conditioners (substructure, natural language, shape, etc.) to realize symmetric assembly design with controllable functions.

Putting together, the composed transformation is:

$$x = \text{subsample}(\text{symmetrize}(\tilde{x}))$$

$$U_f(x, U, t) = U + U_{R_g}(\tilde{x}) + U_{R_g}(\text{subsample}(\text{symmetrize}(\tilde{x})))$$

The system may further condition on other point groups including Cn (cyclic symmetry), Dn (dihedral symmetry), T (tetrahedral symmetry), O (octahedral symmetry), I (icosahedral symmetry). For all the samples, the inverse temperature was set to 8 and the equilibration rate to 8 with the Heun SDE solver that integrates from 1 to 0 for 400 steps. Subunit k-NN sampling with K=6. When K>|G|, K was set to equal |G|.

Shape Conditioning

Proteins often realize particular functions through particular shapes, and consequently being able to sample proteins subject to generic shape constraints would seem to be an important tool for fully realizing the potential of protein design. Pores allow molecules to pass through biological membranes via a doughnut shape, scaffolding proteins spatially organize molecular events across the cell with precise spacing and interlocking assemblies, and receptors on the surfaces of cells interact with the surrounding world through precise geometries. Here methods are introduced to explore and test generalized tools for conditioning on volumetric shape specifications.

The shape conditioning approach is based on Optimal Transport, which provides tools for identifying correspondences and geometric distances between objects, such as the atoms in a protein backbone and a point cloud sampled from a target shape. The system leverages two metrics from the optimal transport theory: (i) the Wasserstein distance which can measure the correspondence between point clouds in absolute 3D space, and (ii) the Gromov-Wasserstein distance, which can measure the correspondences between objects in different domains by comparing their intra-domain distances or dissimilarities. Because it leverages relational comparisons, Gromov-Wasserstein can measure correspondences between unaligned objects with different structures and dimensionalities such as a skeleton graph and a 3D surface or even between unsupervised word embeddings in two different languages.

When adding heuristic gradients to the diffusion based on just the Wasserstein distance, there is huge degeneracy in potential volume-filling conformations would often lead to jammed or high contact-order solutions. The system accelerates convergence by breaking this degeneracy with a very coarse "space-filling plan" for how the fold should map into the target point cloud, which the prior can then realize with a specific protein backbone.

The system can leverage Gromov-Wasserstein (GW) optimal transport. The system (i) generates an idealized distance matrix for a protein based on the scaling law $D_{ij}=7.21\times|i-j|$, (ii) computes the distance matrix for the target shape, and (iii) solves for the Gromov-Wasserstein optimal transport given these two distance matrices yielding a coupling matrix $K_{GromovWasserstein}$ with dimensionality $N_{atoms}\times N_{points}$. This coupling map sums to unity and captures the correspondence between each atom in the abstract protein chain and each point in the target point cloud. The system may incorporate a small amount of entropy regularization to solve the optimal transport problem.

In the inner loop of sampling, the system can combine the Gromov-Wasserstein coupling with simple Wasserstein couplings as a form of regularization towards the fold "plan". The final loss is then:

$$ShapeLoss(x, r) = \sum_{i,j}\left(K_{ij}^{GW} + K_{ij}^{W}(x, r)\right)\|x_i - r_j\|$$

where the system computes the Wasserstein optimal couplings $K_{ij}^{W}$ with the Sinkhorn algorithm. This yields a fast, differentiable loss that can be used directly for sampling.

The system weights the ShapeLoss(x, r) term with the scaling factor:

$$w_t^{(shape)} = \text{Clamp}\left(\sqrt{SNR_t}, [0.001, 3.0]\right)$$

and then add its gradient directly to the loss during sampling. So the weighted objective is:

$$ShapeLoss_t(x, r) = \text{Clamp}\left(\sqrt{SNR_t}, [0.001, 3.0]\right)\sum_{i,j}\left(K_{ij}^{GW} + K_{ij}^{W}(x, r)\right)\|x_i - r_j\|$$

The system successfully rendered letters and numbers from the English alphabet in the Liberation Sans font, extruded these 2D images into 3D volumes, and then sampled isotropic point clouds from these volumes.

Residue, Domain, and Complex-Level Classification

Noised backbone coordinates obtained from the PDB are passed as input to the model, along with a scalar 0<t<1 denoting the time during diffusion (indexed between zero and one) that the noise was sampled at. The model optionally can consume sequence information if available.

The time component is encoded with a random Fourier featurization. The provided sequence is encoded with a learnable embedding layer of amino acid identity. Backbone coordinates are passed to our ProteinFeatureGraph that extracts 2-mer and chain-based distances and orientations. These components are summed and passed to the neural network.

The encoder is a message-passing neural network. The graph is formed by taking K=20 nearest neighbors and sampling additional neighbors from a distribution according to a random exponential method.

Node and edge embeddings are passed to each layer, with each node being updated by a scaled sum of messages passed from neighbors. The message passed from node i to node j is obtained by stacking the embeddings at node i, those at node j, and E, and passing these to a multi-layer perceptron (e.g., implemented with one or more hidden layers). Edges are updated similarly. Each layer also applies layer normalization (along the channel dimension) and dropout (dropout probability=0.1). After processing by the MPNN, node embeddings are passed to a different classification head for each label. If a head corresponds to a chain-level label, residues from each chain are pooled using an attentional pooling layer. The resulting embeddings are then passed to an MLP with 1 hidden layer to output logits for each label.

The model may be trained to predict the following labels: CATH, PFAM, Funfam, Organism, Secondary Structure, Interfacial Residue. The loss for predicting each label is quantified using cross entropy loss, and all components are summed and weighted equally.

The model may be trained for 50 epochs with an Adam optimizer with default momentum settings (betas=(0.9, 0.999)), the learning rate is linearly annealed from 0 up to 0.0001 over the first 10,000 steps then kept constant. During training, first a time stamp $0<t<1$ is sampled uniformly, then noise is sampled from the globular covariance distribution, injected into the backbone coordinates, and fed to the model. Next, label predictions are made, loss are computed, and parameters are updated with the Adam optimizer.

In one or more implementations, the classification model has 4 layers, the size of node feature dimension is 512 and the edge feature dimension is 192, node update MLP has hidden dimension 256 with 2 hidden layers, and edge update MLP has hidden dimension 128 with 2 hidden layers.

Natural Language Annotations

Recent advances in text-to-image diffusion models have produced qualitatively impressive results using a natural language interface. Given the open availability of pre-trained language models and a corpus of protein captions form large scientific databases such as the PDB and UniProt, the system implements a natural language interface to protein backbone generation.

To do so, the system uses a protein captioning model (The protein caption model), which predicts $p(y|x_t)$, where y is a text description of a protein and $x_t$ is a noised protein backbone. This conditional model, when used in conjunction with the structural diffusion model presented in the main text, can be used as a text-to-protein backbone generative model.

To build a caption model, the system may curate a paired dataset of protein structures and captions from both the PDB and UniProt databases. Caption information is collected for the structures used for the backbone diffusion model training, as well as the individual chains within these structures. For each structure, the system uses the PDB descriptive text as an overall caption. For each chain in a structure, the system obtains a caption by concatenating all available functional comments from UniProt. Structures containing more than 1000 residues are not used, corresponding to a minority (10%) of all structures. The final set used to train and validate the caption model contains approximately 45 thousand captions, including those from both PDB and UniProt. The splits used for training are completely random. The small size of the dataset constrained architecture choices to those with relatively few free parameters.

To build the caption model, the system may leverage a pretrained language model and a pretrained protein encoder. For example, the pretrained language model is the GPT-Neo 125 million parameter model. The system also leverages the pretrained graph neural network encoder, the protein structure classification model introduced above, to encode protein backbones. Analogously to the choice of the language model, the purpose of the structure encoder is to start The protein caption model with semantic knowledge of protein structure. To condition the autoregressive language model, GPT-Neo, pseudotokens are formed from structures using the ProClass encoder and prepended to the caption as context.

In one or more embodiments, the protein caption model connects a pretrained graph neural network encoder to an autoregressive language model trained on a large data corpus including scientific documents. Conditioning is achieved with pseudotokens generated from encodings of protein complex 3D backbone coordinates (batch size B, number of residues N, embedding dimension H) and a task token indicating whether a caption describes the whole complex or a single chain. The R relevant pseudotokens for each caption, consisting of the chain/structure residue tokens and the task token, are passed to the language model along with the caption. When used in the forward mode, the protein caption model can describe the protein backbone by outputting the probabilities of each word in the language model's vocabulary of size V for each of the L tokens of a caption. When used in conjunction with the prior model, it can be used for text to protein backbone synthesis. In training, the protein caption model uses a masked cross entropy loss applied only to the caption logits.

The system may perform embedding of the task, caption, and structure data into a shared tensor representation for input to the language model. Captions and task tokens are encoded using a modified version of the GPT-Neo tokenizer, whose vocabulary may be augmented with a special token to distinguish between prediction tasks involving single chains and those relating to entire structures. Structure inputs are converted into pseudotokens with the same shape as text embeddings through the graph neural network encoder of the pre-trained protein caption model. The task, structure, and caption embeddings are concatenated into a representation that is passed to the language model to obtain logits representing the probabilities of caption tokens. The model is trained on a standard masked cross entropy loss of the caption.

Structure encoding in the protein caption model relies on a pretrained classification model. This classifier model may be a GNN with multiple heads to extract different class information, as described previously. The GNN portion of the classifier network is used to obtain embeddings of each residue in the latent space of the classifier, with the intent that the pre-trained classifier weights should help the protein caption model learn the relationship between structures and captions. Besides the 3D information of the atoms in each structure, the diffusion timestep (noise level) is input to the GNN via a Fourier featurization layer which converts the diffusion time to a vector with the same dimension as the GNN node embedding space using randomly chosen frequencies between 0 and 16. To allow for the protein caption model to learn the optional use of sequence information, in 25% of the training data sequences are randomly passed along with structures. In these cases, the amino acid information for each residue is converted through a single embedding layer with output size equal to that of the GNN node embedding space dimension, then added to the time step vector.

Task tokens are added to the model to allow for captions of both single chain and full complex captions. For the prediction of UniProt captions describing single chains within structures, only the embeddings of the residues in the relevant chain are passed to the language model. For the prediction of the PDB captions related to entire structures, all residue embeddings are passed. In addition, a linear layer is added after the classification model embeddings to go between the classification model latent space and the embedding space of the language model, which are of different dimensionality.

Finally, in order to help the model distinguish between PDB and UniProt prediction tasks, the encodings of the entire structures are each prepended with an embedding vector of a newly defined PDB marker token. The system normalizes the components of all structure vectors such that each one has zero mean and unit variance.

In summary, the protein caption model architecture consists of a pre-trained GNN model for structure embedding and a pre-trained language model for caption embedding, with a learnable linear layer to interface between the two and a learnable language model head to convert the raw language model outputs to token probabilities.

The system trains the protein caption model to be compatible with conditional generation using the structural diffusion prior model. Like the other conditional models in this paper, each structure is noised according to the schedule of the structural diffusion model. During the protein caption model training, the graph neural network encoder weights from the pre-trained classification model are frozen. As the system adds a <|PDB|> task token to the GPT-Neo vocabulary to cue the model to predict whole complex captions from the PDB, the system allows the language model to learn in order to optimize the encoding of this new token and refine the embeddings of existing ones.

Low-Temperature Sampling

In one or more implementations, low-temperature sampling implements a hybrid SDE combining temperature-dependent reverse-time SDE and modified Langevin dynamics with an equilibration rate.

Maximum likelihood training of generative models enforces a tolerable probability of all datapoints and, as a result, misspecified or low-capacity models fit by maximum likelihood will 1 typically be overdispersed. This can be understood through the perspective that maximizing likelihood is equivalent to minimizing the KL divergence from the model to the data distribution, which is the mean-seeking and mode-covering direction of KL divergence.

To mitigate overdispersion in generative models, it is common practice to introduce modified sampling procedures that increase sampling of high-likelihood states (mode emphasis, precision) at the expense of reduced sample diversity (mode coverage, recall).

Here a novel algorithm for low-temperature sampling from diffusion models is disclosed. The novel algorithm leverages two concepts, explained in the next two sections. 1. Upscaling the score function of the reverse SDE is insufficient to properly re-weight populations in a temperature perturbed distribution. 2. Annealed Langevin dynamics can sample from low temperature distributions if given sufficient equilibration time.

Reverse-Time SDE

In the isotropic Gaussian case, to determine how the Reverse-Time SDE can be modified to enable (approximate) low temperature sampling, it is helpful to first consider a case that can be treated exactly: transforming a Gaussian data distribution $\mathcal{N}(x_0; \mu_{data}, \sigma_{data}^2)$ to a Gaussian prior $\mathcal{N}(x_1; 0, \sigma_{prior}^2)$.

Under the Variance-Preserving diffusion, the time-dependent marginal density will be given by:

$$p_t(x) = \mathcal{N}\left(x; \alpha_t\mu_{data}, \alpha_t^2\sigma_{data}^2 + (1-\alpha_t^2)\sigma_{prior}^2\right),$$

which means that the score function $s_t$ will be:

$$s_t \triangleq \nabla_x \log p_t(x) = \frac{\alpha_t\mu_{data} - x}{\alpha_t^2\sigma_{data}^2 + (1-\alpha_t^2)\sigma_{prior}^2}.$$

Now, suppose the system wish to modify the definition of the time-dependent score function so that, instead of transitioning to the original data distribution, it transforms to the perturbed data distribution, i.e., so that it transitions to $$\frac{1}{Z}p_0(x)^{\lambda_0}.$$

For a Gaussian, this operation will simply multiply the precision (or equivalently, divide the covariance) by the factor $\lambda_0$. The perturbed score function will therefore be:

$$s_t^{perturb} = \frac{\alpha_t\mu_{data} - x}{\alpha_t^2\sigma_{data}^2/\lambda_0 + (1-\alpha_t^2)\sigma_{prior}^2}.$$

Based on this, the score function can be expressed as a time-dependent rescaling of the original score function with scaling based on the ratios of the time-dependent inverse variances as:

$$s_t^{perturb} = s_t\frac{(1-\alpha_t^2)\sigma_{prior}^2 + \alpha_t^2\sigma_{data}^2}{(1-\alpha_t^2)\sigma_{prior}^2 + \alpha_t^2\sigma_{data}^2/\lambda_0}.$$

Figure 10A:
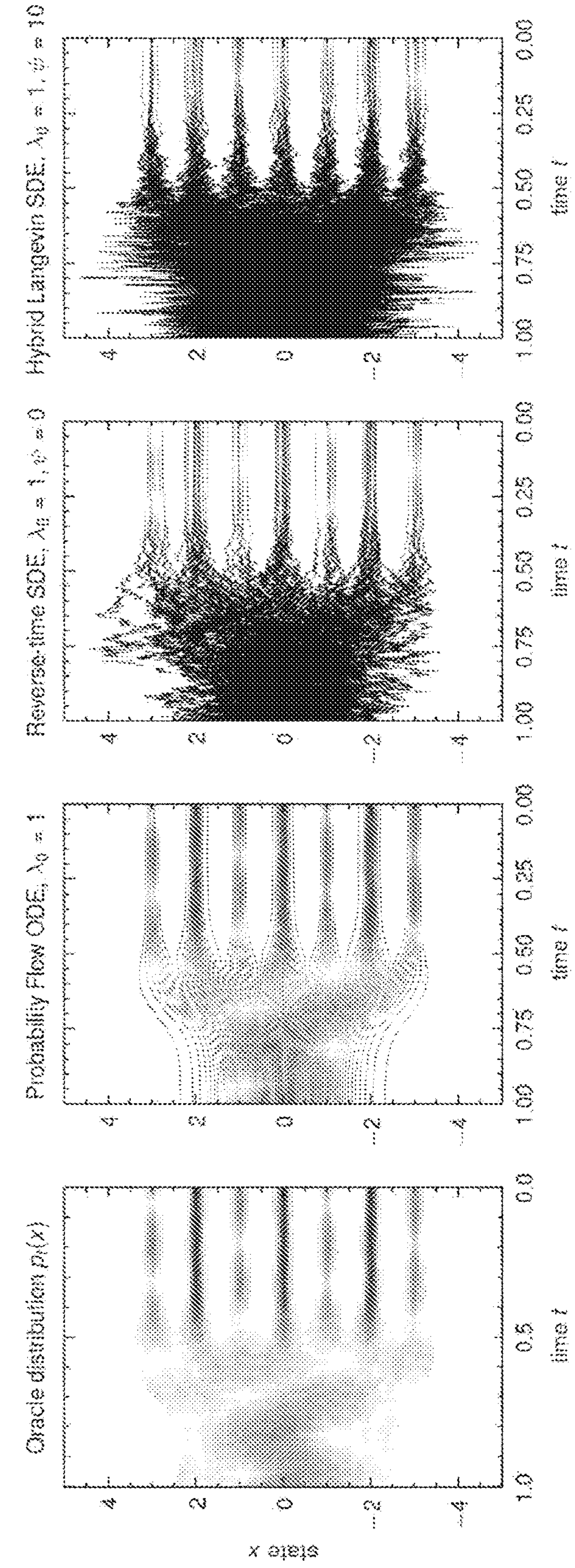
FIGS. 10A-10C illustrate Hybrid Langevin SDE to sample from temperature-perturbed distributions, according to one or more example implementations.
Figure 10B:
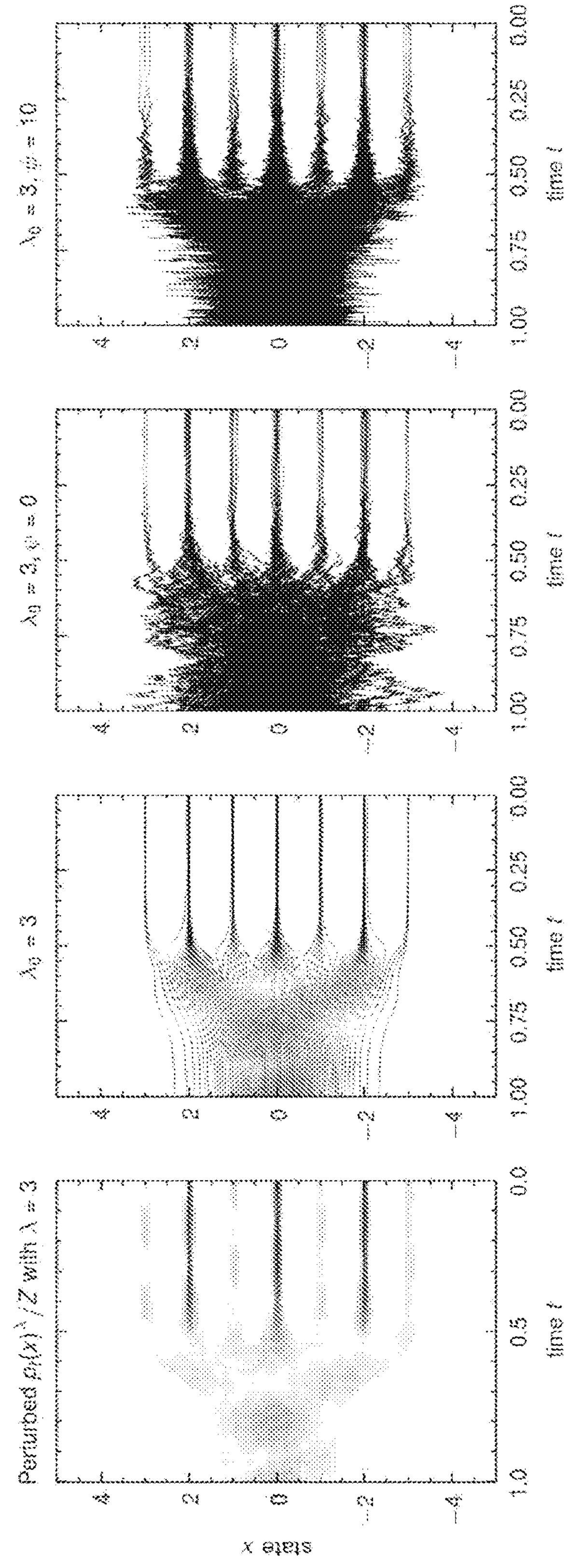
Figure 10C:
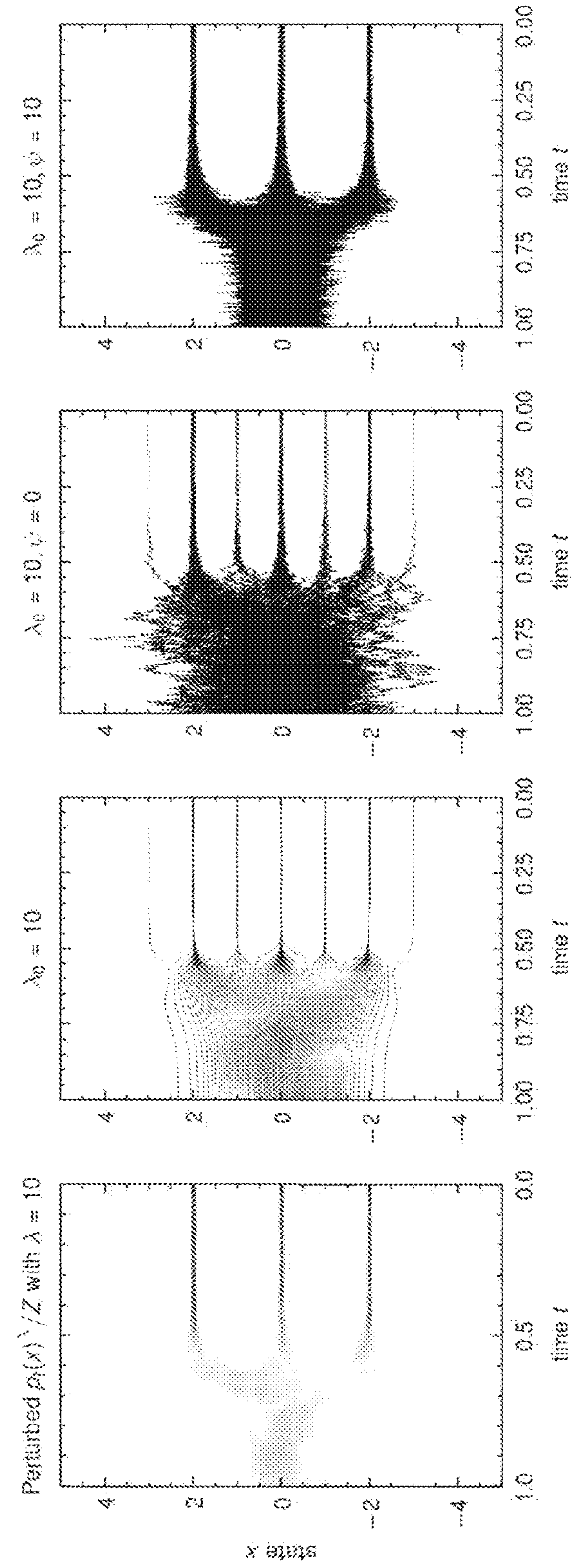

FIGS. 10A-10C illustrate Hybrid Langevin SDE to sample from temperature-perturbed distributions. The marginal densities of the diffusion process $p_t(x)$ (left) gradually transform between a toy 1D data distribution at time t=0 and a standard normal distribution at time t=T. Reweighting the distribution by inverse temperature (FIGS. 13B & 13C) will both concentrate and reweight the population distributions. The annealed versions of the reverse-time SDE and Probability Flow ODEs (middle columns) can concentrate towards local optima but do not correctly reweight the relative population occupancies. Adding in Langevin dynamics with the Hybrid Langevin SDE (right column) increases the rate of equilibration to the time-dependent marginals and, when combined with low temperature rescaling, successfully reweights the populations (right graph of FIG. 10C).

To achieve a particular inverse temperature do for the data distribution, the score function can be rescaled by the time-dependent factor:

$$\lambda_t = \frac{(1-\alpha_t^2)\sigma_{prior}^2 + \alpha_t^2\sigma_{data}^2}{(1-\alpha_t^2)\sigma_{prior}^2 + \alpha_t^2\sigma_{data}^2/\lambda_0} \approx \frac{\lambda_0}{\alpha_t^2 + (1-\alpha_t^2)\lambda_0},$$

where in the last step, $\sigma_{data}^2=\sigma_{prior}^2$ is assumed. So one interpretation of the previously observed insufficiencies of low-temperature sampling based on score-rescaling is that they were hampered by uniform rescaling of the score function in time instead of in a way that accounts for the shift of influence between the prior and the data distribution.

To achieve temperature-adjusted reverse time SDE, the reverse-time SDE is modified by rescaling the score function with the above time-dependent temperature rescaling as:

$$dx = \left(-\frac{1}{2}x - \lambda_t RR^T \nabla_x \log p_t(x)\right)\beta_t dt + \sqrt{\beta_t}\, R d\overline{w} = \left(-\frac{1}{2}x - \lambda_t \frac{\alpha_t \hat{x}_\theta(x, t) - x}{1-\alpha_t^2}\right)\beta_t dt + \sqrt{\beta_t}\, R d\overline{w}.$$

To achieve a temperature-adjusted probability flow ODE, the probability flow ODE can be rescaled as:

$$\frac{dx}{dt} = -\frac{\beta_t}{2}\left(x + \lambda_t RR^T \nabla_x \log p_t(x)\right) = \frac{\beta_t}{2}\left(x\frac{\alpha_t + \lambda_t - 1}{1-\alpha_t^2} - \hat{x}_\theta(x, t)\frac{\lambda_t \alpha_t}{1-\alpha_t^2}\right).$$

The rescaling rationale was derived by considering a unimodal Gaussian, which has the property that the score of the perturbed diffusion can be expressed as a rescaling of the learned diffusion. The above dynamics drive towards local maxima but do not reweight populations based on their relative probability. Accordingly, the low-temperature sampling algorithm incorporates an equilibration process that can be arbitrarily mixed in with the non-equilibrium reverse dynamics.

Annealed Langevin Dynamics Sde

Instead of reversing the forwards time diffusion in a non-equilibrium manner, the low-temperature sampling algorithm can also leverage the learned time-dependent score function $\nabla_x \log p_t(x)$, as expressed in terms of the optimal denoiser $\hat{x}_\theta(x, t)$, to do slow, approximately equilibrated sampling with annealed Langevin dynamics.

The annealed Langevin dynamics is recast in continuous time with the SDE:

$$dx = -\frac{\beta_t \Psi}{2} RR^T \nabla_x \log p_t(x)^{\lambda_0} dt + \sqrt{\beta_t \Psi}\, R d\overline{w} = -\frac{\beta_t \Psi}{2}\lambda_0 RR^T \nabla_x \log p_t(x) dt + \sqrt{\beta_t \Psi}\, R d\overline{w}$$

where $\Psi$ is an equilibration rate scaling the amount of Langevin dynamics per unit time. As $\Psi \rightarrow \infty$, the system will instantaneously equilibrate in time, constantly adjusting to the changing score function. These parameters can be set by considering a single Euler-Maruyama integration step in reverse time with step size $$\frac{1}{T}$$

where T is the total number of steps:

$$x_{t-\frac{1}{T}} \leftarrow x_t + \frac{\beta_t \Psi}{2T}\lambda_0 RR^T \nabla_x \log p_t(x) + \sqrt{\frac{\beta_t \Psi}{T}}\, R\epsilon,\ \epsilon \sim \mathcal{N}(0, I),$$

which is precisely preconditioned Langevin dynamics with step size $$\frac{\beta_t \Psi}{T}.$$

For a sufficiently small interval (t–dt, t), the system can keep the target density approximately fixed while increasing T to do an arbitrarily large number of Langevin dynamics steps, which will asymptotically equilibrate to the current density $\log p_t(x)$.

Hybrid Langevin-Reverse Time Sde

The low-temperature sampling algorithm may combine the annealed Reverse-Time SDE and the Langevin Dynamics SDE into a hybrid SDE that combines both dynamics. Denoting the inverse temperature as $\lambda_0$ and the ratio of the Langevin dynamics to convention dynamics as $\Psi$, the hybrid SDE can be expressed as:

$$dx = \left(-\frac{1}{2}x - \left(\lambda_t + \frac{\lambda_t \Psi}{2}\right) RR^T \nabla_x \log p_t(x)\right)\beta_t dt + \sqrt{\beta_t(1+\Psi)}\, R d\overline{w} = \left(-\frac{1}{2}x - \left(\lambda_t + \frac{\lambda_0 \Psi}{2}\right) RR^T \frac{(RR^T)^{-1}}{1-\alpha_t^2}(\alpha_t \hat{x}_\theta(x, t) - x)\right)\beta_t dt + \sqrt{\beta_t(1+\Psi)}\, R d\overline{w} = \left(-\frac{1}{2}x - \left(\lambda_t + \frac{\lambda_0 \Psi}{2}\right)\frac{\alpha_t \hat{x}_\theta(x, t) - x}{1-\alpha_t^2}\right)\beta_t dt + \sqrt{\beta_t(1+\Psi)}\, R d\overline{w}.$$

where, when the scaling terms are set to unity, the standard reverse-time SDE is recovered.

In one or more generalized embodiments, the low-temperature sampling algorithm differentially scales the reverse-time SDE and/or the annealed Langevin Dynamics SDE. In such embodiments, the reverse-time SDE may be scaled by a first time-dependent factor with the annealed Langevin Dynamics SDE scaled by a second time-dependent factor. One or both of the time-dependent factors may be based on the inverse temperature, the equilibration rate, or some combination thereof. The inverse temperature and/or the equilibration rate may themselves be dependent on a state of the protein backbone on the time continuum.

Figure 11A:
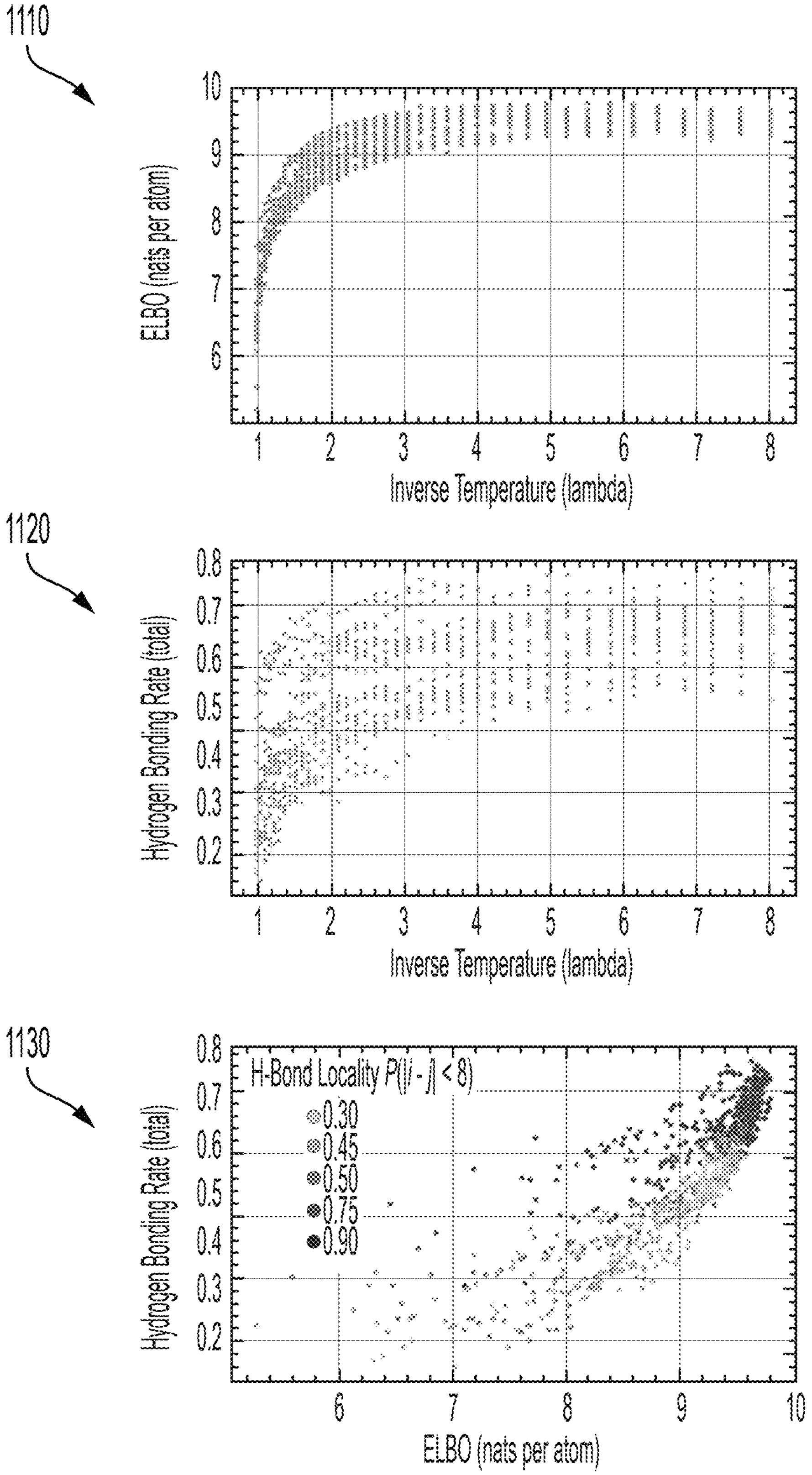
FIGS. 11A-11B illustrate representative samples identified using this modified SDE for low-temperature sampling, according to one or more example implementations.
Figure 11B:
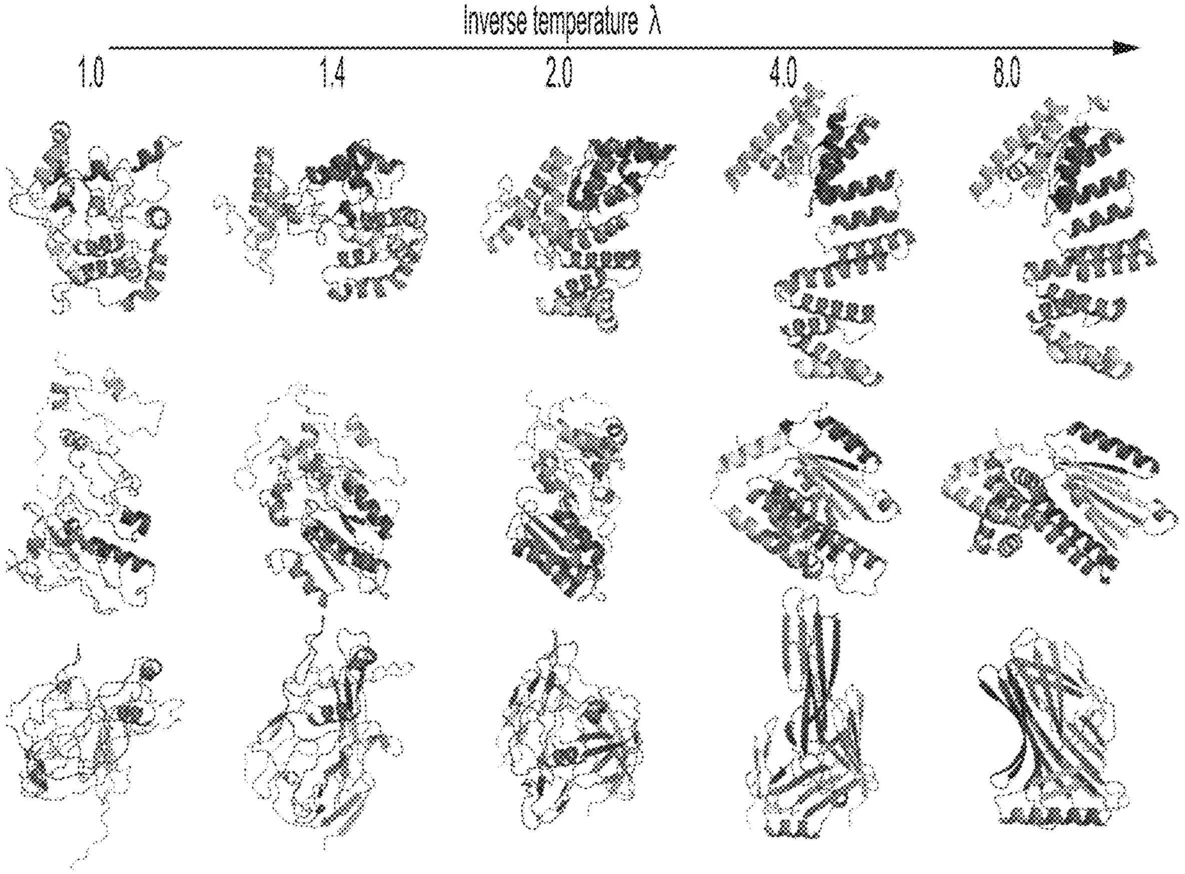

FIGS. 11A-11B illustrate representative samples identified using this modified SDE for low-temperature sampling. Generally, low-temperature sampling drives towards high-likelihood states with increased secondary structure content. Increasing the inverse temperature increases the likelihood (ELBO) for unconditional samples from the backbone diffusion model (Graph 1110). These high-likelihood states exhibit increased rates of backbone hydrogen bonding that underlie secondary structure (Graph 1120). Likewise, the ELBO is strongly associated with the hydrogen bonding rates (Graph 1130). These relationships can be seen within the evolution of single samples under fixed random seeds (each row of sampled backbones), where structures sampled at higher inverse temperature have increased secondary structure content and tighter packing as compact, globular folds.

In additional embodiments, while the Hybrid Langevin-Reverse Time SDE can do an arbitrarily large amount of Langevin dynamics per time interval which would equilibrate asymptotically in principle, these dynamics will still inefficiently mix between basins of attraction in the energy landscape when 0<t><1. The system can further implement simulated tempering or parallel tempering, which would aid in deriving an augmented SDE system with auxiliary variables for the temperature and/or copies of the system at different time points in the diffusion.

Example Results

FIGS. 12A-12D illustrates various structural characteristics of synthetic protein designs generated with the diffusion model, according to one or more example implementations. As shown in Graph 1210, across a set a set of 10,000 single chains, samples from the diffusion model have structural properties that are similar to natural protein structures from the Protein Data Bank (PDB), including secondary structure utilization and length-normalized contact order, radius of gyration, and contact density statistics. Low-temperature samples from the diffusion model tend to favor helices over strands and are more compact than those found in the PDB. As shown in Graphs 1220 and 1230, the synthetic protein designs reproduce length-dependent scaling of contact order and radius of gyration, similar to proteins found in the PDB.

Figure 12A:
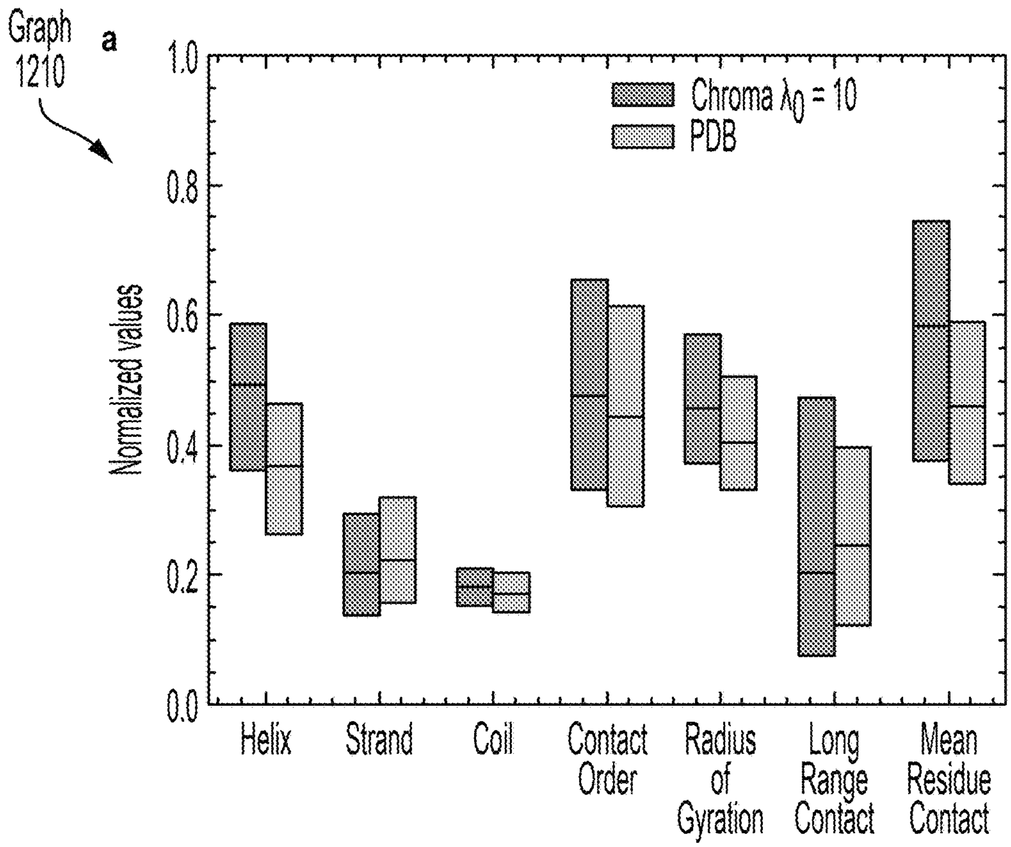
FIGS. 12A-12D illustrate various structural characteristics of synthetic protein designs generated with the diffusion model, according to one or more example implementations.
Figure 12B:
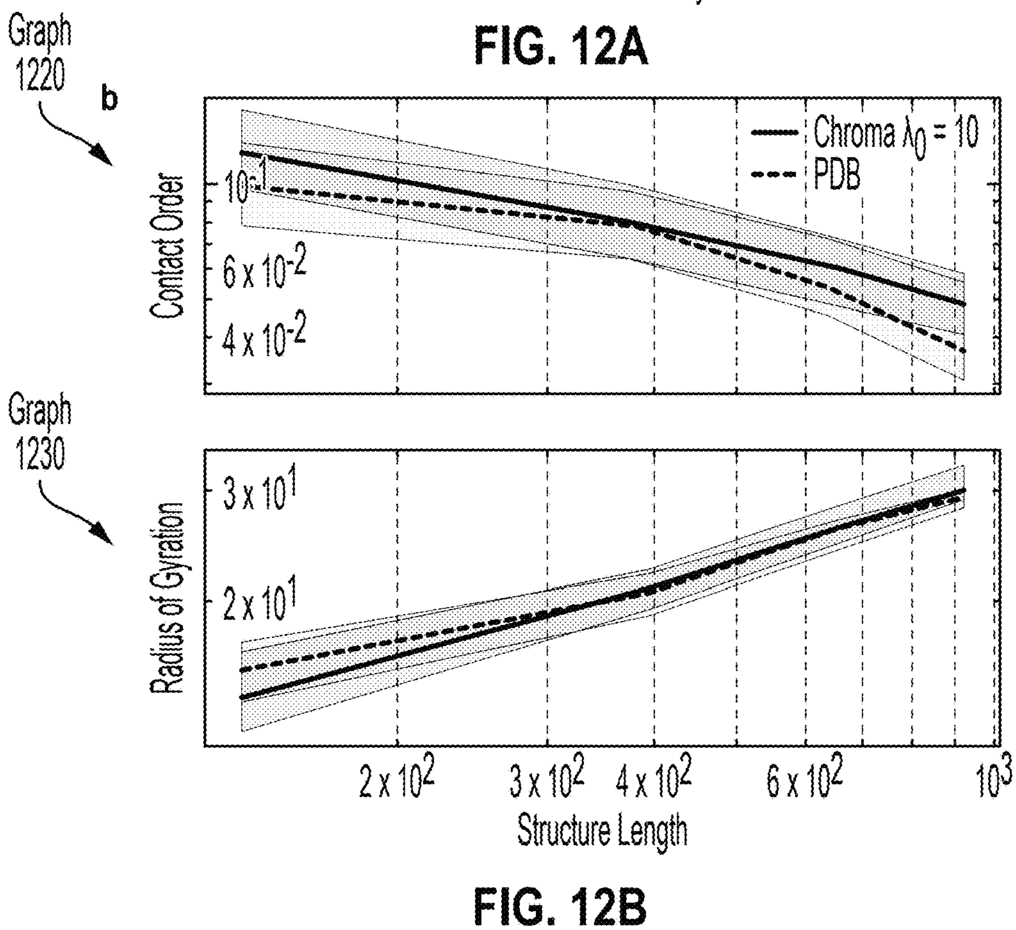
Figure 12C:
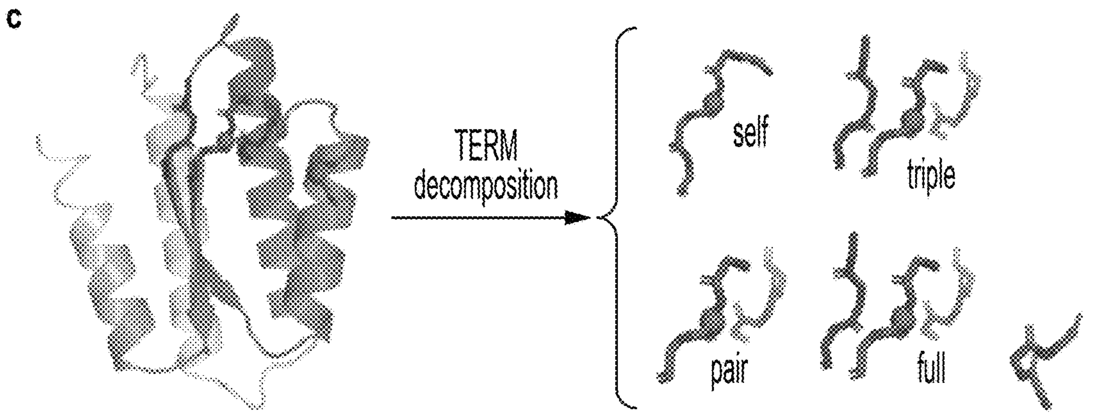
Figure 12D:
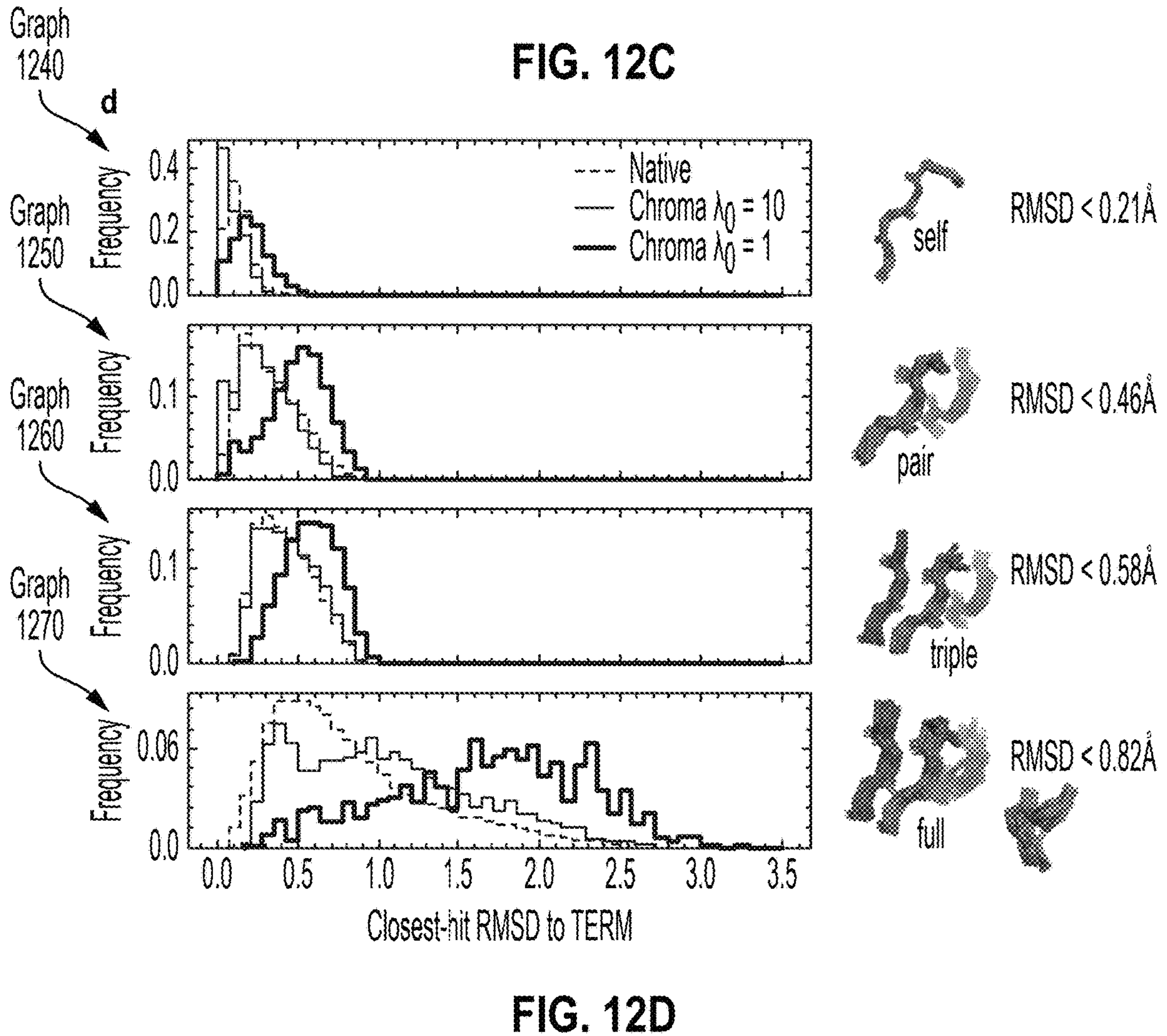

On the right side of FIG. 12C, illustrated is a visual depiction of a tertiary motifs (referred to as "TERMs") decomposition. The distribution of closest-match RMSD for TERMS of increasing order originating from native or Chroma-generated backbones (with inverse temperature $\lambda 0$ being 1 or 10). Diffusion-generated protein backbones are designable by a variety of computational metrics.

Figure 13:
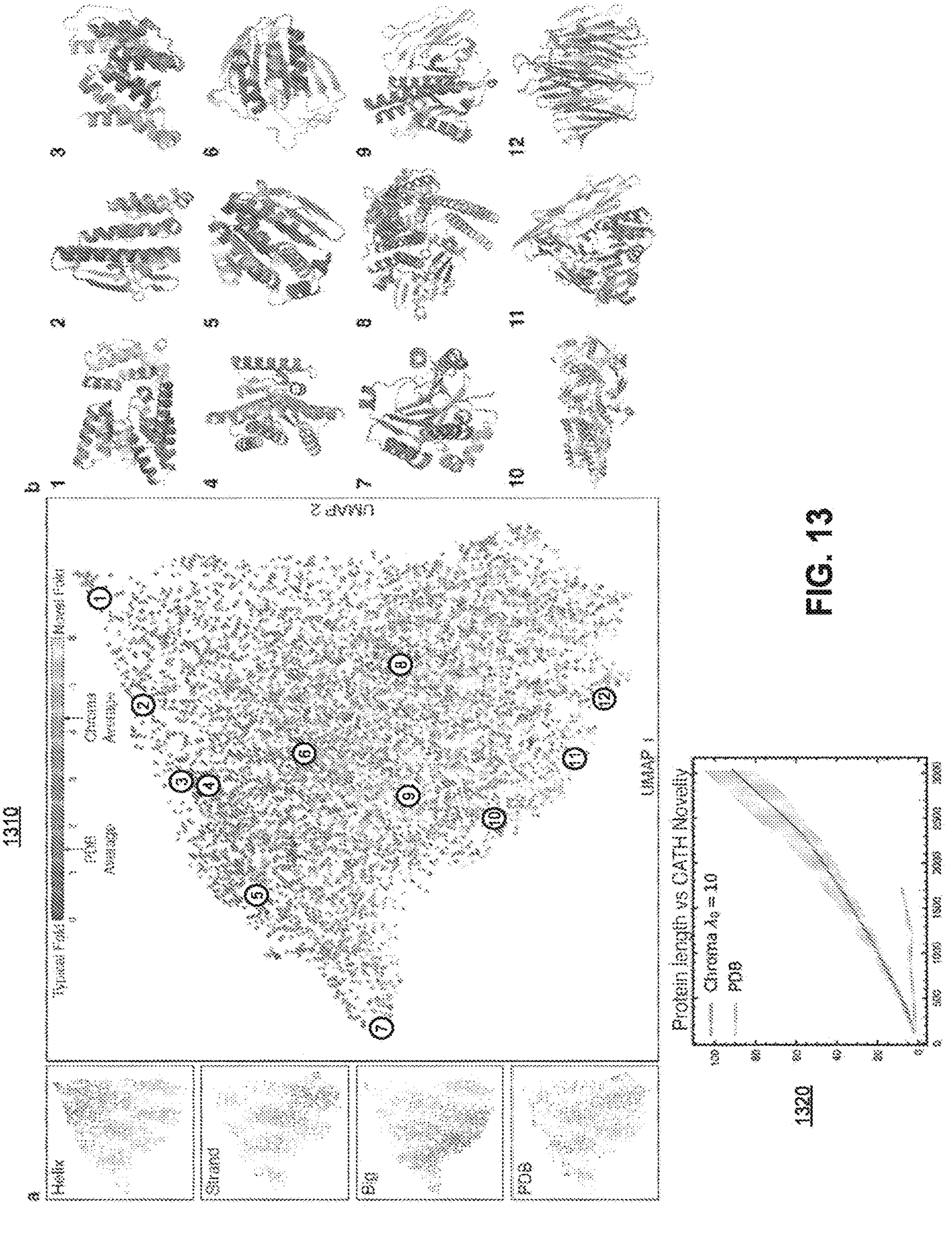
FIG. 13 illustrates synthetic protein designs generated with the diffusion model, according to one or more example implementations.

FIG. 13 illustrates synthetic protein designs generated with the diffusion model, according to one or more example implementations. The synthetic protein designs span natural protein space while also frequently demonstrating high novelty. In Graph 1310, proteins from the PDB and the synthetic proteins generated by the diffusion model are featurized with 31 global-fold descriptors derived from knot theory and are embedded into two dimensions using Uniform Manifold Approximation and Projection (UMAP). The large figure is colored by the CATH coverage novelty measure normalized by protein length. Structural novelty was assessed by counting the number of CATH domains needed to achieve a greedy cover at least 80% of residues with TM>0.5. On average the diffusion model (referred to as "Chroma") needs 4.3 CATH domains per 200 amino acids to cover 80% of its residues while structures from the PDB need only 1.6.

Of note, the synthetic proteins designed by the diffusion model are structurally more diverse and novel compared to structures from the PDB (regardless of protein length). The line represents the median value and is bounded by first (25%) and third (75%) quartile bands. The 4 smaller UMAP plots demonstrate the structure of the embedding by highlighting populations of structures that are mainly helices, strands, large (more than 500 residues), or natural proteins. The panel labeled PDB shows the distribution of natural proteins used to train the model.

On the right-side of the figure, twelve synthetic proteins are shown that were generated by the diffusion model, as a representative set across the embedding space. The twelve synthetic proteins all demonstrate a high novelty score (numbered in the embedding plot). The highlighted structures all have a novelty score of at least one standard deviation greater than the PDB.

FIGS. 14A-14D illustrate example synthetic protein designs satisfying varying design conditions, according to one or more example implementations. Symmetry, substructure, and shape conditioning enable geometric molecular programming.

Figure 14A:
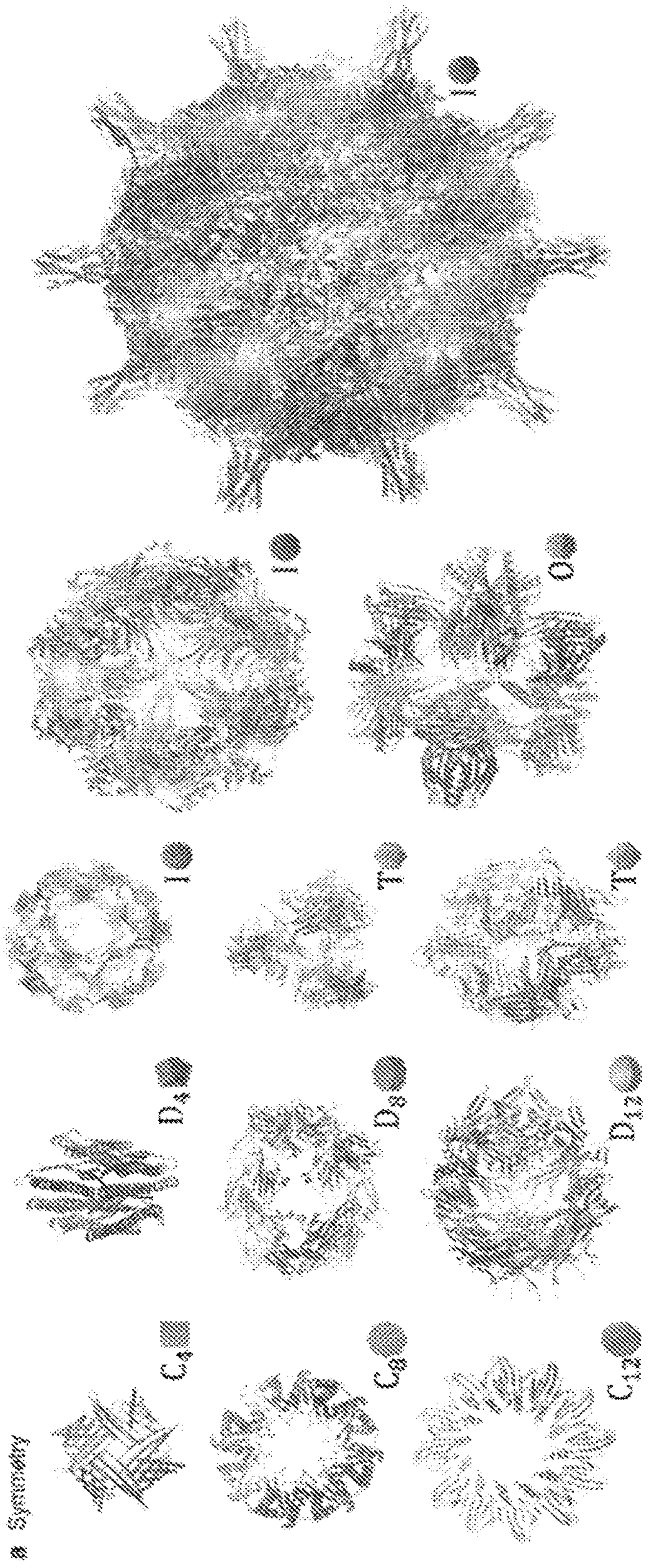
FIG. 14A illustrates conditioning on arbitrary symmetry groups is possible by symmetrizing gradient, noise, and initialization through the sampling process, according to one or more example implementations.

FIG. 14A illustrates conditioning on arbitrary symmetry groups is possible by symmetrizing gradient, noise, and initialization through the sampling process. Cyclic Cn, dihedral Dn, tetrahedral T, octahedral O, and icosahedral I symmetries can produce a wide variety of possible homomeric complexes. The rightmost protein complex contains 60 subunits and 96,000 total residues.

Figure 14B:
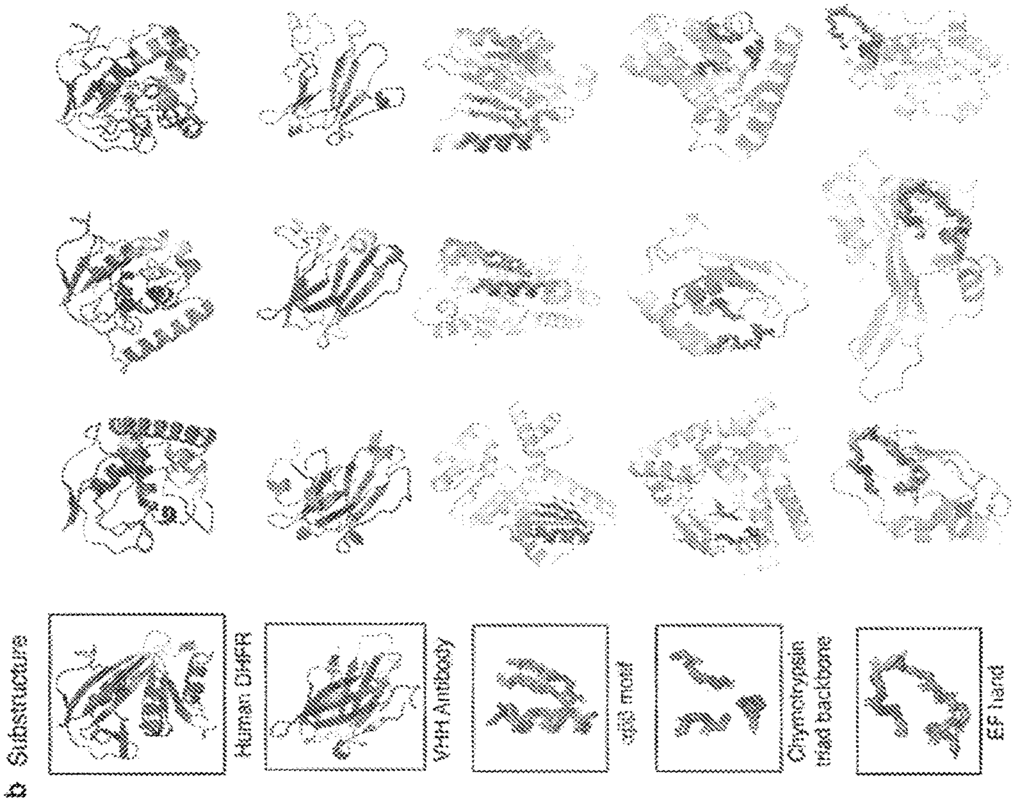
FIG. 14B illustrates conditioning on partial substructure (monochrome) enables protein "infilling" or "outfilling," according to one or more example implementations.

FIG. 14B illustrates conditioning on partial substructure (monochrome) enables protein "infilling" or "outfilling." The top two rows illustrate regeneration (color) of half of a protein (enzyme DHFR, first row) or CDR loops of an antibody (second row). The bottom three rows show conditioning on a pre-defined motif; order and matching location of motif segments is not pre-specified here.

Figure 14C:
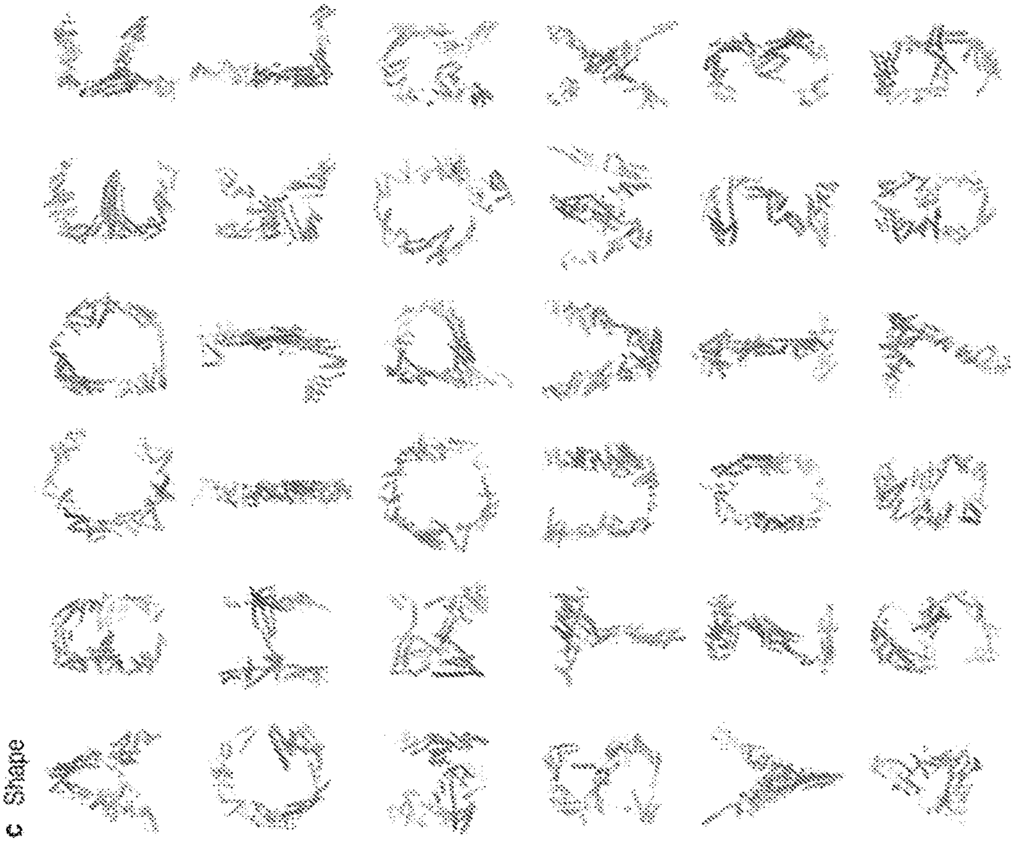
FIG. 14C illustrates conditioning on arbitrary volumetric shapes by using gradients derived from Optimal Transport, according to one or more example implementations.

FIG. 14C illustrates conditioning on arbitrary volumetric shapes by using gradients derived from Optimal Transport. Here, synthetic protein designs were conditioned to have backbone configurations subject to the complex geometries of the Latin alphabet and numerals.

Figure 14D:
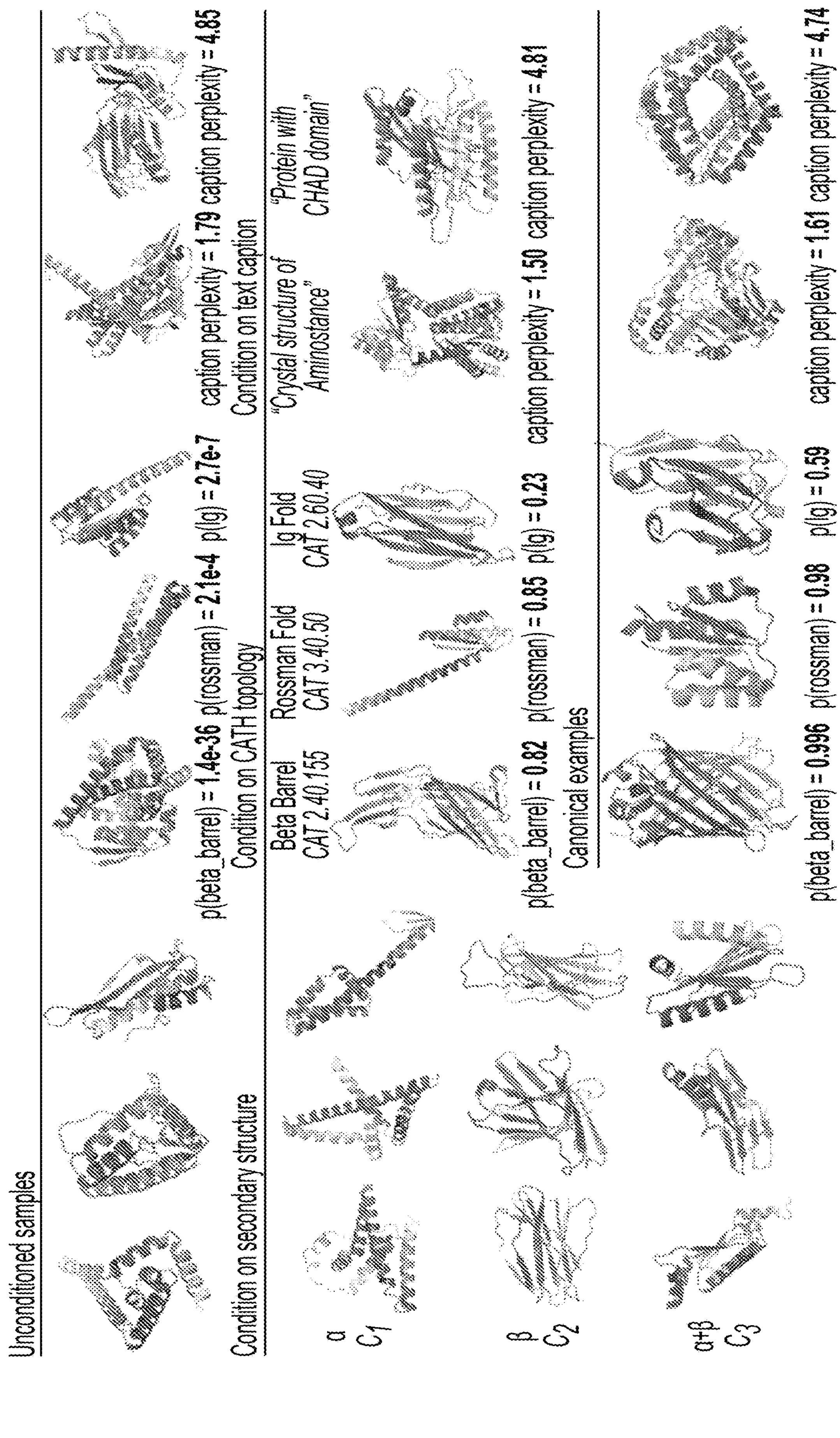
FIG. 14D illustrates further conditioning based on other various design conditions, according to one or more example implementations.

FIG. 14D illustrates further conditioning based on other various design conditions. Protein structure classifiers and caption models can bias the sampling process towards user-specified properties. The top row shows example structures drawn unconditionally from the diffusion model. Below, models trained to predict protein semantics are used to conditionally sample structures with desired secondary structures, belonging to particular topologies, or corresponding to natural language captions. In each column, all conditional samples are drawn starting from the same random seed as the unconditional sample shown at the top of the column. The samples based on secondary structure conditioning show the impact of classifiers trained to predict mainly alpha, mainly beta, and mixed alpha-beta structures. In the columns with topology-conditioned samples, the classifier's predicted probabilities for the intended topology are indicated. Similarly, in the columns with samples based on text conditioning, the caption model's average perplexities are shown. For the topology and text caption columns, PDB structures are shown ("Canonical examples") that exemplify the target condition.

Additional Considerations

The foregoing description of the embodiments has been presented for the purpose of illustration; many modifications and variations are possible while remaining within the principles and teachings of the above description.

Any of the steps, operations, or processes described herein may be performed or implemented with one or more hardware or software modules, alone or in combination with other devices. In some embodiments, a software module is implemented with a computer program product comprising one or more computer-readable media storing computer program code or instructions, which can be executed by a computer processor for performing any or all of the steps, operations, or processes described. In some embodiments, a computer-readable medium comprises one or more computer-readable media that, individually or together, comprise instructions that, when executed by one or more processors, cause the one or more processors to perform, individually or together, the steps of the instructions stored on the one or more computer-readable media. Similarly, a processor may comprise one or more subprocessing units that, individually or together, perform the steps of instructions stored on a computer-readable medium.

Embodiments may also relate to a product that is produced by a computing process described herein. Such a product may store information resulting from a computing process, where the information is stored on a non-transitory, tangible computer-readable medium and may include any embodiment of a computer program product or other data combination described herein.

The description herein may describe processes and systems that use machine-learning models in the performance of their described functionalities. A "machine-learning model," as used herein, comprises one or more machine-learning models that perform the described functionality. Machine-learning models may be stored on one or more computer-readable media with a set of weights. These weights are parameters used by the machine-learning model to transform input data received by the model into output data. The weights may be generated through a training process, whereby the machine-learning model is trained based on a set of training examples and labels associated with the training examples. The training process may include: applying the machine-learning model to a training example, comparing an output of the machine-learning model to the label associated with the training example, and updating weights associated for the machine-learning model through a back-propagation process. The weights may be stored on one or more computer-readable media, and are used by a system when applying the machine-learning model to new data.

The language used in the specification has been principally selected for readability and instructional purposes, and it may not have been selected to narrow the inventive subject matter. It is therefore intended that the scope of the patent rights be limited not by this detailed description, but rather by any claims that issue on an application based hereon.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or". For example, a condition "A or B" is satisfied by any one of the following: A is true (or present) and B is false (or not present); A is false (or not present) and B is true (or present); and both A and B are true (or present). Similarly, a condition "A, B, or C" is satisfied by any combination of A, B, and C being true (or present). As a not-limiting example, the condition "A, B, or C" is satisfied when A and B are true (or present) and C is false (or not present). Similarly, as another not-limiting example, the condition "A, B, or C" is satisfied when A is true (or present) and B and C are false (or not present).

ILLUMINATING PROTEIN SPACE WITH A PROGRAMMABLE GENERATIVE MODEL

Abstract

Three billion years of evolution have produced a tremendous diversity of protein molecules [1], but the full potential of this molecular class is likely far greater. Accessing this potential has been challenging for computation and experiments because the space of possible protein molecules is much larger than the space of those likely to host function. Here we introduce Chroma, a generative model for proteins and protein complexes that can directly sample novel protein structures and sequences and can be conditioned to steer the generative process towards desired properties and functions. To enable this, we introduce a diffusion process that respects conformational statistics of polymer ensembles, an efficient neural architecture for molecular systems that enables long-range reasoning with sub-quadratic scaling, layers for efficiently synthesizing 3D structures of proteins from predicted inter-residue geometries, and a general low-temperature sampling algorithm for diffusion models. Chroma realizes protein design as Bayesian inference under external constraints, which can involve symmetries, substructure, shape, semantics, and even natural-language prompts. Experimental characterization of 310 proteins shows that sampling from Chroma results in proteins that express, fold, and have favorable biophysical properties. Crystal structures of two designed proteins exhibit atomistic agreement with Chroma samples (backbone RMSD of ~1.0 Å). With this unified approach to protein design, we hope to accelerate the prospect of programming protein matter for human health, materials science, and synthetic biology.

Introduction

Protein molecules carry out most of the biological functions necessary for life, but inventing them is a complicated task that has taken billions of years of evolution. The field of computational protein design aims to shortcut this by automating the design of functional proteins in a manner that is programmable. While there has been significant progress towards this goal over the past three decades [2,3], including the design of novel topologies, assemblies, binders, catalysts, and materials[4-7], most de-novo designs have yet to approach the complexity and variety of macromolecules that are found in nature. Reasons for this include 1) modeling the relationship between sequence, structure, and function is difficult, and 2) most computational design methods rely on iterative search and sampling processes which, just like evolution, must navigate a rugged fitness landscape incrementally [8]. While many computational techniques have been developed to accelerate this search [3] and to improve the prediction of natural protein structures [9], the space of possible proteins remains combinatorially large and only partially accessible by traditional computational methods. Determining how to efficiently explore the space of designable protein structures remains an open challenge.

An alternative and potentially appealing approach to protein design would be to directly sample from the space of proteins that are compatible with a set of desired functions. While this could address the fundamental limitation of iterative search methods, it would require a way to parameterize a-priori "plausible" protein space, a way to draw samples from this space, and a way to bias this sampling towards desired properties and functions. Deep generative models have proven successful in solving these kinds of high-dimensional modeling and inference problems in other domains, for example, in the text-conditioned generation of photorealistic images [10-12]. For this reason, there has been considerable work developing generative models of protein space, applied to both protein sequences [13-19] and structures [20-26].

Despite recent advances in generative models for proteins, we argue that there are three properties that have yet to be realized simultaneously in one system. These are 1) to model the joint, all-atom likelihood of sequences and 3D structures of full protein complexes, 2) to do so with computation that scales sub-quadratically with the size of the protein system, and 3) to enable conditional sampling under diverse design contraints without re-training. The first, generating full complexes, is important because proteins function by interacting with other molecules, including other proteins. The second, sub-quadratic scaling of computation, is important because it has been an essential ingredient for managing complexity in other modeling disciplines, such as in computer vision, where convolutional neural networks scale linearly with the number of pixels in an image, and in computational physics, where fast N-body methods are used for efficient simulation of everything from stellar to molecular systems [27]. And lastly, the requirement to sample conditionally from a model without having to retrain it on new target functions is of significant interest because protein design projects often involve many complex and composite requirements which may vary over time.

Here we introduce Chroma, a generative model for proteins that achieves all three of these requirements by modeling full complexes with quasi-linear computational scaling and by admitting arbitrary conditional sampling at generation time. It builds on the framework of diffusion models [28,29], which model high-dimensional distributions by gradually transforming them into simple distributions and learning to reverse this process, and of graph neural networks [30,31], which can efficiently reason over complex molecular systems. We show that Chroma generates high-quality, diverse, and novel structures which refold both in silico and in crystallographic experiments, and that it enables programmable generation of proteins conditioned on diverse properties such as symmetry, shape, protein class, and even textual input. We anticipate that scalable generative models like Chroma will enable a widespread and rapid increase in our ability to design and build protein systems fit for function.

Results

A Scalable Generative Model for Protein Systems

Figure 15A:
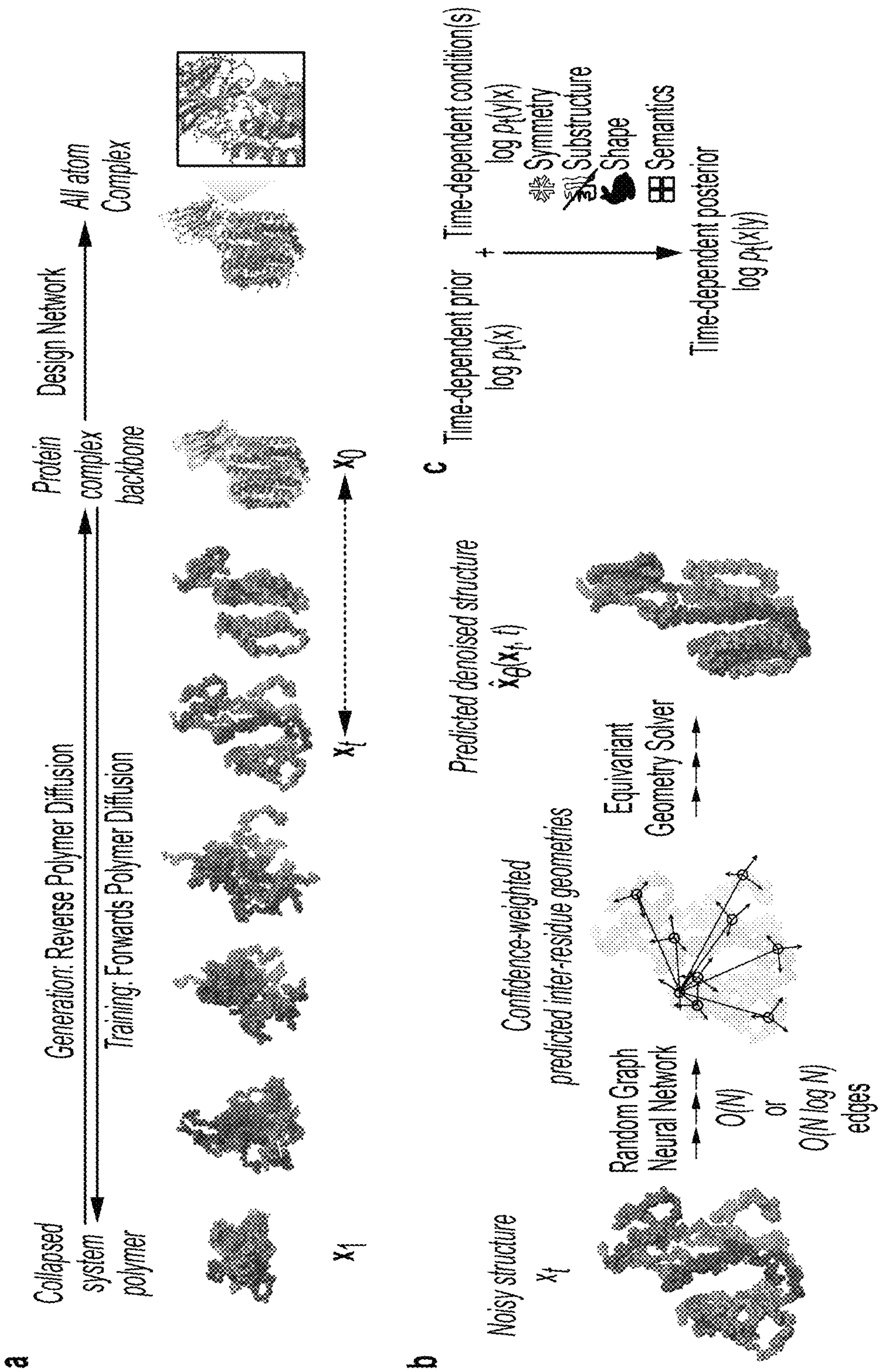
FIG. 15A shows that Chroma is a generative model for proteins and protein complexes that combines structured diffusion for protein backbones with scalable molecular neural networks for backbone synthesis and all-atom design.
Figure 37A:
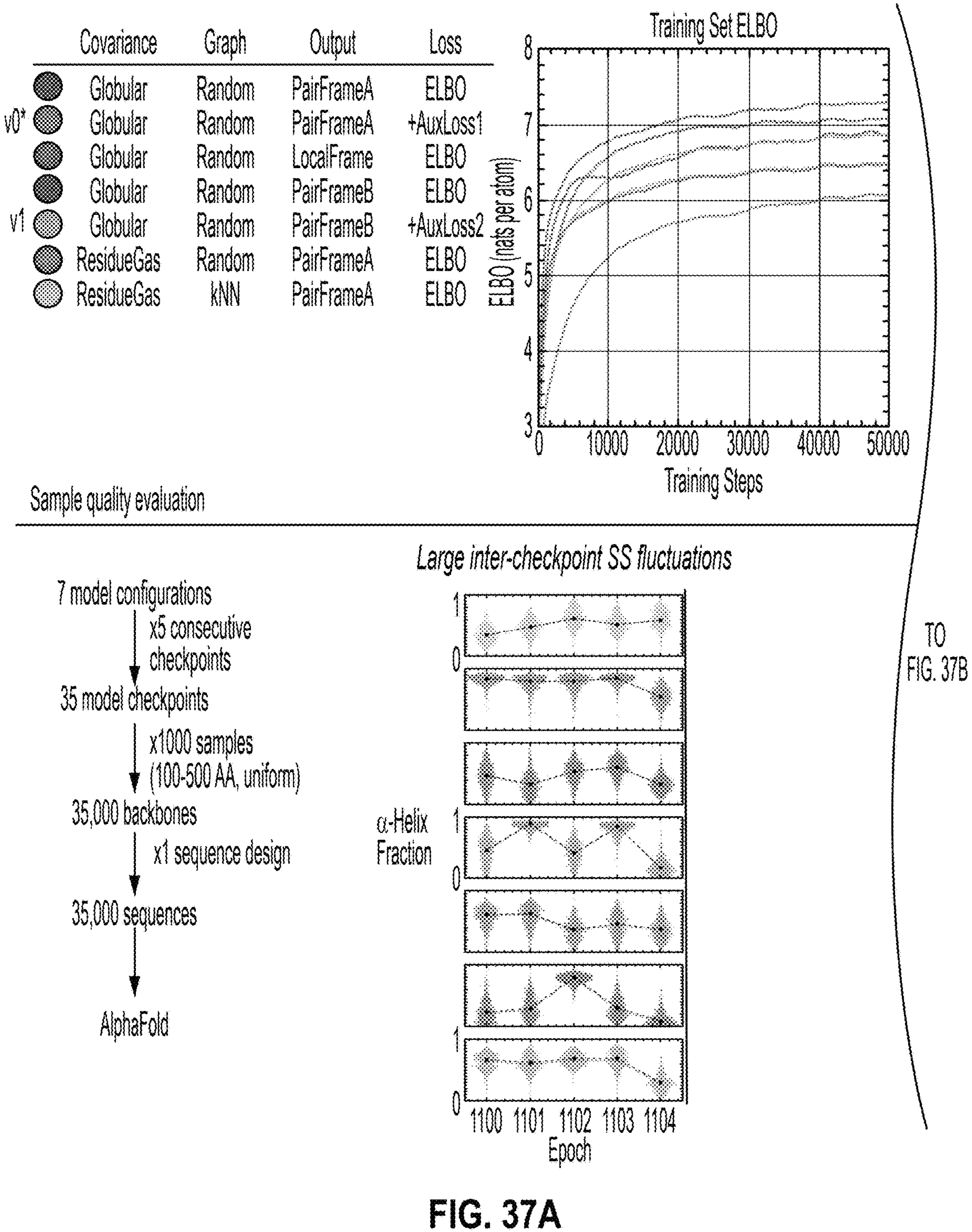
FIGS. 37A-37B show results of ablation study demonstrating utility of novel model components as measured by likelihood and sample quality.
Figure 37B:
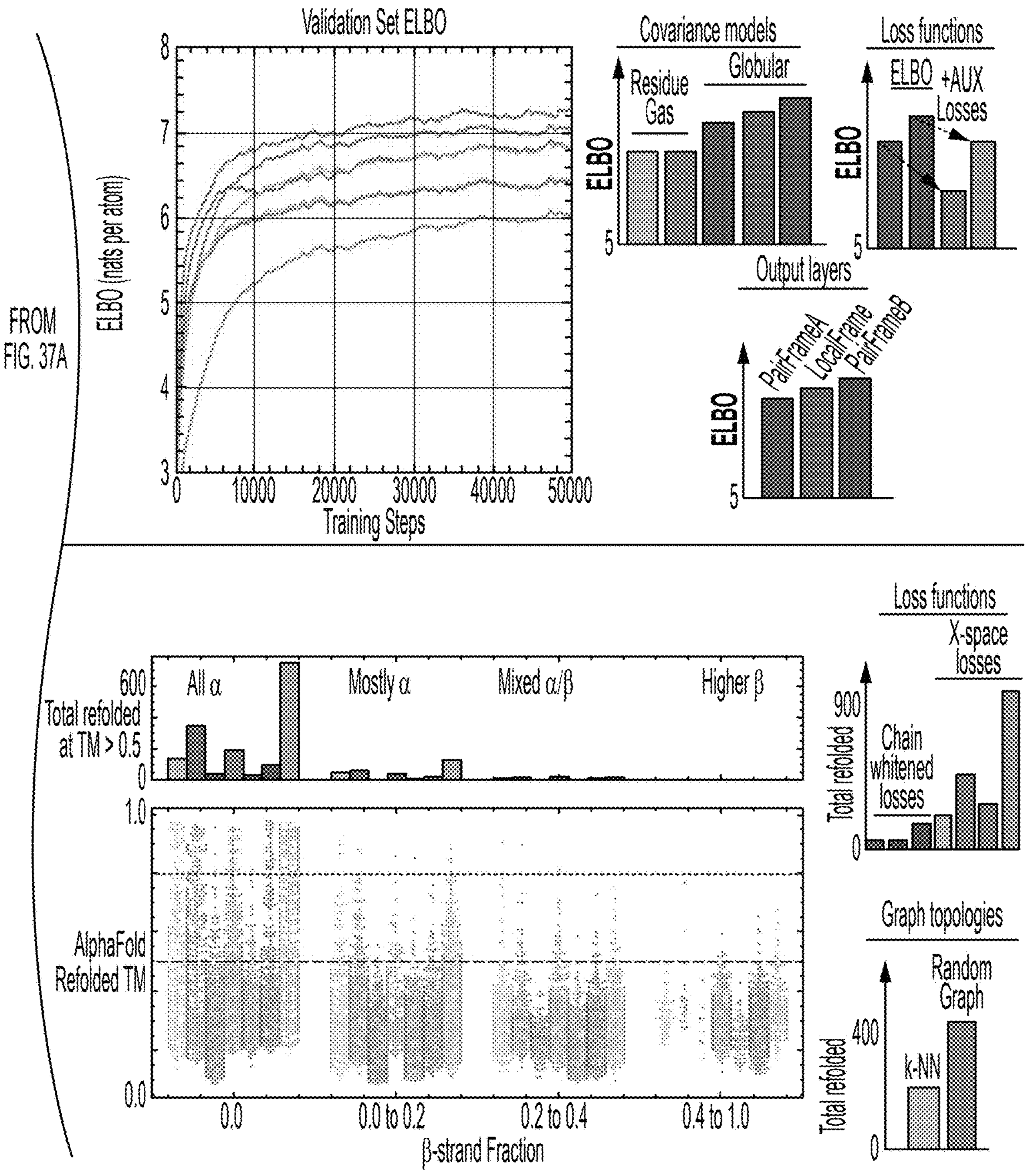

Chroma achieves high-fidelity and efficient generation of proteins by introducing a new diffusion process, neural network architecture, and sampling algorithm based on principles from contemporary generative modeling and biophysical knowledge. Diffusion models generate data by learning to reverse a noising process, which for previous image modeling applications has typically been uncorrelated Gaussian noise. In contrast, our model learns to reverse a correlated noise process to match the distance statistics of natural proteins, which have well-understood scaling laws from biophysics (FIG. 15A, Appendix C). Prior generative models for protein structure have typically leveraged computation that scales quadratically $\mathcal{O}(N^2)$[24,25] or cubically $\mathcal{O}(N^3)$[9,23] in the number of residues N, which has limited their application to small systems or required large amounts of computation for modestly sized systems. To overcome this, Chroma introduces a novel neural network architecture (FIG. 15A, Appendices D-F) for processing and updating molecular coordinates that uses random long range graph connections with connectivity statistics inspired by fast N-body methods [27] and that scales sub-quadratically (O(N) or $\mathcal{O}$(Nlog N), Appendix D). We found that these modeling components improve performance as measured by likelihood and in-silico refolding across an ablation study of seven different model configurations (FIGS. 37A-37B, Appendix K). Finally, we introduce methods for low-temperature sampling with a modified diffusion process that allows us to trade increased quality of sampled backbones (increasing likelihood) for reduced conformational diversity (reducing entropy). Given backbones from this diffusion process, the Chroma design network then generates sequence and side-chain conformations conditioned on the sampled backbone to yield a joint generative model for the sequences and structure of a protein complex. The design network is based on a similar graph neural network architecture, but with conditional sequence and side-chain decoding layers that build on prior works [15,16] that have recently seen further refinement and experimental validation [32-34].

An important aspect of our diffusion-based framework is that it enables programmability of proteins through conditional sampling under combinations of user-specified constraints. This is made possible by a key property of diffusion models: they learn a process that transforms a simple distribution into the complex data distribution through a sequence of many infinitesimal steps; these 'microscopic' steps, therefore, can be biased or constrained by different user-specified requirements to produce a new conditional diffusion process at design time. We build on this with a diffusion Conditioners_framework that allows us to automatically sample from arbitrary mixtures of hard constraints and soft penalties implemented as composable primitives (FIG. 15A, Appendix L). We explore several conditioner primitives including geometrical constraints which can "outfill" proteins from fixed substructures (Appendix M), enforce particular distances between atoms (Appendix M), graft motifs into larger structures (Appendix N), symmetrize complexes under arbitrary symmetry groups (Appendix P), and enforce shape adherence to arbitrary point clouds (Appendix Q). We also explore the possibilities of semantic prompting by training neural guidance networks which predict multi-scale protein classifications (Appendix R) and natural language annotations (Appendix S) from protein structures. We can invert these predictive models by sampling proteins which optimize classifier predictions. Any subset of conditioners may then be composed for bespoke, on-demand protein generation subject to problem-specific requirements.

Analysis of Unconditional Samples

Figures 1, 15B:
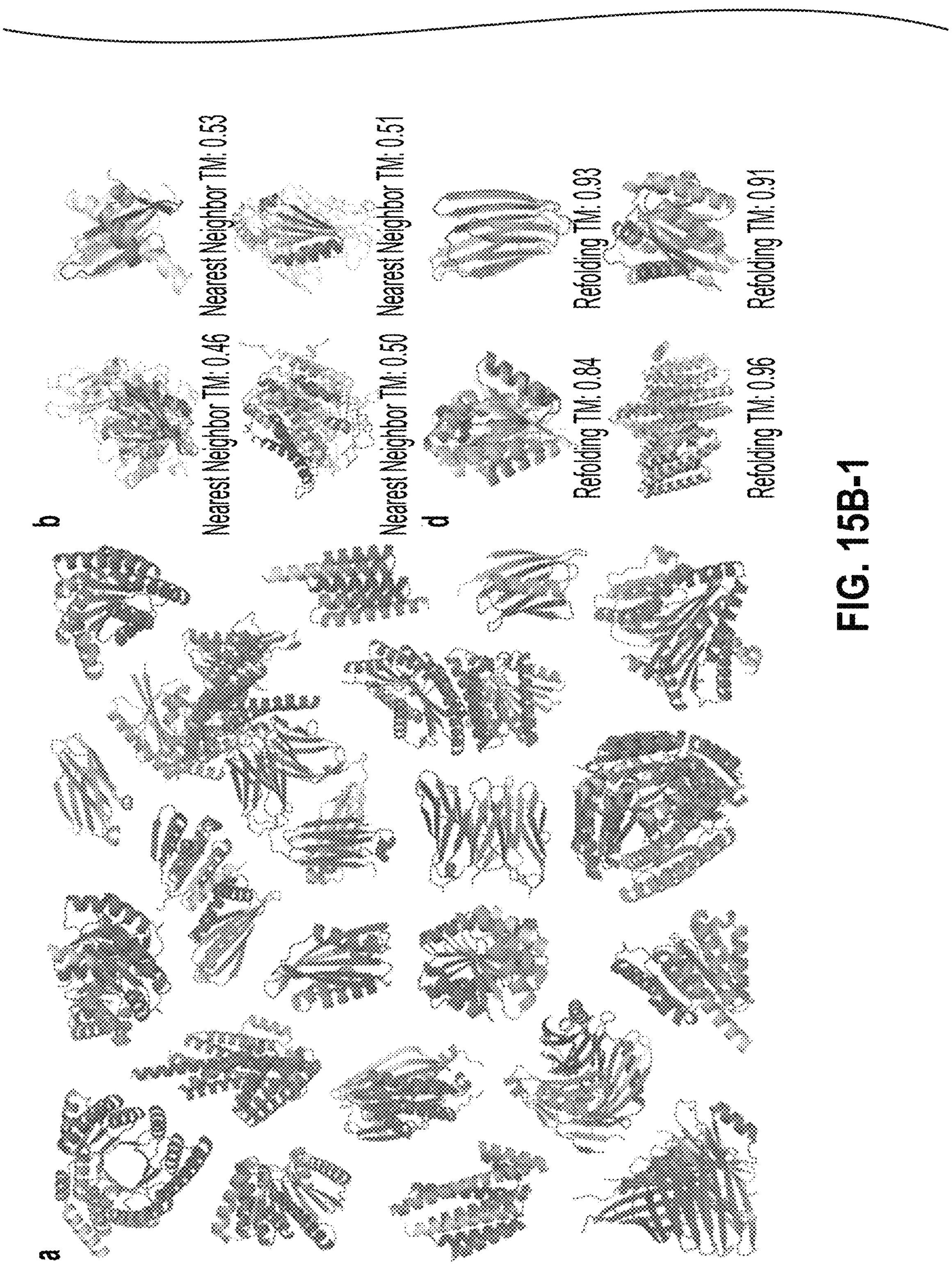
Figure 25:
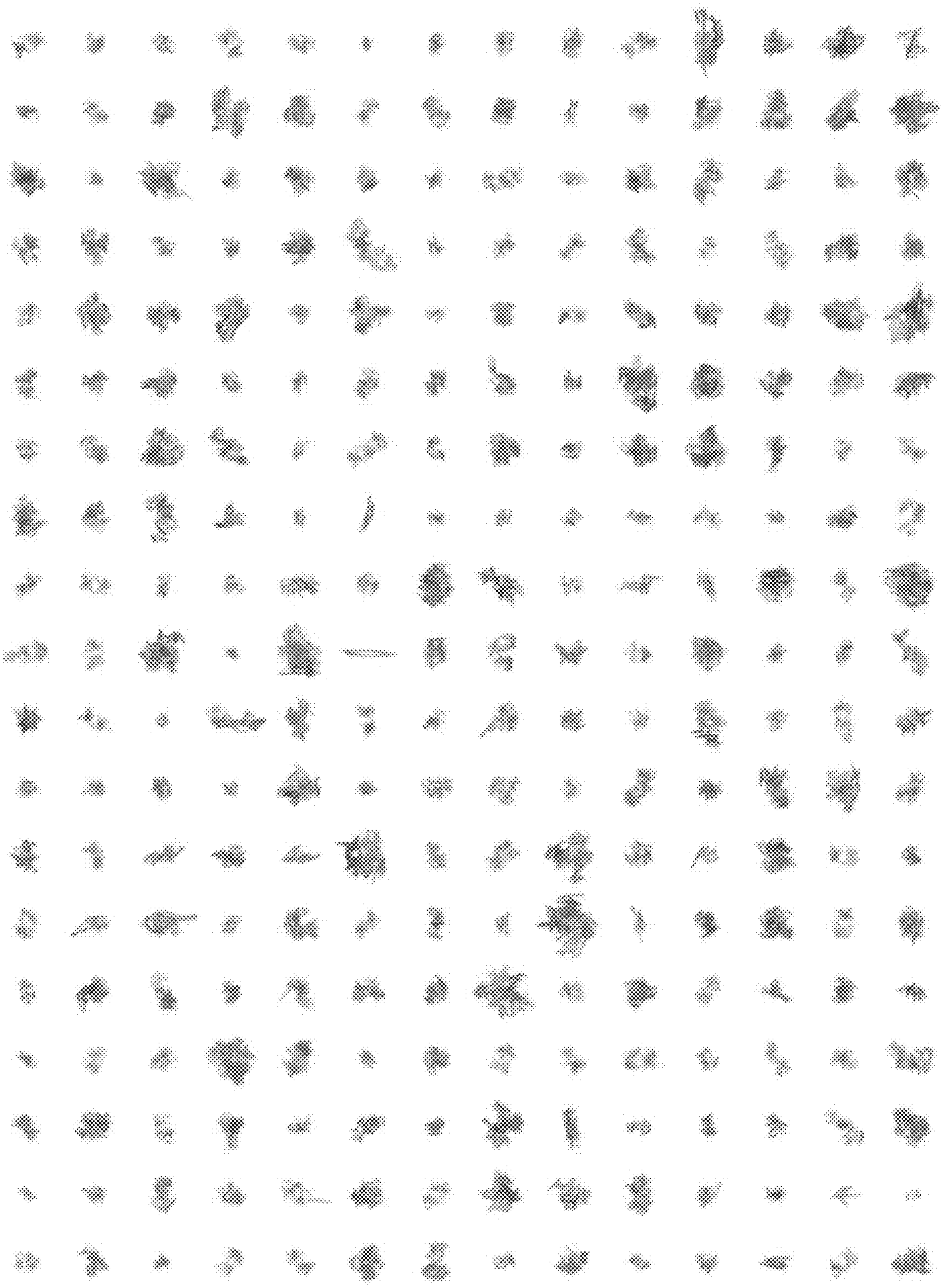
FIG. 25 shows random complex samples from ChromaBackbone-v1.
Figure 26:
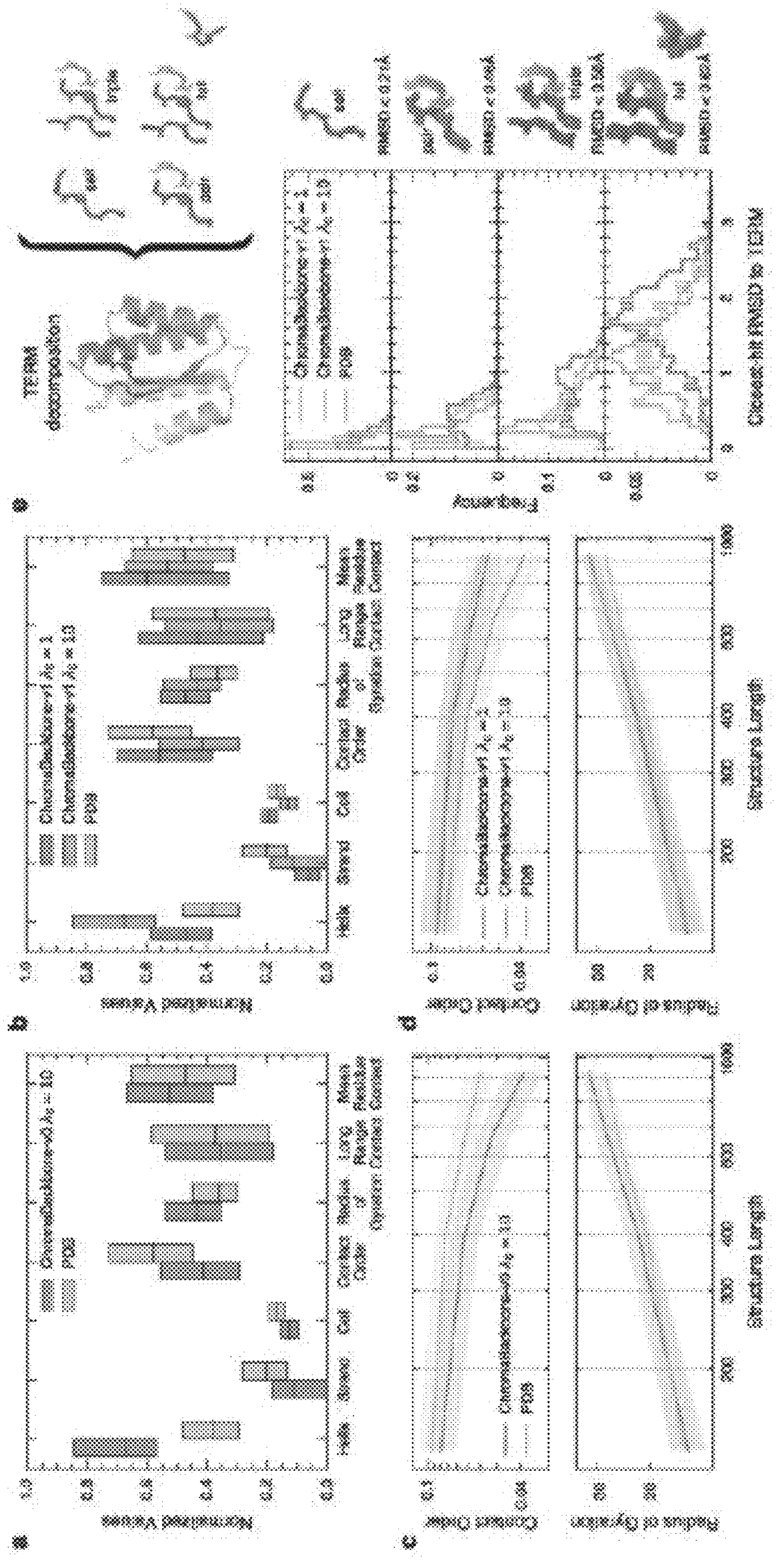
FIG. 26 shows that unconditional backbone samples reproduce both low and high order structural statistics of natural proteins.

We sought to characterize the space of possible proteins parameterized by Chroma by generating a large number of unconditional samples of protein and protein complexes (100,000 single-chain proteins and 20,000 complexes across two model versions (v0 and v1); Appendix F and Supplementary Table 2). As can be seen in FIGS. 15B-1-15B-2, unconditional samples display many properties shared by natural proteins, such as complex layering of bundled alpha helices and beta sheets in cooperative, unknotted folds. In some cases, we observe recognizable protein complex configurations, such as what appears to be an antibody-antigen complex in FIGS. 15B-1-15B-2 (center-right; note that the closest PDB structural matches to the two "antigen" chains of this complex are at TM-scores of 0.46 and 0.43, indicating that this sample is not a result of memorization). We provide grids of random samples in FIG. 24 and FIG. 25 for single-chain and complex structures, respectively. To quantitatively characterize the agreement of Chroma samples with natural proteins, we computed distributions of several key structural properties, including secondary structure utilization, contact order [35], length-dependent radius of gyration [36], length-dependent long-range contact frequency and density of inter-residue contacts (Appendix I). We observe general agreement of these statistics to corresponding distributions from the PDB (FIG. 26), although we do see an overrepresentation of α-helices in the later version of Chroma (v1) that appears to be a consequence of low-temperature sampling (i.e., low-temperature sampling accentuates the already increased frequency helices exhibit over strands in natural proteins; FIG. 26). Since these protein properties focus on low-order structural statistics, we also sought to characterize the extent to which they reproduce higher-order atomic geometries of natural protein structures. Natural protein structures exhibit considerable degeneracy in their use of local tertiary backbone geometries, such that completely unrelated proteins tend to utilize very similar tertiary motifs or TERMs [37,38]. Chroma-generated structures exhibit the same type of degeneracy, utilizing natural TERMs in a way closely resembling native proteins, including complex tertiary geometries with four or five disjoint backbone fragments (see FIG. 26 and Appendix I).

Figure 30:
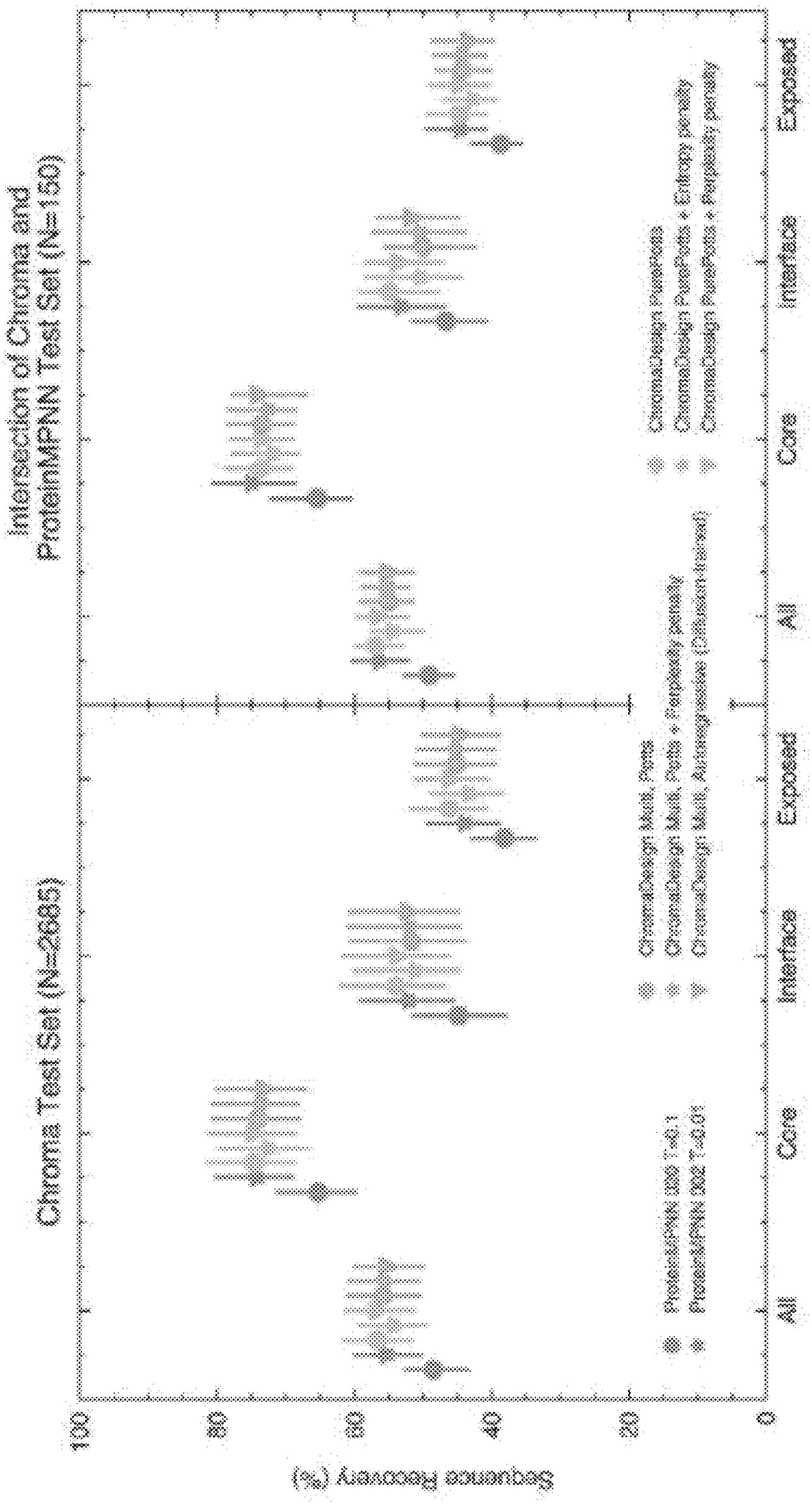
FIG. 30 shows that ChromaDesign and ProteinMPNN have comparable sequence recovery.
Figure 31A:
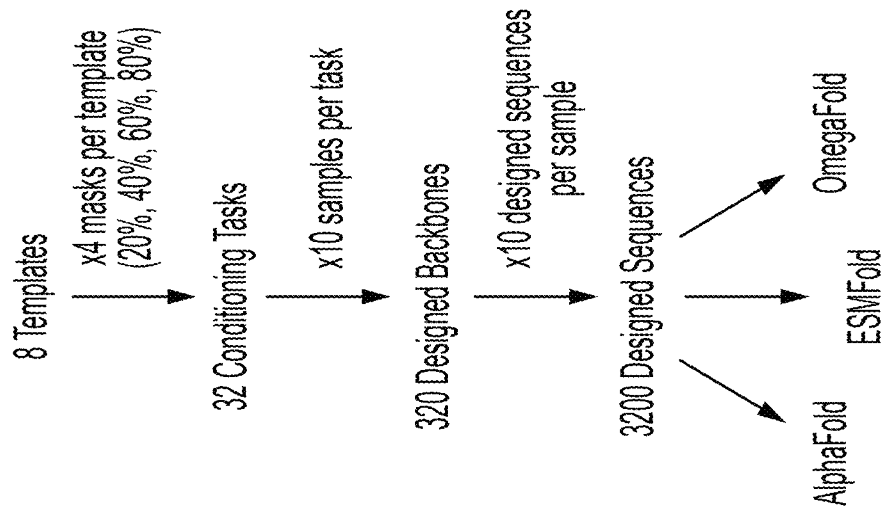
FIGS. 31A-31D show that substructure-conditioned samples can refold in silico.
Figure 31B:
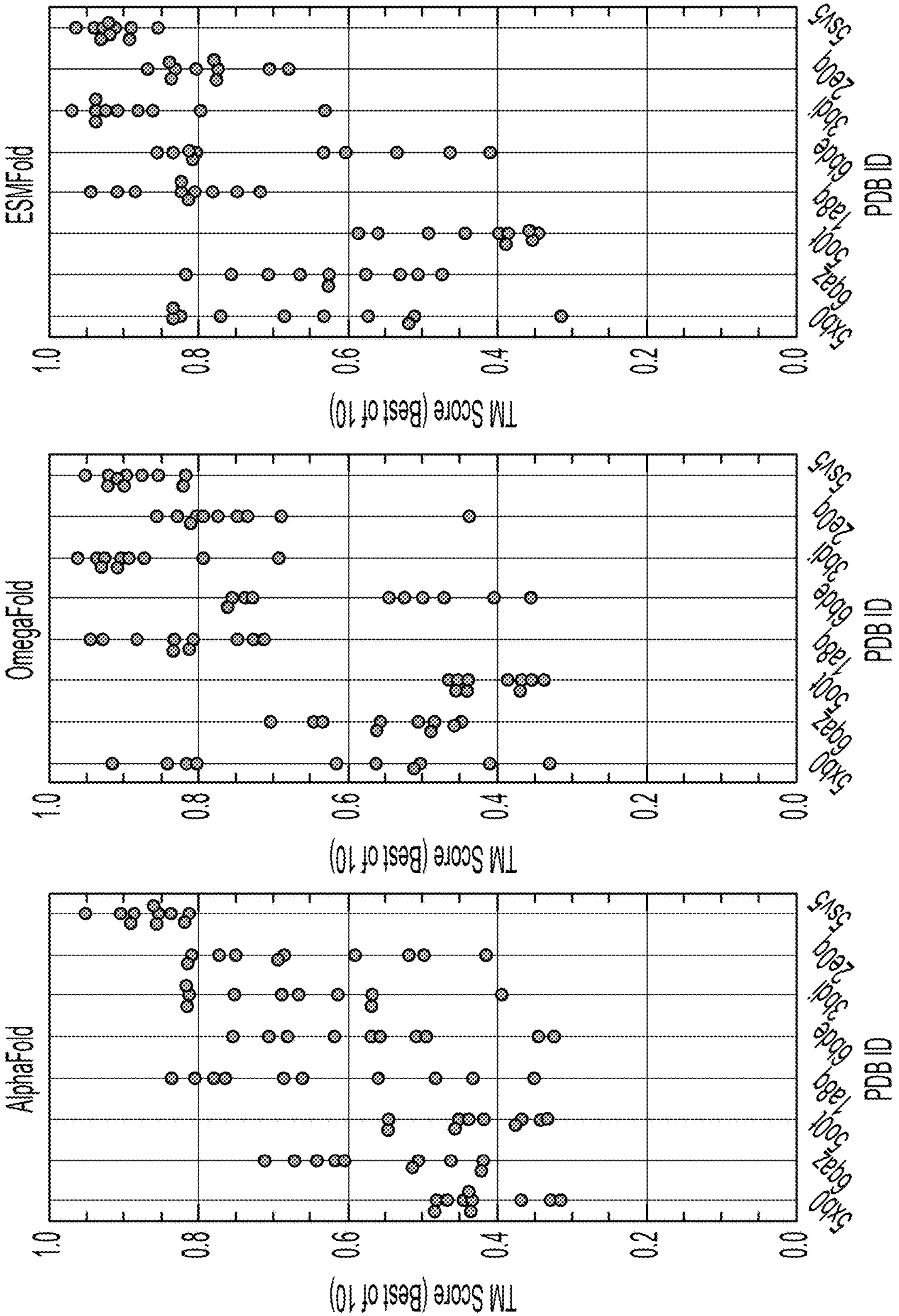
Figure 31D:
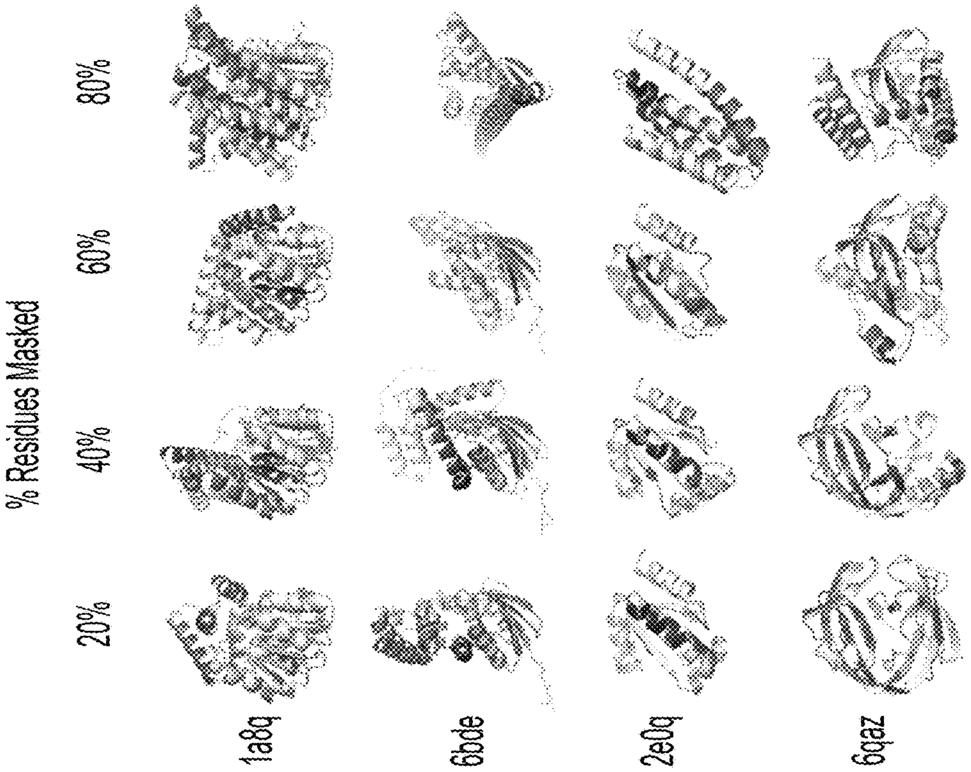
Figure 31C:
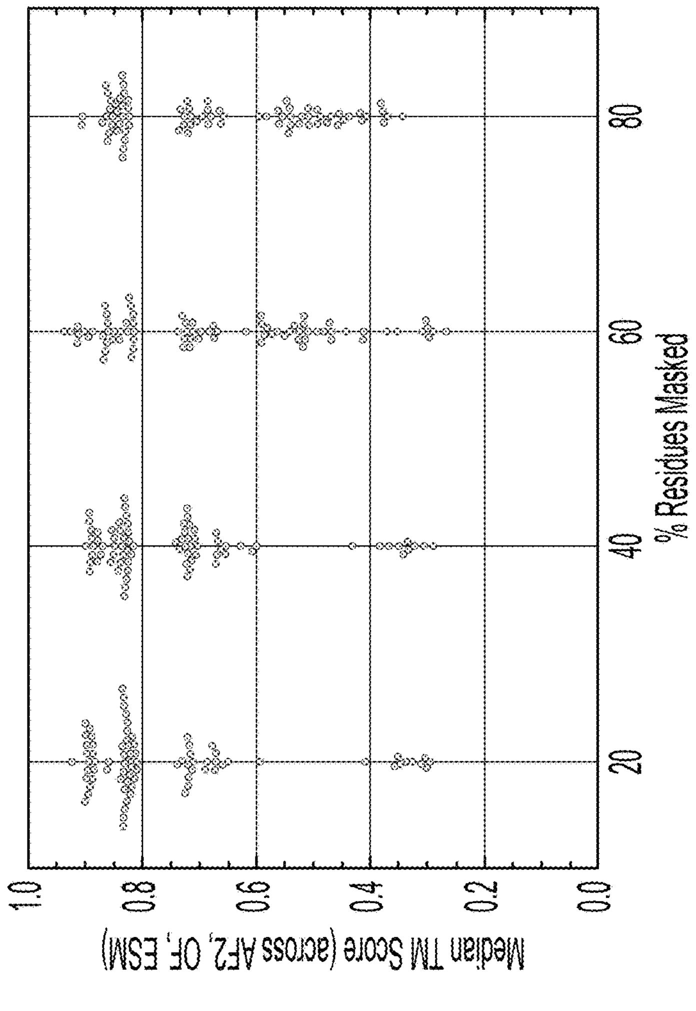

While reproducing native-like properties of backbone geometries is important in design, we ultimately care about the extent to which they can be realized as sequences that fold and function as intended. The definitive answer to this question involves experimental characterization (see below), but in-silico evidence can be gathered more systematically. We sought to evaluate the fidelity of sequence-structure pairs generated by Chroma by measuring their agreement with three state-of-the-art structure prediction models [9,39,40]. We sampled one sequence for each backbone with Chroma's design network and assessed whether each structure prediction method would predict these sequences to fold into the corresponding generated structures (Appendix I, FIG. 30). We observe widespread refolding of Chroma samples whether stratified by protein length (FIGS. 15B-1-15B-2) or helical content and novelty (FIG. 30). While it is not surprising that successful refolding is less frequent for longer proteins, it is remarkable that high TM-scores [41] are routinely achieved even for proteins of over 800 residues in length. Interestingly, helix content does not appear to be a strong predictor of refolding but the distance to the nearest neighbor in the PDB does (FIG. 30, middle and bottom rows, respectively). We note that this sequence-structure consistency test is not perfect, as it rests on the assumption that structure prediction models will generalize to novel folds and topologies. However, the test does provide partial supporting evidence for the generation of realizable protein models in instances where the predicted and generated structures have strong agreement.

Figure 27:
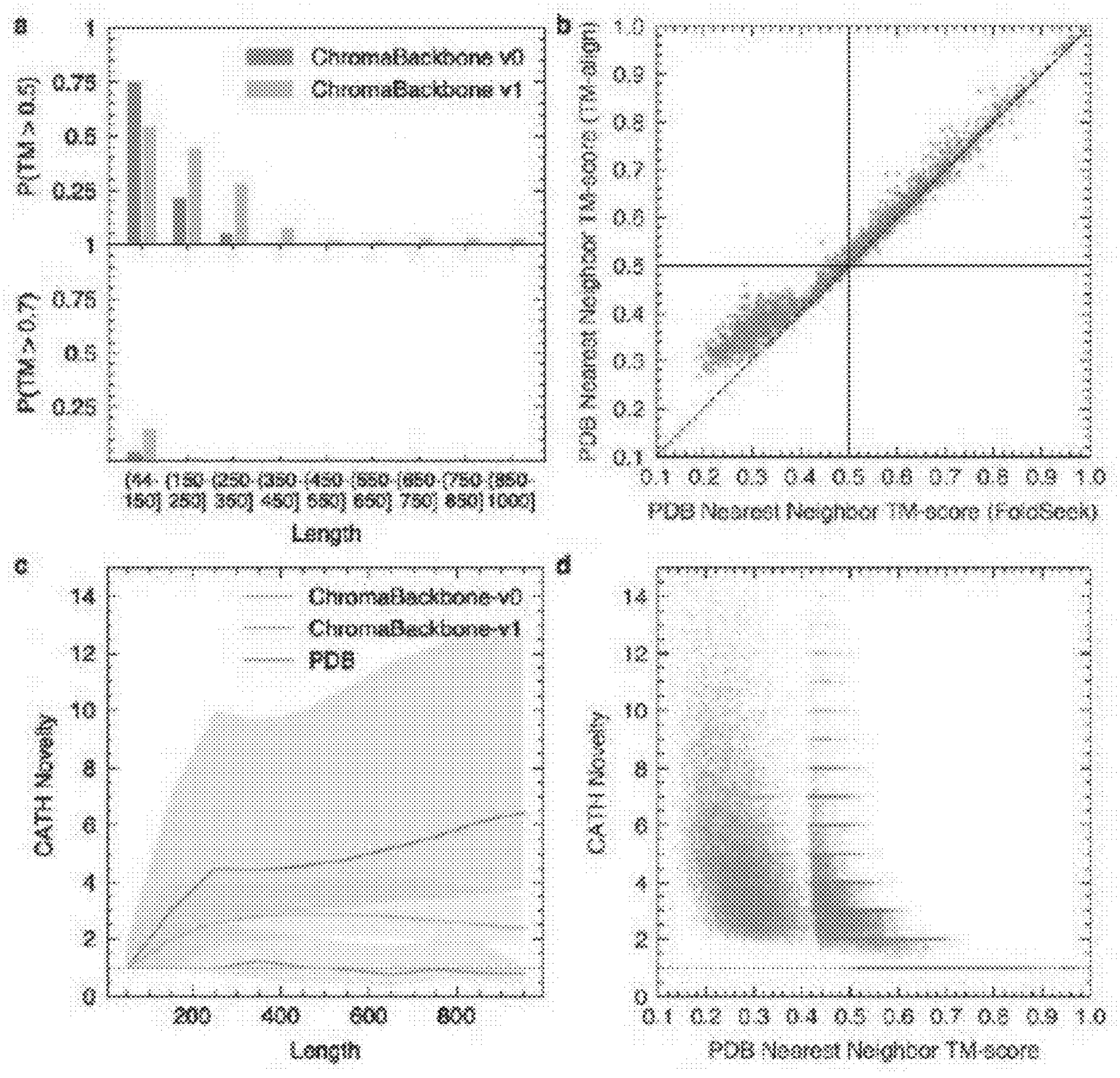
FIG. 27 shows that unconditional backbone samples demonstrate structural novelty across different metrics and protein sizes

Quantification of the structural homology between Chroma-generated samples and proteins in the PDB suggests that the model generates novel structures at a frequency that increases sharply with length (FIGS. 15B-1-15B-2 and FIG. 27). However, this analysis suffers from the issue that coverage of longer structures is expected to be lower in any finite database. To get a better understanding how novel Chroma samples are across lengths, we defined a novelty score as the number of CATH [42] domains required to greedily cover 80% of the residues in a protein at a TM score above 0.5, normalized by protein length (see Appendix I). Note that most valid proteins will be covered by at least some finite number of CATH domains, as we retain even very small domains (e.g., single secondary-structural elements) in the coverage test. As shown in FIG. 27, there is a clear gap between native and Chroma-generated proteins by this metric, with most native backbones covered by a roughly constant number of CATH domains per length, while Chroma-generated structures require an increasing number of domains per length as length increases.

Figure 28:
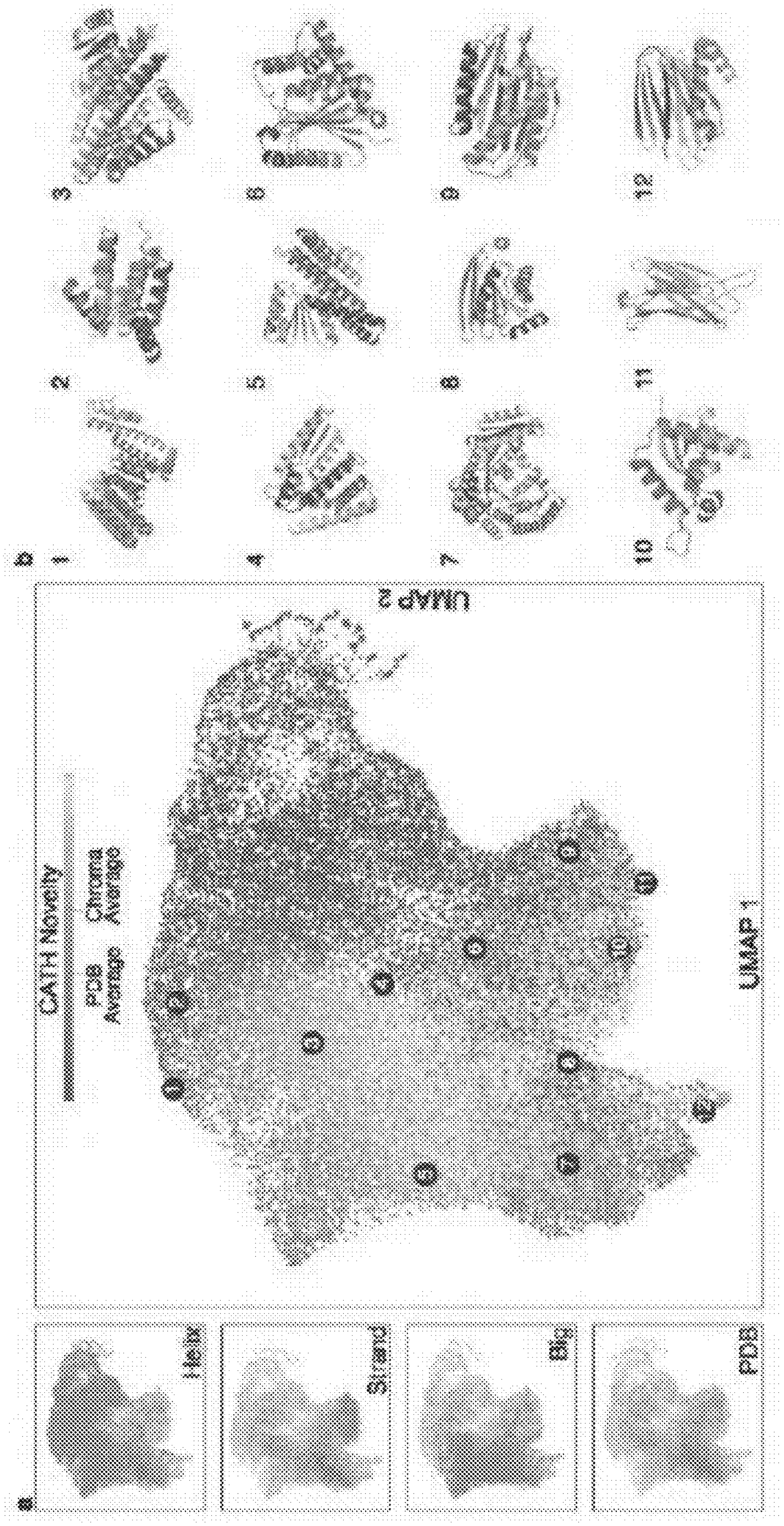
FIG. 28 shows that unconditional backbone samples span natural protein space while also frequently demonstrating high novelty.

We further find that samples from Chroma are diverse and cover all of natural protein space. In FIG. 28, we jointly represent samples from Chroma and a set of native structures with global topology descriptors derived from knot theory [43,44], and embed these into two dimensions with UMAP [45]. The resulting embedding appears to be semantically meaningful as sub-sets of structures belonging to different categories by size and secondary structures cluster in this projection (sub-panels on the left in FIG. 28). False color of the points in the embedding shows that novelty is spread broadly and not biased to only certain types of structure space. This is especially clear when looking at a representative selection of novel samples shown in FIG. 28.

Programmability

An important aspect of Chroma is its programmability, which means that it is straightforward to specify high-level protein properties (e.g., symmetry groups) that are complied into a set of sampling conditioners that bias the diffusion process towards desired properties (see FIG. 15A and Appendix L). To demonstrate the range of protein properties that can be programmed with conditional generation, we explored several composable conditioning primitives (see Methods and Appendices M-S). While we believe that each of these represents only a preliminary demonstration of possible conditioning modes, they provide a glimpse of the potential for programmable protein design.

Figures 1, 15C:
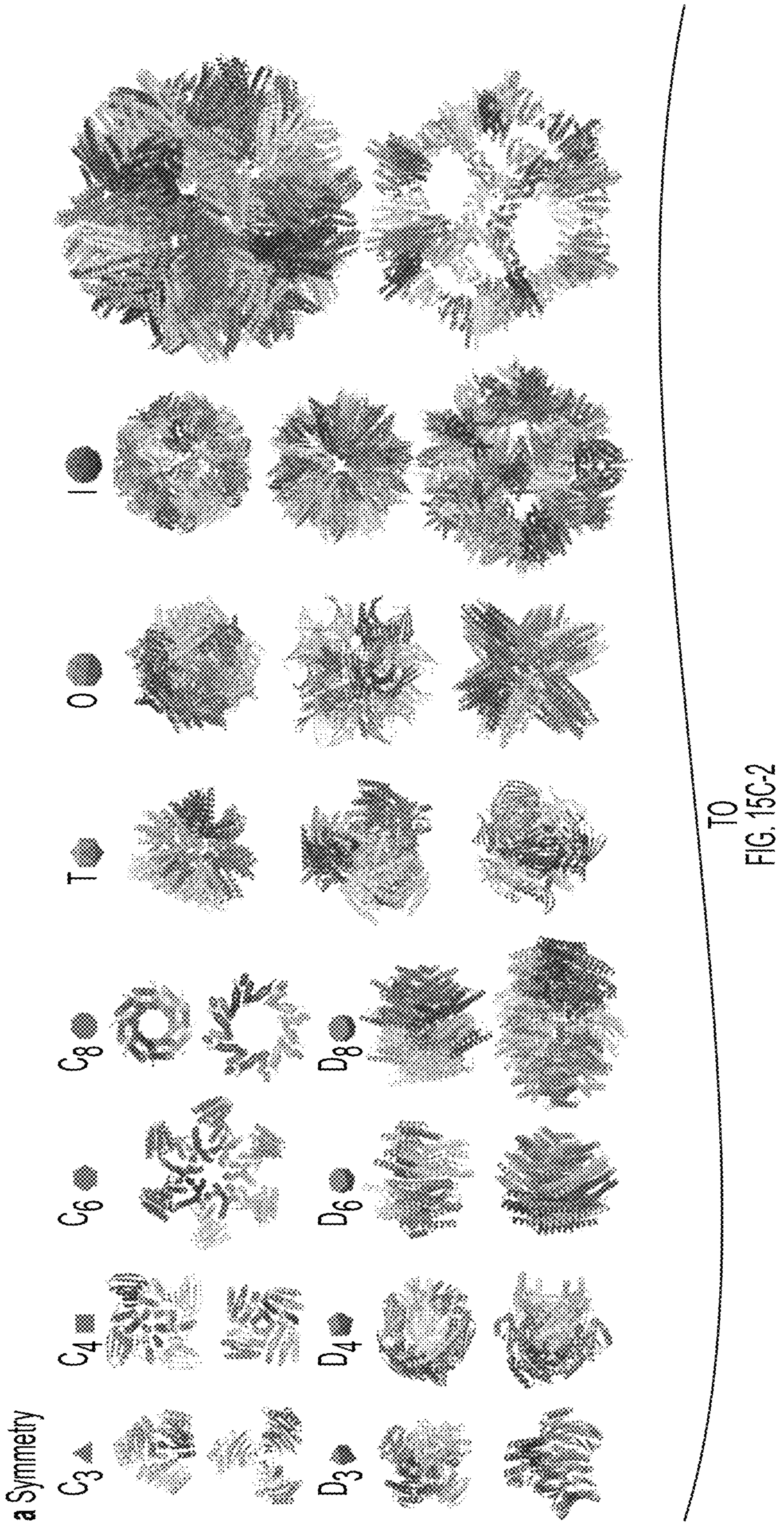
Figures 2, 15C:
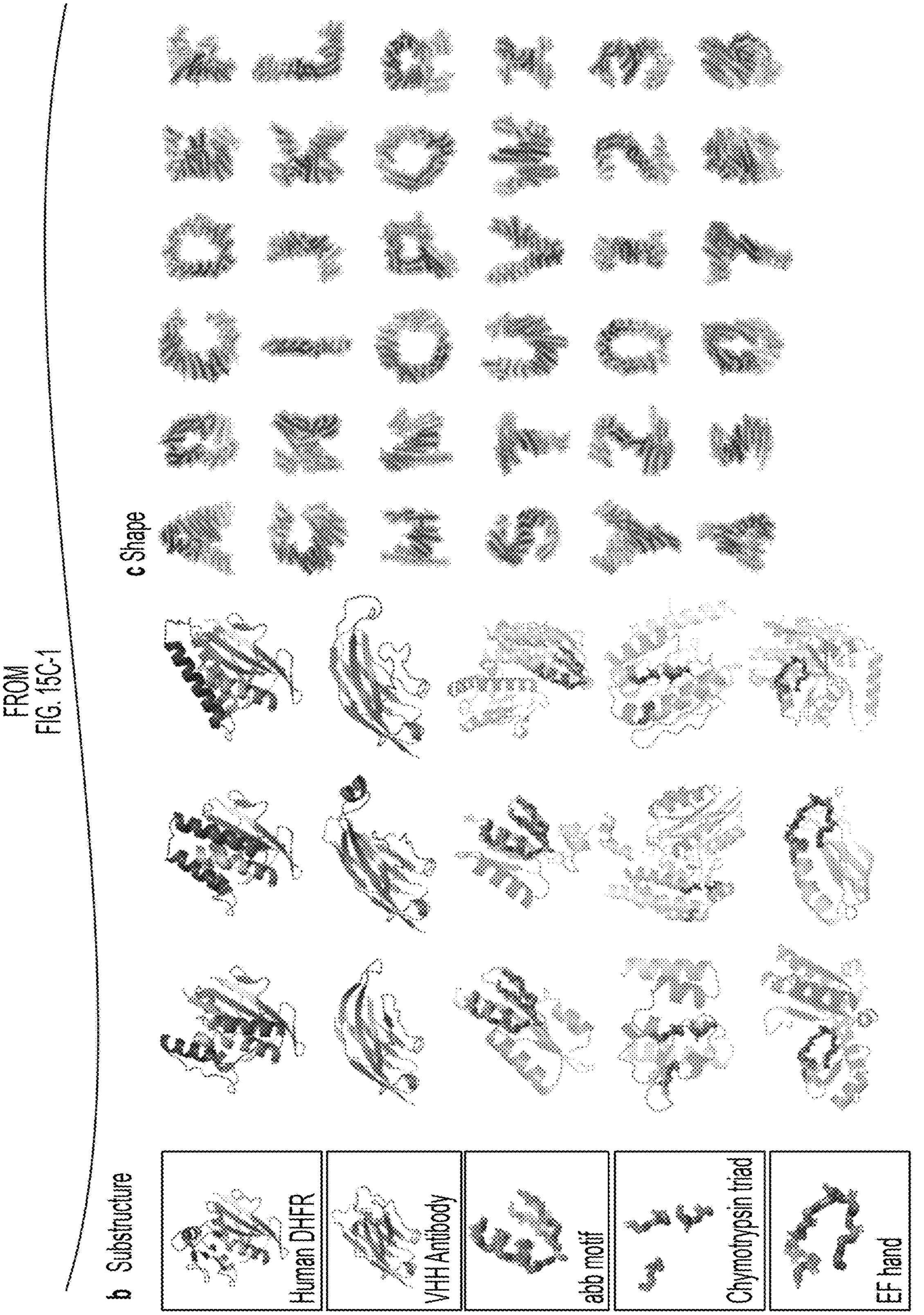

We begin by considering analytic conditioners that can control protein backbone geometry. We found that conditioning on the symmetry of protein complexes can readily generate samples under arbitrary symmetry groups (FIGS. 15C-1-15C-2, Appendix P). FIGS. 15C-1-15C-2 illustrate symmetry-conditioned generation across many groups, from simple 4-subunit cyclic symmetries up to a capsid-sized icosahedral complex with 60,000 total residues and over 240,000 atoms. This also demonstrates why favorable computational scaling properties, such as quasilinear computation time (Appendix D), are important, as efficient computation facilitates scaling to larger systems. Symmetric assemblies are common in nature and there have been some successes with de novo symmetric designs [46,47], but it has been generally challenging to simultaneously optimize for both the molecular interaction details between protomers and the desired overall symmetry in design. Symmetry conditioning within the generation process in Chroma should make it simpler to sample structures that simultaneously meet both requirements.

Next, we explore substructure conditioning in FIGS. 15C-1-15C-2, which is a central problem for protein design as it can facilitate preserving one part of a protein's structure (e.g., an active site) while modifying another part of the structure (and potentially function). In the top row, we "cut" the structure of human dihydrofolate reductase (PDB code 1DRF) into two halves with a plane, remove one of the halves, and regenerate the other half anew. The cut plane introduces several discontinuities in the chain simultaneously, and the generative process needs to sample a solution that satisfies these boundary conditions while being biophysically plausible. Nevertheless, the samples achieve both goals and, interestingly, do so in a manner very different from both each other and from natural DHFR. In the second row of FIGS. 15C-1-15C-2, we cut out the complementarity-determining regions of a VHH antibody and rebuild them conditioned on the remaining framework structure. Lastly, in the bottom three rows of FIGS. 15C-1-15C-2 condition on substructure in an unregistered manner, meaning that the exact alignment of the substructure (motif) within the chain is not specified a priori as it was in the prior examples. We "outfill" the protein structure around several structural and functional motifs, including an αββ packing motif, backbone fragments encoding the catalytic triad active site of chymotrypsin, and the EFhand Ca-binding motif. Again, these motifs are accommodated in a realistic manner using diverse and structured solutions.

In FIGS. 15C-1-15C-2 we provide an early demonstration of a more exotic kind of conditioning in which we attempt to solve for backbone configurations subject to arbitrary volumetric shape specifications. We accomplish this by adding heuristic classifier gradients based on optimal transport distances [48] between atoms in the structures and user-provided point clouds (Appendix Q). As a stress test of this capability, we conditioned the generation of 1,000-residue single protein chains on the shapes of the Latin alphabet and Arabic numerals. We see the model routinely implementing several core phenomena of protein backbones such as high secondary structure content, close packing with room for designed sidechains, and volumespanning alpha-helical bundle and beta sheet elements. Although these shapes represent purely a challenging set of test geometries, more generally, shape is intimately related to functions in biology, for example, with membrane transporters, receptors, and structured assemblies that organize molecular events in space. Being able to control shape would be a useful subroutine for generalized programmable protein engineering.

Figure 15D:
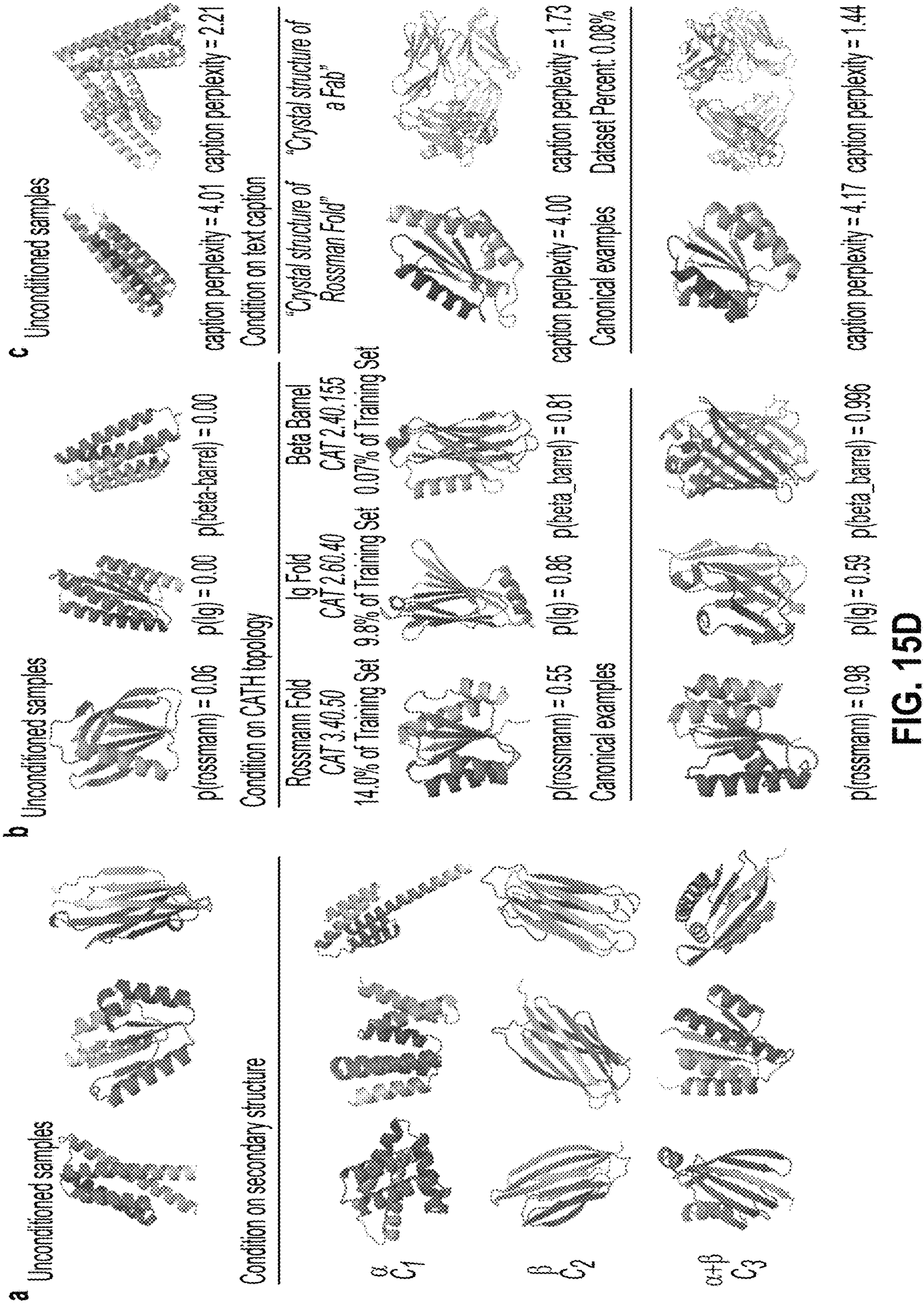
FIG. 15D shows that protein structure classifiers and caption models can bias the sampling process towards user-specified properties.

Finally, we demonstrate in FIG. 15D that it is possible to condition on protein semantics such as secondary structure, fold class (FIG. 15D) and natural language (FIG. 15D). Unlike geometric conditioning where the classifier is correct by construction (e.g., the presence of a motif under a certain RMSD is unambiguous), here the classifiers are neural networks trained on structure data, so there can be a discrepancy between the label assigned by the classifier and the ground truth class. Thus, looking at the fold-conditioned generation (FIG. 15D), we see that conditional samples always improve classifier probabilities over unconditioned samples taken from the same random seed, but the classification is not always perfect. For example, for the cases of "beta barrel" and "Ig fold" classes, the generated samples look like believable representatives of the respective class. On the other hand, in the "Rossman fold" example, the structure has some of the features characteristic of the class (i.e., two helices packed against a sheet on one side), but does not contain all such features (e.g., the opposing side of the sheet is not fully packed with helices like in a classical Rossman fold). In FIG. 15D we demonstrate semantic conditioning on natural language captions, which similarly improves probabilities while not generically being valid. It is exciting to imagine the potential of such a capability—i.e., being able to request desired protein features and properties directly via natural language prompts.

Generative models such as Chroma can reduce the challenge of function-conditioned generation to the problem of building accurate classifiers for functions given structures. While there is clearly much more work to be done to make this useful in practice, high-throughput experiments and evolutionary data can likely make this possible in the near term.

Appendix J demonstrates extensive refolding studies of samples generated under the above mentioned conditions. As shown in FIGS. 31-35, all of these conditional-generation processes can produce samples that refold quite accurately to their generated backbones. The rates at which this happens do vary based on the specific condition and protein length (and are subject to the caveats of this test mentioned above), but even the very challenging cases of shape-, complex symmetry-, class-, and language-conditioned designs, we find many examples of successful refolds.

Experimental Validation

To experimentally validate Chroma, we built a simple design protocol (based on Chroma v0) intended to generate high-likelihood samples drawn from the model. Specifically, the protocol involved three steps: 1) generate backbones by drawing independent samples from Chroma at low temperature, 2) design sequences for each backbone using ChromaDesign, and 3) automatically select a sub-set for experimental characterization, to match the desired: experimental scale, driven primarily by sequence and/or structure likelihoods (see Appendix T. 1 and Supplementary Table 7). Notably, we intentionally did not filter designs for refolding by a structure-prediction method or based on any structure-energetic calculations. This is not to say that such filtering could not be, in principle, employed to improve the success rate of design.

Figures 1, 2, 15E:
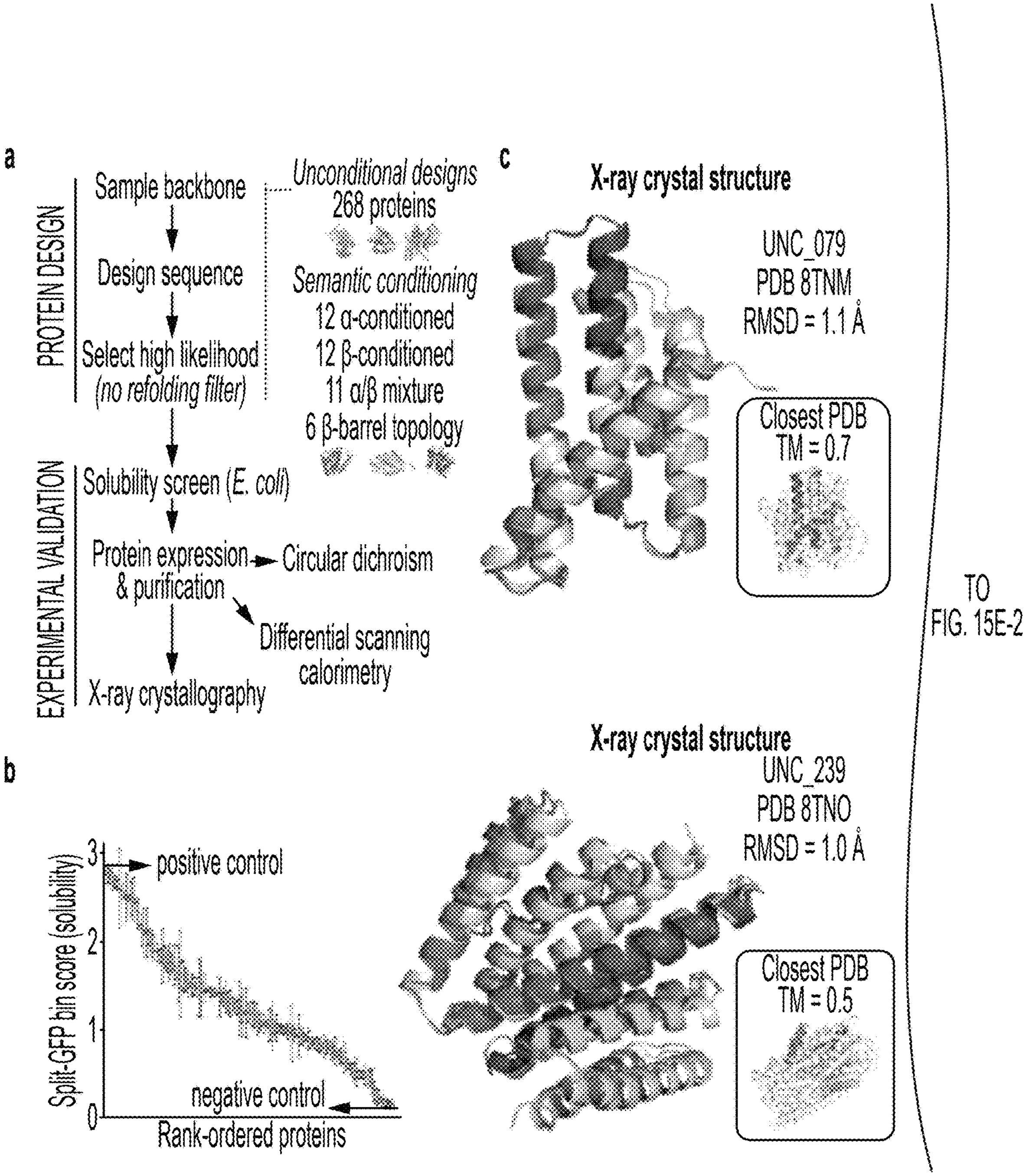
Figures 1, 2, 3, 15E:
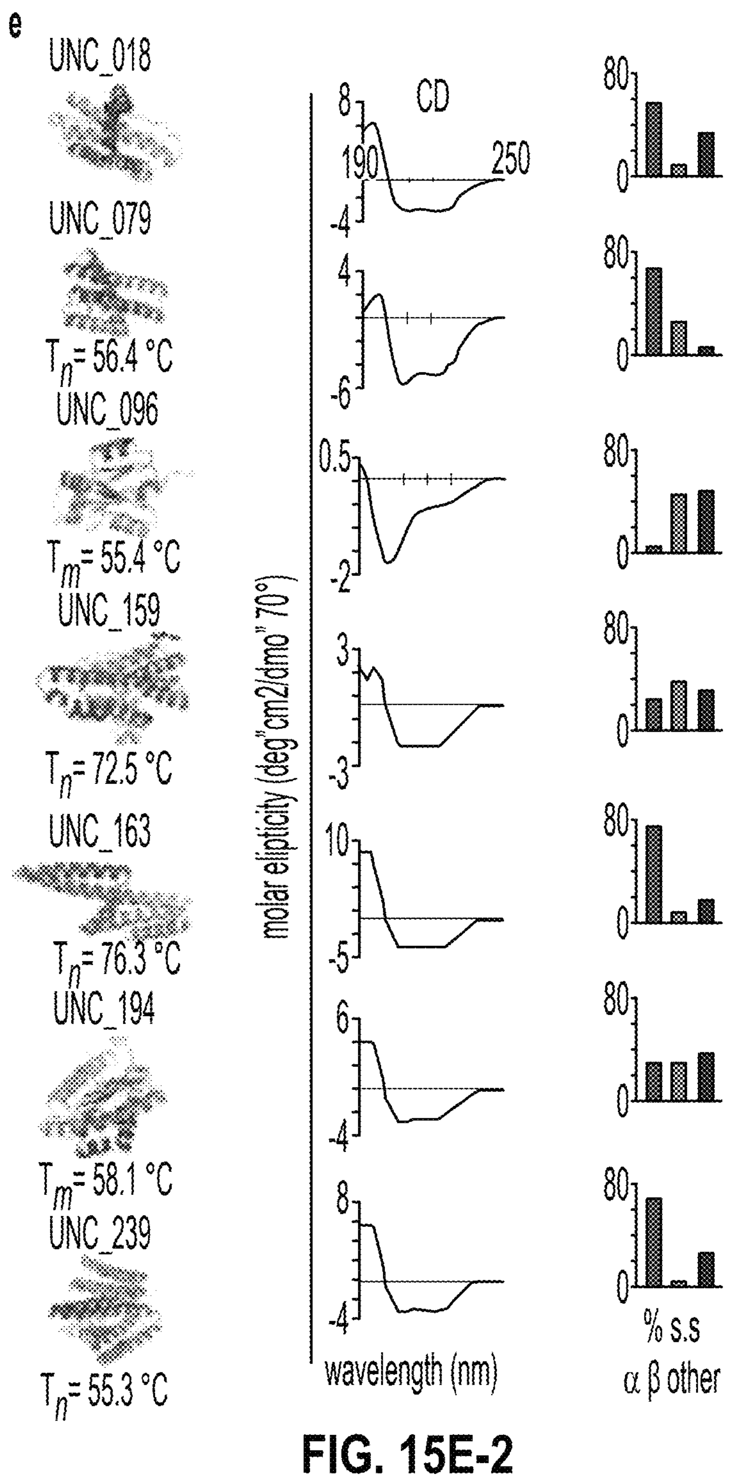
Figures 2, 3, 15E:
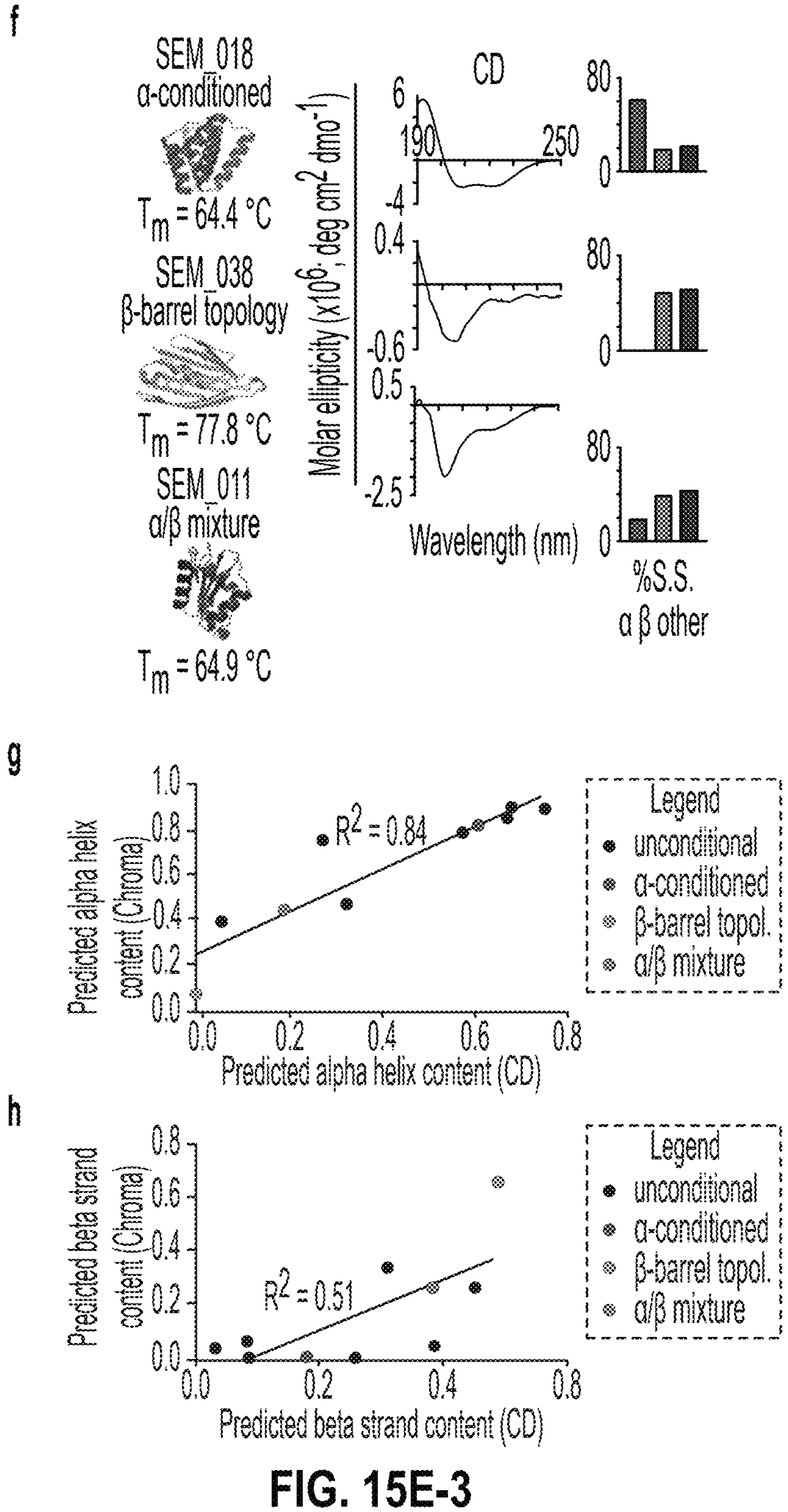
Figure 51:
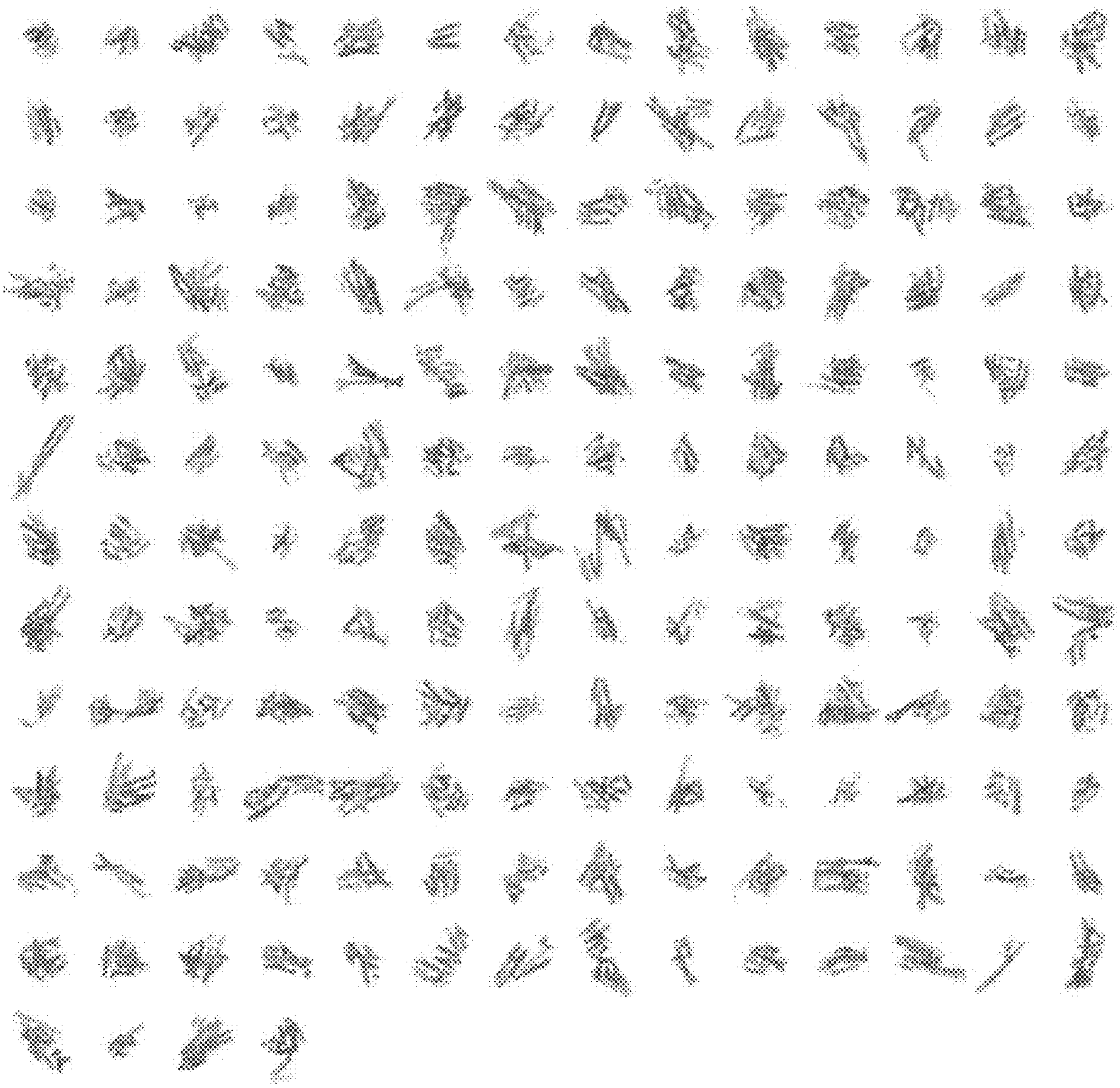
FIG. 51 shows unconditional protein designs.
Figure 53:
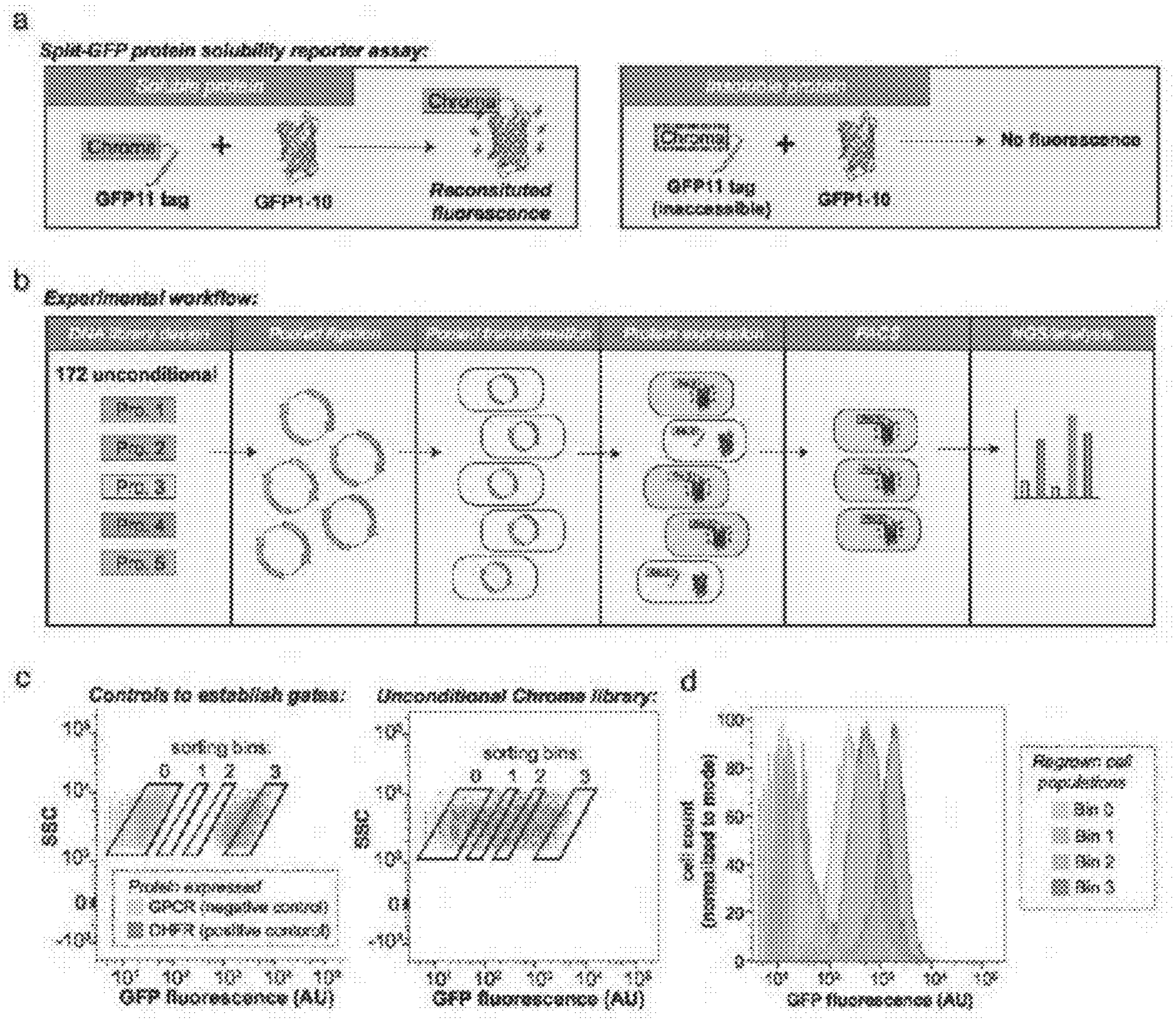
FIG. 53 shows split GFP protein solubility assay.
Figure 54A:
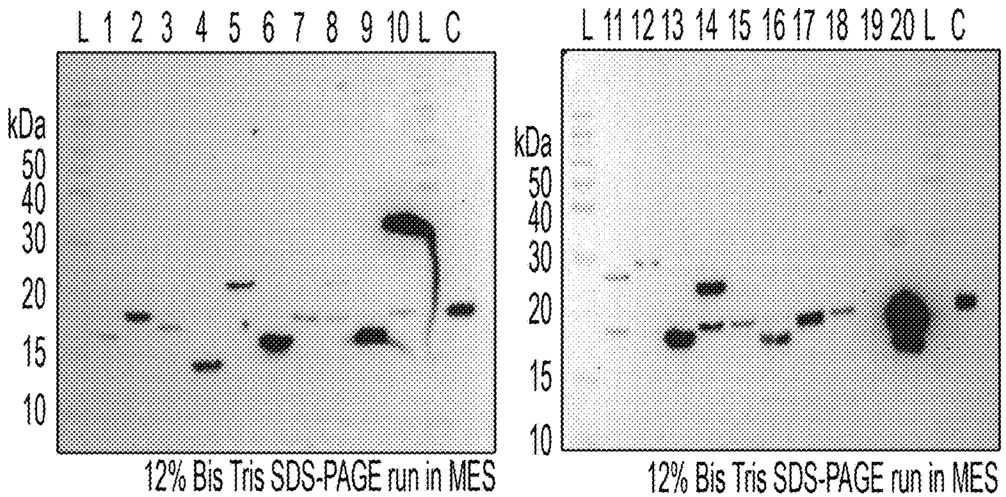
FIGS. 54A-54D show soluble protein expression confirmation via western blot.
Figure 54B:
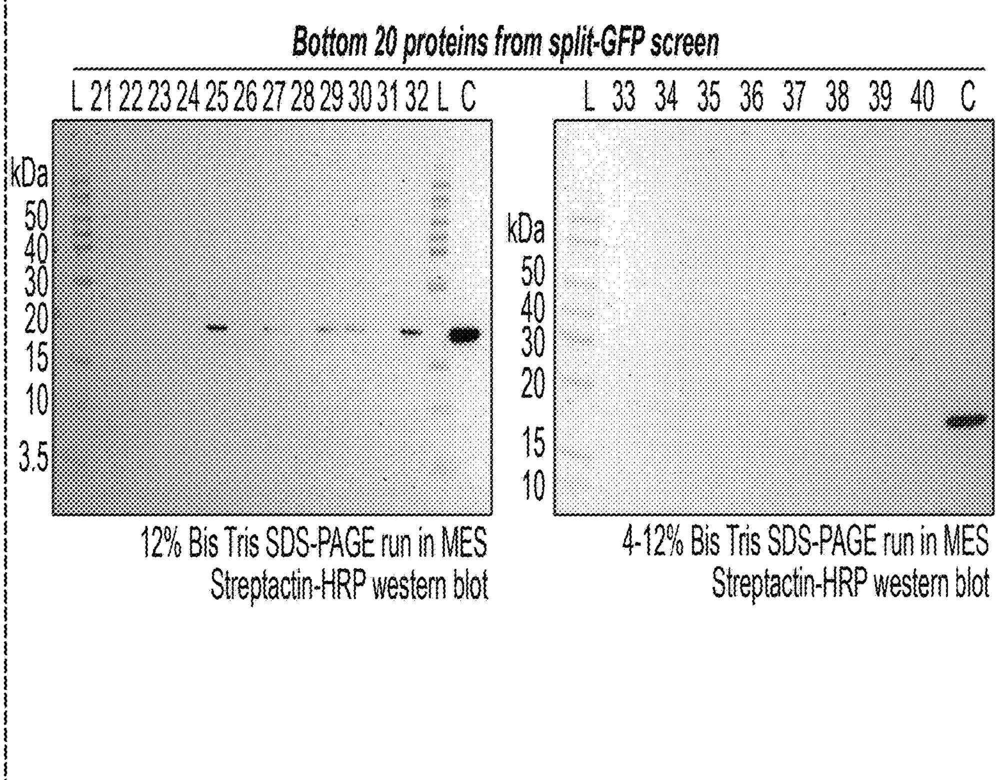
Figure 54C:
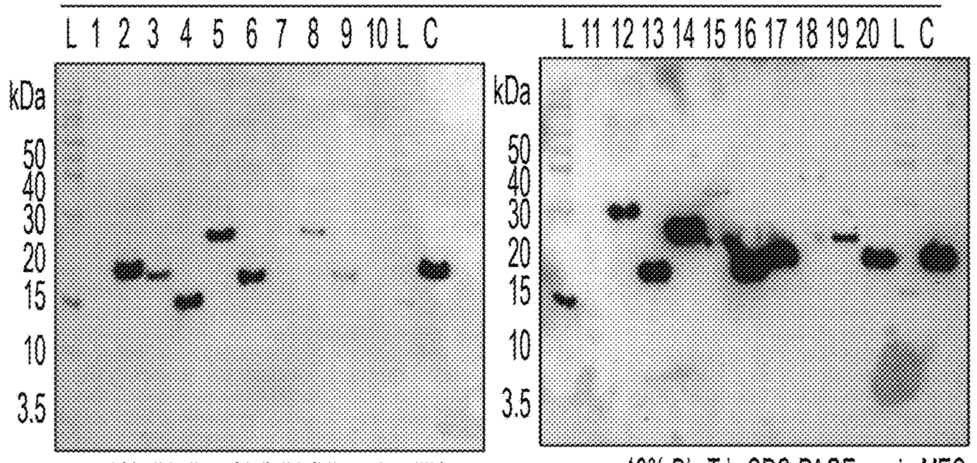
Figure 54D:
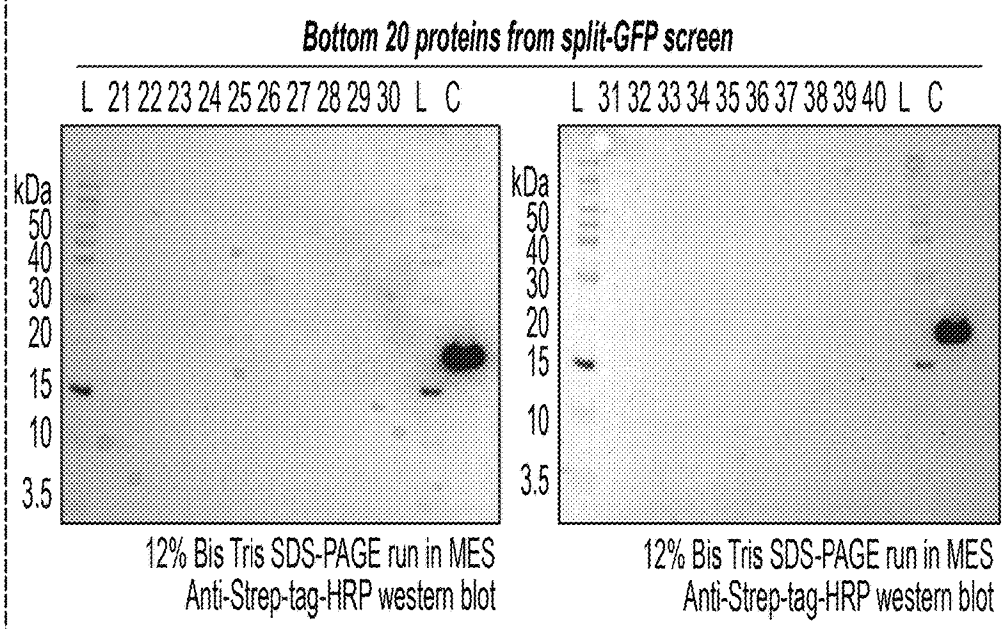
Figure 55A:
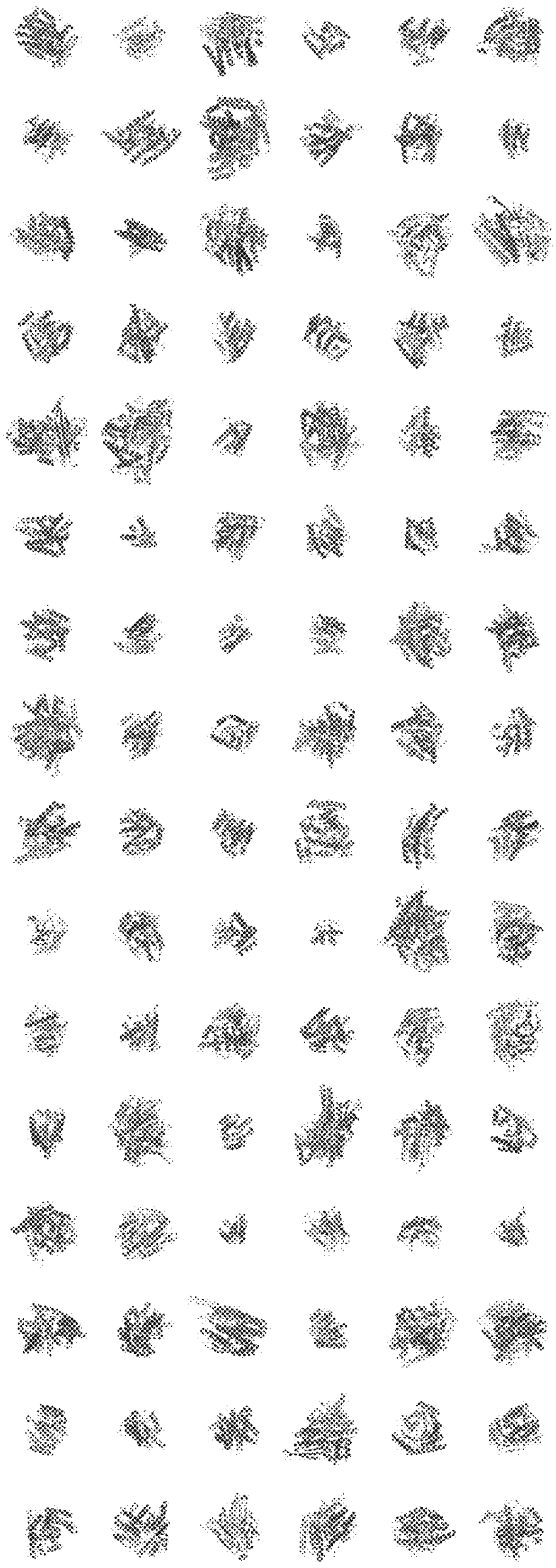
Figure 55B:
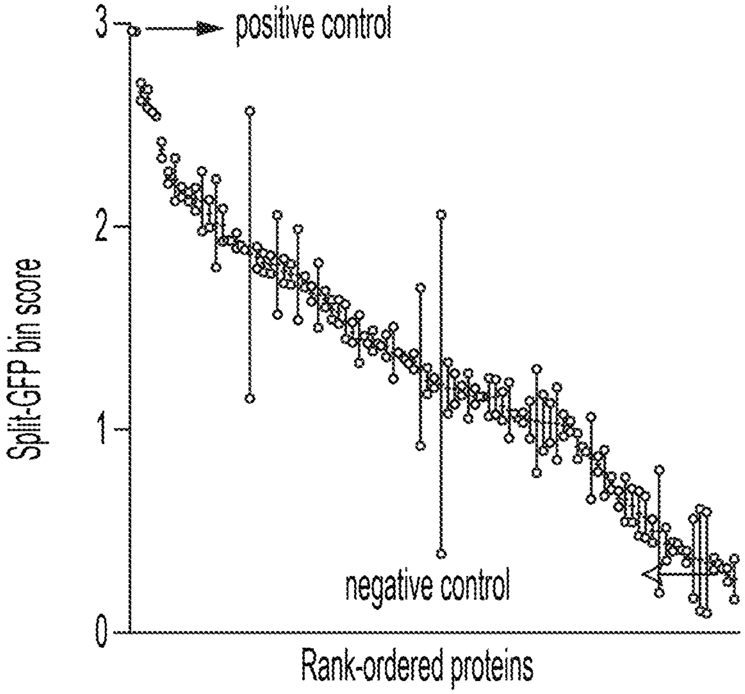
Figure 55C:
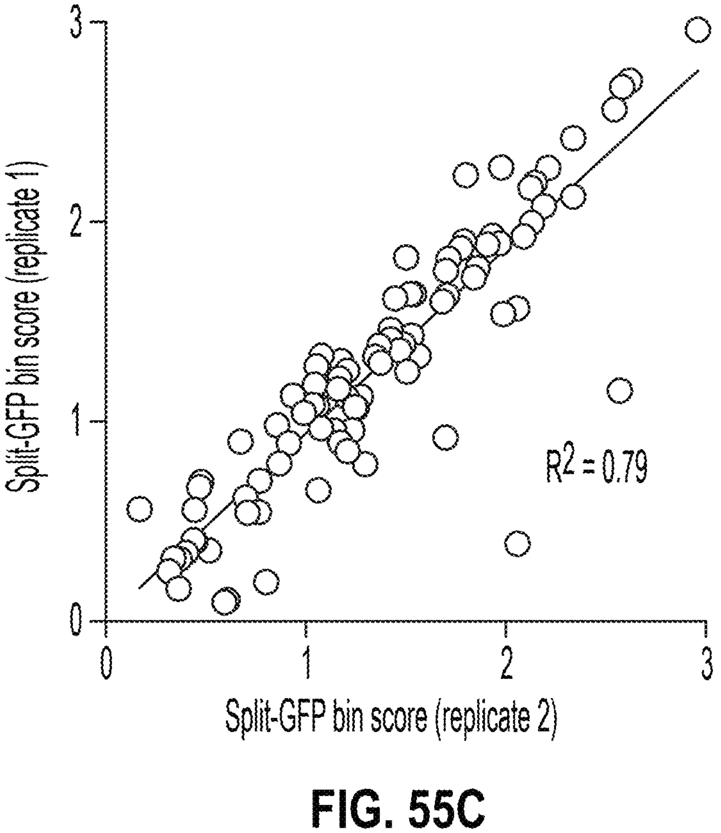

We generated a total of 310 proteins (unconditional or semantically-conditioned on CATH class or topology) for attempted expression and structural characterization (FIGS. 15E-1-15E-3). We first addressed an initial set of 172 unconditional proteins, ranging between 100 and 450 amino acids in length (FIG. 51). We employed a pooled protein solubility assay based on the split-GFP reporter system [49] to prioritize tractable proteins for subsequent characterization (FIG. 53). After fluorescence-activated cell sorting (FACS) and Nanopore sequencing (FIG. 53), enrichment scores were assigned to categorize the soluble expression levels of each protein (FIG. 53). All of the 172 tested proteins were assigned higher enrichment scores than the negative control (human beta-3 adrenergic receptor), suggesting that a wealth of Chroma-designed unconditional proteins can be solubly expressed in *E. coli* (FIGS. 15E-1-15E-3). We confirmed stable fluorescence in sorted cell populations (FIG. 53) and corroborated our split-GFP screen results via western blot, observing soluble expression of 19 out of 20 of the top-scoring proteins and 0 out of 20 of the lowest-scoring proteins (FIGS. 54A-54D). We created an additional set of 96 unconditional Chroma proteins encompassing a wider range of lengths (from 100 to 950 amino acids; FIGS. 55A-55D), which performed similarly to the first unconditional protein set via the split-GFP reporter assay (FIGS. 55A-55D). In this additional set, soluble expression of 9/10 of the top-scoring proteins was confirmed by western blot (FIGS. 55A-55D).

Figure 56A:
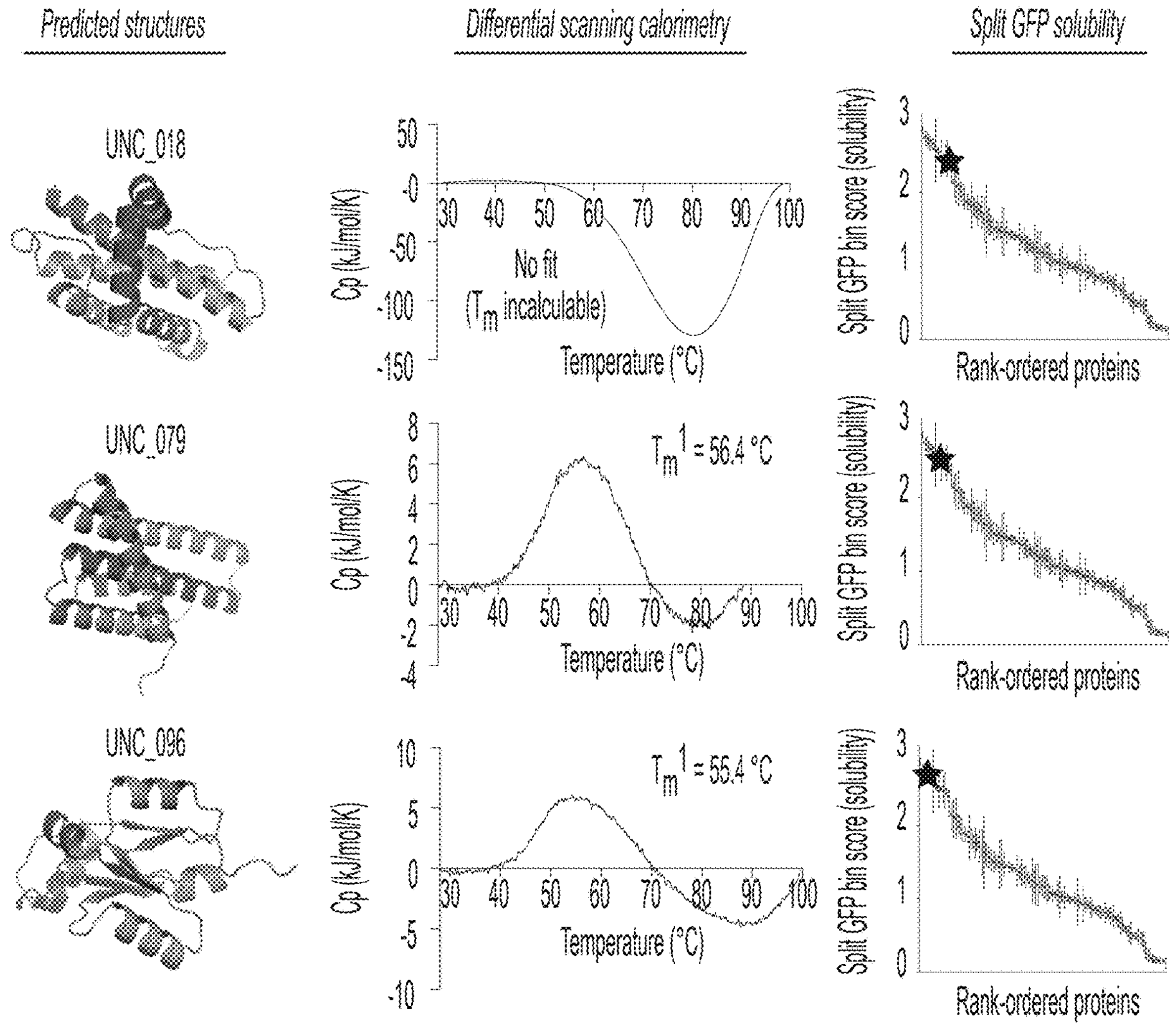
FIGS. 56A-56B show differential scanning calorimetry experiments.
Figure 56B:
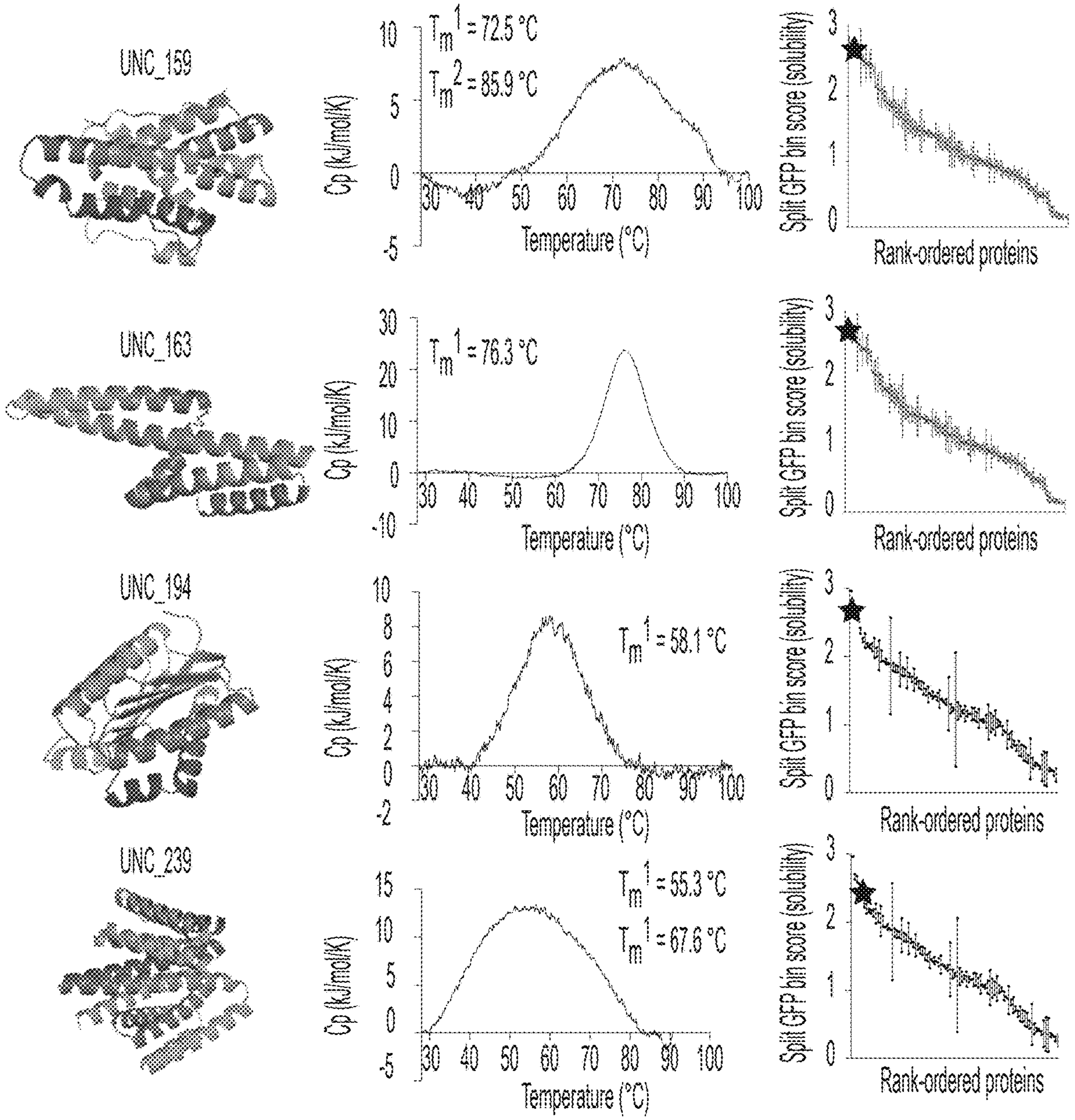

From the proteins identified in the top 10% of the split-GFP solubility screen, we purified 7 for interrogation using circular dichroism (CD, FIGS. 15E-1-15E-3) and differential scanning calorimetry (DSC, FIGS. 56A-56B). The results indicate that the majority of isolated proteins were stably folded with appreciable secondary structure. From these proteins, we were able to obtain X-ray crystal structures for UNC_079 (PDB 8TNM, FIGS. 15E-1-15E-3) and UNC_239 (PDB 8TNO, FIGS. 15E-1-15E-3). The observed structures matched the anticipated designs to a high degree (RMSD=1.1 Å and 1.0 Å, respectively), strongly suggesting Chroma-generated structures are realizable. Importantly, these structures are unique with respect to the PDB, with the top PDB hit to UNC_079 (PDB entry 4NH2, chain E) having query and target TM-scores of 0.7 and 0.3, respectively, and the top hit to UNC_239 (PDB entry 6AFV, chain A) having query and target TM-scores 0.5 and 0.23, respectively (FIGS. 15E-1-15E-3).

Figure 49:
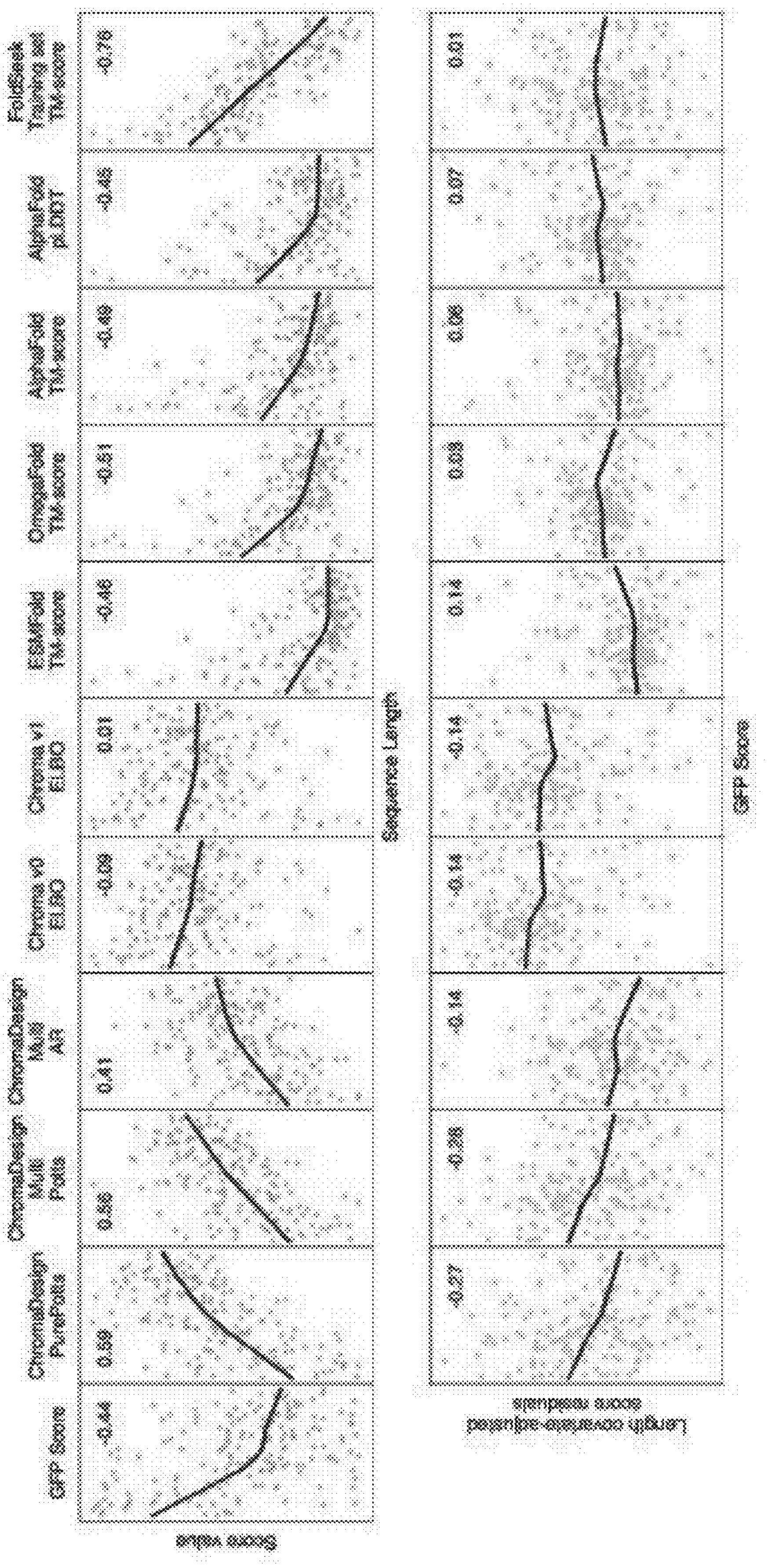
FIG. 49 shows in silico scores compared to Unconditional I split-GFP and sequence length.
Figure 50:
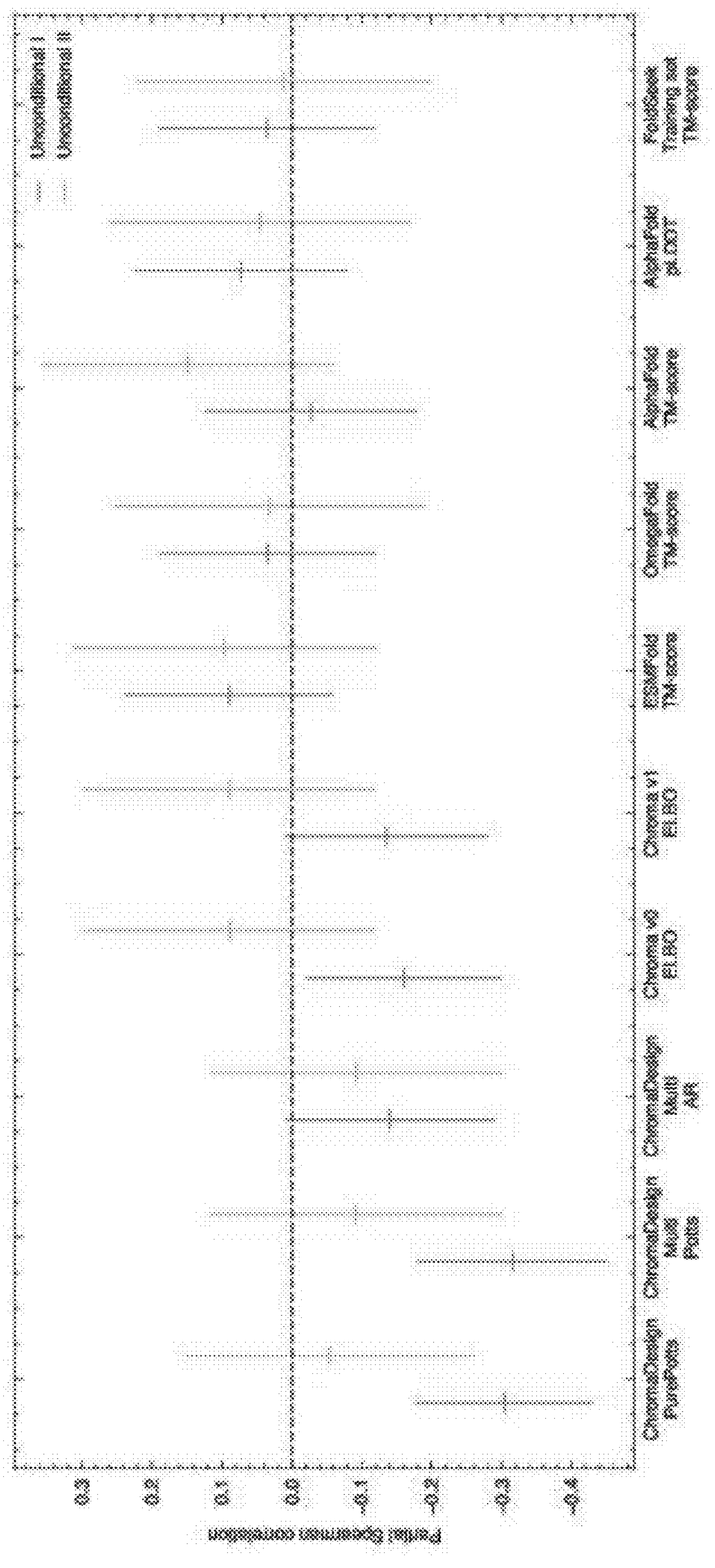
FIG. 50 shows in silico scores partial Spearman correlation to split GFP controlling for sequence length

Results of the split-GFP assay clearly show that it is more difficult to succeed with longer designs, as there is a clear inverse correlation between length and split-GFP score (FIG. 49). Interestingly, while one might expect extent of refolding by structure prediction to also correlate with experimental success, we saw no correlation once length is corrected for (FIG. 49). Similarly, we saw no correlation between soluble expression and structural novelty. We did find model likelihoods to be weakly predictive of experimental success for the first conditional set, but this did not hold true for the second set where lengths were extended up to 950 amino acids (FIG. 50).

Figure 52:
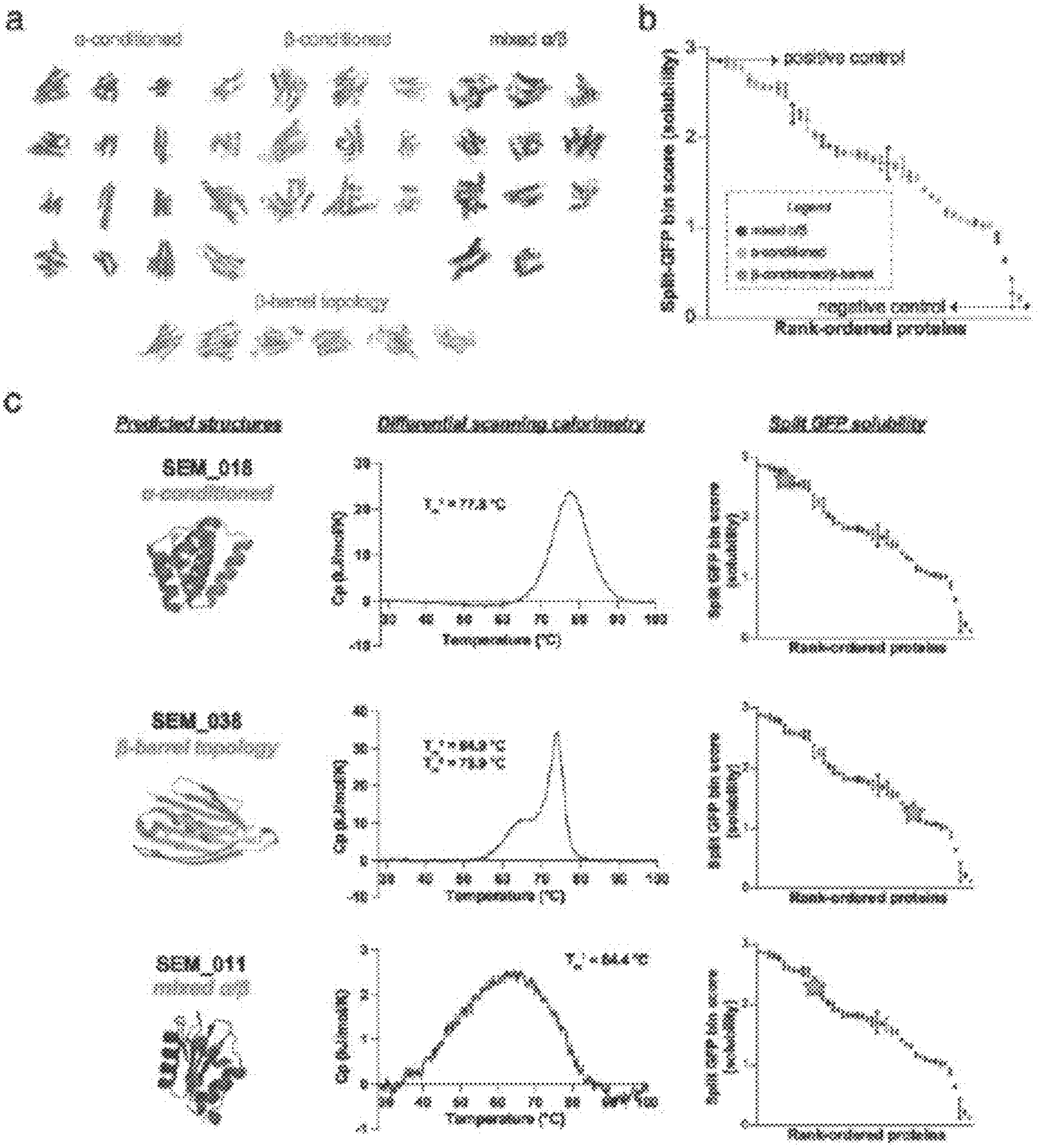
FIG. 52 shows secondary structure conditional designs.

To test Chroma's ability to propose well-behaved proteins in a conditioned setting, we next evaluated a set of 42 proteins conditioned via ProClass on CATH class (36 total designs split among classes mainly-α, mainly-β, and mixed α/β) and on CATH topology (6 designs conditioned on the β-barrel topology 2.40.155; FIG. 52). In the split-GFP solubility assay, 40 of these proteins (95%) scored above the negative control, indicating a high success rate of soluble protein expression (FIG. 52). We purified one representative protein from each secondary-structure category (two designs conditioned on mainly-α and mixed α/β classes and one design conditioned on the β-barrel topology). DSC data for these proteins were consistent with relatively stable folding, with melting temperatures ranging from 64° C. to 78° C. (FIG. 52). Based on secondary structure predictions from CD spectra [50], we observed higher α-helical content in the mainly-α design, higher β-sheets in the β-barrel design, and mixed secondary structure in the mixed-content protein (FIGS. 15E-1-15E-3). In fact, across both conditional and unconditional designs, the inferred secondary structure content from CD was closely correlated with the secondary structure content calculated from Chroma-generated models, for both the fraction of α-helices ($R^2$=0.84, FIGS. 15E-1-15E-3) and β-sheets ($R^2$=0.51, FIG. 20), suggesting that proteins with various structural makeups can be designed by Chroma.

Discussion

In this work, we present Chroma, a new generative model capable of generating novel and diverse proteins across a broad array of structures and properties. Chroma is programmable in the sense that it can sample proteins with a wide array of user-specified properties, including: inter-residue distances and contacts, domains, sub-structures, and semantic specifications from classifiers. Chroma is able to generate proteins that have arbitrary and complex shapes, and even begins to demonstrate the ability to accept descriptions of desired properties as free text. Due to an efficient design with a new diffusion process, quasilinear scaling neural architecture, and low-temperature sampling method, Chroma can generate extremely large proteins and protein complexes (e.g., with ≥3000 residues) on a commodity GPU (e.g., an NVIDIA V100) in a few minutes.

We reasoned that the best way to determine the plausibility of the protein space parameterized by Chroma was to draw independent samples from the model and test them experimentally. Note that this is a departure from the prototypical protein design protocol, where initial proposal designs are down-selected using a custom set of filters intended to avoid known or hypothesized model deficiencies and help focus on designs more likely to work experimentally. While the latter practice, broadly adopted in the field, can be quite effective at increasing design success rates, it does require a custom set of filters for each design project and makes fully automated design difficult to achieve. Further, such an approach would detract from our intention of characterizing the distribution learned by Chroma.

Our experimental validation shows that Chroma has learned an accurate enough distribution such that sampling from it results in proteins that express, fold, have favorable biophysical properties, and conform to intended structures at non-trivial rates. Even under the very conservative view that only the proteins we purified and characterize individually in solution constitute successful designs (versus other ones that performed comparably by split-GFP, for example), we would still arrive at a 3% success rate. Additionally, the two designs with experimentally determined crystal structures demonstrate that a non-trivial fraction of this distribution should be expected to be atomistically accurate. Given the breadth and novelty of the structure space learned by Chroma (e.g., see FIG. 5B and FIGS. 24, 25, and 28), even these conservative success rate estimates would translate into immense swaths of unexplored actionable protein space that can now be accessible through commodity computing hardware.

The task of exploring protein structure space in a way that can produce physically reasonable and designable conformations has been a long-standing challenge in protein design. In a few protein systems, it has been possible to parameterize the backbone conformation space mathematically-most notably the α-helical coiled coil [51] and a few other cases with high symmetry [52]-and in these cases design efforts have benefited tremendously creating possibilities not available in other systems [52,53]. For all other structure types, however, a great amount of computational time has been spent on the search for reasonable backbones, often leaving the focus on actual functional specifications out of reach. Chroma has the potential to address this problem, enabling a shift from focusing on generating feasible structures towards a focus on the specific task at hand—i.e., what the protein is intended to do. By leveraging proteins sampled over the first 3+ billion years of evolution on Earth and finding new ways to assemble stable protein matter, generative models such as Chroma are well poised to drive another expansion of biomolecular diversity for human health and bioengineering.

Methods

Model

Chroma is a joint generative model for the sequences and all-atom structure of a protein complex given a set of chain lengths. We factorize this high-dimensional distribution into parameterized components as $$\log p_\theta(x, s, \chi) = \underbrace{\log p_\theta(x)}_{\text{backbone likelihood}} + \underbrace{\log p_\theta(s \mid x)}_{\text{sequence likelihood}} + \underbrace{\log p_\theta(\chi \mid x, s)}_{\text{side-chain likelihood}},$$

where $x \in \mathbb{R}^{4N \times 3}$ represents the backbone heavy atom coordinates (i.e. N, $C_\alpha$, C, O), $s \in [[20]]^N$ represents the discrete sequences over all residues, $\chi \in (-\pi, \pi]^{4N}$ represents the torsional angles of the side-chains, θ represents the model parameters, and N is the total number of residues in the complex (we drop explicit dependence on chain lengths to simplify notation). We parameterize these component distributions in terms of two neural networks: a backbone network which uses diffusion modeling to estimate $\log p_\theta(x)$ and a design network which uses discrete factorizations to estimate $\log p_\theta(\chi, s|x)$. Both networks are based on a graph neural network architecture which takes SE(3)-invariant features as inputs and outputs SE(3)-invariant scalars and SE(3)-equivariant coordinates as needed (Appendix F).

Our diffusion modeling approach builds upon standard methods with extensions for correlated diffusion processes (Appendix A). Briefly, we define a forwards noising process which destroys structure in data as $$x_t \sim N\left(x; \alpha_t x_0, \left(1 - \alpha_t^2\right) R R^T\right),$$

where $RR^T$ is the covariance matrix of the diffusion process and at is a noise schedule which decays monotonically from 1 to 0 as the time t goes from 0 to 1. We design the covariance matrix $RR^T$ to respect the distance statistics of natural proteins, including local chain constraints as well as global density constraints based on the well-known scaling law $R_g \approx 2.\times N^{0.4}$ (Appendix C). Given this forwards process, we train a neural network $\hat{x}_\theta(x_t, t)$ to predict the optimally denoised structure by optimizing a bound on the likelihood $$\log p(x_0) \geq$$

$$-\frac{1}{2}\log \det\left(2\pi eRR^T\right)\frac{1}{2}E_{p(x_t|x_0)p(t)}\left[SNR_t'\left(\frac{N}{1+SNR_t}-\left|R^{-1}(\hat{x}_\theta(x_t, t)-x_0)\right|_2^2\right)\right]$$

together with auxiliary training objectives which emphasize accurate denoising of specific types of sub-structural features (Appendix A).

We parameterize the optimal denoiser in terms of a graph neural network with random long-range connectivity for global context (Appendix D) which predicts denoised structures via a weighted consensus of inter-residue geometry predictions (Appendix E). To draw samples, we simulate a non-equilibrium reverse diffusion process enriched with equilibrating Langevin dynamics (Appendix B) by integrating the stochastic differential equation $$dx = \left(-\frac{1}{2}x - \left(\lambda_t + \frac{\lambda_0\psi}{2}\right)RR^T\nabla_x \log p_t(x; \theta)\right)\beta_t\, dt + \sqrt{\beta_t(1+\psi)}\, R\, d\overline{w}$$

where $\lambda_t$ are $\lambda_0$ inverse temperature parameters, $\psi$ sets the rate of Langevin equilibration per unit time, $d\overline{w}$ is a reverse-time Wiener process, and $\nabla_x \log p_t(x; \theta)$ is the time-dependent score function which can be expressed as an affine transform of the optimal denoiser. These Langevin-enriched dynamics allow us to adjust the time-dependent distribution to account for perturbations such as external conditioning cues or lower sampling temperatures which bias towards high-likelihood states (Appendix B).

For the design network, we train a graph neural network to predict discrete sequence states via either conditional Potts models or conditional language models and predict side chain conformations via an autoregressive decomposition and an empirical histogram parameterization binned at 10° resolution. Sampling is performed via a combination of penalized Markov Chain Monte Carlo and/or either ancestral sampling (Appendix H).

Conditioners

To make protein design with Chroma programmable, we introduce a Conditioners framework based on arbitrarily composable mixtures of soft restraints which bias the distribution of states from the prior and hard constraints which directly restrict the underlying sampling process (Appendix L). Briefly, we cast conditioners as composable mapping functions which transform the implicit energy function and unconstrained coordinates of the diffusion process to a modified energy function and potentially transformed coordinate system that enforce constraints. We then implement and evaluate several conditioners within this framework capturing a variety of potential protein design criteria including fixed substructures and motifs (Appendices M-O), multi-chain symmetries (Appendix P), and arbitrary shape biases (Appendix Q) as well as guidance with neural network classifiers (Appendix R) and natural language prompts (Appendix S).

Training

We constructed a dataset of 28,819 protein complex structures from the Protein Data Bank circa Mar. 20, 2022 (Appendix G). These complexes were filtered for X-ray crystal structures at resolution≤2.6 Å and were then redundancy-reduced via general sequence clustering at 50% identity followed by re-enrichment of 1726 highly-variable antibody systems with clustering at 10% sequence identity. We split these data into 80/10/10 trainining/validation/test components based on a graph-based annotation overlap reduction procedure.

We trained two configurations of the backbone network on 8 V100 GPUs for approximately 1.6 and 1.8 million training steps with target batch sizes of approximately 32,000 residues per step, with each model having approximately 19 million parameters (Supplementary Table 2). To test the influence of different components of our framework, we also carried out an ablation study of 7 different model configurations each trained with 8 V 100 GPU s and similar batch sizing for approximately 500,000 steps (Appendix K, FIGS. 37A-37B). Additionally, we trained two configurations of the design network on 1 or 8 V 100 GPUs with each model having approximately 4 or 14 million parameters, respectively, based on the inclusion of side chain and autoregressive decoding layers.

Experimental Characterization

We analyzed all 310 Chroma proteins (FIGS. 51, 52, and 55) using the split-GFP pooled solubility assay in *E. coli* (FIG. 53, Supplementary Table 8), quantitating protein solubility scores by Nanopore sequencing-based enrichment analysis after fluorescence-activated cell sorting (FIGS. 15E, 52, and 55, Extended Data Table 1) and performing additional assay corroboration by western blot (FIGS. 54 and 55). We analyzed purified Chroma proteins by differential scanning calorimetry (FIGS. 52 and 56, Extended Data Table 3) and circular dichroism (FIGS. 15E-1-15E-3) to analyze stability and secondary structure components, respectively. We structurally validated two unconditional proteins by X-ray crystallography (FIGS. 15E-1-15E-3, Extended Data Table 2). All experimental details can be found in the Experimental Validation section (Appendix T) of the Supplementary Information.

Data Availability

All experimental and computational results are available in the Supplementary Information document.

Code Availability [Omitted]

Acknowledgements [Omitted]

Author Contributions [Omitted]

Competing Interests [Omitted]

References [Omitted]

Figure Captions

FIG. 15A Chroma is a generative model for proteins and protein complexes that combines structured diffusion for protein backbones with scalable molecular neural networks for backbone synthesis and all-atom design. a, A correlated diffusion process with chain and radius of gyration constraints gradually transforms protein structures into random collapsed polymers (right to left). The reverse process (left to right) can be expressed in terms of a time-dependent optimal denoiser $\hat{x}_\theta(x_t, t)$ (b), which we parameterize in terms of a random graph neural network with long-range connectivity inspired by efficient N-body algorithms (b, middle) and a fast method for solving for a global consensus structure given predicted inter-residue geometries (b, right). a (top right), Another graph-based design network generates protein sequences and side-chain conformations conditionally based on the sampled backbone. c, The time-dependent protein prior learned by the diffusion model can be combined with composable restraints and constraints for programmable generation of protein systems.

FIGS. 15B-1-15B-2 Analysis of unconditional samples reveals diverse geometries that exhibit novel higher-order structure that refold in silico. a, A representative set of Chroma-sampled proteins and protein complexes exhibits complex and diverse topologies with high secondary structure content, including familiar TIM-barrel like folds, antibody: antigen-like complexes, as well as new arrangements of helical bundles and β-sheets. b, Despite these qualitative similarities, samples frequently have low nearest neighbor similarity to structures in the PDB as measured by nearest-neighbor TM-score (Appendix 1.4), with structures demonstrating frequent novelty across length ranges. c, When we attempt to refold samples in-silico using only a single sequence sample per structure, we observe widespread refolding, including occasionally in the very high size range of 800+residues.

FIGS. 15C-1-15C-2 Symmetry, substructure, and shape conditioning enable geometric molecular programming. a, Sampling oligomeric structures with arbitrary chain symmetries is possible via a conditioner which tessellates an asymmetric subunit in the energy function. Cyclic $C_n$, dihedral $D_n$, tetrahedral T, octahedral O, and icosahedral I symmetry groups can produce a wide variety of possible homomeric complexes. The rightmost protein complex contains 60 subunits and 60,000 total residues, which is enabled via leveraging symmetries and our sub-quadratically scaling architecture. b, Conditioning on partial substructure (monochrome) enables protein "infilling" or "outfilling". The top two rows illustrate regeneration (color) of half of a protein (enzyme DHFR, first row) or CDR loops of an antibody (second row). Next three rows show conditioning on a pre-defined motif; order and matching location of motif segments is not pre-specified here. c, Conditioning on arbitrary volumetric shapes exemplified by the complex geometries of the Latin alphabet and Arabic numerals. All structures were selected from protocols with high rates of in-silico refolding (Appendix J).

FIG. 15D Protein structure classifiers and caption models can bias the sampling process towards user-specified properties. a, Neural networks trained to predict protein properties can bias unconditional samples (top) towards states which optimize predicted properties, such as secondary structure composition (bottom). b, A neural network trained to predict CATH topology annotations can routinely drive generation towards samples with high classification probabilities, which sometimes aligns with our intended fold topology for highly abundant labels. c, Fine-tuning a multi-label predictor to bias a pretrained large language model into a structure caption predictor can enable natural language conditioning. We begin to see examples of semantic alignment between prompts and output structures for highly abundant classes of structures, and consistently see that we can sample structures assigned high likelihood by the language model (whether or not this aligns with our objectives).

FIGS. 15E-1-15E-3 Experimental validation of Chroma-designed proteins. a, Protocol for protein design and experimental validation. b, Rank-ordered unconditional Chroma protein solubility scores by the split-GFP assay for 172 tested proteins. Error bars show standard deviations for 3 biological replicates. c, d, X-ray crystal structures (rainbow) of UNC_079 (1.1 Å resolution, PDB 8TNM) and UNC_239 (2.4 Å resolution, PDB 8TNO) overlaid with Chroma-generated models (gray). Insets compare each crystal structure (rainbow) with its nearest PDB match (4 NH 2 and 6 AFV, respectively; gray). e, Circular dichroism data on seven purified Chroma proteins. Fraction of a helical and 8-strand content was determined using BestSel [50]. $T_m$ is the melting temperature determined by differential scanning calorimetry and s.s. designates secondary structure. f, Circular dichroism data on three purified Chroma conditional designs. g, h Correlation between predicted secondary-structure content in Chroma designs compared to prediction from CD (a helical and β-strand content shown in g and h, respectively).

Supplementary Information for: Illuminating Protein Space with a Programmable Generative Model

SUPPLEMENTARY INFORMATION

Table of Contents

A Diffusion Models with Structured Correlations
A.1 Correlated diffusion as uncorrelated diffusion in transformed space
A.2 Training with likelihood on an Evidence Lower Bound (ELBO)
A.3 Auxiliary training objectives
A.4 Reverse-time SDE
A.5 Probability Flow ODE
A.6 Conditional sampling from the posterior under auxiliary constraints
A.7 Related work
B Low-Temperature Sampling for Diffusion Models
B.1 Reverse-time SDE with temperature annealing
B.2 Annealed Langevin Dynamics SDE
B.3 Hybrid Langevin-Reverse Time SDE
C Polymer-Structured Diffusions
C.1 Diffusion processes predictably affect molecular distances
C.2 Covariance model #1: Ideal Chain
C.3 Covariance model #2: $R_g$-confined Globular Polymer
C.4 Alternative covariance model: Residue Gas
D Random Graph Neural Networks
D.1 Background: efficient N-body simulation
D.2 Random graph generation
D.3 Computational complexity
E Structure from Inter-residue Geometry Predictions
E.1 Background and motivation
E.2 Equivariant structure updates via convex optimization
E.3 Equivariant prediction of backbone atoms
E.4 Time-dependent post-prediction scaling
F Chroma Architecture
F.1 Graph neural networks for protein structure
F.2 ChromaBackbone
F.3 ChromaDesign
F.4 Related Work
G Training
G.1 Dataset
G.2 Optimization
H Sampling
H.1 Sequence design
I Evaluation: Unconditional Samples
I.1 Sample generation
I.2 Backbone geometry statistics
I.3 Tertiary motif analysis
I.4 Novelty analysis
I.5 Refolding analysis
I.6 Sequence design analysis
J Evaluation: Conditional Samples
J.1 Refolding substructure-conditioned samples
J.2 Refolding symmetry-conditioned samples
J.3 Refolding shape-conditioned samples
J.4 Refolding class-conditioned samples
J.5 Refolding language-conditioned samples
J.6 Refolding analysis of confidence -continued Table of Contents

| | |
|---|---|
| K | Evaluation: Ablation Study |
| | K.1 Alternate model configurations and training |
| | K.2 Ablation results |
| L | Programmability: Conditioners framework |
| | L.1 Bayes' theorem for score functions |
| | L.2 Conditioners: motivation |
| | L.3 Conditioners |
| | L.4 Example applications of constraint composition |
| | L.5 Related work |
| M | Programmability: Substructure Constraints |
| | M.1 Motivation |
| N | Programmability: Substructure Distances |
| | N.1 Motivation |
| | N.2 Approach |
| O | Programmability: Substructure Motifs |
| | O.1 Motivation |
| | O.2 Approach |
| P | Programmability: Symmetry |
| | P.1 Motivation |
| | P.2 Symmetry breaking in sampling |
| | P.3 Symmetric transformation as a conditioner |
| | P.4 Practical implementation with additional transformation blocks |
| | P.5 Additional symmetric samples |
| Q | Programmability: Shape |
| | Q.1 Motivation |
| | Q.2 Approach |
| R | Programmability: Classification |
| | R.1 Motivation |
| | R.2 Approach |
| | R.3 Model inputs |
| | R.4 Featurization |
| | R.5 Architecture |
| | R.6 Labels and loss functions |
| | R.7 Training |
| | R.8 Hyperparameters |
| S | Programmability: Natural Language Annotations |
| | S.1 Motivation |
| | S.2 Dataset curation |
| | S.3 Model architecture |
| | S.4 Model training |
| | S.5 Performance |
| T | Experimental Validation |
| | T.1 Protein design |
| | T.2 Experimental methods |
| | T.3 Experimental Figures |
| | T.4 Experimental Tables |

LIST OF FIGURES

1 Low temperature sampling with Hybrid Langevin SDE
2 Low temperature sampling analysis, proteins
3 Polymer-structured diffusions for proteins
4 Random graph sampling for random graph neural networks
5 Equivariant structure updates from inter-residue geometries
6 Anisotropic confidence models for predicted inter-residue geometries.
7 Chroma architecture
8 Randomized autoregression orders with varying spatial clustering
9 Random single-chain samples
10 Random complex samples
11 Unconditional sample metric analysis
12 Structure novelty evaluation
13 The protein space of Chroma samples
14 Structure backbone statistic
15 Sequence recovery evaluation
16 Refolding analysis for substructure conditioning
17 Refolding analysis for symmetry conditioning
18 Refolding analysis for shape conditioning
19 Refolding analysis for class conditioning
20 Refolding analysis for natural language conditioning
21 Evaluation of structure prediction confidence versus agreement
22 Ablation study of novel model components
23 Programmable design with diffusion conditioners
24 Substructural infilling with globular covariance
25 Substructural infilling examples
26 RMSD conditioning: Motifs can occur in entirely unrelated structural contexts
27 Constrained transformations for symmetry operations.
28 Symmetric complex samples
29 Symmetric complexes with poor contacts
30 Architecture: ProClass model
31 Architecture: ProCap model
32 ProCap evaluation metrics
33-ProCap-guided sample predictions of CATH class
34 In silico scores scatter plot to split GFP and length
35 In silico scores partial correlation to split GFP.
36 Unconditional protein designs
37 Secondary structure conditional designs
38 Split-GFP protein solubility assay
39 Soluble protein expression confirmation via western blot
40. Evaluation of additional set of unconditional protein designs
41 Differential scanning calorimetry experiments

LIST OF TABLES

1 Notation
2 Hyperparameters for the backbone network
3 Hyperparameters for the design network
4 Hyperparameters for sampling
5 Structural metrics for backbones
6 Conditioners
8 Split-GFP control sequences

TABLE 1

Table of notation

| Symbol | Definition |
|---|---|
| N | number of atoms or residues |
| $x_t \in \mathbb{R}^{N\times 3}$ | coordinates sampled at time t |
| $x_t^{\mathcal{M}} \in \mathbb{R}^{\lvert\mathcal{M}\rvert\times 3}$ | motif-sliced coordinates based on index set $\mathcal{M} \subset [[1, N]]$ |
| $x_t^{(i)} \in \mathbb{R}^3$ | the $i_{th}$ coordinate in $x_t$ |
| $\mathcal{G} = (\mathcal{V}, \varepsilon)$ | a graph composed of sets of vertices and edges |
| $D^{ij}$ | Euclidean distance between i and j $\lVert x^{(i)} - x^{(j)}\rVert_2$ for structures at t = 0 |
| $d_t^{ij}$ | time-dependent noised Euclidean distance between i and j |
| $z \in \mathbb{R}^{N\times 3}$ | whitened noise, and $z_i$ is the individual noise component |
| $\Sigma = RR^T$ | covariance matrix for polymer-structured prior, $[Rz]_{ik} = \Sigma_j [R]_{ij} z_{jk}$ |
| T = (t, O) | Euclidean transformation with translation t and rotation O |
| $\beta_t$ | time-dependent noise schedule |
| $\alpha_t$ | integrated noise in the forward diffusion |
| $\lambda_t$ | time-dependent inverse temperature |
| $\psi$ | Langevin equilibration rate in Hybrid SDE |
| T | number of integration time steps |

TABLE 1-continued

| Table of notation | |
|---|---|
| Symbol | Definition |
| $\hat{x}_i$ | denoising network in Cartesian space |
| $\hat{z}_\theta$ | denoising network in the whitened space |
| $\nabla_x \log p_t(x, t)$ | score estimator network |
| dw, $d\bar{w}$ | forward Brownian noise, reverse Brownian noise |

A Diffusion Models with Structured Correlations

A.1 Correlated Diffusion as Uncorrelated Diffusion in Transformed Space

Correlation and diffusion Most natural data possess a hierarchy of correlation structures, some of which are very simple (e.g., most nearby pixels in natural images will tend to be a similar color) and some of which are very subtle (e.g., complex constraints govern the set of pixels forming an eye or a cat). With finite computing resources and modeling power, it can be advantageous to design learning systems that capture simple correlations as efficiently as possible such that most model capacity can be dedicated to nontrivial dependencies (see Appendix C).

Diffusion models capture complex constraints in the data by learning to reverse a diffusion process that transforms data into noise [51, 52]. While most of these original diffusion frameworks considered the possibility of correlated noise, it is typical in contemporary models to use isotropic noise that is standard normally distributed. In this configuration, models must learn both simple correlations and complex correlations in data from scratch.

Whitening transformations and linear generative models One classical approach for removing nuisance correlations in the data is to apply a "whitening transformation", i.e., an affine linear transformation $$z = \sum^{-\frac{1}{2}} (x - \mu)$$

that decorrelates all factors of variation by subtracting the empirical mean μ and multiplying by a square root of the inverse covariance matrix $$R = \sum^{-\frac{1}{2}}.$$

Whitening data can also be related to fitting the data to a Gaussian model x=F(z)=Rz+b where the whitened factors z are standard normally distributed as $z \sim \mathcal{N}(O, I)$ [53]. The density in the whitened space can be related to the density in the transformed space by the change of variables formula as $$\begin{aligned}\log p(x) &= \log p_z(F^{-1}(x)) - \log\left|\det\frac{dF}{dx}\right| \\ &= \log p_z(R^{-1}(x-b)) - \log|\det R| \\ &= \log \mathcal{N}(R^{-1}(x-b); 0, I) - \log|\det R| \\ &= \log \mathcal{N}(x; b, RR^\top).\end{aligned}$$

From uncorrelated diffusion to correlated diffusion If we have a linear Gaussian prior for our data $p(x)=\mathcal{N}(x; b, RR^T)$ which can be sampled as x=Rz with $z\sim\mathcal{N}(O, I)$ [1], then an uncorrelated diffusion process on the whitened coordinates $z_t \sim p_t(z|z_0)$ will induce a correlated diffusion process on the original coordinates $x_t \sim p_t(x|x_0)$. When the diffusion process is the socalled Variance-Preserving (VP) diffusion [51, 54], then the diffusion will transition from the data distribution at time t=0 to the Gaussian prior distribution at time t=T. Throughout this work we use the continuous-time formulation of VP diffusion in whitened space. This process evolves in time $t\in(0,1)$ according to the Stochastic Differential Equation (SDE)

[1] We will assume the data are centered (have zero mean) for ease of notation.

$$dz = -\frac{\beta_t}{2} z\,dt + \sqrt{\beta_t}\,dw,$$

where w is a standard Wiener process and $\beta_t$ is the time-dependent schedule at which noise is injected into the process. We can also write the correlated SDE in terms of $x_t$ if we substitute[2] x=Rz as

[2] This can be justified by Ito's lemma.

$$dx = Rdz = -\frac{\beta_t}{2} Rz\,dt + \sqrt{\beta_t}\,R\,dw = -\frac{\beta_t}{2} x\,dt + \sqrt{\beta_t}\,R\,dw.$$

Sampling from the diffusion This diffusion process is simple to integrate forward in time [51, 52]. Given an initial data point $x_0$, then $x_t$ will be distributed as $x_t \sim \mathcal{N}(x; \alpha_t x_0, (1-\alpha_t^2) RR^T)$ where $\alpha_t = \int_0^t \exp(-\beta_s)ds$ is the integrated noise (variance). Samples at any time t can thus be generated from standard normally distributed noise as $$x_t = \alpha_t x_0 + \sqrt{1-\alpha_t^2}\,R\epsilon,\ \epsilon \sim \mathcal{N}(0, I).$$

A.2 Training with Likelihood on an Evidence Lower Bound (ELBO)

Denoising loss Diffusion models can be parameterized in terms of a denoising neural network $\hat{x}_\theta(x, t)$ that is trained to predict $x_0$ given a noisy sample $x_t$. Typically this is done by minimizing a denoising loss $$\mathcal{L}(x_0; \theta) = \mathbb{E}_{x_t \sim p(x_t|x_0), t \sim Unif(0,1)}\left[\tau_t \|\hat{x}_\theta(x_t, t) - x_0\|_2^2\right]$$

where $\tau_t$ is a time-dependent weighting to emphasize the loss at particular points in time (noise levels) [52]. Training with this loss can be directly related to score matching and noise prediction which can be cast as alternative parameterizations of the target output of the network [55].

ELBO We train our diffusion models by optimizing a bound on the log marginal likelihood of data together with optional auxiliary losses. As shown in Information-Theoretic Diffusion models [56] and building on Variational Diffusion models [55], we can express a lower bound on the the log-likelihod of data in terms of the weighted average of mean-square error across diffusion time as $$\log p(z_0) = -\frac{N}{2}\log(2\pi e) + \frac{1}{2}\int_0^\infty \left(\frac{N}{1+SNR} - mmse(z_0, SNR)\right) dSNR$$

-continued $$= -\frac{N}{2}\log(2\pi e) - \frac{1}{2}\int_0^1\left(\frac{N}{1+SNR_t} - mmse(z_0, SNR_t)\right)SNR_t'\,dt$$

$$\geq -\frac{N}{2}\log(2\pi e) - \frac{1}{2}\int_0^1\left(\frac{N}{1+SNR_t} - \mathbb{E}_{p(z_t|z_0)}\left[\|\hat{z}(z_t,t) - z_0\|_2^2\right]\right)SNR_t'\,dt$$

where N is the dimensionality of $z_0$, the Signal-to-Noise Ratio (SNR) is defined $$SNR_t = \frac{\alpha_t^2}{\sigma_t^2}$$

with $\sigma_t^2=1-\alpha_t$ for VP diffusions, and mmse is the minimum achievable mean square error under the forwards noising model as a function of the SNR. We can then apply the change of variables formula to transform this bound as log $p(x_0)$=log $p(z_0)$−log detR $$\log p(x_0) = \log p(z_0) - \log detR$$

$$\geq -\frac{N}{2}\log(2\pi e) - \log\det R - \frac{1}{2}\int_0^1\left(\frac{N}{1+SNR_t} - \mathbb{E}_{p(x_t|x_0)}\left[\left\|R^{-1}(\hat{x}(x_t,t) - x_0)\right\|_2^2\right]\right)SNR_t'\,dt$$

$$= \underbrace{-\frac{1}{2}\log\det(2\pi eRR^\top)}_{\text{Entropy of the Gaussian prior}} - \underbrace{\frac{1}{2}\mathbb{E}_{p(x_t|x_0)p(t)}\left[SNR_t'\left(\frac{N}{1+SNR_t} - \left\|R^{-1}(\hat{x}(x_t,t) - x_0)\right\|_2^2\right)\right]}_{\text{Deviation from Gaussianity (Bound)}}$$

$$\triangleq \mathcal{L}(x;\theta),$$

where p(t) is uniformly distributed on 0;1.

It is important to note that, for continuous data, probability density and information content is unbounded and can become pathologically high (e.g. with infinite precision one could encode the entire Protein Data Bank in the decimal expansion of a single coordinate). In practice we may handle this by manipulating the noise schedule to bound the maximum attainable $SNR_t$ [56].

A.3 Auxiliary Training Objectives

There has been consistent tension in the diffusion modeling literature between training on likelihood-based objectives, likelihood-related objectives, and auxiliary domain-specific objectives [52, 57]. Here we consider a few objectives in the latter category. Generally, diffusion models can be equivalently treated in the frameworks of score matching, noise prediction, denoising, which all can be considered as different parameterizations of the problem of learning a posterior-optimal denoiser which minimizes mean square denoising error across time.

ELBO-weighted unwhitened MSE While the information content of the structures is measured by a SNR-weighted average of mean square error in whitened space, we also consider similarly-weighted objective measuring errors in x-space as $$\mathcal{L}_x(x_0;\theta) = \mathbb{E}_{x_t\sim p(x_t|x_0),t\sim Unif(0,1)}\left[\omega^{-2}SNR_t'\|\hat{x}_\theta(x_t,t) - x\|_2^2\right]. \quad (1)$$

where we set the scale factor ω to give x units of nanometers. We found this regularization to be important because in practice we care about absolute errors in x space, i.e. absolute spatial errors, at least as much as we care about errors in z space, which will correspond under our covariance models (Appendix C) to relative local geometries. These objectives share the same minima, i.e. they will be minimized by the posterior optimal denoiser under the diffusion process, but for an approximately trained trained parametric model with limited capacity will trade off different errors in which statistics of data are emphasized in reconstruction.

Substructure MSE and Perceptually-motivated metrics As has often been emphasized in the literature in generative models of images, not all bits are equally important to perception or, more generally, sample utility. For example, it takes the same number of bits to encode the average color of an image as it does to encode the color of one single pixel, but mis-estimation of the average color will generally be much more noticeable to humans.

As a result of this, many diffusion models eschew training purely on likelihood-based metrics, for example using flat weightings of the denoising loss across diffusion time which implicitly emphasize the importance of low-frequency statistics [52]. Other generative models have used domain-specific metrics such as FAPE for proteins [58] as the denoising objective for diffusion training [59].

Here we consider auxiliary training objectives for protein backbone diffusion models which emphasize some conventionally important aspects of structural similarity. Since diffusion models trained to optimality will learn the posterior mean denoising function, which minimizes mean squared error of reconstruction from the forward process, we consider only squared-error objectives.

Substructure Aligned Squared Error Minimizing ELBO-weighted mean squared error trains a diffusion model to learn all statistics of the data at all length scales, but for proteins we know that there are some substructural statistics which may be stronger and more important to correctly estimate than others. For example, proteins often exhibit substructures, such as secondary structural elements or domains connected by more flexible linkers. We can encourage the denoiser to prioritize these substructural statistics of the data by optimizing the mean squared error under optimal superposition as $$\mathcal{D}_{substructure}(x, x') = \sum_{\mathcal{M}_i\in\{\mathcal{M}_i\}} \min_{T\in SE(3)} \left\|x^{\mathcal{M}_i} - T\cdot x'^{\mathcal{M}_i}\right\|_2^2$$

where $\{\mathcal{M}_i\}$ is a set of substructures and the inner optimization problem can solved via the optimal superposition with a Kabsch or quaternion-based method [60, 61]. We consider the following substructures for measuring aligned squared error:

- Global structure. $\mathcal{M}$=[[1, N]]. In this case, the substructure aligned MSE will simply be a rescaling of the squared optimal RMSD after superposition.
- Fragment structure. $\mathcal{M}_i$={i−m, . . . , i+m}. We consider fragments of radius m=7 residues centered around each residue i.

Distance Squared Error Many aspects of protein geometry are driven by specific packing and steric interactions that depend more strongly on interatomic distances and less strongly on relative orientations. We consider a loss measuring the squared error of proteins when represented by distance matrices of their $C_\alpha$ carbon atoms as $$\mathcal{D}_{distance}(x, x') = \sum_{ij}\left(D_{ij}^{CA}(x) - D_{ij}^{CA}(x')\right)^2.$$

Normalizing Auxiliary Losses Across Time and Schedules All of the aforementioned losses can be used as denoising losses by minimizing $\mathbb{E}_{p(x_0, x_t, t)}[\mathcal{D}(\hat{x}(x_t, t), x_0)]$, but (i) an unweighted average will be dominated by loss values at high t and (ii) values of these losses will be incomparable if the noise schedule of the diffusion is changed, complicating evaluation. To address both of these issues, we propose (i) to normalize the losses with an approximate estimate of the time-dependent error magnitude and (ii) to reweight the average with respect to time t as an average with respect to a schedule-invariant statisic via importance weights.

One intuitive schedule-invariant statistic is the signal to signal plus noise ratio $SSNR_t$ $$SSNR_t \triangleq \frac{\alpha_t^2}{\alpha_t^2 + \sigma_t^2} = \frac{SNR_t}{SNR_t + 1}.$$

For Variance-Preserving diffusion, this value simplifies to $SSNR_t = \alpha_t \in [0,1]$. Since t is uniformly distributed on (0,1) and $SSNR_t$ goes from 1 to 0, we can interpret $SSNR_{1-t}$ as a CDF and compute $$p(SSNR_t) = \frac{d}{dt} SSNR_t^{-1}(SSNR_t).$$

We can then compute importance weights as $$\frac{1}{p(SSNR_t)}$$

and combine that with normalization to yield normalized denoising training losses as $$\mathcal{L}_D(x_0; \theta) = \mathbb{E}_{x_t x_t' \sim p(x_t|x_0), t \sim Unif(0,1)}\left[\frac{1}{p(SSNR_t)} \frac{\mathcal{D}(x(x_t, t); x_0)}{\mathcal{D}(x_t'; x_0)}\right].$$

Transform Squared Error Our proposed method for parameterizing predicted structure in terms of predicted inter-residue geometries (Appendix E) leverages predicted inter-residue transforms $T_{ij}$ between every pair of residues on the graph. When training on ELBO, these predicted inter-residue transforms are only indirectly supervised by backpropagation but we can also directly supervise their values towards the true denoised inter-residue geometries to potentially stabilize and accelerate learning. This is not dissimilar from auxiliary prediction of inter-residue distances as done in end to end structure prediction methods such as AlphaFold [58]. Training these quantities directly can be useful because (i) they are SE(3) invariant and typically lower-variance targets than raw coordinates and (ii) they are aligned with the overall denoising objective in the sense that perfect inter-residue geometry prediction will yield a perfectly denoised structure (assuming sufficient equilibration time of the backbone solver).

We score the agreement between the predicted $\hat{T}_{ij}^{\theta}(x_t)$ and actual $T_{ij}(x_0)$ inter-residue geometries as the sum of a squared errors in the predicted translation vectors and rotation matrices, i.e.

$$\mathcal{L}_{transform}(x_0; \theta) = \sum_{ij \in \mathcal{G}(x)} \left\| t_{ij}(x_0) - \hat{t}_{ij}^{\theta}(x_t) \right\|_2^2 + \left\| R_{ij}(x_0) - \hat{R}_{ij}^{\theta}(x_t) \right\|_2^2,$$

where the translational disagreement is scaled to give it units of nanometers.

A.4 Reverse-Time SDE

In whitened space, we can express the reverse-time dynamics for the forwards-time SDE in terms of another SDE [52,62] that depends on the score function of the time-dependent marginals $\nabla_z \log p_t(z)$ as $$dx = \left(-\frac{1}{2}z - \nabla_z \log p_t(z)\right)\beta_t\, dt + \sqrt{\beta_t}\, d\overline{w}$$

We can similarly express this in the score function of the transformed coordinate system as $$dx = \left(-\frac{1}{2}x - RR^T \nabla_x \log p_t(x)\right)\beta_t\, dt + \sqrt{\beta_t}\, R\, d\overline{w}$$

To sample from the diffusion model by taking a sample from the "prior" (time 1 distribution) and integrate the SDE above backward in time from t=T to t=0. We can rewrite the above SDE in terms of our optimal denoising network $\hat{x}_\theta(x, t)$ (trained as described above) by leveraging the relationship [52,55] that $$\nabla_x \log p_t(x) = \left((1 - \alpha_t^2)RR^T\right)^{-1}(\alpha_t \hat{x}_\theta(x, t) - x).$$

Therefore we can express the reverse-time SDE in terms of the optimal denoising network $\hat{x}_\theta(x,t)$ as $$\begin{aligned} dx &= \left(-\frac{1}{2}x - RR^T \frac{(RR^T)^{-1}}{1 - \alpha_t^2}(\alpha_t \hat{x}_\theta(x, t) - x)\right)\beta_t dt + \sqrt{\beta_t}\, R\, d\overline{w} \\ &= \left(-\frac{1}{2}x - \frac{\alpha_t \hat{x}_\theta(x, t) - x}{1 - \alpha_t^2}\right)\beta_t dt + \sqrt{\beta_t}\, R\, d\overline{w} \\ &= \left(\frac{-\alpha_t \hat{x}_\theta(x, t) + x - \frac{1}{2}x(1 - \alpha_t^2)}{1 - \alpha_t^2}\right)\beta_t dt + \sqrt{\beta_t}\, R\, d\overline{w} \\ &= \left(\frac{\alpha_t + 1}{2(1 - \alpha_t)}x - \frac{\alpha_t}{1 - \alpha_t^2}\hat{x}_\theta(x, t)\right)\beta_t dt + \sqrt{\beta_t}\, R\, d\overline{w} \end{aligned}$$

A.5 Probability Flow ODE

Probability Flow ODE for deterministic encoding and sampling Remarkably, it is also possible to derive a set of deterministic ordinary differential equations (ODEs) whose marginal evolution from the prior is identical to above SDEs

65

[52,63]. In the context of our covariance model this can be expressed either in terms of the score function $\nabla_x \log p_t(x)$ as $$\frac{dx}{dt} = -\frac{\beta_t}{2}\left(x + RR^T \nabla_x \log p_t(x)\right)$$

or in terms of the optimal denoiser network $\hat{x}_\theta(x, t)$ as $$\frac{dx}{dt} = -\frac{\beta_t}{2}\left(x + RR^T\left((1-\alpha_t)RR^T\right)^{-1}(\alpha_t \hat{x}_\theta(x, t) - x)\right)$$

$$= -\frac{\beta_t}{2}\left(x + (1-\alpha_t)^{-1}(\alpha_t \hat{x}_\theta(x, t) - x)\right)$$

$$= -\frac{\beta_t}{2}\left(x\left(1 - \frac{1}{1-\alpha_t^2}\right) + \hat{x}_\theta(x, t)\frac{\alpha_t}{1-\alpha_t^2}\right)$$

$$= \frac{\beta_t}{2}\left(x\frac{\alpha_t}{1-\alpha_t^2} - \hat{x}_\theta(x, t)\frac{\alpha_t}{1-\alpha_t^2}\right)$$

$$= \frac{1}{2}\frac{\alpha_t \beta_t}{1-\alpha_t^2}\left(x - \frac{\hat{x}_\theta(x_t, t)}{\alpha_t}\right).$$

The ODE formulation of sampling is especially important because it enables reformulating the model as a Continuous Normalizing Flow [64, 65], which can admit efficient and exact likelihood calculations using the adjoint method [65].

A.6 Conditional Sampling from the Posterior Under Auxiliary Constraints

Bayesian posterior SDE for conditional sampling An extremely powerful aspect of the reverse diffusion formulation is that it can also be extended to enable conditional sampling from a Bayesian posterior p(x|y) by combining with auxilliary classifiers $\log p_t(y|x)$ and without retraining the base diffusion model [52]. When extended to the correlated diffusion case, this gives the SDE $$dx = \left(-\frac{1}{2}x - RR^T(\nabla_x \log p_t(x) + \nabla_x \log p_t(y|x))\right)\beta_t \, dt + \sqrt{\beta_t}\, R\, d\overline{w} \quad (2)$$

$$= \left(\frac{\alpha_t + 1}{2(1-\alpha_t)}x - \frac{\alpha_t}{1-\alpha_t^2}\hat{x}_\theta(x, t) - RR^T \nabla_x \log p_t(y|x)\right)\beta_t \, dt + \sqrt{\beta_t}\, R\, d\overline{w} \quad (3)$$

Bayesian posterior ODE for conditional sampling In the context of our covariance model and conditional constraints, the Probability Flow ODE for sampling from the posterior is $$\frac{dx}{dt} = -\frac{\beta_t}{2}\left(x + RR^T(\nabla_x \log p_t(x) + \nabla_x \log p_t(y|x))\right) \quad (4)$$

$$= \frac{1}{2}\frac{\alpha_t \beta_t}{1-\alpha_t^2}\left(x - \frac{\hat{x}_\theta(x, t)}{\alpha_t}\right) - \frac{\beta_t}{2}RR^T \nabla_x \log p_t(y|x) \quad (5)$$

A.7 Related Work

Subspace diffusion models also consider correlated diffusion, with a particular emphasis on focusing the diffusion to most relevant factors of variation for statistical and computational efficiency. Additionally, latent-space diffusion models [67] might be viewed as learning a transformed coordinate system in which the diffusion process can more efficiently model the target distribution. Our work provides further evidence for how correlated diffusion may be an underutilized approach to distributional modeling and shows

66 how domain knowledge can be incorporated in the form of simple constraints on the covariance structure of the noise process.

B Low-Temperature Sampling for Diffusion Models

Maximum likelihood training of generative models enforces a tolerable probability of all data-points and, as a result, misspecified or low-capacity models fit by maximum likelihood will typically be overdispersed. This can be understood through the perspective that maximizing likelihood is equivalent to minimizing the KL divergence from the model to the data distribution, which is the mean-seeking and mode-covering direction of KL divergence.

To mitigate overdispersion in generative models, it is common practice to introduce modified sampling procedures that increase sampling of high-likelihood states (mode emphasis, precision) at the expense of reduced sample diversity (mode coverage, recall). This includes approaches such as shrunken encodings in normalizing flows [68], low-temperature greedy decoding algorithms for language models [69], and stochastic beam search [70].

A powerful but often intractable way to trade diversity for quality in generative models is low-temperature sampling. This involves perturbing a base distribution p(x) by exponentiating with an inverse temperature rescaling factor $\lambda$ and renormalizing as $p_\lambda(x) = \frac{1}{2}p(x)^\lambda$. As the inverse temperature becomes large $\lambda \ll 1$, this perturbed distribution will trade diversity (entropy) for sample quality (likelihood) and ultimately will collapse into the global optimum as $\lambda \to \infty$. Unfortunately, low temperature sampling in the general case will require expensive iterative sampling methods such as Markov Chain Monte Carlo which typically offer no guarantee of convergence in a practical amount of time [71].

Low temperature and diffusion models The issue of trading diversity for sample quality in diffusion models has been discussed previously, with some authors reporting that simple modifications like upscaling the score function and/or downscaling the noise were ineffective [72]. Instead, classifier guidance and classifier-free guidance have been widely adopted as critical components of contemporary text-to-image diffusion models such as Imagen and DALL-E 2 [73-75].

Equilibrium versus Non-Equilibrium Sampling Here we offer an explanation for why these previous attempts at low temperature sampling did not work and produce a novel algorithm for low-temperature sampling from diffusion models. We make two key observations, explained in the next two sections 1. Upscaling the score function of the reverse SDE is insufficient to properly re-weight populations in a temperature perturbed distribution.

2. Annealed Langevin dynamics can sample from low temperature distributions if given sufficient equilibration time.

B.1 Reverse-Time SDE with Temperature Annealing

The isotropic Gaussian case To determine how the Reverse SDE can be modified to enable (approximate) low temperature sampling, it is helpful to first consider a case that can be treated exactly: transforming a Gaussian data distribution $\mathcal{N}(x_0; \mu_{data}, \sigma_{data}^2)$ to a Gaussian prior $\mathcal{N}(x_1; 0, \sigma_{prior}^2)$. Under the Variance-Preserving diffusion, the time-dependent marginal density will be given by $$p_t(x) = \mathcal{N}\left(x; \alpha_t \mu_{data}, \alpha_t^2 \sigma_{data}^2 + (1-\alpha_t^2)\sigma_{prior}^2\right)$$

which means that the score function $s_t$ will be $$s_t \triangleq \nabla_x \log p_t(x) = \frac{\alpha_t \mu_{data} - x}{\alpha_t^2 \sigma_{data}^2 + (1-\alpha_t^2)\sigma_{prior}^2}$$

Now, suppose we wish to modify the definition of the time-dependent score function so that, instead of transitioning to the original data distribution, it transforms to the perturbed data distribution, i.e. so the it transitions to $$\frac{1}{z} p_0(x)^{\lambda_0}.$$

For a Gaussian, this operation will simply multiply the precision (or equivalently, divide the covariance) by the factor $\lambda_0$. The perturbed score function will therefore be $$s_t^{perturb} = \frac{\alpha_t \mu_{data} - x}{\alpha_t^2 \sigma_{data}^2/\lambda_0 + (1-\alpha_t^2)\sigma_{prior}^2}$$

Figure 16A:
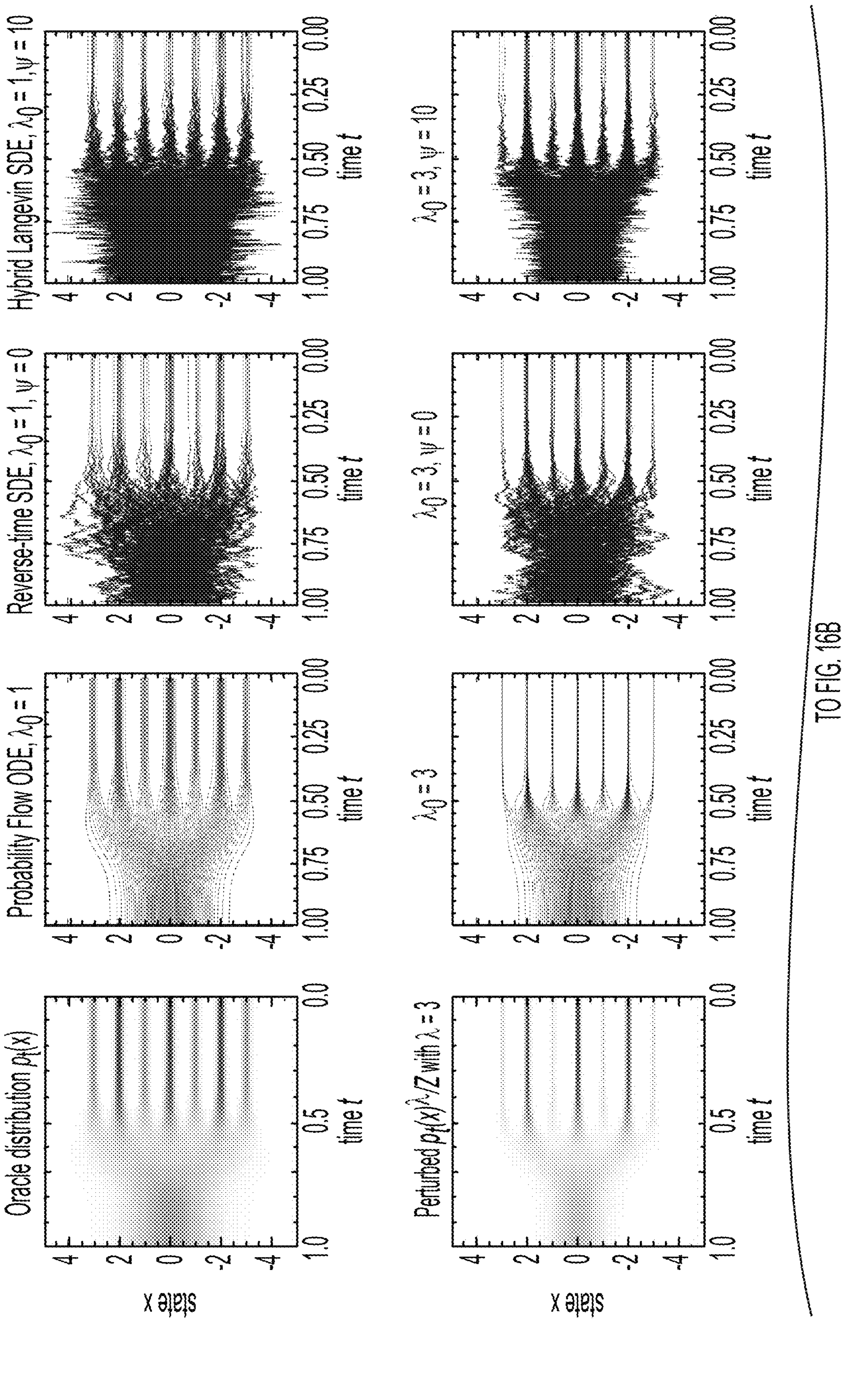
FIGS. 16A-16B show that the Hybrid Langevin SDE can sample from temperature perturbed distributions.
Figure 16B:
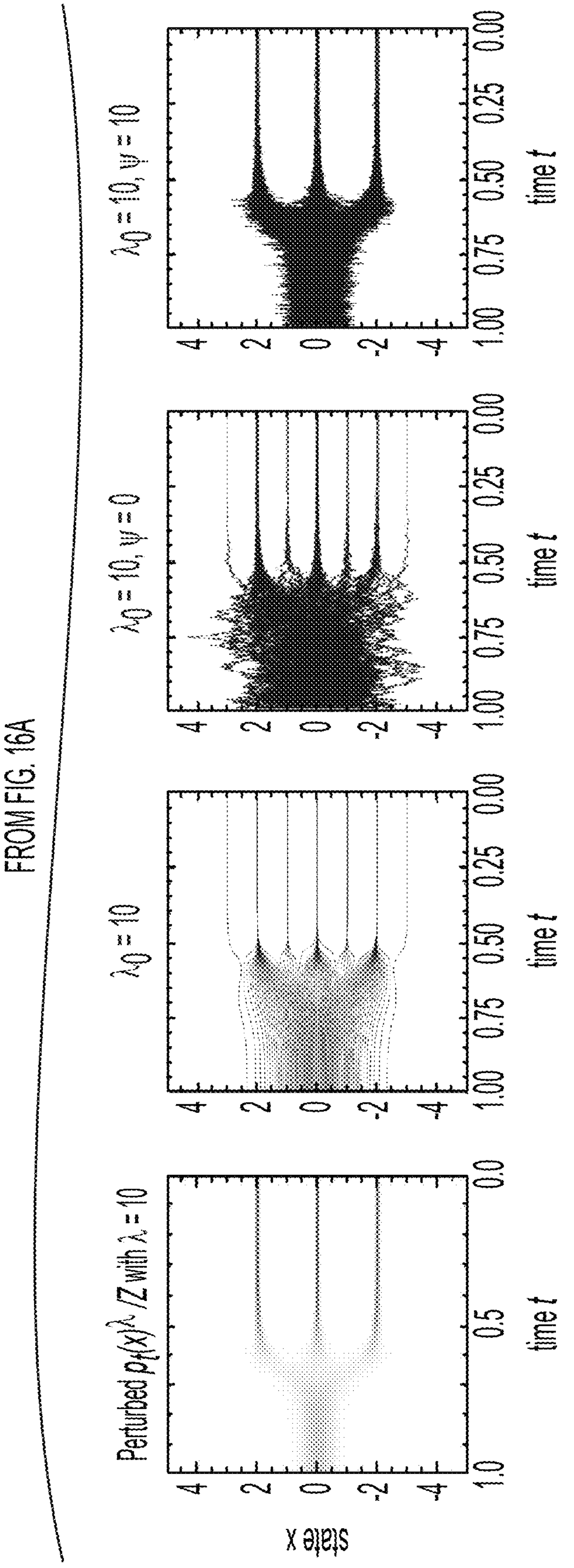

FIGS. 16A-16B: The Hybrid Langevin SDE can sample from temperature-perturbed distributions. The marginal densities of the diffusion process $p_t(x)$ (top left) gradually transform between a toy 1D data distribution at time t=0 and a standard normal distribution at time t=T. Reweighting the distribution by inverse temperature $\lambda_0$ as $$\frac{1}{z} p_t(x)^{\lambda_0}$$

(left column, bottom two rows) will both concentrate and reweight the population distributions. The annealed versions of the reverse-time SDE and Probability Flow ODEs (middle columns) can concentrate towards local optima but do not correctly reweight the relative population occupancies. Adding in Langevin dynamics with the Hybrid Langevin SDE (right column) increases the rate of equilibration to the time-dependent marginals and, when combined with low temperature rescaling, successfully reweights the populations (bottom right).

Based on this, we can express the perturbed score function as a time-dependent rescaling of the original score function with scaling based on the ratios of the time-dependent inverse variances as $$s_t^{perturb} = s_t \frac{(1-\alpha_t^2)\sigma_{prior}^2 + \alpha_t^2 \sigma_{data}^2}{(1-\alpha_t^2)\sigma_{prior}^2 + \alpha_t^2 \sigma_{data}^2/\lambda_0}$$

Therefore we see that, to achieve a particular inverse temperature do for the data distribution, we should rescale the learned score function by time-dependent factor $$\lambda_t = \frac{(1-\alpha_t^2)\sigma_{prior}^2 + \alpha_t^2 \sigma_{data}^2}{(1-\alpha_t^2)\sigma_{prior}^2 + \alpha_t^2 \sigma_{data}^2/\lambda_0} \approx \frac{\lambda_0}{\alpha_t^2 + (1-\alpha_t^2)\lambda_0}$$

where in the last step we assumed $\sigma_{data}^2 = \sigma_{prior}^2$. So one interpretation of the previously observed insufficienes of low temperature sampling based on score-rescaling [72] is that these were hampered by uniform rescaling the score function in time instead of in a way that accounts for the shift of influence between the prior and the data distribution.

Temperature-adjusted reverse time SDE We can modify the reverse-time SDE by simply rescaling the score function with the above time-dependent temperature rescaling as $$dx = \left(-\frac{1}{2}x - \lambda_t R^T \nabla_x \log p_t(x)\right)\beta_t\, dt + \sqrt{\beta_t}\, R\, d\overline{w} = \left(-\frac{1}{2}x - \lambda_t \frac{\alpha_t \hat{x}_\theta(x,t) - x}{1-\alpha_t^2}\right)\beta_t\, dt + \sqrt{\beta_t}\, R\, d\overline{w}$$

Temperature adjusted probability flow ODE Similarly for the Probability Flow ODE we can rescale as $$\frac{dx}{dt} = -\frac{\beta_t}{2}\left(x + \lambda_t R^T \nabla_x \log p_t(x)\right) = \frac{\beta_t}{2}\left(x\frac{\alpha_t + \lambda_t - 1}{1-\alpha_t^2} - x_\theta(x,t)\frac{\lambda_t \alpha_t}{1-\alpha_t^2}\right).$$

Rescaling does not reweight We derived the above rescaling rationale by considering a unimodal Gaussian, which has the simple property that the score of the perturbed diffusion can be expressed as a rescaling of the learned diffusion. This will not be true in general, and sure enough we find that the above dynamics do drive towards local maxima but do not reweight populations based on their relative probability (FIGS. 16A-16B) as true low temperature sampling does. To address this, we next introduce an equilibration process that can be arbitrarily mixed in with the non-equilibrium reverse dynamics. Concurrent with this work, [76] identified this problem as well and proposed several potential solutions based on MCMC.

B.2 Annealed Langevin Dynamics SDE

Instead of reversing the forwards time diffusion in a non-equilibrium manner, we can also use the learned time-dependent score function $\nabla_x \log p_t(x)$ (expressed in terms of the optimal denoiser $\hat{x}_\theta(x, t)$) to do slow, approximately equilibrated sampling with annealed Langevin dynamics [77].

While the annealed Langevin dynamics of [77] was originally framed via discrete iteration, we can recast it in continuous time with the SDE $$dx = -\frac{\beta_t \psi}{2} R R^T \nabla_x \log p_t(x)^{\lambda_0} dt + \sqrt{\beta_t \psi}\, R\, d\overline{w} = -\frac{\beta_t \psi}{2} \lambda_0 R R^T \nabla_x \log p_t(x) dt + \sqrt{\beta_t \psi}\, R\, d\overline{w}$$

where ψ is an "equilibration rate" scaling the amount of Langevin dynamics per unit time. As ψ→∞ the system will instantaneously equilibrate in time, constantly adjusting to the changing score function. In practice, we can think about how to set these parameters by considering a single Euler-Maruyama integration step in reverse time with step size 1/T where T is the total number of steps $$x_{t-\frac{1}{T}} \leftarrow x_t \frac{\beta_t \psi}{2T} \lambda_0 R R^T \nabla_x \log p_t(x) + \sqrt{\frac{\beta_t \psi}{T}} R\epsilon \qquad \epsilon \sim \mathcal{N}(o, I)$$

which is precisely preconditioned Langevin dynamics with step size $$\frac{\beta_t \psi}{T}.$$

For a sufficiently small interval (t−dt, t) we can keep the target density approximately fixed while increasing T to do an arbitrarily large number of Langevin dynamics steps, which will asymptotically equilibrate to the current density log $p_t(x)$.

B.3 Hybrid Langevin-Reverse Time SDE

We can combine the annealed Reverse-Time SDE and the Langevin Dynamics SDE into a hybrid SDE that infinitesimally combines both dynamics. Denoting the inverse temperature as do and the ratio of the Langevin dynamics to conventional dynamics as ψ, we have $$\begin{aligned} dx &= \left(-\frac{1}{2}x - \left(\lambda_t + \frac{\lambda_0 \psi}{2}\right) RR^T \nabla_x \log p_t(x)\right)\beta_t dt + \sqrt{\beta_t(1+\psi)}\, Rd\overline{w} \\ &= \left(-\frac{1}{2}x - \left(\lambda_t + \frac{\lambda_0 \psi}{2}\right) RR^T \frac{(RR^T)^{-1}}{1-\alpha_t^2}(\alpha_t \hat{x}_\theta(x,t) - x)\right)\beta_t dt + \sqrt{\beta_t(1+\psi)}\, Rd\overline{w} \\ &= \left(-\frac{1}{2}x - \left(\lambda_t + \frac{\lambda_0 \psi}{2}\right)\frac{\alpha_t \hat{x}_\theta(x,t) - x}{1-\alpha_t^2}\right)\beta_t dt + \sqrt{\beta_t(1+\psi)}\, Rd\overline{w} \end{aligned}$$

where we highlight in pink the terms that, when set to unity, recover the standard reverse time SDE.

Figure 17A:
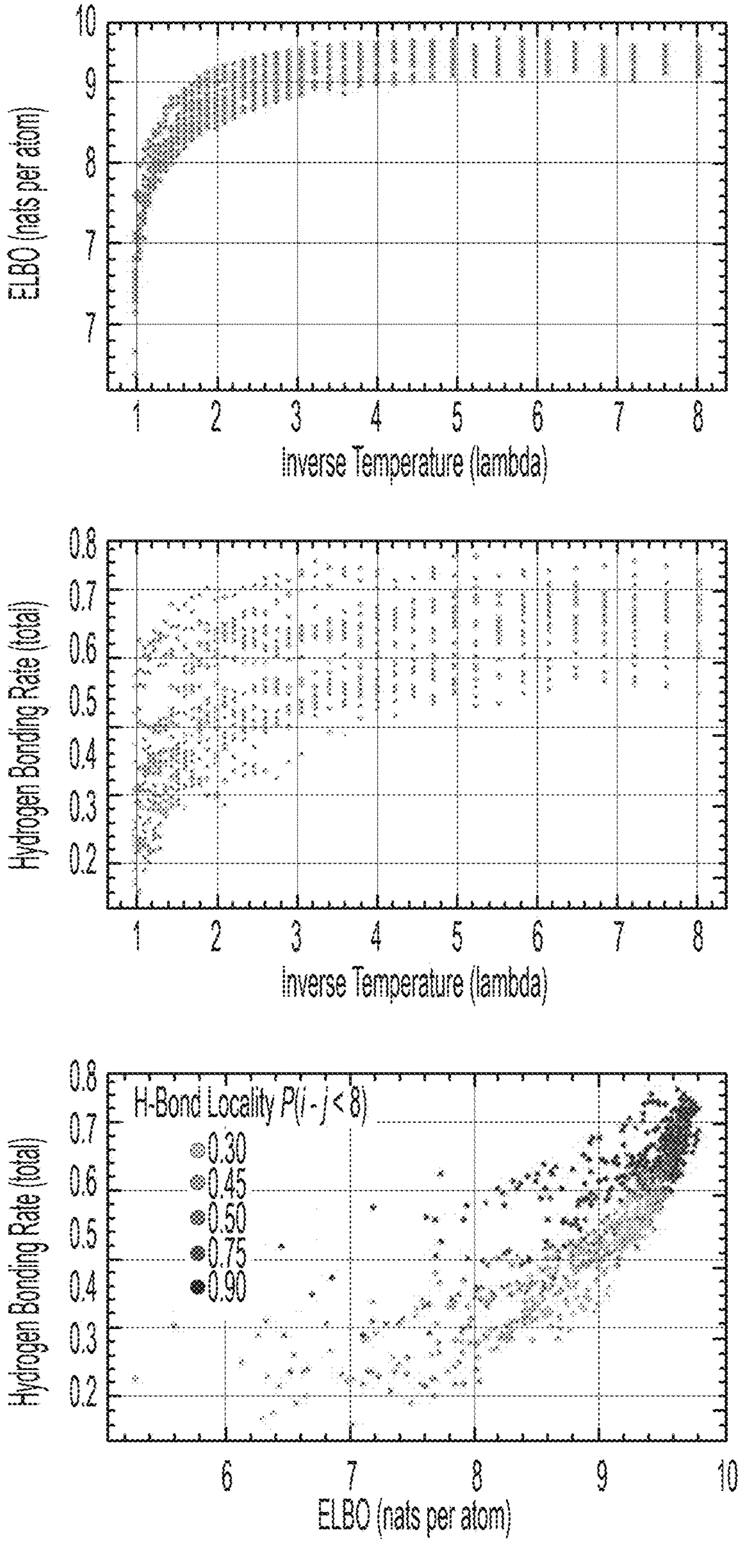
FIGS. 17A-17B show that low-temperature sampling drives towards high-likelihood states with increased secondary structure content.
Figure 17B:
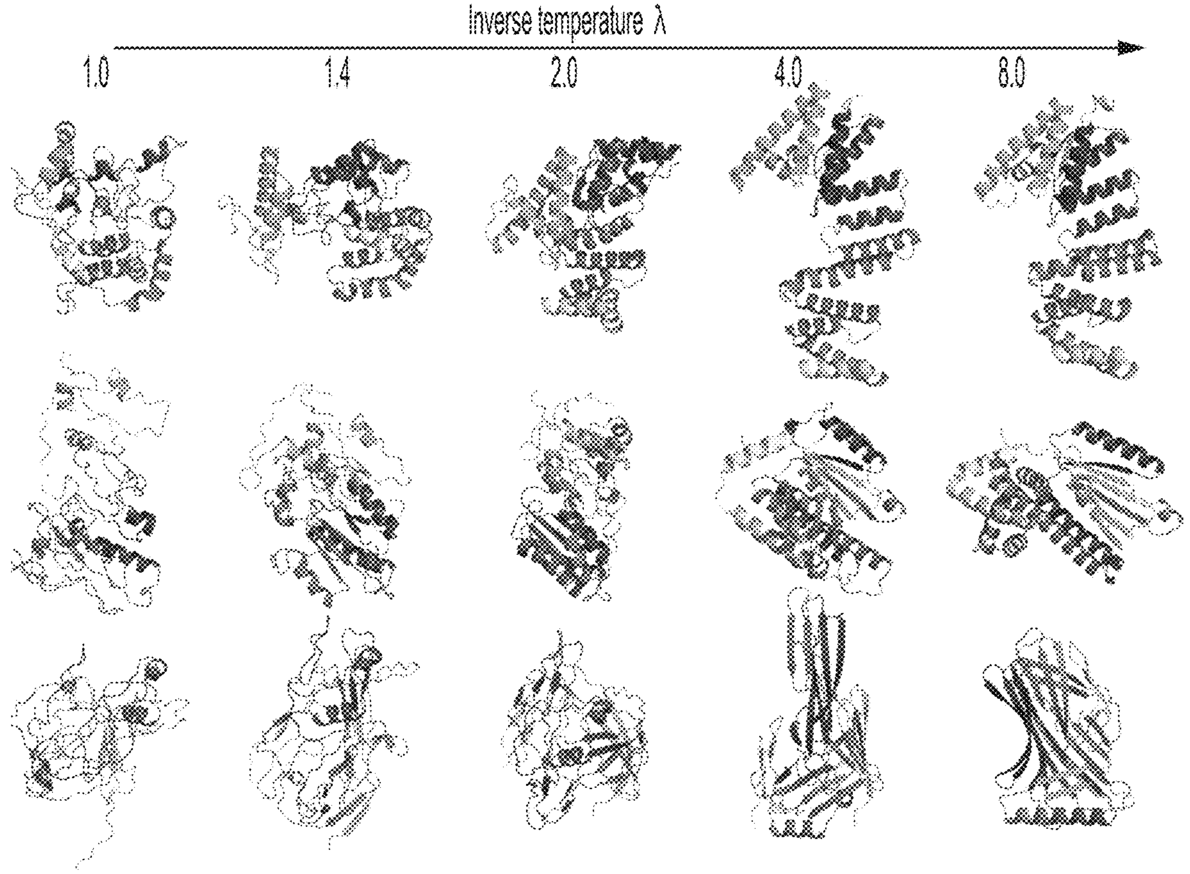

Representative samples using this modified SDE are shown in FIGS. 17A-17B. Without the low temperature modification, this idea is very reminiscent of the Predictor Corrector sampler proposed by [52], where those authors explicitly alternated between reverse-time diffusion and Langevin dynamics while we fuse them into a single SDE.

FIGS. 17A-17B: Low-temperature sampling drives towards high-likelihood states with increased secondary structure content. Increasing the inverse temperature λ increases likelihood (ELBO) for unconditional samples from the backbone diffusion model (left, top). These high-likelihood states exhibit increased rates of backbone hydrogen bonding that underlie secondary structure (left, middle). We observe that the ELBO itself (which is sequence-independent) is strongly associated with hydrogen bonding rates, and the highest likelihood states are particularly associated with increased locality of hydrogen bonding at primary sequence distance |i<j|<8 (left, bottom). These relationships can be seen within the evolution of single samples under fixed random seeds (each row, right), where structures sampled at higher inverse temperature λ have increased secondary structure content and tighter packing as compact, globular folds. The model shown is ChromaBackbone v0, while ChromaBackbone v1 generally has higher secondary structure compositions at lower inverse temperature.

Equilibration is not free Generally speaking, as we increase the amount of Langevin equilibration with ψ, we will need to simultaneously increase the resolution of our SDE solution to maintain the same level of accuracy. However, we found that even a modest amount of equilibration was sufficient to significantly improve sample quality in practice with ψ∈[1,5].

Even more equilibration Lastly, while the Hybrid Langevin-Reverse Time SDE can do an arbitrarily large amount of Langevin dynamics per time interval which would equilibrate asymptotically in principle, these dynamics will still inefficiently mix between basins of attraction in the energy landscape when 0<t<<1. We suspect that ideas from variable-temperature sampling methods, such as simulated tempering [78] or parallel tempering [79], would be useful in this context and would amount to deriving an augmented SDE system with auxiliary variables for the temperature and/or copies of the system at different time points in the diffusion. Additionally, momentum-aware approaches such as those based on Hamiltonian Monte Carlo [76] may help increase rates of equilibration and thus enable better satisfication of conditioning criteria with fewer objective function evaluations.

C Polymer-Structured Diffusions

Most prior applications of diffusion models to images and molecules have leveraged uncorrelated diffusion in which data are gradually transformed by isotropic Gaussian noise. We found this approach to be non-ideal for protein structure applications for two reasons. First, noised samples break simple chain and density constraints that almost all structures satisfy such as basic size scaling laws of the form $R_g \propto N^v$, where the scaling exponent is approximately v≈0.4 [80, 81]. These mismatches between the data distribution and the noising process force the model to allocate capacity and training time towards re-learning basic and well-understood constraints. Second, when high-noise samples are highly "out-of-distribution" from the data distribution, this can limit the performance of efficient domain-specific neural architectures for molecular systems, such as sparsely-connected graph neural networks. To this end, we introduce multivariate Gaussian distributions for protein structures that (i) are SO(3) invariant, (ii) enforce protein chain and radius of gyration statistics, and (iii) can be computed in linear time.

Throughout this section, we will introduce covariance models for protein polymers (which can be thought of as a de-whitening transform R, see Appendix A) with parameters that can be fit offline from training the diffusion model. We provide an overview figure illustrating the different Gaussian distributions presented in this section, their corresponding diffusion processes, and the respective distance statistics which they capture in FIG. 18.

C.1 Diffusion Processes Predictably Affect Molecular Distances

Here we show how variance-preserving diffusion processes (Appendix A) will predictably affect molecular geometry as a function of the covariance structure of the noising process. We will use this result to reflect on how the covariance structure should be designed. Squared distance $D_{ij}^2$ and the squared radius of gyration $R_g^2$ are both functions that can be expressed as quadratic forms in the coordinates. That means they can be expressed as a function $\mathcal{F}(x)=x^T Ax$ where A is a matrix weighting the different cross-terms as $\mathcal{F}(x)=\Sigma_{i,j} A_{ij}x_i x_j$. Suppose we want to understand the behavior of these quantities as they evolve under the forward process of a diffusion model. Recall that we can write samples from the forward diffusion process as $$x_t = \alpha_t x_0 + \sqrt{1-\alpha_t^2}\,Rz, \quad z \sim \mathcal{N}(0, I)$$

So we can write the time-expectation of any quadratic form as $$\begin{aligned}
\mathbb{E}_{p(x_t|x_0)}[\mathcal{F}(x)] &= \mathbb{E}_z\left[\left(\alpha_t x_0 + \sqrt{1-\alpha_t^2}\,Rz\right)^T A\left(\alpha_t x_0 + \sqrt{1-\alpha_t^2}\,Rz\right)\right] \\
&= \mathcal{F}(\alpha_t x_0) + \mathbb{E}_z\left[\mathcal{F}\left(\sqrt{1-\alpha_t^2}\,Rz\right) + \right. \\
&\qquad \left. \alpha_t\sqrt{\left(1-\alpha_t^2\right)}\left(x_0^T Rz + Rz^T x_0\right)\right] \\
&= \alpha_t^2\mathcal{F}(x_0) + \mathbb{E}_z\left[\mathcal{F}\left(\sqrt{1-\alpha_t^2}\,Rz\right)\right] \\
&= \alpha_t^2\mathcal{F}(x_0) + \left(1-\alpha_t^2\right)\mathbb{E}_{p_{model}(x)}[\mathcal{F}(x)].
\end{aligned}$$

Squared distance is a quadratic form, so diffusion processes will simply linearly interpolate to the behavior of the prior as $$\mathbb{E}_{p(x_t|x_0)}\left[D_{ij}^2(x_t)\right] = \alpha_t^2 D_{ij}^2(x_0) + \left(1-\alpha_t^2\right)\mathbb{E}_{p_{prior}(x)}\left[D_{ij}^2(x)\right]$$

and squared radius of gyration will similarly evolve under the diffusion as $$\mathbb{E}_{p(x_t|x_0)}\left[R_g^2(x_t)\right] = \alpha_t^2 R_g^2(x_0) + \left(1-\alpha_t^2\right)\mathbb{E}_{p_{prior}(x)}\left[R_g^2(x)\right]$$

Punchline Because variance-preserving diffusion models will do simple linear interpolations between the average squared distances and $R_g$ of the data distribution and of the prior, we should focus on covariance structures that empirically match these properties as closely as possible. Two primary ways will be in the chain constraint, i.e., that $D_{i,i+1}(x_t)$ should always be small and match the data distribution, and the density constraint of how $R_g^2(x_t)$ should behave as a function of protein length and typical packing statistics.

C.2 Covariance Model #1: Ideal Chain

In this section, we introduce one of the simplest covariance models that enforces the chain constraint but ignores the $R_g$ scaling. It will interpolate between the data distribution and the ensemble of unfolded random coils.

Noise process We index our amount of noise with a diffusion time $t \in [0,1]$. Given a denoised structure $x_0$, a level of noise t, and a noise schedule $\alpha_t$, we sample perturbed structures from a Multivariate Gaussian distribution $p(x_t|x_0) = \mathcal{N}(\alpha_t x_0, (1-\alpha_t^2)\Sigma)$ as $$x_t = \alpha_t x_0 + \sqrt{1-\alpha_t^2}\,Rz, \; z \sim \mathcal{N}(0, I)$$

where the covariance matrix enforcing our chain constraint $\Sigma = RR^T$ can be expressed in terms of its square root R, which is defined below.

Key to our framework is a matrix R whose various products, inverse-products, and transposeproducts with vectors can be computed in linear time. We define the matrix R in terms of its product with a vector $f(z) = Rz$ as $$f(z)_i = \tilde{x}_i + \delta\tilde{x}_1 - \sum_k \frac{\tilde{x}_k}{N}, \text{ where } \tilde{x}_i = a\sum_{k=1}^{i} z_k$$

The inverse product $f^{-1}(x) = R^{-1}x$ is then $$f^{-1}(x)_i = \frac{\tilde{x}_i - \tilde{x}_{i-1}}{a}, \text{ where } \tilde{x}_i = x_i - x_1 + \frac{1}{\delta}\sum_k \frac{x_k}{N}.$$

This definition of R induces the following inverse covariance matrix on the noise, which possesses a special structure of:

$$\Sigma^{-1} = \left(RR^T\right)^{-1} = \frac{1}{a^2}\begin{bmatrix} 1 & -1 & & & & \\ -1 & 2 & -1 & & & \\ & -1 & 2 & -1 & & \\ & & \ddots & \ddots & \ddots & \\ & & & -1 & 2 & -1 \\ & & & & -1 & 1 \end{bmatrix} + \frac{1}{(Na\delta)^2}11^T.$$

The parameter a sets the length scale of the chain and the parameter δ sets the allowed amount of translational noise about the origin. This latter parameter is important for training on complexes where each chain may not have a center of mass at 0.

Figure 18:
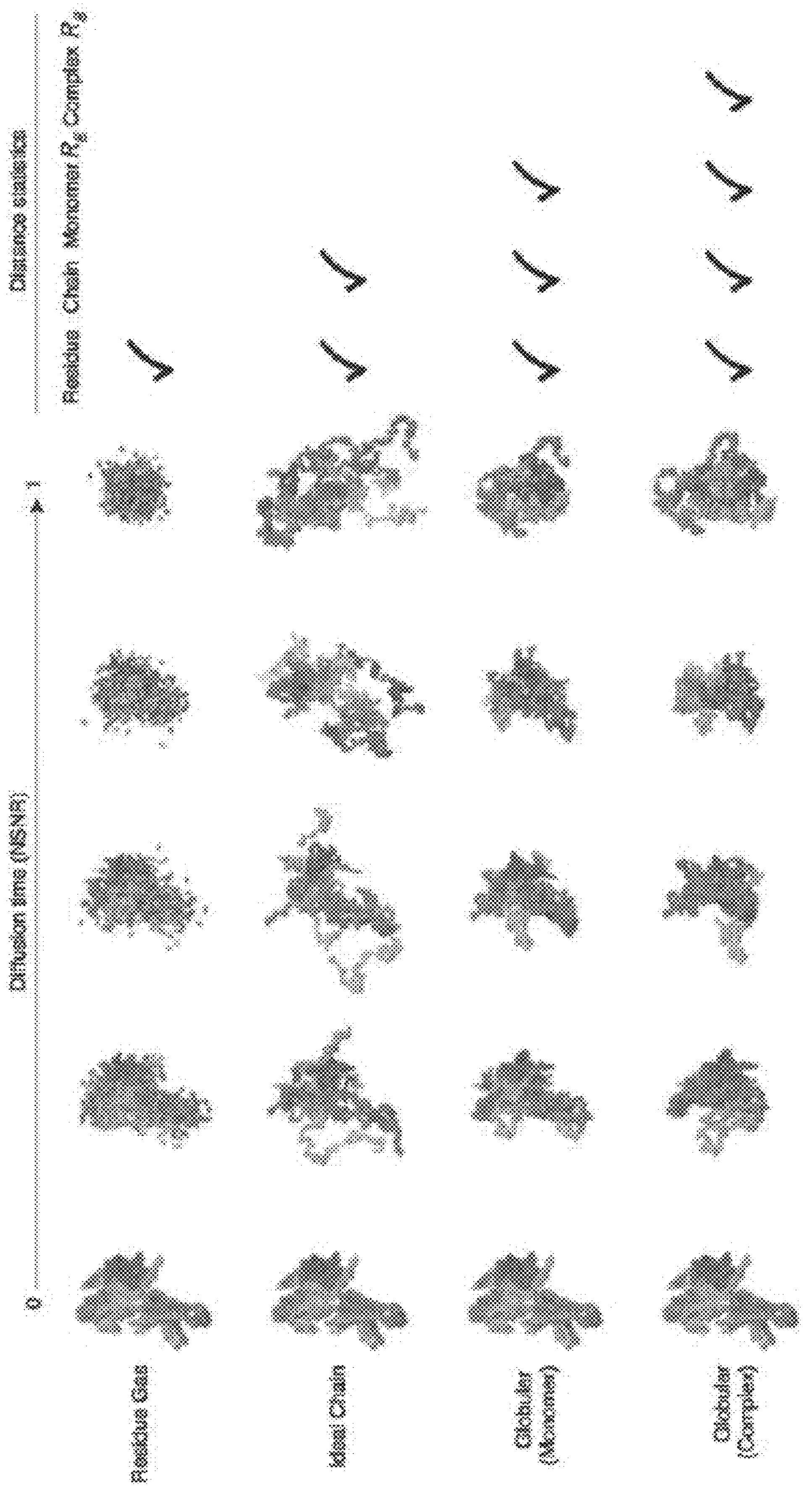
FIG. 18 shows that polymer-structured diffusions capture multiple scales of distance statistics in proteins.

FIG. 18: Polymer-structured diffusions capture multiple scales of distance statistics in proteins. A residue gas covariance model (top row, Appendix C.4) enforces atomic proximity within residues, but ignores chain correlations and length-dependent scaling effects. The ideal chain covariance model (second row, Appendix C.2), a standard entry point for polymer physics, captures atomic proximity along a chain but does not capture the length-dependent scaling driven by polymer collapse. The globular covariance model (third and fourth rows, Appendix C.3), combines chain covariance with an analytic scaling law that reproduces the empirical scaling of globular proteins and complexes. All of these covariance models admit computation of matrix-vector products involving covariance and inverse-covariance matrices with linear time complexity.

C.2.1 Covariance Model #1 has Ideal Chain Scaling $R_g \propto N^{(1/2)}$

Our ideal-chain model is a simple Brownian motion and so the interatomic residual is Gaussian distributed with zero mean and a $^2|i-j|$ variance, i.e., $$\Gamma_{ij} \sim \mathcal{N}\left(0, a^2|i-j|\right)$$

The expected squared norm for a Multivariate Normal Distribution (MVN) with spherical covariance is $\|\mu\|_2^2 + k\sigma^2$ where k is the dimensionality, so we have $$\mathbb{E}_{p(x_t|x_0)}\left[D_{ij}^2(x_t)\right] = \alpha_t^2 D_{ij}^2(x_0) + \left(1-\alpha_t^2\right)3a^2|i-j|$$

When $\alpha_t=0$, the expected squared distances are those of the data distribution, while when $\alpha_t=T$, they are those on an ideal Gaussian chain.

To compute the expected radius of Gyration, we can use the identity that it is simply half of the root mean square of inter-residue distances $$\frac{1}{2N^2}\sum_{i,j}\mathbb{E}_{p_{prior}}\left[\|x_t^j - x_t^i\|_2^2\right] = +\frac{1}{2N^2}\sum_{i,j}(1-\alpha)3a^2|i-j|$$

$$= 3a^2\frac{1}{2N^2}\sum_{i,j}|i-j|$$

$$= 3a^2\frac{1}{N^2}\sum_{i=1}^{N}\sum_{j=1}^{N} j-i$$

$$= 3a^2\frac{N}{6}\left(\frac{N^2-1}{N^2}\right)$$

Therefore, we can also view the mean behavior of the diffusion as linearly interpolating the squared radius of gyration as $$\mathbb{E}_{p(x_t|x_0)}\left[R_g^2(x)\right] = \alpha_t^2\left(R_g^{(0)}\right)^2 + \left(1-\alpha_t^2\right)3a^2\frac{N}{6}\left(\frac{N^2-1}{N^2}\right)$$

When $\alpha \rightarrow 0$ and $N<<0$, the term $$\left(\frac{N^2-1}{N^2}\right) \approx 1$$

we recover the well-known scaling for an ideal chain with $$\mathbb{E}_{p(x_t|x_0)}\left[\left(R_g^2(x_t)\right)\right] = \frac{Na^2}{6}$$

where the segment length is $a=\sqrt{3}a$.

C.3 Covariance Model #2: $R_g$-Confined Globular Polymer

In this section we consider how to extend the previous model in a way that preserves the chain constraint while further restricting the scaling of the radius of gyration $R_g$. We consider a family of two-parameter linear chain models that include the previous model as a special case. Specifically, consider the following linear recurrence $$x_i = az_i + bx_{i-1}$$

$$= \alpha\sum_{j=2}^{i} b^{i-j}z_j + b^{i-1}x_1.$$

Here, the parameter a is a global scale parameter setting the "segment length" of the polymer and b is a "decay" parameter which sets the memory of the chain to fluctuations. Informally, at each step along the chain, we bury 1−b percent of the way to the origin and step in a random direction with step scale a. We recover a spherical Gaussian when b=0 and the ideal Gaussian chain when b=1.

This system can also be written in matrix form as x=Rz with $$R = a\begin{bmatrix} vb^0 & & & & & \\ vb^1 & b^0 & & & & \\ vb^2 & b^1 & b^0 & & & \\ \vdots & & \ddots & \ddots & & \\ vb^{N-2} & & & b^1 & b^0 & \\ vb^{N-1} & & \dots & b^2 & b^1 & b^0 \end{bmatrix}$$

where $v=\sqrt{\mathrm{Var}(x_1)}$.

We can solve for the equilibrium value of v via the condition $\mathrm{Var}(x_1)=a^2v^2=\mathrm{Var}(x_i)=\mathrm{Var}(x_{i-1})$. The solution is $$\mathrm{Var}(x_i) = a^2\mathrm{Var}(z_i) + b^2\mathrm{Var}(x_i)$$

$$\mathrm{Var}(x_i)\left(1-b^2\right) = a^2$$

$$a^2v^2 = \frac{a^2}{1-b^2}$$

$$v = \frac{1}{\sqrt{1-b^2}}.$$

So our final recurrence is $$x_i = a\sum_{k=2}^{i} b^{i-k}z_k + a\frac{b^{i-1}}{\sqrt{1-b^2}}z_1$$

C.3.1 Expected Radius of Gyration $\mathbb{E}[R_g^2]$ as a Function of b

To compute the expected Radius of Gyration, we will use the identity $$R_g^2(x) = \frac{1}{2N^2}\sum_{i,j} D_{ij}^2(x),$$

which we can compute via the variance of the residual between $x_i$ and $x_j$. Assuming j>i, we have $$\frac{x_j - x_i}{a} = \sum_{k=i+1}^{j} b^{j-k}z_k + \sum_{k=2}^{j}\left(b^{j-k} - b^{i-k}\right)z_k + \frac{b^{j-1} - b^{i-1}}{\sqrt{1-b^2}}z_1,$$

the variance of which is $$\frac{1}{a^2}\mathbb{E}\left[D_{ij}^2(x)\right] = \frac{1}{a^2}\mathrm{Var}(x_j - x_i)$$

$$= \mathrm{Var}\left(\sum_{k=2}^{j} b^{j-k}z_k + \frac{b^{j-1}}{\sqrt{1-b^2}}z_1 - \sum_{k=2}^{i} b^{i-k}z_k - \frac{b^{i-1}}{\sqrt{1-b^2}}z_1\right)$$

$$= \mathrm{Var}\left(\sum_{k=i+1}^{j} b^{j-k}z_k + \sum_{k=2}^{i}\left(b^{j-k} - b^{i-k}\right)z_k + \frac{b^{j-1} - b^{i-1}}{\sqrt{1-b^2}}z_1\right)$$

$$= \sum_{k=i+1}^{j} b^{2(j-k)} + \sum_{k=2}^{i}\left(b^{j-k} - b^{i-k}\right)^2 + \frac{\left(b^{j-1} - b^{i-1}\right)^2}{1-b^2}$$

$$= \frac{2\left(1 - b^{j-i}\right)}{1-b^2}.$$

So the expected $R_g^2$ is $$\frac{1}{a^2}\mathbb{E}\left[R_g^2(x)\right] = \frac{1}{a^2}\mathbb{E}\left[\frac{1}{N^2}\sum_{i=1}^{N}\sum_{j=i}^{N}D_{ij}^2(x)\right]$$

$$= \frac{1}{N^2}\sum_{i=1}^{N}\sum_{j=i}^{N}\frac{1}{a^2}\mathbb{E}\left[D_{ij}^2(x)\right]$$

$$= \frac{1}{N^2}\sum_{i=1}^{N}\sum_{j=i}^{N}\frac{2\left(1-b^{j-i}\right)}{1-b^2}$$

$$= \frac{2b^{N+1}-b^2N(N+1)+2b\left(N^2-1\right)-N(N-1)}{(b-1)^3(b+1)N^2}$$

$$\approx \left(\frac{6b}{N}+1-b^2\right)^{-1} \text{ for } b \text{ on } (0, 1) \text{ and } N \gg 1$$

$$= \frac{N}{6b+N\left(1-b^2\right)}.$$

The approximation in the penultimate step works quite well in practice and becomes more accurate with growing N, which we can verify with the limit $$\forall\, b \in (0, 1) \lim_{N\to\infty}\frac{2b^{N+1}-b^2N(N+1)+2b\left(N^2-1\right)-N(N-1)}{(b-1)^3(b+1)N^2}\left(\frac{6b}{N}+1-b^2\right) = 1.$$

Limiting Behaviors We can verify that this result reproduces the expected limiting behavior of an ideal unfolded chain when b→1 as $$\lim_{b\to 1}\frac{1}{a^2}\mathbb{E}\left[R_g^2(x)\right] = \frac{N}{6},$$

and of a standard normal distribution when b→0 as $$\lim_{b\to 0}\frac{1}{a^2}\mathbb{E}\left[R_g^2(x)\right] = 1$$

$R_g^2$ Scaling To finish up, we can add back in our global scaling factor a to give $$\mathbb{E}_{x\sim p_{prior}(x)}\left[R_g^2(x)\right] \approx \frac{Na^2}{6b+N\left(1-b^2\right)}.$$

C.3.2 How to Implement any $R_g^2$ Scaling

Empirical analysis and biophysical models suggest that protein radii of gyration $R_g$ will scale with the number of residues N with scaling law $$R_g = rN^{\nu},$$

where r≈2.0 Å and ν≈0.4 [80,81].

Given this expected behavior of $R_g^2$ as a function of N, we can solve for the value of b(N) that implements the correct scaling by solving $$\mathbb{E}_{x\sim p_{prior}(x)}\left[R_g^2(x)\right] = (rN^{\nu})^2 = \frac{Na^2}{6b+N\left(1-b^2\right)}.$$

This gives a quadratic equation with the solution $$b_{effective}(N, a, r, \nu) = \frac{3}{N} \pm N^{-\nu}\sqrt{N^{2(\nu-1)}\left(N^2+9\right)-\frac{a^2}{r^2}},$$

where the positive branch is the relevant one to us (the negative branch corresponds to a pathological solutions for small N), giving us the final result $$b_{effective}(N, a, r, \nu) = \frac{3}{N} + N^{-\nu}\sqrt{N^{2(\nu-1)}\left(N^2+9\right)-\frac{a^2}{r^2}}$$

C.3.3 Standardizing the Translational Variance

Initializing the above recurrence relationship at equilibrium yields diverging marginal variance as b→1. We can arbitrarily re-tune the translational variance of each chain with the following mean-deflation operation enforcing $$\sum\nolimits_k \frac{x_k}{N} = (1-\xi)\sum\nolimits_k \frac{\tilde{x}_k}{N}$$

as $$x_i = \tilde{x}_i - \xi\sum_k \frac{\tilde{x}_k}{N}.$$

This operation has inverse $$\tilde{x}_i = x_i + \frac{\xi}{1-\xi}\sum_k \frac{x_k}{N},$$

C.3.4 Setting the Parameters

First, we set the dimension-wise segment scaling factor a=1.559 by fitting uniformly random ϕ, ψ chains with ideal geometry. We then dynamically set b for each chain to satisfy its predicted $R_g$ scaling with the relationship $$b_{effective}(N_{atoms}, a, r, \nu) = \frac{3}{N_{atoms}} + N_{atoms}^{-\nu}\sqrt{N_{atoms}^{2(\nu-1)}\left(N_{atoms}^2+9\right)-\frac{a^2}{r^2}},$$

ν=0.4, r=0.66, and $N_{atoms}=4N_{residues}$. We have two procedures for setting the values of ζ, leading to two different named covariance models:

1. Monomer $R_g$ scaling. Set ζ so that the translational variance of each chain is unity. This will cause chains to have a realistic radius of gyration but pile up at the origin.
2. Complex $R_g$ scaling. Set ζ per chain by solving for the translational variance that also implements the correct whole-complex $R_g$ scaling as a function of the number of residues. This will cause chains to preserve a realistic complex-level radius of gyration and also intrachain radius of gyration that scales as that of individual globular proteins.

C.3.5 Covariance Factors and their Inverses

When also including a centering transform, we can factorize the square root of the covariance matrix, $$\Sigma^{\frac{1}{2}} \triangleq R,$$

as a product of three matrices, $$R = aR_{center}R_{sum}R_{init} =$$

$$a\left(I - \frac{\xi}{N}11^T\right)\begin{bmatrix} b^0 & & & & & \\ b^1 & b^0 & & & & \\ b^2 & b^1 & b^0 & & & \\ \vdots & & \ddots & \ddots & & \\ b^{N-2} & & & b^1 & b^0 & \\ b^{N-1} & \dots & b^2 & b^1 & b^0 & \end{bmatrix}\begin{bmatrix} \frac{1}{\sqrt{1-b^2}} & & & & & \\ & 1 & & & & \\ & & 1 & & & \\ & & & \ddots & & \\ & & & & 1 & \\ & & & & & 1 \end{bmatrix}.$$

Each of these matrices can each be multiplied with a vector with linear time and space complexity, as $R_{center}$ is a global shift, $R_{sum}$ is a simple linear filter, and $R_{init}$ is a single-element adjustment. Similarly we may build up the inverse of the matrix square root as $$R^{-1} = \frac{1}{a}R_{init}^{-1}R_{sum}^{-1}R_{center}^{-1},$$

where the factor-wise inverses are $$R_{init}^{-1} = \begin{bmatrix} \sqrt{1-b^2} & & & & & \\ & 1 & & & & \\ & & 1 & & & \\ & & & \ddots & & \\ & & & & 1 & \\ & & & & & 1 \end{bmatrix}$$

and, via solving $x_i = \Sigma_{j=1}^{i} b^{i-j} z_i$ for $z_i$, $$R_{sum}^{-1} = \begin{bmatrix} 1 & & & & & \\ -b & 1 & & & & \\ & -b & 1 & & & \\ & & \ddots & \ddots & & \\ & & & -b & 1 & \\ & & & & -b & 1 \end{bmatrix},$$

and, via the matrix inversion lemma, $$R_{center}^{-1} = I - \frac{\xi}{(1-\xi)N}11^T.$$

C.3.6 Covariance Determinant

Computing likelihoods of protein chains under the multivariate normal prior introduced in this section or computing the Diffusion ELBO from Appendix A requires computation of the determinant of the covariance matrix. Fortunately, the simple form of our covariance model in turn leads to a simple form for the determinant. With a chain length of N, we have $$\begin{aligned} \log detR &= N\log a + \log detR_{center} + \log detR_{sum} + \log detR_{init} \\ &= N\log a + \log\det\left(I + \left(-\frac{\xi 1}{N}\right)1^T\right) + N\log b^0 + -\frac{1}{2}\log\left(1-b^2\right) \\ &= N\log a + \log\left(1 + 1^T\left(-\frac{\xi 1}{N}\right)\right) + 0 + -\frac{1}{2}\log\left(1-b^2\right) \\ &= N\log a + \log(1-\xi) + 0 + -\frac{1}{2}\log\left(1-b^2\right), \end{aligned}$$

where log $detR_{center}$ follows from the matrix determinant lemma. Thus, $$detR = \frac{a^N(1-\xi)}{\sqrt{1-b^2}}.$$

C.3.7 Inverse Covariance and Intuition

We may examine the inverse of the globular covariance matrix to build intuition on the underlying factors driving correlations in our system. For simplicity, we analyze[3] the simpler case of the uncentered covariance model with $\Sigma_{uncentered} = aR_{sum}R_{init}aR_{init}^TR_{sum}^T$. It will be helpful to define $D \triangleq R_{init}^{-T}R_{init}^{-1}$ and to note that the inverse sum operator can be expressed as $R_{sum}^{-1} = I - bP$, where P is a nilpotent shift matrix with ones on the first lower diagonal. We then have

[3] We thank Rian Kormos for this proof and analysis.

$$D = \begin{bmatrix} 1-b^2 & & & & & \\ & 1 & & & & \\ & & 1 & & & \\ & & & \ddots & & \\ & & & & 1 & \\ & & & & & 1 \end{bmatrix}$$

and $$\begin{aligned} \Sigma_{uncentered}^{-1} &= \frac{1}{a^2}R_{sum}^{-T}R_{init}^{-T}R_{init}^{-1}R_{sum}^{-1} \\ &= \frac{1}{a^2}\left(I - bP^T\right)D(I - bP) \\ &= \frac{1}{a^2}\left(D - b\left(P^TD + D^TP\right) + b^2P^TDP\right) \\ &= \frac{1}{a^2}\left(D - b\left(P^T + P\right) + b^2P^TP\right) \\ &= \frac{1}{a^2}\begin{bmatrix} 1 & -b & & & & \\ -b & 1+b^2 & -b & & & \\ & -b & 1+b^2 & -b & & \\ & & \ddots & \ddots & \ddots & \\ & & & -b & 1+b^2 & -b \\ & & & & -b & 1 \end{bmatrix}, \end{aligned}$$

where the penultimate line follows from the behavior of the shift operator P.

We can identify within this precision matrix a linear combination of two well known precision matrices: the precision of Brownian motion, i.e. the chain Laplacian matrix, and the precision for a spherical Gaussian, i.e. an identity matrix, along some nuisance boundary conditions as $$\Sigma^{-1} = \frac{1}{a^2}\left(\begin{bmatrix} 1 & -1 & & & & \\ -1 & 2 & -1 & & & \\ & -1 & 2 & -1 & & \\ & & \ddots & \ddots & \ddots & \\ & & & -1 & 2 & -1 \\ & & & & -1 & 1 \end{bmatrix} + (1-b)^2 I + \begin{bmatrix} b(1-b) & & \\ & & \\ & & b(1-b) \end{bmatrix}\right).$$

This provides another simple characterization of our globular covariance model as being the result of a combination of 'chain springs' holding the polymer together locally along with 'burial springs' pulling the chain to the origin. This simple energetic structure has been leveraged in prior biophysical 'toy models' of hydrophobic collapse in proteins [82].

C.4 Alternative Covariance Model: Residue Gas

One useful parameterization of protein structure that strikes a balance between capturing the strong spatial dependencies induced by covalent bonds while avoiding the accumulated lever effects of internal coordinates is the so-called "Residue Gas" approach of AlphaFold [58]. In this parameterization, each residue is treated as a rigid body with local geometries fixed to their ideal values. This will ensure idealized intra-residue geometries by construction, though inter-residue covalent bond geometries, i.e. $C_i$–$N_{i+1}$ bonds, will need to be fixed by the predictor.

Prior work applying diffusion models for protein backbones has modeled the $C_\alpha$ carbons as independently distributed with a fixed variance, i.e. $x_1^{C_\alpha}, \ldots, x_N^{C_\alpha} \sim \mathcal{N}(0, \sigma_{C_\alpha}^2)$ [59, 83]. While previous frame-based approaches then model the remaining N, C, O atoms as locked to the $C_\alpha$ carbon with variable rotation and ideal geometry, we can simply model these atoms as normally distributed around $C_\alpha$ with a fixed standard deviation $\sigma_{intra}$. At full noise levels this will induce an isotropic distribution over implied frame orientations while keeping these atoms close to the parent $C_\alpha$, and as such can be considered an off-ideality relaxation of frame diffusion models or an all-backbone-atom extension of IID $C_\alpha$ diffusion models [83].

This sequential Gaussian dependency structure within residues will imply that all coordinates are jointly Gaussian with square root of the covariance matrix $$R_{gas} = \begin{bmatrix} R_{residue} & & & \\ & R_{residue} & & \\ & & \ddots & \\ & & & R_{residue} \end{bmatrix}$$

and with block diagonal elements $$R_{residue} = \begin{bmatrix} \sigma_{intra} & \sigma_{C_\alpha} & 0 & 0 \\ 0 & \sigma_{C_\alpha} & 0 & 0 \\ 0 & \sigma_{C_\alpha} & \sigma_{intra} & 0 \\ 0 & \sigma_{C_\alpha} & 0 & \sigma_{intra} \end{bmatrix}.$$

In our experiments we set the intra-residue standard deviation to $\sigma_{intra}=1$ and the residue standard-deviation to $\sigma_{C_\alpha}=10$. As can be seen in FIG. 18, this covariance implies trajectories that are extremely similar to frame-based diffusion [59], but with the added benefit that we can treat non-ideal bond stretch and angle fluctuations. We do lose the guarantee of fixed internal ideal geometries, but this is only requires learning the equivalent of ~6 additional numbers.

D Random Graph Neural Networks

Prior approaches to predicting or generating protein structure have relied on neural network architectures with $\mathcal{O}(N^2)$ or $\mathcal{O}(N^3)$ computational complexity [58,59,83], in part motivated by the need to process the structure at multiple length scales simultaneously and/or to reason over triples of particles as is done during distance geometry methods. Here we introduce an effective alternative to these approaches with sub-quadratic complexity by combining Message Passing Neural Network [84] layers with random graph generation processes. We design random graph sampling methods that reproduce the connectivity statistics of efficient N-body simulation methods, such as the Barnes-Hut algorithm [85].

D.1 Background: Efficient N-Body Simulation

One of the principal lessons of computational physics is that N-body simulations involving $\mathcal{O}(N^2)$ dense interactions (e.g. gravitational simulations and molecular physics) can often be effectively simulated with only $\mathcal{O}(N \log N)$-scaling computation. Methods such as Barnes-Hut [85] and the Fast Multipole Method take advantage of a common particular property of (and inductive bias for) physical systems that more distant interactions can be modeled more coarsely for the same level of accuracy. For example, in cosmological simulations, you can approximate the gravitational forces acting on a star in a distant galaxy by approximating that galaxy as a point at its center of mass.

So far, most relational machine learning systems [86] for protein structure have tended to process information in a manner that is either based on local connectivity (e.g. a k-Nearest Neighbors or cutoff graphs) [87] or all-vs-all connectivity [58,59,83]. The former approach is natural for highly spatially localized tasks such as structure-conditioned sequence design and the characterization of residue environments, but it is less clear if local graph-based methods can effectively reason over global structure in a way that is possible with fully connected Graph Neural Networks, such as Transformers [88]. Here we ask if there might be reasonable ways to add in long-range reasoning while preserving sub-quadratic scaling simply by random graph construction.

Related work Our method evokes similarity to approaches that have been used to scale Transformers to large documents by combining a mixture of local and deterministically [89] or randomly sampled long-range context [90]. Distant-dependent density of context has also been explored in multiresolution attention for Vision transformers and in dilated convolutional neural networks [92].

D.2 Random Graph Generation

Figure 19:
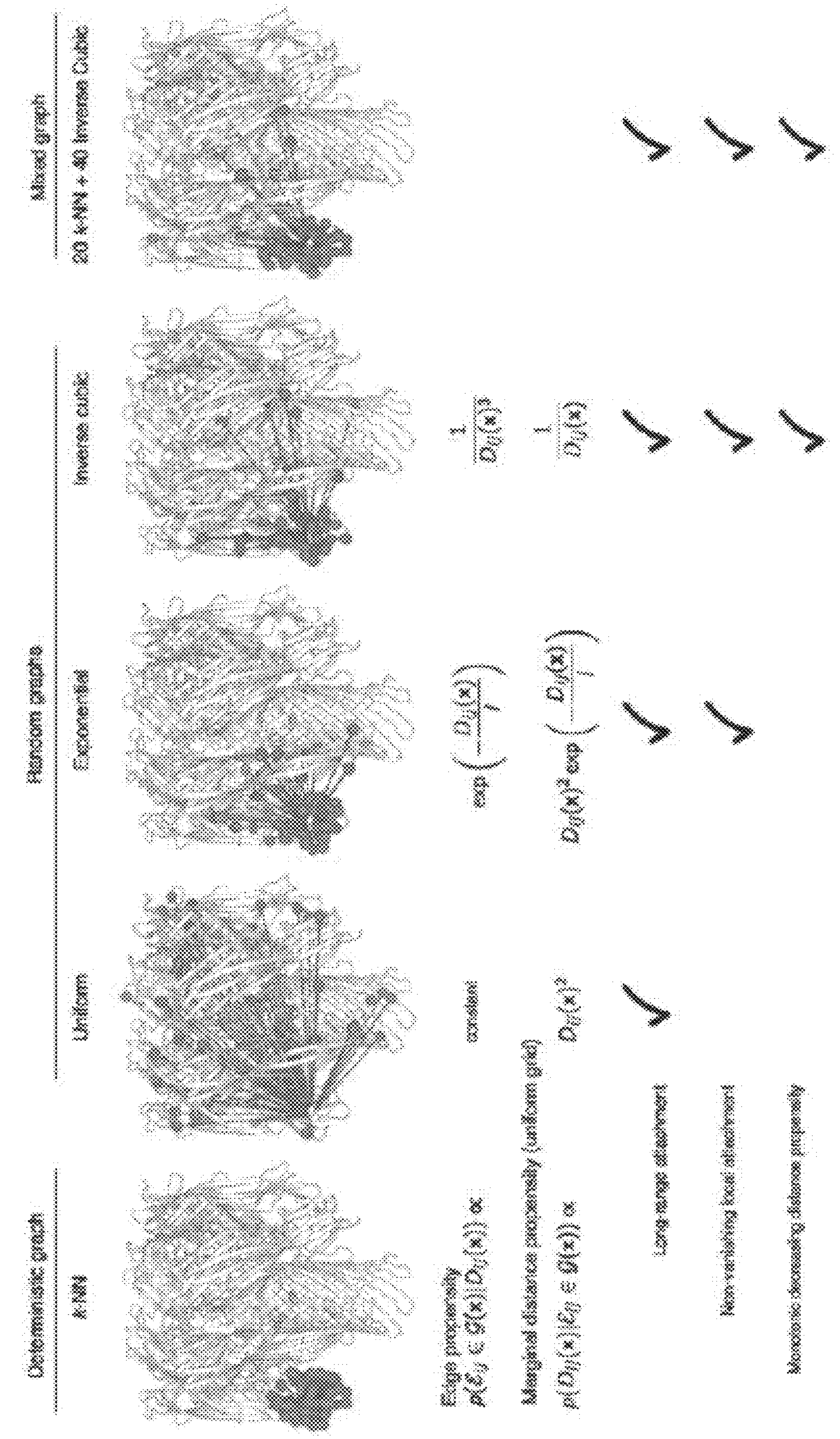
FIG. 19 shows that random graphs with distance-weighted attachment efficiently capture long-range context.

We propose to build scalable graph neural networks for molecular systems by sampling random graphs that mix short and long-range connections. We define the graph $\mathcal{G}=(\mathcal{V}, \mathcal{E})$ where $\mathcal{V}$ is the node set and $\mathcal{E}$ is the edge set. A protein can be represented as a point set $x \in \mathbb{R}^{N \times 3}$. We define the process of constructing the geometric graph as $\mathcal{G}(x)=(\mathcal{V}, \mathcal{E}(x))$ with $|\mathcal{V}|=N$. Different from the usual graph construction scheme, the edges are generated stochastically, and $\mathcal{E}(x)$ describes the process. We consider schemes in which edges for each node are sampled without replacement from the set of possible edges, weighted by an edge propensity function based on spatial distance (FIG. 19). In practice, we implement this weighted sampling without replacement using Gumbel Top-k sampling [70] (Algorithm 1). Throughout this work, we use hybrid graphs which include the 20 nearest neighbors per node together with 40 randomly sampled edges under the inverse cubic edge propensity function so that both short-range and long-range interactions are sampled with appropriate rates.

FIG. 19: Random graphs with distance-weighted attachment efficiently capture long-range context. Contemporary graph neural networks for learning from molecular systems achieve efficiency via spatial locality, e.g. with a spatial k-Nearest Neighbors graphs or cutoff graph (top left, $\mathcal{O}(Nk)$). We propose methods that retain this efficiency while incorporating longrange context through random edge sampling weighted by spatial distance (middle columns). We consider three different graph sampling schemes: (i) Uniformly random sampling (middle left) introduces long-range context but at the expense of vanishing local attachment. (ii) Exponential distance weighting (middle center), which can be related to dilated convolutions [92], includes both short- and long-range attachment but introduces a typical length scale as it induces Gamma-distributed distances. (iii) Inverse cubic distance weighting (middle right), which is the effective connectivity scaling of fast N-body methods such as Barnes-Hut [85], retains a balance of both short and long-term distances with a marginal distance propensity that gently and monotonically decays with D. In practice, we combine inverse cubic sampled random graphs with deterministic k-NN graphs to guarantee coverage of the k closest nodes while adding in long-range context (top right).

D.3 Computational Complexity

Under the inverse cubic attachment model, the cumulative edge propensity as a function of distance will scale as $$\int_{D_{min}}^{D_{max}} \frac{1}{r^3} r^2 dr = \int_{D_{min}}^{D_{max}} \frac{1}{r} dr = \log D_{max} - \log D_{min}.$$

As we increase the total size (radius) of the system by $D_{max}$, we only need to increase the total number of of edges per node by a factor of $\log D_{max}$ to keep up with the increase in total edge propensity (and to therefore ensure that increasingly distant parts of the system do not “steal” edge mass from closer parts of the system). This means that, even if we were to scale to extremely large systems such as large, solvated molecular dynamics systems with millions of atoms, the total amount of computation required for a system of N atoms will scale as $\mathcal{O}(N \log N)$. In practice, we found that for protein sizes considered in this work (complexes containing up to 4000 residues[4]) it was sufficient to simply set the number of edges per node to a constant k=60, which means that the graph and associated computation will scale within this bounded size as $\mathcal{O}(N)$. This is a considerable improvement on previous approaches for global learning on protein structure such as methods based on fully connected graph neural networks [83] $\mathcal{O}(N^2)$ or Evoformer-based approaches [58] which scale as $\mathcal{O}(N^3)$. These sparse graphs also combine favorably with our method for synthesizing updated protein structures based on predicted inter-residue geometries (Section E).

[4] In some of our symmetry examples we find that models still generalize well to systems larger than they were trained on Algorithm 1 Random graph generation Require: Inter−node distances $\{D_{ij}\}_{i,j=1}^{N}$, inverse temperature $\lambda_G$, attachment propensity

```
log p((i, j) ∈ ε(x) | D_ij) ∝ e^{c(D_ij)}, number of edges to sample k
for each i ∈ [N] do
  for each j ∈ [N] do
    U_ij~Uniform(0,1)                     ▷ Sample uniform noise per edge
    Z_ij ← λ_G c(D_ij) − log (−log (U_ij))   ▷ Perturb log probabilities with Gumbel noise
  end for
  ε ← ⋃_i^N {(i, j) | j ∈ TopK(Z_i)}        ▷ Sample top k edges
end for
```

E Structure from Inter-Residue Geometry Predictions

E.1 Background and Motivation

Prior neural network layers for generating molecular geometries in proteins have typically relied on either (i) direct prediction of backbone internal coordinates (i.e., dihedral angles) [93, 94], which incurs accumulating errors along the chain in the form of “lever effects” that hinder performance beyond small systems; (ii) prediction of inter-residue geometries followed by offline optimization [95, 96], which builds on the successes of predicting protein structure from contacts [97] but is difficult to make end-to-end trainable; or (iii) iterative local coordinate updates based on the entire molecular system [58,98], which can benefit from end-to-end learning but also face computational and stability challenges that may come with that.

Predicting structure as predicting constraints In principle, protein structures arise from a balance of competing intra- and inter-molecular forces. In that sense, protein structure may be regarded of as the solution to a constraint satisfaction problem with many competing potential interactions across multiple length scales. It is therefore natural to think about protein structure prediction as a so-called “Structured Prediction” problem [99], in which predictions are cast as the low-energy configurations of a learned potential function. Structured Prediction formulations of tasks often learn in a data efficient manner because it can be simpler to characterize the constraints in a system the the outcomes of those constraints. This perspective can be leveraged for molecular geometries via differentiable optimization or differentiable molecular dynamics [98, 100, 101], but these approaches are often unstable and can be cumbersome to integrate as part of a larger learning system.

Figure 20:
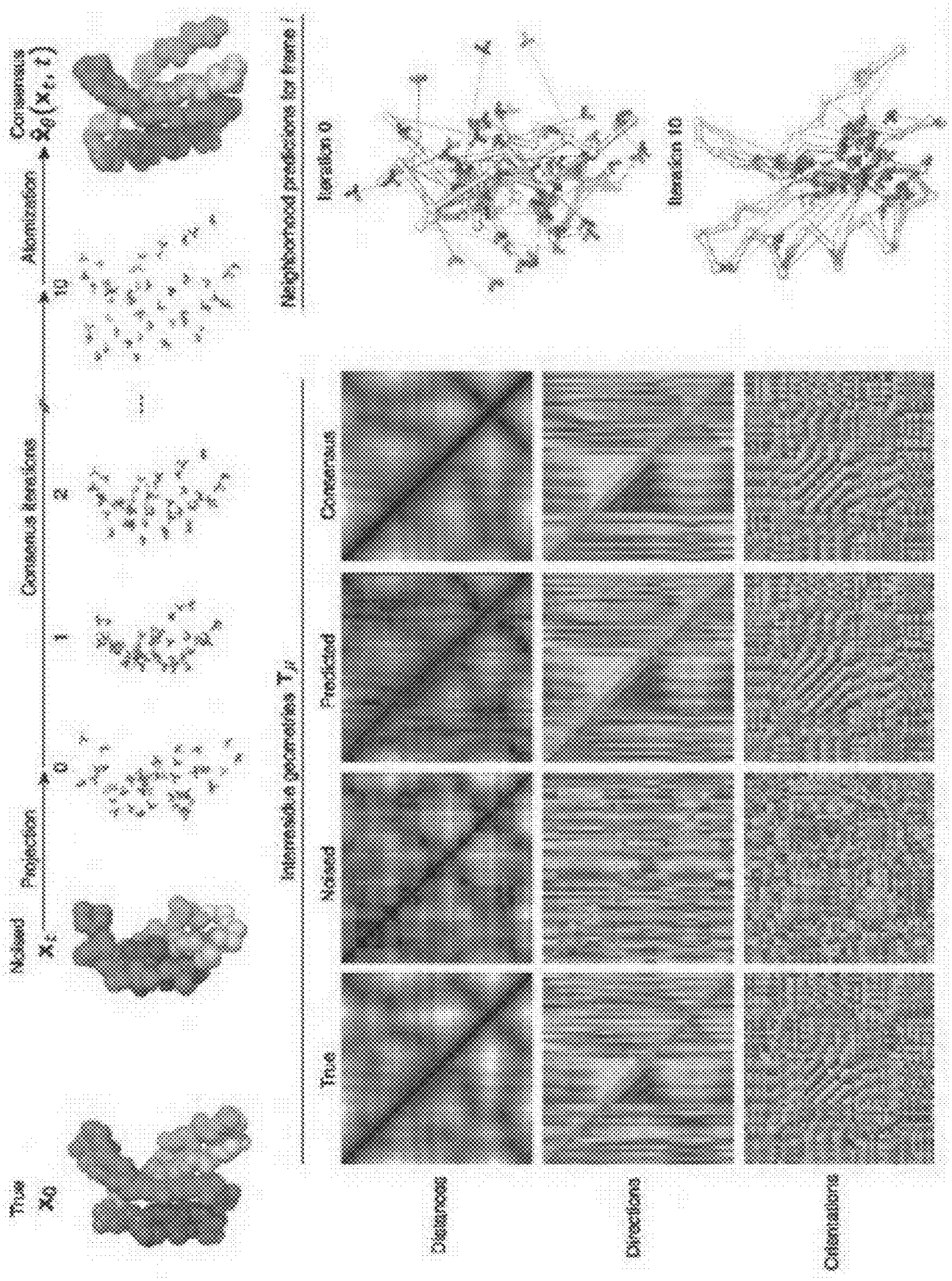
FIG. 20 shows that an iterative consensus algorithm resolves coordinates from predicted inter-residue geometries.

FIG. 20: An iterative consensus algorithm resolves coordinates from predicted inter-residue geometries. An initially noised structure (top left) is processed by a graph neural network which predicts denoised inter-residue geometries between every pair of residues on the graph (bottom left), along with confidence weights for each prediction (not shown, Appendix E). The problem of finding the optimal structure satisfying the confidence-weighted inter-residue geometry predictions forms a convex problem which can be solved by iteratively replacing residue poses with their neighborhood weighted-average consensus pose (parallel coordinate descent, top). The equilibrated poses are then imputed with relative local atom positioning also predicted by the graph neural network, forming the overall denoised structure prediction $\hat{x}_\theta(x_t,t)$ (top right). This entire procedure can be optimized end-to-end via automatic differentiation. As the parallel coordinate descent iterations proceed, the initially discordant geometry predictions for any given residue (right center, orange tube widths denote confidence), i.e. $\{T_j \cdot \hat{T}_{ji}\}_{j \in N(i)}$ begin to coalesce (right bottom). The inter-residue direction and orientation visualizations (bottom left) map the normalized translation vector and rotation matrix of $T_{ij}$ to RGB colors, respectively (using the last three elements of a quaternion representation of the rotation matrix).

E.2 Equivariant Structure Updates Via Convex Optimization

Here we introduce a framework which combines the benefits of inter-residue geometry prediction and end-to-end differentiable optimization in an efficient and stable formulation based on convex optimization. We show how predicting pairwise inter-residue geometries as pairwise rigid translation transformations with potentially anisotropic uncertainty models induces a convex optimization problem which can be solved by a simple iteration that quickly drives towards a global consensus configuration. Throughout this section we will build on the widely adopted approach representing the rigid orientations of residues in proteins via coordinate reference frames [58, 59, 98].

The key idea of our update is that we ask the network to predict a set of inter-residue geometries $T_{ij}$ together with confidences $w_{ij}$ (which will initially be simple but can be extended to anisotropic uncertainty) and we then attempt to either fully or approximately solve for the consensus structure that best satisfies this set of pairwise predictions. We visualize the method in FIG. 20.

Transform preliminaries Let $T=(O, t) \in SE(3)$ be a transformation consisting of a rotation by an orthogonal matrix $O \in SO(3)$ followed by a translation by a vector $t \in \mathbb{R}^3$. These transformations form a group with identity, inverse, and composition given by $$T_{id} = (I, O),$$

$$T^{-1} = (O^{-1}, -O^{-1}t)$$

$$T_a \circ T_b = [O_a, t_a) \circ (O_b, t_b) = (O_a O_b, O_a t_b + t_a).$$

We denote the transformation to the frame of each residue a as $T_a$, and denote the relative transformation from residue a to residue b as $$T_{ab} \triangleq T_a^{-1} \circ T_b = (O_a^{-1} O_b, O_a^{-1}(t_b - t_a)).$$

These relative transformations satisfy equations $$T_{ab} \circ T_{bc} = T_{ac},$$

$$T_{ba} = T_{ab}^{-1}.$$

Converting from backbones to transforms We represent the rigid pose of a residue as an absolute translation and rotation in space $T_i \triangleq (O_i, t_i)$. We can compute these residue poses by building an orthonormal basis from three backbone coordinates at a residue i, i.e. from the set of atoms $\{x_i^N, x_i^{C\alpha}, x_i^C\}$. To do this, we define the vectors $v_1 = x_i^N - x_i^{C\alpha}$ and $v_2 = x_i^C - x_i^{C\alpha}$, and then build an orthonormal basis as $$u_1 = \frac{v_1}{\|v_1\|},$$

$$u_2 = \frac{v_2}{\|v_2\|},$$

$$n_1 = u_1,$$

$$n_2 = \frac{n_1 \times u_2}{\|n_1 \times u_2\|},$$

$$n_3 = \frac{n_1 \times n_2}{\|n_1 \times n_2\|},$$

which gives the final transform as $$T_i = ([n_1, n_2, n_3]^T, x_i^{c\alpha})$$

We note that pose representations are SE(3) equivariant but are not invertible unless one forces coordinates to adopt ideal geometries, as is the choice in many structure prediction and diffusion methods [58,59, 102, 103]. Many backbone geometries with differing internal bond lengths and angles) will give rise to same transform $T_i$ (though it is also true that many structures are not resolved at a resolution to meaningfully distinguish these degrees of freedom). Nevertheless, we can retain the benefits of both coarse transformation frames for predictiona and fine all-atom granularity via a hierarchical decomposition in which we predict coarse residue-transform based inter-residue geometries along with sub-frame deviations from ideality, which can be in turn be composed (equivariantly) to yield the final structure.

Convex problem How can we define a consensus structure given a set of predictions of inter-residue geometries, some of which may agree and some of which may disagree? This problem is naturally formulated as an optimization problem. Given a collection of pairwise inter-residue geometry predictions and confidences $\{T_{ij}, w_{ij}\}_{ij \in \varepsilon}$, we score a candidate structure $\{T_i\}_{i=1}^N$ via a weighted loss U that measures the agreement between the current pose of each residue $T_i$ and the predicted pose of the residue given each neighbor $T_i$ and the predicted geometry $T_{ji}$ as $$U(\{T_i\}; \{w_{ij}, T_{ij}\}) = \sum_{i,j} w_{ij} |T_i - T_j \circ T_{ji}|^2$$

$$= \sum_{i,j} w_{ij} |O_i - O_j O_{ji}|^2 + w_{ij} |t_i - (O_j t_{ji} + t_j)|^2$$

We wish to optimize each local pose $T_i$ with neighbors fixed as $$T_i^\star \leftarrow \underset{T_i}{\operatorname{argmin}} U(\{T_i\}; \{w_{ij}, T_{ij}\}).$$

This problem of finding the local "consensus pose" for a residue $T_i^*$ given its neighborhood is a convex optimization problem, the solution to which can be realized analytically as a weighted average with projection, $$T_i^\star = \left( Proj_{SO(3)}\left( \sum_j p_{ij} O_j O_{ji} \right), \sum_j p_{ij}(O_j t_{ji} + t_j) \right), \text{ where } p_{ij} = \frac{w_{ij}}{\sum_j w_{ij}}$$

where the projection operator may be implemented via SVD as in the Kabsch algorithm [60] for optimal RMSD superposition. If we iterate this update multiple times to all positions in parallel, we obtain a parallel coordinate descent algorithm which can rapidly equilibrate towards a global consensus (FIG. 20).

Two-parameter uncertainty models The above iteration leverages an isotropic uncertainty model in which the error model for the translational component is spherically symmetric and coupled to the uncertainty in the rotational component of the transform. We may also consider anisotropic uncertainty models where these confidences are decoupled. In the first of these, we decouple the weight $w_{ij}$ into separate factors for the translational and rotational components of uncertainty as $w_{ij}^T$ and $w_{ij}^\angle$ respectively. The overall error model being optimized is then $$U(\{T_i\}; \{w_{ij}, T_{ij}\}) = \sum_{i,j} w_{ij}^\angle |O_i - O_j O_{ji}|^2 + w_{ij}^T |t_i - (O_j t_{ji} + t_j)|^2$$

This makes intuitive sense when the network will possess high confidence about the relative position of another residue but not its relative orientation, and may still be solved analytically by weighted averaging with projection.

Three-parameter uncertainty models In a more sophisticated form of anisotropic uncertainty, we extend this framework to ellipsoidal error models bespoke to each ij, while retaining a closedform iteration update using approaches from sensor fusion. We parameterized this anisotropic error model by separating this precision term w into three components: $w_{ij}^\angle$ for rotational precision and two components for position: $w_{ij}^\parallel$ for radial distance precision, and $w_{ij}^\perp$ for lateral precision. The radial and lateral precision terms are each eigenvalues of the full 3×3 precision matrix $P_{ij}$ for translation errors (i.e., inverse covariance matrix under a multivariate normal error model):

$$P_{ij} = w_{ij}^\parallel \pi_{ij} + w_{ij}^\perp (I - \pi_{ij}), \quad \pi_{ij} = \frac{(O_j t_{ji})(O_j t_{ji})^T}{(O_j t_{ji})^T (O_j t_{ji})}$$

where $\pi_{ij}$ is the projection matrix onto the radial direction from $t_j$ to the predicted position $O_j t_{ji} + t_j$ of $t_i$, and $I - \pi_{ij}$ is the projection matrix onto lateral translations (spanned by the remaining two eigenvectors). These anisotropic terms finally combine as $$U(\{T_i\}; \{w_{ij}, T_{ij}\}) = \sum_{i,j} (O_j t_{ji} + t_j - t_i)^T P_{ij} (O_j t_{ji} + t_j - t_i) + w_{i,j}^\angle |O_i - O_j O_{ji}|^2$$

$$= \sum_{i,j} w_{ij}^\parallel |\pi_{ij}(O_j t_{ji} + t_j - t_i)|^2 + w_{ij}^\perp |(I - \pi_{ij})(O_j t_{ji} + t_j - t_i)|^2 + w_{ij}^\angle |O_i - O_j O_j|^2.$$

As we expect that the radial precision always exceeds the lateral precision, our neural predictor outputs three positive parameters ($w^\perp$, $w^\parallel - w^\perp$, $w^\angle$). Whereas the isotropic objective above is solved by weighted averaging, the anisotropic translation part of this objective is solved by a standard Gaussian product operation from sensor fusion [104], $$t_i^\star = t_i + \left( \sum_j P_{ij} \right)^{-1} \sum_j P_{ij} (O_j t_{ji} + t_j - t_i).$$

Figure 21:
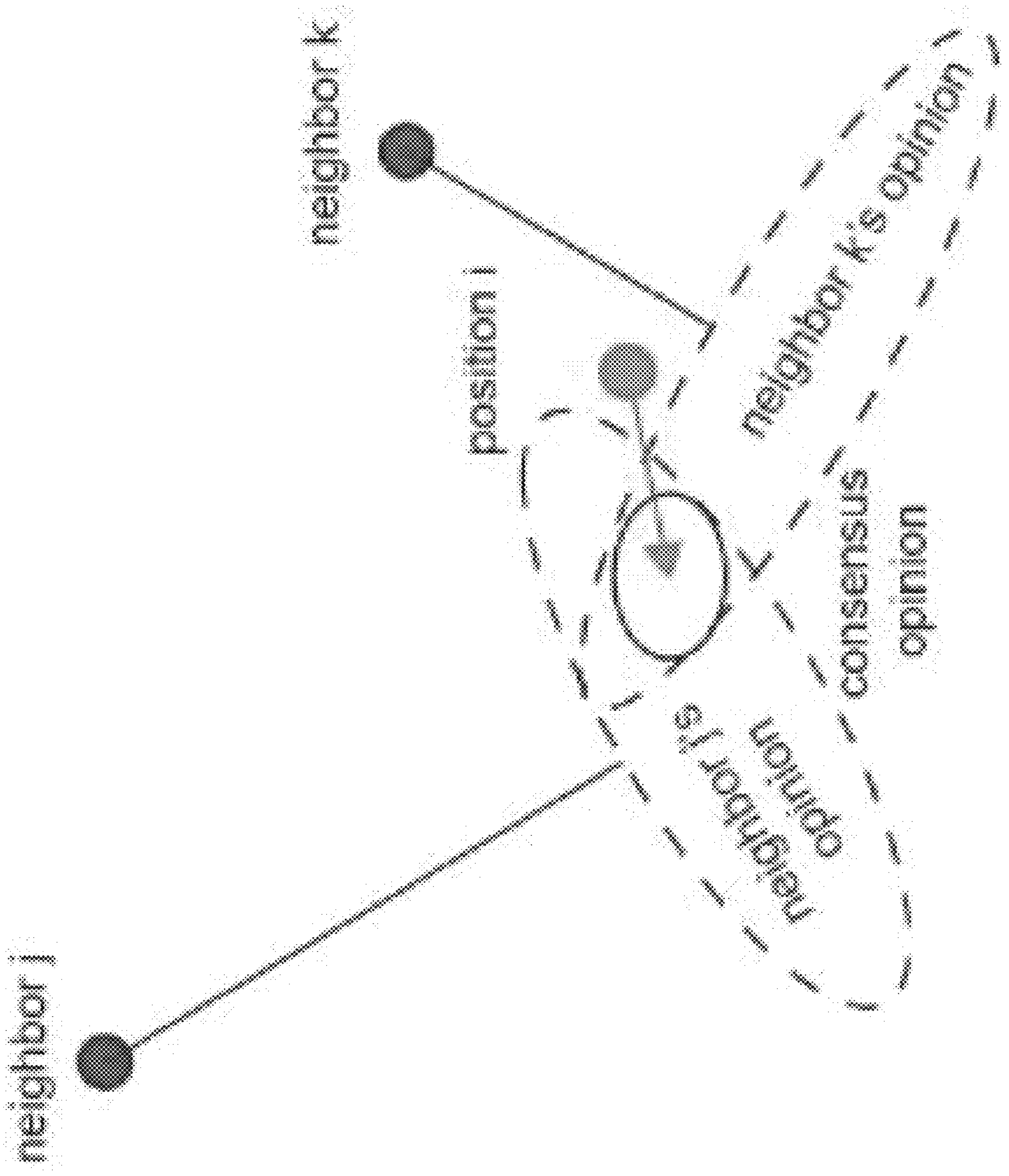
FIG. 21 shows that anisotropic confidence models capture asymmetric uncertainty in predicted inter-residue geometries.

We illustrate this anisotropic Gaussian fusion operation in FIG. 21.

E.3 Equivariant Prediction of Backbone Atoms

The parallel coordinate descent procedure optimizes residue poses $\{T_i\}$ but our diffusion model (Appendix C) requires unconstrained atomic prediction of all backbone heavy atoms. We can straightforwardly augment the above predictions in an equivariant manner by predicting local coordinates $\{t_{iN}, t_{iC_\alpha}, t_{iC}, t_{iO}\}_{i=1}^N$ for each atom position relative to the parent residue pose from graph node embeddings. To ease learning, we parameterize these predictions as residual updates from the ideal backbone geometry positions. To build the final atomic structure, we simply right-compose these local coordinate predictions $t_{i\,ATOM}$ with each parent pose $T_i$ as $$(0, x_i^{ATOM}) = T_i \circ (0, t_{i\,ATOM})$$

We schematize this combined method in Algorithm 2. These predictions will be equivariant because they are right-composed with the parent residue poses, which are equivariant because they are built from relative, equivariant projection from the initial geometry $x_t$.

Algorithm 2 Equivariant Consensus Structure from Inter-residue Geometries

Require: $\{T_{ij}, w_{ij}\}_{ij \in \varepsilon_g(x)}$ ▹ Predicted inter-residue geometries and confidence weights
Require: $\{t_{iN}, t_{iC_\alpha}, t_{iC}, t_{iO}\}]_{i=1}^{N}$ ▹ Predicted local atomic geometries
Require: $\{T_i\}_{i=1}^{N}$ ▹ Initial residue poses
Require: M ▹ Number of parallel coordinate descent iterations $\forall$ i, j, $p_{ij} \leftarrow \frac{w_{ij}}{\sum_j w_{ij}}$ ▹ Compute confidence weights for each $m \in 1 \ldots M$ do
  $\forall i\ T_i \leftarrow (\mathrm{Proj}_{SO(3)}(\Sigma_j\, p_{ij} O_j O_{ji}), \Sigma_j\, p_{ij}(O_j t_{ji} + t_j))$ ▹ Locally optimize poses
end for
for each ATOM $\in$ {N, $C_\alpha$, C, O] do
  $\forall i(0, x_i^{ATOM}) \leftarrow T_i \circ (0, t_{i\ ATOM})$ ▹ Build atoms
end for
return x ▹ Output atomic backbone geometry FIG. 21: Anisotropic confidence models capture assymetric uncertainty in predicted inter-residue geometries. Position i is forced towards its consensus position which is the mean of a fusion of anisotropic Gaussians. Here we visualize the covariance ellipsese of component the 1 Gaussians, i.e. the inverses of the precision matrices predicted by our network.

E.4 Time-Dependent Post-Prediction Scaling

It has been helpful in prior diffusion modeling works to parameterize the denoising network output in a way that can behave as an identity function for low noise levels early in training [57]. We found this to be helpful as well and parameterized the final prediction as.

$$\hat{x}_\theta(x_t, t) = \eta_t \tilde{x}_\theta(x_t, t) + (1 - \eta_t) x_t,$$

where $\tilde{x}_\theta(x_t, t)$ is the output from the inter-residue consensus and the time dependent 'gate' $\eta_t$ was set in two ways:

Output Scaling A Set $\eta_t$ to scale as $\sqrt{1\text{-SSNR}_t}$ with a learnable offset by parameterizing as $\eta_t = S(S^{-1}(\mathrm{SSNR}_t) + u_t^\theta)$ where S(·) is the sigmoid function and up is parameterized by a small MLP.

Output Scaling B Set $\eta_t$ to scale as $\sqrt{1-\mathrm{SSNR}_t}$ with a learnable offset by parameterizing as $\eta_t = 1-(1-S(S^{-1}(\mathrm{SSNR}_t)+u_t^\theta)) \| (\mathrm{SSNR}\ _t > \mathrm{CUTOFF})$ where S(·) is the sigmoid function, $u_t^\theta$ is parameterized by a small MLP, and CUTOFF=0.99. This is similar to the previous scaling but almost always disabled except for the highest values of the signal-to-noise ratio.

F Chroma Architecture

Chroma builds a joint distribution of the sequence and and all-atom structure of protein complexes via the factorization $$\log p(x, s, \chi) = \underbrace{\log p(x)}_{\text{backbone likelihood}} + \underbrace{\log p(s \mid x)}_{\text{sequence likelihood}} + \underbrace{\log p(\chi / x, s)}_{\text{side-chain likelihood}}.$$

We model these likelihoods with two networks: a backbone network trained as a diffusion model to model p(x) and a design network which models sequence and side chain chains conditioned on backbone structure. Both networks are based on a common graph neural network architecture, and we visualize the overall system in FIGS. 22A-22B. We list important hyperparameters for the backbone network in Supplementary Table 2 and for the design network in Supplementary Table 3. We design sequences by extending the framework of [87] and factorizing joint rotamer states autoregressively in space, and then locally autoregressively per side-chain $\chi$ angle within a residue as done in [105]. For the sequence decoder, we explore both autoregressive decoders of sequence (pictured in FIGS. 22A-22B) and conditional-random field decoding of sequence, which was also explored in concurrent work [106].

F.1 Graph Neural Networks for Protein Structure

Figure 22A:
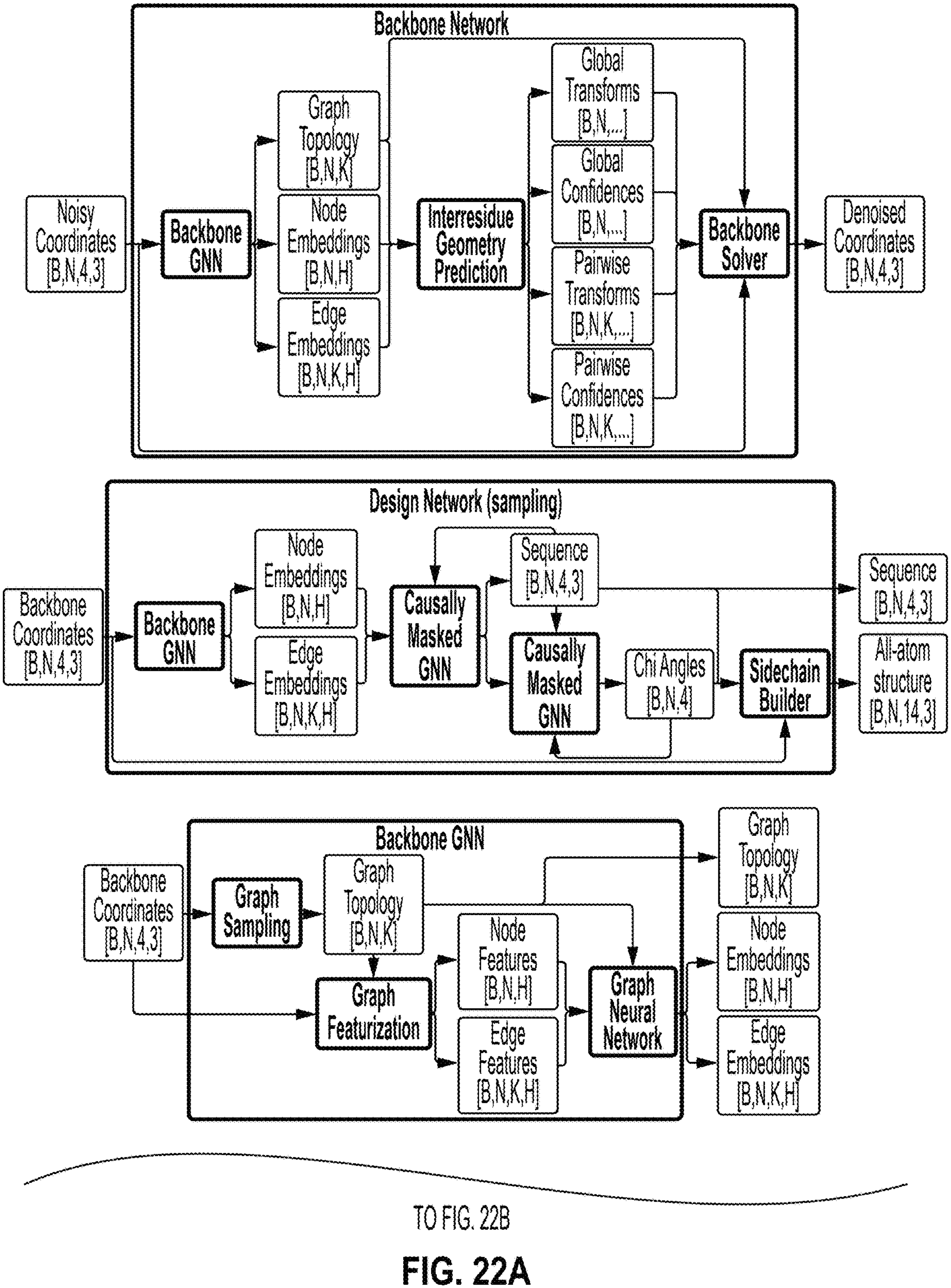
FIGS. 22A-22B show that Chroma is composed of graph neural networks for backbone denoising and sidechain design.
Figure 22B:
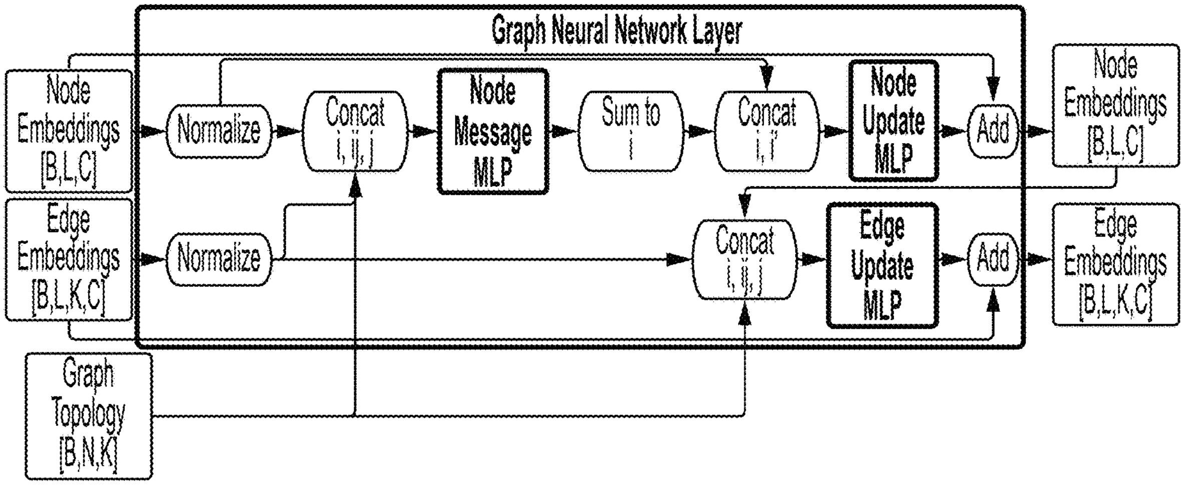

Graph Neural Network All of our neural network models are based on graph neural networks that reason over 3D structures of proteins by transforming them into attributed graphs built from rigid transformation invariant (SE(3)-invariant) features. The building block from which these models are built is presented in Algorithm 3. This approach has been pursued in several prior works for sequence design [87,107,108] and our primary architectural innovations to extend this to all-atom protein complex generative modeling are two-fold:

FIGS. 22A-22B: Chroma is Composed of Graph Neural Networks for Backbone Denoising and Sidechain Design.

- We propose random graph neural networks that add in long-range connections and reasoning while preserving sub-quadratic computational complexity (Appendix D)
- We introduce a method for efficiently and differentiably generating protein structures from predicted inter-residue geometries based on parallel coordinate descent (Appendix E)

Algorithm 3 Graph Neural Network Layer

Require: $n_i$, $e_{ij}$ ▹ Node and edge embeddings with shapes (B, N, C) and (B, N, K, C)
Require: N(i) ▹ Graph topology specifying neighbors of each residue
 for each $i \in [L]$ do
  $\tilde{n}_i \leftarrow \mathrm{NodeLayerNorm}(n_i)$
  $\tilde{e}_{ij} \leftarrow \mathrm{EdgeLayerNorm}\ (e_{ij})$
  $p_{ij} \leftarrow \mathrm{Concatenate}_{j \in N(i)}(\tilde{n}_i, \tilde{n}_j, \tilde{e}_{ij})$
  $m_{ij} \leftarrow \mathrm{MessageMLP}\ (p_{ij})$
  $m_i \leftarrow \mathrm{Aggregate}_j(m_{ij})$ -continued

| Algorithm 3 Graph Neural Network Layer | |
|---|---|
| $p_i \leftarrow$ Concatenate ($\tilde{n}_i$, $m_i$) | |
| $n_i \leftarrow n_i$ + NodeUpdateMLP ($p_i$) | |
| end for | |
| for each $i \in [N]$ do | |
| for each $ij \in N(i)$ do | |
| $p_{ij} \leftarrow$ Concatenate$_{j \in N(i)}$($\tilde{n}_i$, $\tilde{n}_j$, $\tilde{e}_{ij}$) | |
| $e_{ij} = e_{ij}$ + EdgeUpdateMLP ($p_{ij}$) | |
| end for | |
| end for | |
| return $n_i$, $e_{ij}$ | ▹ Updated node and edge embeddings |

Featurization We represent protein structure as an attributed graph with node and edge embeddings computed as SE(3)-invariant features of the input backbone. For the node features we encode local geometry via bond lengths and the backbone dihedral angles lifted to the unit circle via paired sin and cos featurization. We encode the inter-residue geometries between each pair of nodes ij with the following edge features:

Inter-atomic distances: The distances among all atoms at residues i and j, i.e. the 8×8 distance matrix, lifted into a radial basis via $f_i(D_{ab})=e^{(D_{ab}-\mu_i)^2/\sigma_i^2}$ of for $1 \leq i \leq 20$ and centers $\rho_i$ spaced linearly on [0,20] and $\sigma_i=1$.

Inter-atomic directions: The unit vector from $x_i^{C_\alpha}$ at residue i to atom b in residue j, concatenated over all atoms $b \in \{N, C, C_\alpha, O\}$ in j.

Chain distance: Tuple encoding (1) chain distance featurized as (log (|i−j|+1) for residues i, j lying along the same chain, else 0, and (2) a binary flag indicating if i and j are in different polymer chains.

Transform features: For two frames $T_a=(R_a, t_a)$ and $T_b=(R_b, t_b)$ let $T_{a\rightarrow b}$ denote the transform that maps coordinates in frame $T_a$ to coordinates in frame $T_b$. For each residue i, define two frames, a local frame $T_i$ and chain frame $T_{c(i)}$. The chain frame is obtained by using Grahm-schmidt to pass to an orthonormal set of vectors [$n_1$, $n_2$, $n_3$] starting with N–$C_\alpha$ and $C_\alpha$–C vectors averaged across the chain. The following transforms are computed: $T_{i\rightarrow j}$, $T_{i\rightarrow c(j)}$, $T_{c(i)\rightarrow c(j)}$. For each of these transforms, the features log (|t|), t, and quanterion (R) are computed and concatenated.

TABLE 2

ChromaBackbone Hyperparameters.

| Category | Hyperparameter | Value in ChromaBackbone v0 | Value in ChromaBackbone v1 |
|---|---|---|---|
| Diffusion Process | Covariance Model | Globular Monomer | Globular Complex |
| | Noise Schedule | Log-linear SNR (−7, 13.5) [55] | Log-linear SNR (−7, 13.5) |
| Graph Features | Node Features | Internal Coordinates | Internal Coordinates |
| | Edge Features | Atom distances, Atom directions, Chain distances, Transforms | Atom distances, Atom directions, Chain distances, Transforms |
| | Edges per Node, k | 60 | 60 |
| | Number of Nearest Neighbor Edges | 20 | 20 |
| | Number of Random Edges | 40 | 40 |
| | Random Edge Type | Inverse Cubic | Inverse Cubic |
| Graph Neural Network | Number of GNN layers | 12 | 12 |
| | Node Embedding Dimension | 512 | 512 |
| | Edge Embedding Dimension | 256 | 256 |
| | Node MLP Dimension | 512 | 512 |
| | Edge MLP Dimension | 128 | 128 |
| | Dropout p | 0.1 | 0.1 |
| Denoising Solver | Inter-residue Parameterization | Direct $T_{ij}$ prediction | Update from $T_{ij}(x_t)$ |
| | Uncertainty Model | Isotropic (1-parameter) | Decoupled (2-parameter) |
| | Number of Iterations | 3 | 10 |
| | Post-Process Scaling | A | B |
| Loss Function | Likelihood Loss | ELBO | ELBO |
| | Auxilliary Losses | ELBO-weighted/MSE | $\mathcal{D}_{global}$, $\mathcal{D}_{fragment}$, $D_{ij}$SE, $\hat{T}_{ij}$SE |
| Total Number of Parameters | | 18.6M | 18.6M |
| Total Number of Training Steps | | 1.6M | 1.8M |

Equivariance Because the input features are SE(3) invariant and the update layer (see section E for details) is SE(3) equivariant, the ChromaBackbone network is SE(3) equivariant and the ChromaDesign network is SE(3) invariant.

F.2 ChromaBackbone

The backbone network parameterizes an estimate of the optimal denoiser $\hat{x}_\theta(x_t, t)$ and combines a graph neural network described in the previous section with the inter-residue consensus layer described in Appendix E. We trained two major versions used throughout this work (aside from the ablation study), with hyperparameters described in Table 2.

F.3 ChromaDesign

The design network parameterizes the conditional distribution of sequence given structure $p_\theta(s|x)$ by combining the graph neural network encoder described in the previous section with sequence and side-chain decoding layers. We consider both a Potts decoder architecture which admits compact and fast constrained sampling with conditioning or auxiliary objectives, as well as an autoregressive decoder architecture for capturing higher-order dependencies in the sequence and modeling sidechain conformations given sequence and structure.

F.4 Related Work

Generative models based on diffusion There has been significant interest in generative models of protein structure, and diffusion models have seen particularly rapid adoption towards the problem.

TABLE 3

ChromaDesign Hyperparameters.

| Category | Hyperparameter | Value in ChromaDesign Potts | Value in ChromaDesign Multi |
|---|---|---|---|
| Diffusion Process | Covariance Model | None | Globular Complex |
| | Noise Schedule | N/A | Log-linear SNR (−7, 13.5) |
| Graph Features | Node Features | Internal Coordinates | Internal Coordinates |
| | Edge Features | Atom distances, Atom directions, Chain distances | Atom distances, Atom directions, Chain distances, Transforms |
| | Number of edges per node, k | 40 | 60 |
| | Number of kNN edges | 40 | 60 |
| | Number of inverse cubic edges | 0 | 0 |
| | Number of GNN layers | 6 | 10 |
| Graph Neural Network | Node embedding dimension | 128 | 128 |
| | Edge embedding dimension | 128 | 128 |
| | Node MLP hidden dimension | 512 | 512 |
| | Edge MLP hidden dimension | 128 | 128 |
| | Dropout p | 0.1 | 0.1 |
| | Label smoothing | 0.1 | 0.1 |
| Sequence Decoder | Type | Potts model, First order | Potts model, First order, Autoregressive |
| Sidechain Decoder | Type | N/A | Autoregressive |
| Chi decoder | Number of $\chi$ bins | N/A | 36 |
| Total Number of Parameters | | 3.9M | 13.8M |

This has included diffusion models for protein monomers represented as coarse $C_\alpha$ coordinates [83], internal coordinates [94], and rigid frames [109, 110], as well as for protein complexes represented as rigid frames [111]. Beyond backbone-only models, there have also been joint generative frameworks which model all-atom protein structure with mixed diffusions over backbone, sequence, and side-chain degrees of freedom [59, 112]. Furthermore, we are beginning to see experimental validation of diffusion-based models for structure and/or sequence [111, 113] and for partially joint sequence-structure models that combine a language model prior with deterministic structure prediction [114].

One common theme of generative models for proteins thus far has been dense reasoning in which, to generate complex molecular systems like proteins or protein complexes, learning frameworks must reason over all possible pairs of interactions in a system. While these approaches will, by construction, always be able to perform as well as sparsely-connected approaches, Chroma provides evidence that simpler frameworks based entirely on sparse reasoning and knowledge of domain structure can be sufficient to build a complete joint model for complex multi-molecular systems such as protein complexes. We anticipate that this sufficiency argument may be important for two reasons: Firstly, subquadratic scaling $\mathcal{O}(N \log N)$ of algorithms has been a foundational paradigm for modeling the physical world from molecular [115] to cosmological systems [85]. Second, and perhaps more speculatively, it may be argued that, given multiple algorithms with similar performance, simpler and more computationally efficient algorithms are more likely to be robust and to generalize [116].

Potts Decoder In the Potts formulation of the ChromaDesign network, we factorize the conditional distribution of sequence as a conditional Potts model, a type of conditional random field [53], with likelihood $$p_\theta(s \mid x) = \frac{1}{Z(x, \theta)} \exp\left(-\sum_i h_i(s_i; x) - \sum_{i<j} J_{ij}(s_i, s_j; x)\right)$$

where the conditional fields $h_i(s_i; x)$ and conditional couplings $J_{ij}(s_i; s_j; x)$ are parameterized by the node and edge embeddings of the graph neural network, respectively. Advantages of the Potts decoders include that they admit fast global optimization even when combined with conditioning constraints or co-objectives via as simulated annealing or gradient-based samplers ([117]) and that they have been highly validated experimentally as sufficient generative models for generating diverse and functional samples when trained on protein families. A disadvantage is that they are limited beyond modeling second order effects and require many more iterations of Monte Carlo sampling than one-shot ancestral sampling of autoregressive models.

Figure 23:
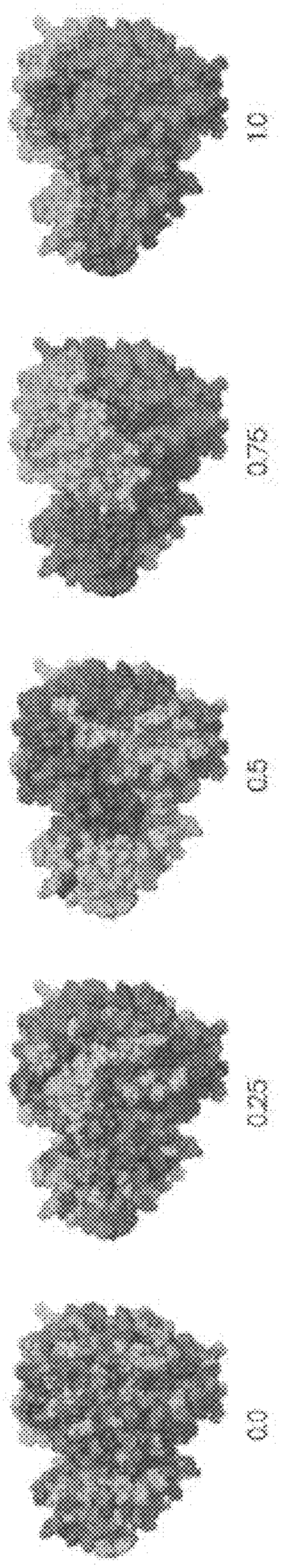
FIG. 23 shows that randomized autoregression orders with spatial smoothing vary the typical spatial context for sequence modeling.

FIG. 23: Randomized autoregression orders with spatial smoothing vary the typical spatial context for sequence modeling. Uniformly random autoregression orders (left) are spatially uncorrelated and as a result induce highly disordered contexts which are unlike the conditionals used during sub-structure design tasks. Uniformly random orderings can be transformed into spatially coherent orderings by applying tunable spatial smoothing to the original ordering values, followed by ARGSORT. We apply spatial smoothing with by local neighborhood averaging on a k-NN graph. Intermediate strengths of spatial smoothing produce locally coherent orderings (middle), while strong smoothing producing crystallization-like, coherent traversals of the entire structure (right).

We uniformly sample $\mu_{smooth} \sim \mathcal{U}(0,1)$ at training time.

Autoregressive Decoder We build on the theme of using graph neural networks with autoregressive decoders for sequence design [98, 107, 108] and factorize the conditional distribution of sequence given structure autoregressively as $$p_\theta(s \mid x) = \prod_i p_\theta(s_{\pi_i} \mid s_{\pi_{i-1}}, \ldots, s_{\pi_1}, x)$$

where $\pi$ is a permutation specifying an decoding order for the sequence. We sample random traversals with a randomly sampled amount of spatial correlation, as shown in FIG. 23, that may better align with conditionals encountered at design time and enable more spatially structured decompositions that mix more effectively in causally-masked message passing.

Sidechain Decoding We model the a conditional distribution of side chain conformations given sequence and backbone structure by modeling the $\chi$ angles with an autoregressive decomposition as $$p_\theta(\chi \mid s, x) = \prod_i p_\theta(\chi_{\pi_i} \mid \chi_{\pi_{i-1}}, \ldots, \chi_{\pi_1}, s, x)$$

where the conditional joint distributions $p_\theta(\chi_{\pi_i} | \chi_{\pi_{i-1}}, \ldots, \chi_{\pi_1}, s, x)$ at each residue locally factorize as up to four discrete, sequential decisions as in [105]. We model model these with empirical histograms for each angular degree of freedom binned at 36 bins, i.e. with 10° angular resolution. During sampling, we convert the discrete binned probability masses into linearly interpolated probability densities, giving a distribution over angles that is fully supported on the hypertorus.

G Training

G.1 Dataset

Processing We constructed our training dataset from a filtered version of the Protein Data Bank [118] queried on 2022 Mar. 20. We filtered for non-membrane X-ray protein structures with a resolution of 2.6 Å or better and reduced redundancy by clusteing homologous sequences with USEARCH [119] at 50% sequence identity and selecting one sequence per cluster. Additionally, because antibody folds exhibit a large amount of sequence and structural diversity along with significant biotherapeutic relevance, we enriched our redundancy-reduced set 1726 non-redundant antibodies that were clustered at a 90% sequence identity cutoff. This yielded 28,819 complex structures which were transformed into their biological assemblies by favouring assembly ID where the authors and software agreed, followed by authors and finally by software only. Missing side-chain atoms were added with pyRosetta [120].

Splitting We split the data set with into 80%/10%/10% train, validation and test splits by minimizing the sequence similarity overlap using entries of PFAM family ID, PFAM clan ID [121], UniProt ID [122] and MMSEQ2 cluster ID at a 30% threshold [123]. To accomplish this, we construct a similarity graph in which each PDB entry is represented by a node connected to other entries that share at least one identical annotation. Connected sub-graphs are identified and broken apart by iteratively deleting the most central annotations until there are 50 or fewer connected nodes. Using this procedure, we increased the fraction of test annotations with no representation in the training set (versus a random split) from 0.1% to 9% for Pfam clan, from 10% to 59% for Pfam family, from 50% to 82% for MMSEQ30 cluster, and from 70% to 89% for Uniprot ID.

G.2 Optimization

Backbone network We trained ChromaBackbone v1 on 8 Tesla V100-SXM2-16 GB using the Adam optimizer to optimize a sum of the regularized ELBO loss (Appendix A) and an unweighted sum of the losses described in (Appendix A.3). We linearly annealed the learning rate from 0 to $2\times10^{-4}$ over the first 10,000 steps and trained for a total of 1,796,493 steps. Due to the linear scaling memory footprint of our model, we dynamically pack complexes into mini-batches to approach a target number of residues per batch which was 4,000 residues per GPU and thus 32,000 residues per step. We estimated the final model parameters with an exponential moving average (EMA) of per-step parameter values with a decay factor of 0.999 [125]. We trained ChromaBackbone v0 similarly but without EMA estimation, and we refer to checkpoints from specific epochs of training as ChromaBackbone vo. XXXX where XXXX is the epoch number.

Design network We trained ChromaDesign Potts and ChromaDesign Multi with the same framework as the backbone networks but a few specific modifications: We trained ChromaDesign, Potts in a time-invariant manner on uncorrupted samples $x_0$ to optimize a pairwise composite log-likelihood approximation of the Potts log-likelihood [126], averaged to nats per residue. We trained ChromaDesign Multi in a time-aware manner on samples $x_t$ from the diffusion process. As a training objective we used the sum of the pairwise composite log likelihood loss for the Potts decoder (residue-averaged) along with the average per residue log likelihood losses for the three other decoder 'heads': the autoregressive sequence decoder, the marginal sequence decoder (which independently predicts each residue identity $s_i$ from structure $X_i$), and the autoregressive side chain predictor.

TABLE 4

Sampling hyperparameters. We review all configurations for sampling used across both in silico and wet lab experiments. The (★) symbol in the T column indicates integrating with an Improved-Euler-like integrator. The (◇) symbol in the λ column corresponds to keeping inverse temperature fixed throughout integration instead of the annealing presented in Appendix A.

| Experiments | Sample Type | T | λ | ψ | Backbone Model | Design Model | Complexity Penalty |
|---|---|---|---|---|---|---|---|
| Computational | Unconditional | 500 | 10 | 2 | Multiple | Multiple | LCP |
| | Ablation Study | 500 | 10 | 2 | Multiple | ChromaDesign Potts | LCP |
| | Substructure | 400 | 8◇ | 2 | ChromaBackbone v1 | ChromaDesign Multi | LCP |
| | Symmetry | 500★ | 8◇ | 8 | ChromaBackbone v1 | ChromaDesign Multi | LCP |
| | Shape | 3000★ | 10 | 2.3 | ChromaBackbone v1 | ChromaDesign Multi | LCP |
| | Classification | 2000 | 10 | 2 | ChromaBackbone v1 | ChromaDesign Multi | LCP |
| | Language | 500 | 10 | 2 | ChromaBackbone v1 | ChromaDesign Multi | LCP |
| Wet Lab | Unconditional I | 1000 | 10 | 2 | ChromaBackbone v0.4999 | ChromaDesign Potts | UP |
| | Unconditional II | 2000 | 10 | 0.1 | ChromaBackbone v0.4998 | ChromaDesign Potts | LCE |
| | Conditional I | Multiple | 10 | 2 | ChromaBackbone v0.4999 | ChromaDesign Potts | UP |
| | Conditional II | 2000 | 10 | 0.9 | ChromaBackbone v0.4999 | ChromaDesign Potts | UP |

Sampling

We sampled proteins from Chroma by first generating backbone structures and then designing sequences conditioned on the backbone. Unless otherwise specified, we generated structures by integrating the reverse SDE with $\lambda_0=10$.

H.1 Sequence Design

For all design tasks we experimented with both autoregressive and Potts-based sequence sampling but ultimately decided on Potts-based samples as they facilitated more thorough global global optimization with sequence complexities penalties. It has been widely observed that low temperature sampling from likelihood-based models often biases towards low complexity sequences [69], and we also have observed this phenomenon to happen on occasion during conditional sequence design. While it is not impossible that low-complexity sequences may still fold in silico and in vivo, we wish to be able to control the level of sequence complexity at design time.

We control sequence complexity via penalized Markov-Chain Monte Carlo (MCMC) with our conditional Potts models. We define the total energy as the sum of the conditional Potts energy, plus an optional sequence complexity penalty, and sample sequences using 10 independent cycles of simulated annealing Monte Carlo (MC), each with 4000·N steps, where N is the length of the protein.

H.1.1 Unique Permutations (UP) Restraint

The first restraint type that we used is based on the number of unique permutations of the designed sequence, Ω[127]:

$$\Omega = \log\left(\frac{L!}{\prod_{i=1}^{N} n_i!}\right) \tag{6}$$

where N is the number of different amino acids in the sequence, $n_i$ is the number of occurrences of amino acid type i. This restraint simply applied a linear penalty when Ω dropped below a desired threshold $\hat{\Omega}$:

$$C_1 = \begin{cases} \hat{\Omega} - \Omega, & \text{if } \Omega < \hat{\Omega} \\ 0, & \text{otherwise} \end{cases} \tag{7}$$

We chose $\hat{\Omega}$ to be one standard deviation below the empirical mean for PDB sequences of length L. Specifically, we found the empirical mean and standard deviation among PDB sequences to depend on L as $2.855\cdot(1+9.927\cdot L^{-0.894})^{-1}$ and $0.287\cdot(1+0.0447\cdot L^{0.810})^{-1}$, respectively.

H.1.2 Local Composition Entropy (LCE) Restraint

Our second sequence complexity restraint was based on the mean sequence entropy over all local windows:

$$C_2 = \frac{L}{L-w+1}\sum_{i=1}^{L-w+1} S_i \tag{8}$$

where w is window length (we used w=30 throughout this study) and $S_i$ is the entropy of the i-th window.

H.1.3 Local Composition Perplexity (LCP) Restraint

Our third sequence complexity restraint also used local-window entropies, but applied a quadratic penalty on corresponding perplexities when the entropy fell below a predefined threshold:

$$C_3 = \frac{L}{L-w+1}\sum_{i=1}^{L-w+1}\left(e^{\hat{S}} - e^{S_i}\right)^2 \Delta(S_i < \hat{S}) \tag{9}$$

where $\hat{S}$ is the threshold entropy value and $\Delta(S_i<\hat{S})$ is an indicator variable of whether $S_i$ falls below $\hat{S}$. Here, we used w=30 and as $\hat{S}$ we chose the 5th percentile of 30-residue local window entropies in PDB sequences (~2.32 nats). All three restraints effectively restricted the sampling of sequences from Potts models to regions of expected sequence complexity for native-like sequences, with the last two having the advantage of not introducing potentially undesired global inter-residue correlations.

I Evaluation: Unconditional Samples

I.1 Sample Generation

Figure 24:
FIG. 24 shows random single-chain samples from ChromaBackbone-v1.

We generated three sets of unconditional protein samples using Chroma. All sets used the same parameters: 200 steps, $\lambda_0$=10, and $\psi$=2. Of these three sets, we used ChromaBackbone v0 and V1 to generate two sets of single-chain proteins and ChromaBackbone v1 to generate one set of multi-chain proteins. The single-chain sets each contained 50,000 samples and the lengths were drawn from a "1/length" distribution, where the probability of a protein chain's length was inversely proportional to its length constrained to a minimal length of 50 and a maximal length of 1,000 residues. The multi-chain set contained 10,000 samples with the length distribution taken from the empirical statistics of chain lengths in PDB complexes. Specifically, for each Chroma sample, we drew a random protein complex from the PDB and took the number of chains and their lengths from that complex. FIG. 24 and FIG. 25, show randomly-chosen (i.e., non-cherry picked) samples from the resulting sets for single-chain and multi-chain examples, respectively.

FIG. 24: Random single-chain samples from ChromaBackbone-v1.

FIG. 25: Random complex samples from ChromaBackbone-v1.

TABLE 5

Structural metrics used for characterizing backbone geometries

| Metric | Description | Normalization |
|---|---|---|
| Secondary structure content ($SS_i$) | Distribution of Helix, Strand, Coil for given structure | none |
| Mean Residue Contact ($C_{mean}$) | Average number of contacts per residue for any given structure | none |
| Long-range Residue Contact ($C_{long}$) | Number of long-range contacts per residue per residue; long-range residue interaction means a pair of interacting residues separated by 24 or more residues in sequence | none |
| Contact Order (CO) | Average sequence distance between contacting residues normalized by the total length of the protein; higher contact orders generally indicate longer folding times | $CO/N^{-0.3}$[133] |
| Radius of Gyration ($R_g$) | Root mean square distance of structure's atomic coordinates from its center of mass | $R_g/N^{0.4}$[81] |

I.2 Backbone Geometry Statistics

We evaluated the structural validity of Chroma generated single chain structures by characterizing their secondary structures and residue interactions alongside a non-redundant subset of PDB database (Table 5). We evaluated the distribution of secondary structures (α-helix, β-strands, and coil) using Stride [132]. We determined residue interaction by any pairwise residue (C–α to C–α) distance less than 8 Å and computed mean and long-range residue contacts. We computed contact order [133] and radius of gyration [81] by length normalizing them according to their corresponding empirical power laws. We normalized all metrics except for secondary structures for FIG. 26.

1.3 Tertiary Motif Analysis

We previously described that native protein structures exhibit considerable degeneracy in their use of local tertiary backbone geometries, such that relatively few local tertiary motifs account for the majority of the observed structure space [134]. These tertiary motifs, or TERMs, consist of a central residue, its backbone-contiguous neighbors, neighboring residues capable of contacting the central residue, and their backbone-contiguous neighbors [134, 135]. Depending on how many contacting residues are combined into the motif, TERMs can be distinguished as self, pair, triple, or higher-order, corresponding to having zero, one, two, or more contacting neighbors (FIG. 26). To compare the local geometry of Chroma-generated backbones with that of native structures, we randomly sub-sampled self, pair, triple, and full TERMs (i.e., TERMs containing all contacting residues for a given central residue) within Chroma backbones and identified the closest neighbor (by backbone RMSD) to each within "search database"—i.e., the training set used for Chroma. We performed a similar analysis on a set of native proteins not contained within the search database—i.e., the test set used for Chroma. Although the test and training sets had been split by chain-level sequence homology, we took further care to exclude any apparent homologs of native TERMs from consideration as matches. To this end, we compared the local 31-amino acid sequence windows around each TERM segment and its corresponding match, with any pairings reaching 60% or more sequence identity not being allowed to participate in a match.

FIG. 26: Unconditional backbone samples reproduce both low and high order structural statistics of natural proteins. a. A set of 50,000 single-chain samples from the unconditional ChromaBackbone-v0 at inverse temperature $\lambda_0$=10 has structural properties that are similar to natural protein structures from the PDB. ChromaBackbone-v0 samples reproduce length-dependent scaling of contact order [128] and radius of gyration. b. Across a set of 50,000 single-chain samples from the unconditional ChromaBackbone-v1 at inverse temperature $\lambda_0$=10 and a set of 500 single-chain samples from the unconditional ChromaBackbone-v1 at inverse temperature $\lambda_0$=1, there are differences in secondary structure content and contact order compared to natural protein structures from the PDB. There is generally higher preference for helices over strands and the samples are more compact than those found in the PDB. c. The distribution of closest-match RMSD for TERMs of increasing order originating from native or Chroma-generated backbones (with inverse temperature $\lambda_0$ being 1 or 10).

FIG. 26 shows the distribution of closest-neighbor RMSDs for TERMs derived from both native and Chroma-sampled backbones that were generated at inverse temperatures $\lambda_0$=10 and $\lambda_0$=1. The distributions of nearest-neighbor RMSD were very close for lowtemperature samples from Chroma and native proteins, indicating that Chroma geometries are valid and likely to be as designable as native proteins, including complex motifs.

FIG. 27: Unconditional backbone samples demonstrate structural novelty across different metrics and protein sizes a, Fraction of backbones that have a PDB highest TM-score above 0.5 (top) or 0.7 (bottom) by length for ChromaBackbone v0 and v1. b, Highest TM-score against CATHdb for TM-align and FoldSeek. c, Lenght normalized number of CATH domains required to cover at least 80% of backbone versus length for ChromaBackbone v0, v1 and PDB. d, Lenght normalized number of CATH domains required to cover at least 80% of backbone versus PDB nearest neighbour TM-score (FoldSeek) for both ChromaBackbone datasets joint fragments (see FIG. 26). Because native amino-acid choices are driven by these local geometries [136], and adherence to TERM statistics has been previously shown to correlate with structural model accuracy and success in de-novo design [135, 136], this argues for the general designability of Chroma-generated backbones in a model-independent manner. Notably, the samples from Chroma at its natural temperature (i.e. $\lambda_0$=1) still utilize quite quite precedented low-order TERMs, while their geometries do begin to depart from native for higher-order motifs.

I.4 Novelty Analysis

We assessed the novelty of Chroma generated samples by comparing them to natural protein folds from CATHdb S40 [137] and PDB100 with FoldSeek (5-53465f0) [138]. For each sample, we identified the closest hit in the PDB (with the highest TM-score) by using FoldSeek to search against the highest resolution experimental structure within each cluster of PDB100. We estimated novelty by computing fractions of entries with TM-scores above 0.5,0.7 or 0.9; see FIG. 27 for results using ChromaBackbone v0 and v1.

FIG. 28: Unconditional backbone samples span natural protein space while also frequently demonstrating high novelty. a. We co-embedded ≈50,000 samples from ChromaBackbone v1. along with a small set of about ~500 samples from from our PDB test set using UMAP [129] on 31 global fold descriptors derived from knot theory [130, 131]. We visualize in the largest embedding plot all of these points colored by our length-adjusted CATH novelty metric, which estimates the normalized number of CATH domains needed to achieve a greedy cover at least 80% of residues at TM>0.5. We use this score because it continues to grade the novelty of longer proteins which almost all have a PDB nearest-neighbor TM<0.5. On average Chroma has a CATH novelty score of 2.7 and PDB has a CATH novelty score of 1.9. The four embedding insets (left) demonstrate the specific distributions of properties of interest by highlighting populations of structures that are mainly helices, strands, large (>500 residues), or from the PDB test set. b, We highlight twelve proteins from across the embedding space with a high novelty score (with embedding locations numbered).

Additionally, we aligned all Chroma-generated samples against the full CATHdb dataset (all-toall) using FoldSeek. We greedily determined the number of domains needed to cover at least 80% of the query by identifying the hits with the highest number of residues within 5 Å of the query that were not already covered. The number of domains required increases with query size given that CATH domains typically have a length ranging between 50 and 200 amino acids. We defined a length-normalized CATH novelty metric as the number of domains required to cover 80% divided by the highest number between 300 and the protein length, multiplied by 300. As a baseline, we analyzed our PDB test set using the same algorithm (see FIG. 27).

Finally, we embedded single-chain structures from Chroma and the test set in 31 Gauss Integral dimensions using the pdb2git program from the Phaistos suite [131, 139]. Discarding the structures that failed to embed, the remaining 47,786 Chroma samples and 561 natural folds were projected onto a two-dimensions space using UMAP [129] with default parameters of 25 neighbors and a minimal distance of 0.5 (see FIG. 28).

I.4.1 TM-Align Versus FoldSeek

While TM-score produced by the program TM-align is a well-established standard for comparing structures, we used FoldSeek for computational efficiency (allowing all-to-all comparisons) and parameterized it to very closely reproduce TM-align results. Specifically, by comparing a subset of 3,000 unconditional structures to the ~32k structurally conserved domains from CATHdb S40 set with TM-align and FoldSeek, we found that using FoldSeek with the following parameters:--alignment-type 1--min-seq-id 0-s 20-e inf--max-seqs 17000-k 5--num-iterations 2 provided the best trade-off between compute time and retrieval. There is an overall good agreement between the two programs when the highest TM-score is above 0.45, with the median difference of −0.003, 95% CI [−0.013, −0.0003]. FoldSeek tends to overestimate novelty below this cutoff by a median difference of 0.057, 95% CI [−0.08, −0.024]. Comparison between FoldSeek and TM-align is summarized in FIG. 27.

I.5 Refolding Analysis

Figure 29:
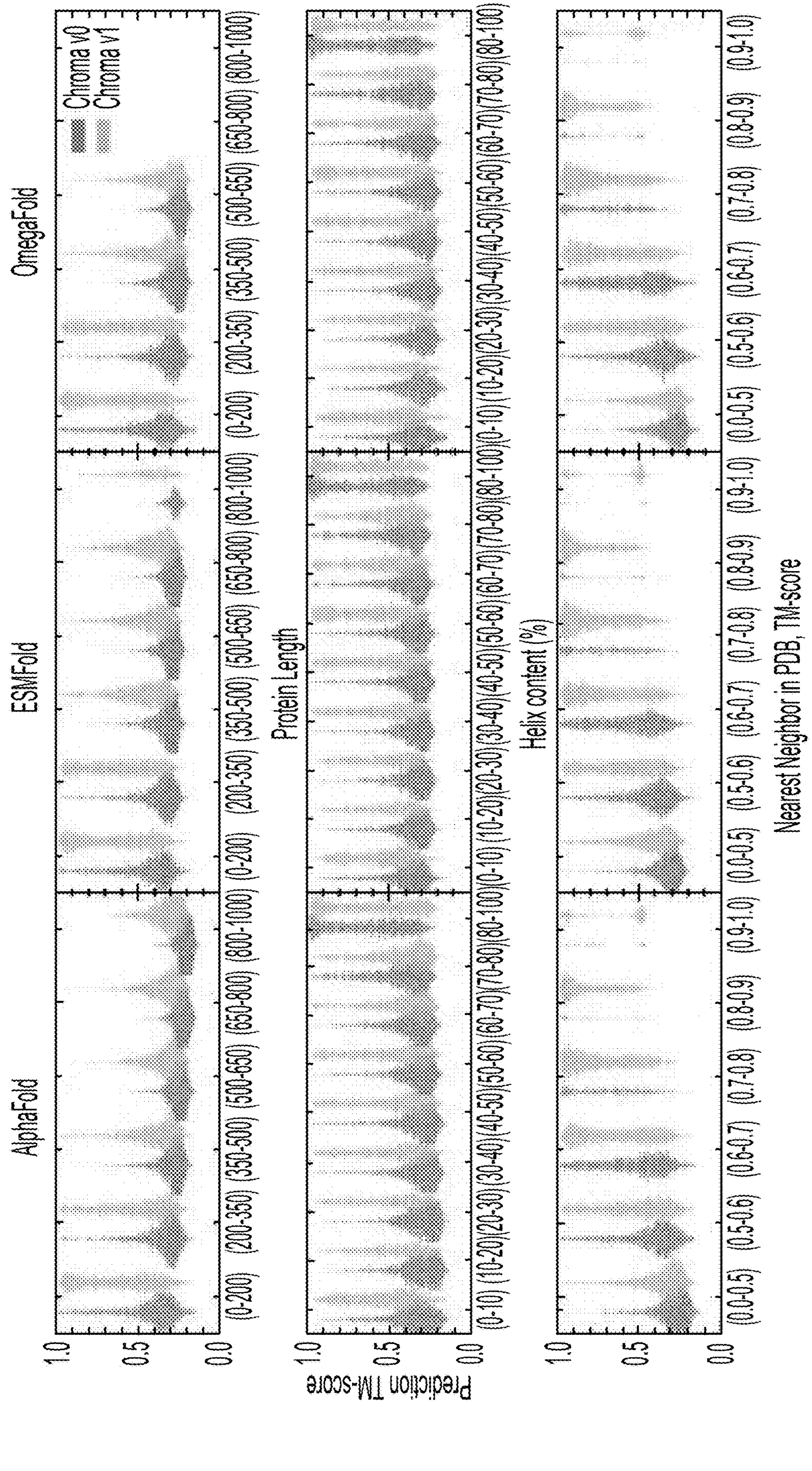
FIG. 29 shows ChromaBackbone v0 and v1 refolding TM-scores across length, secondary structure and novelty

We designed one sequence conditioned on each of the generated single-chain unconditional structures (see section I.1), for both Chroma v0 and v1. To this end we used our sequence design module with a Potts decoder as described in section H. 1 in conjunction with the flat-bottom restraint energy in equation 9. For each generated structure, we ran the above MC procedure once to produce one sequence, each of which was used as input into AlphaFold [58, 141], ESMFold [142], and OmegaFold [103] for structure prediction. A summary of the results is presented in (FIG. 29). While shorter sequences refold successfully more frequently, there is a non-trivial fraction of even very long designs (e.g., 800-1000 residues) that do refold quite accurately (FIG. 29). Interestingly, helix content does not appear to be a strong predictor of refolding (FIG. 29), but the distance to the nearest neighbor in the PDB does (FIG. 29). Validation through refolding is most challenging for novel structures, as both the generation and prediction tasks are most challenging in this limit and require strong generalization of the underlying methodology.

I.6 Sequence Design Analysis

We used Potts and Multi versions of ChromaDesign to generate protein sequences on the test set using different complexity penalty methods, reflecting the experimental validation approach. We assessed sequence recovery for all residues, as well as over exposed, core, and interface regions. We compared performances to ProteinMPNN [108] using the 002 checkpoint at a temperature of 0.01, as well as the 020 checkpoint at a temperature of 0.1. Considering that a substantial portion of Chroma's test set was incorporated into ProteinMPNN's training set, performance was assessed on the overlapping entries of both test sets.

FIG. 29: ChromaBackbone v0 and v1 refolding TM-scores across length, secondary structure and novelty TM-scores of Chroma compared to predicted structures for AlphaFold, ESMfold and OmegaFold across different length, helical content and novelty. A maximum of 2000 points per model and bin is shown.

A summary of the performances is shown in FIG. 30. Chroma designs and ProteinMPNN 002 exhibited comparable performance across all regions and subsets, while ProteinMPNN 020 tended to have lower sequence recovery. Neither of the complexity penalty methods appeared to have a significant impact on Chroma design's performance.

J Evaluation: Conditional Samples

In this section, we demonstrate the effectiveness of our integrated approach of programmable generation and design in creating protein structures capable of refolding in silico. We focus on evaluating our methods against state-of-the-art protein structure models such as AlphaFold [58,141], ESMFold [142], and OmegaFold [103]. Our expectation is that the proteins generated by our design exhibit novel structures and sequences. Therefore, we do not anticipate multiple sequence alignment (MSA) hits, prompting us to deploy AlphaFold with a high number of cycles. To compare refolded structures with generated ones, we compute the Template Modeling (TM) score using the TM-align software [140]. For each generated backbone, we design one sequence following the methodology described in section T.1 and report the TM score between the original and refolded backbones.

J.1 Refolding Substructure-Conditioned Samples

Eight PDBs were selected for this evaluation by sampling from the test set restricted to monomers with lengths between 60 and 500 amino acids and no missing structural data. For each template, we explore refolding rate on four conditional generation tasks, each of which consists of masking out a fraction (20%, 40%, 60%, and 80%) of the residues and conditioning on the atomic coordinates of the unmasked residues. Masks are obtained by shifting a plane normal to the first principal component of the atomic coordinates until the desired percentage of residues are masked. For a formal description of the conditioning task as well as the method under evaluation, see section M.

FIG. 30: ChromaDesign and ProteinMPNN have comparable sequence recovery. We plot the median and interquartile ranges of per-protein sequence recoveries when evaluated on the Chroma test set (left) and an intersection of the Chroma and ProteinMPNN test sets (right).

For each of the 32 conditioning tasks, 100 backbones. For each task, ten of these 100 backbones were sampled subject to a filtering which excluded samples containing discontinuities, clashes, or stereochemical violations, resulting in a total of 3,200 backbones. For each backbone, ten sequences were designed using the method described in H, and the resulting 32000 sequences are refolded with AlphaFold2 [58], OmegaFold [103], and ESMFold [102].

TM scores between predicted and designed models are evaluated, the results are summarized in FIGS. 31A-31D. Calling a backbone a hit at a best-of-ten TM score cutoff of 0.5, we see non-zero hitrate across all PDBs considered for all three structure prediction method, with 100% hit-rate achieved on several PDB-task-structure-predictor combinations. At a TM score cutoff of 0.8, when restricting our analysis to the task of masking out 60% of the template backbone, we see non-zero hit rate on half of the sampled PDBs for each of the three structure prediction methods. We see that refolding becomes less likely as more of the template is masked (and hence more of the monomer backbone is infilled).

FIGS. 31A-31D: Substructure-conditioned samples can refold in silico. a, Schematic outlining the refolding pipeline generating these data b, Best-of-ten TM scores for each sampled backbone for each PDB, aggregated across task for each structure prediction method (AlphaFold2, OmegaFold, and ESMFold). Sub-structure conditioned samples are able to achieve best-of-ten TM scores higher than 0.5 for every PDB considered with each structure prediction method. c, Median TM score (across structure predictors) per task. Distribution of median TM score shifts down as more of the protein backbone is occluded. d, Example samples along with predicted structures (drawn in white) for three PDBs across each task.

J.2 Refolding Symmetry-Conditioned Samples

We conducted an investigation into the designability of symmetric assemblies generated by ChromaBackbone v1 using AlphaFold v2 and our refolding experiments showed remarkable refolding rate, indicating that Chroma can generate highly designable assemblies. Our study involved two sets of refolding experiments across various point groups, including Cyclic ($C_2$, $C_3$, $C_4$), Dihedral ($D_2$, $D_3$, $D_4$), Tetrahedral (T), Octahedral (O), and Icosahedral (I) groups. For each symmetry group, we explored single chain lengths of 50,100,150, and 200 residues. For each combination of symmetry and backbone length, we generated 50 backbones without applying any filtering, resulting in a total of 1,800 backbones. To ensure consistency, we used the sequence design method described in appendix H, which enforced identical sequences for all chains. For each backbone, we sampled 20 sequences and used AlphaFold v2 for folding prediction, employing 10 cycles without Multiple Sequence Alignment (MSA). This process involved a total of 36,000 structure prediction jobs.

In the case of higher-symmetry groups (T, O, and I), which consist of 12, 24, and 60 subunits, respectively, we limited our validation to symmetric trimers that repsect $C_3$ symmetry. This choice was reasonable due to the presence of a three-fold axis in these groups. Unfortunately, reliable and rapid structure prediction models for large and high-symmetry assemblies are currently un-available. It is important to note that while the poorer refolding results observed in the trimer-only setting might result from excluding interface interactions from neighboring chains, this does not necessarily imply that the designed proteins will not assemble. Based on the results obtained from the aforementioned protocol, we observed a considerable number of successfully refolded designs across the selected symmetry groups and sequence lengths (see FIG. 32). The probability of success in refolding, defined as a TM-score greater than 0.5, was found to be higher for assemblies with a smaller number of subunits and shorter chain lengths. We have included selected refolded structures in FIG. 32.

Figure 32:
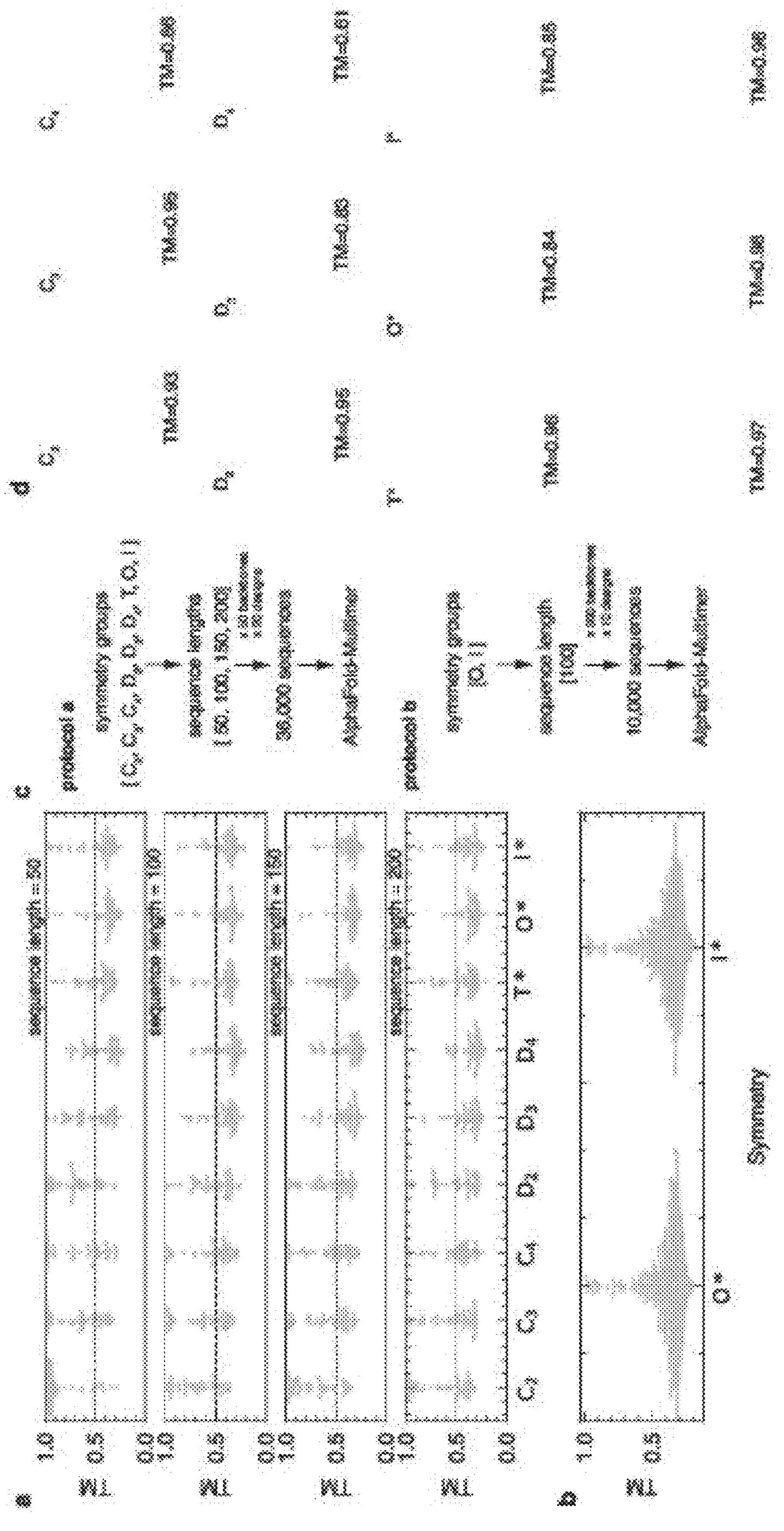
FIG. 32 shows that symmetry-conditioned samples can refold in silico.

FIG. 32: Symmetry-conditioned samples can refold in silico. a, b, Refolding statistics for all the generated backbones (no filtering). c, Computational protocol for refolding analysis. d, representative refolded samples for different symmetry groups.

Furthermore, we conducted a separate set of refolding validation experiments that focused specifically on assemblies with O and I symmetries, generating 500 backbones instead of 50. We observed a notable number of successful trimer refoldings. However, how trimer refolding correlates with assembly formation success rate requires further investigation.

J. 3 Refolding Shape-Conditioned Samples

While shape-conditioned samples may drive towards folds that are highly atypical of what is found in natural proteins, we sought to characterize to what extent they can be refolded in silico. For each of the 26 letters in the Latin alphabet and each of the 10 digits in the Arabic numeral system, we sampled 120 backbones representing a combination of sizes (length 500,750, or 1000) and conditioner hyperparameters. For the conditioner hyperparameters, we considered two configurations: (i) one with fixed point cloud scaling, ψ=2, and the hybrid SDE and (ii) the other with autoscaling, ψ=3 and purely annealed Langevin dynamics. Ultimately we found both methods gave a large number of refolding hits so these may be primarily regarded as a mechanism for diversity.

Figure 33:
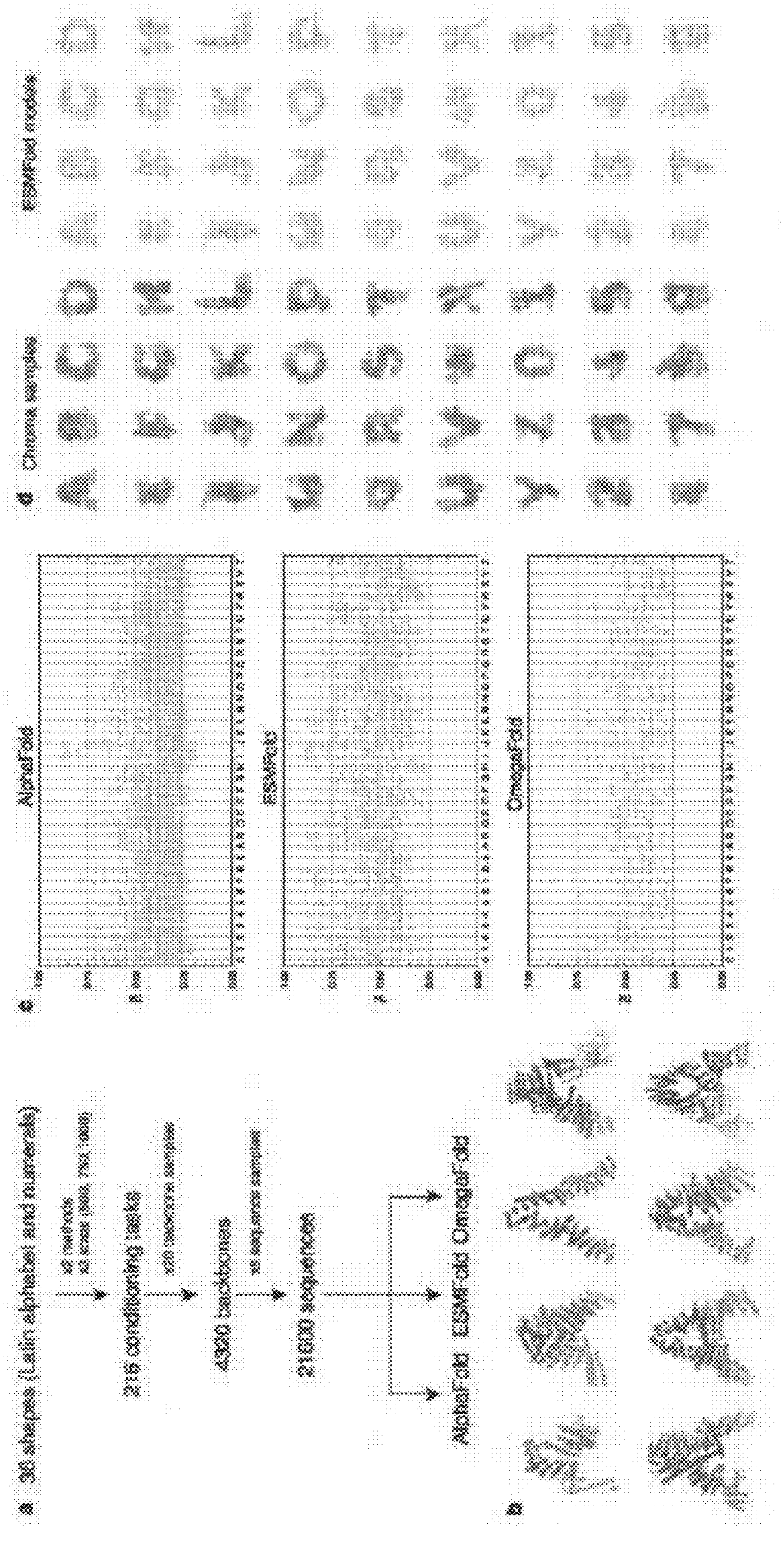
FIG. 33 shows that shape-conditioned samples can refold in silico.

FIG. 33: Shape-conditioned samples can refold in silico. a, Experimental protocol for refolding analysis of shape-conditioned samples. b, Samples for even the same shape cue, such as the letter A, can exhibit significant topological variations. c, Top TM-scores per backbone out of 5 designed sequences across three different folding methods. d, The ESMfold models (white) with the highest level of TM-score agreement with the Chroma model (rainbow).

For each of the backbones sampled in this workflow we sampled 5 sequences and refolded with all three structure prediction methods. We outline the overal workflow and results in FIG. 33.

Remarkably, we observe refolding with high TM-scores across all 36 shape classes and all 3 structure prediction methods (FIG. 33), even though samples were at minimum 500 residues long which is often a difficult regime for in silico refolding. Every shape shown in FIGS. 15C-1-15C-2 scored at least an ESMfold TM-score of 0.65 (many higher than this), and when we visualize the ESMfold models with the highest TM-score correspondence to our Chroma designs in Supplementary FIG. 33, we see that many of them successfully refold into the intended 3D. shapes. We emphasize that the only information being passed to ESMfold is the amino acid sequence, and we in no way use ESMfold during the sampling process itself other than for final selection of models to examine based on agreement. Thus, it would appear that both structure predictors and Chroma are capturing sufficiently similar sequence-structure relationships to agree how they might be leveraged to propose folds.

J.4 Refolding Class-Conditioned Samples

Figure 34:
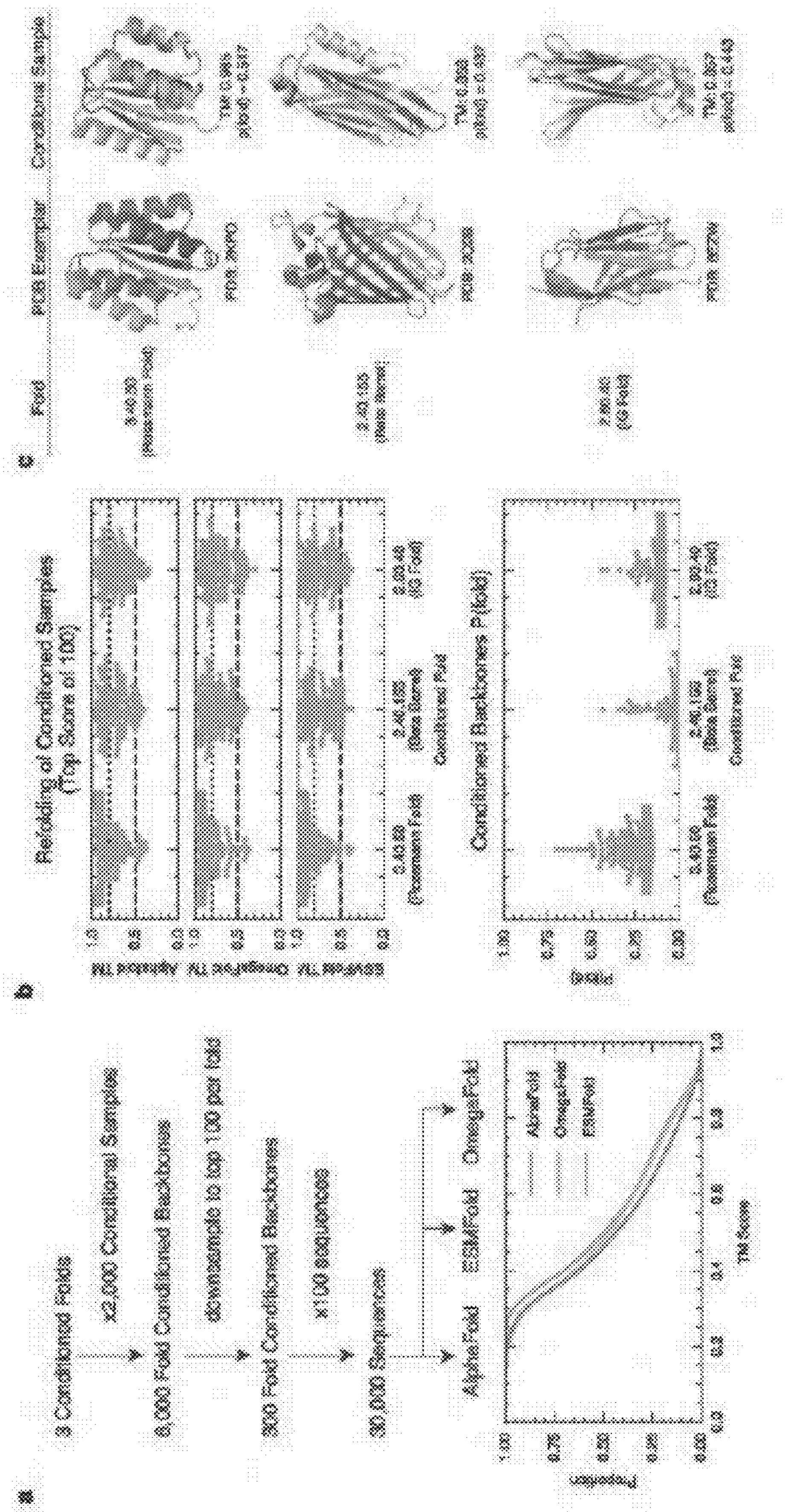
FIG. 34 shows that class-conditioned samples can refold in silico.

Refolding on CATH class (fold) conditioned samples works in silico. To illustrate the performance of the ProClass conditioner and provide in silico evidence that the designs can be made in the lab, a computational sampling protocol was run as illustrated in FIG. 34. Three canonical folds were selected, beta barrel, Rossmann fold, and IG fold. For each fold, 2000 conditional backbones were sampled.

FIG. 34: Class-conditioned samples can refold in silico. a, Conditional generation protocol diagram. Three canonical folds were chosen to conditionally design the beta barrel, Rossmann fold, and IG fold. 2000 conditional samples were generated for each fold. The best 100 of each fold were selected for downstream refolding analysis. There is close agreement in TM score for all folding algorithms for these samples. b, Each backbone was designed 100 times and refolded under each folding model. Almost all of the structures refold with a TM score greater than 0.5 in best of 100 sequence designs. In the bottom plot, Conditioned backbones have a range of probabilities of being the correct fold. In general conditioning on CAT class requires many samples before high quality examples are generated. Some are easier to optimize than others. c, A selection of the best examples for each fold in conditional design. The middle column illustrates an example of the same class from the PDB for reference. The right column is an exemplar protein generated from Chroma. In white is the refolded structure, in rainbow is the sampled backbone.

For each fold, the top 100 samples (evaluated by p (fold) under ProClass) were selected for design and refolding. Sequence design was performed 100 times for each backbone, then each of the resulting 30,000 resulting sequences were folded by three folding models: AlphaFold, OmegaFold, and ESMFold. To evaluate if the refolding was successful for each model a TM score was calculated against the generated backbone. If that TM score was greater than 0.5 it was considered a successful refolding event. Overall success of a backbone was evaluated by choosing the best TM score out of 100 designs.

Choosing hyperparamers that allow for successful optimization of the backbones requires tuning. Two key hyperparameters are guidance scale, and max_norm. Both need to be tuned to achieve high-quality samples. guidance scale rescales the gradient of the conditioner for sampling, max_norm, provides a maximum gradient norm above which the gradient is clipped. If the guidance scale is too low the sample looks like an unconditioned sample. If the guidance scale is too high, it breaks local backbone bond length constraints. In effect, the protein explodes. For max_norm, if its chosen to be too low, it clips gradients in a way that prevents optimization. If its chosen to be too high random outlier gradients can cause the sampling trajectory to fail, as occasionally the gradients explode and destroy the sample. This random gradient explosion does not occur for all conditional sampling problems, and so is evaluated on a case by case basis.

The conditional parameters depend on various other sampling hyperparameters, so must be determined for each sampling problem separately. The best choice for guidance scale tends to vary based on inverse temperature, Langevin factor, and number of steps. Practically, the guidance scale and max_norm are found by a small sampling hyperparameter search. A small number of seed-controlled samples are run at different choices of guidance scale and max norm (e.g. 0.1, 1,10,100). Then the best performing values are chosen for a production run. After appropriate hyper parameters are found a large run is executed as outlined in FIG. 34.

Refolding successes were observed across all three conditioned folds. Refolding had high agreement across models, as seen in FIG. 34. Further in FIG. 34, about 40% of the designs meet the threshold for refolding success. For a design to be considered successful, it also has to have a high p (fold). Qualitatively this cutoff can vary on what is acceptable, however, the best samples tend to be close to 1. In FIG. 34, the top 100 backbones are seen to vary substantially in the best optimization performance achieved. Some CAT annotations are very difficult to optimize, whereas others are relatively easy and good samples can be found quickly. In all three cases, structures that refolded and match the desired fold were found. These examples can be seen in FIG. 34.

J.5 Refolding Language-Conditioned Samples

To demonstrate the designability of samples conditioned on natural language, we draw the backbone with reverse diffusion guided by the gradients of a model that predicts $p(y|x_t)$, where y is a particular caption. Details about the underlying model are given in Appendix S. For each of the four captions, we sample 50 backbones using three different guidance scales to combine the conditioning gradient with the gradient from the diffusion model. The backbone length and number of chains are chosen separately per caption to be similar to representative examples in the PDB. Subsequently, we design ten sequences for each backbone and refold as in appendix J.1. For backbones with more than one chain, when using OmegaFold we only fold the first chain, rather than the entire complex. We find that larger guidance scales can result in incoherent backbones with particularly low likelihood, and reject those structures derived from backbones with ELBO below 0. The TM scores between each surviving designed backbone and its best refolded structure are shown in FIG. 35.

We find examples of designability for structures conditioned on each caption, though the success rate varies considerably. The single chain structures refold with larger TM scores to their Chroma predictions than complexes (antibody example). Nevertheless, for all captions we observe instances where our design protocol is successful, as measured by refolding with a TM score above 0.5. We also show some comparisons of Chroma and successfully refolded structures in the right panel of FIG. 35, alongside canonical examples of each caption from the PDB.

Figure 35:
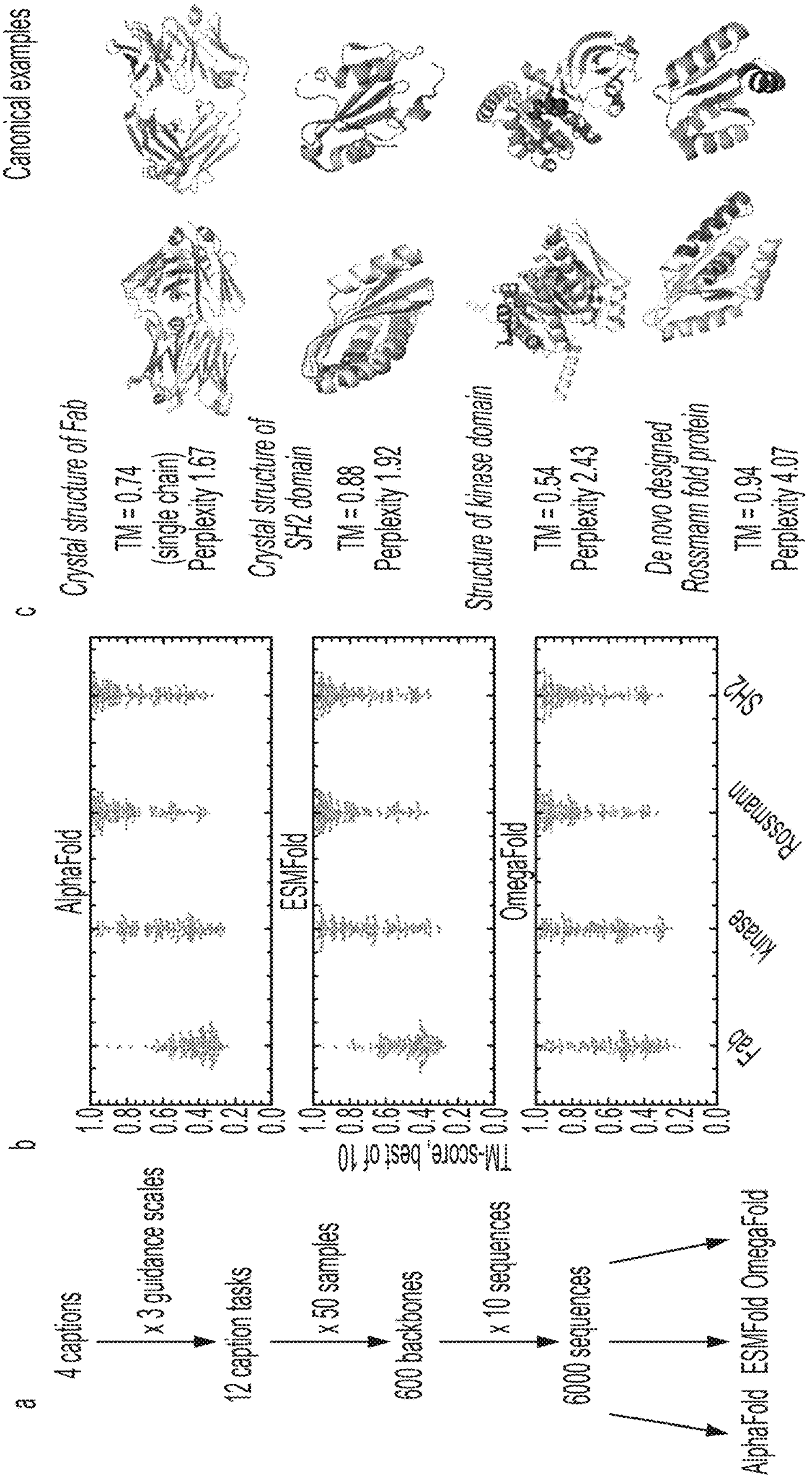
FIG. 35 shows that natural language-conditioned samples can refold in silico.

FIG. 35: Natural language-conditioned samples can refold in silico. a, Schematic outlining the refolding pipeline generating these data. Structures conditioned on the caption “Crystal structure of Fab” have two chains of length 200 residues. Structures conditioned on SH2 domain, kinase domain and Rossmann fold captions have single chains of length 110, 300 and 125 residues, respectively. In all cases, a task token is passed to the caption model specifying that the caption represents the entire structure; see appendix S for further details. Other sampling parameters are listed in appendix H. b, Best-of-ten TM scores for structures sampled with guidance from each caption and refolded using different structure prediction methods (AlphaFold2, ESMFold, and OmegaFold). OmegaFold is run on only the first chain for complexes. c, Chroma backbones (rainbow) superimposed on OmegaFold predicted structures (white), alongside examples from the PDB for each caption for comparison.

J.6 Refolding Analysis of Confidence

We observe a correlation between TM-Score and pLDDT for ESMFold, AlphaFold, and OmegaFold across 35,000 unconditional samples generated in the ablation study. For all three predictors, we see a correlation predictor consistency, i.e. the TM-score between the generated protein and the refolded protein, and predictor confidence, i.e. the pLDDT of the predicted structural model model. We visualize this correspondence in FIG. 36.

K Evaluation: Ablation Study

To better understand the influence of our proposed covariance model (Appendix A), graph neural network topology (Appendix D), atomic output layer parameterization (Appendix E), and losses (Appendix A), we trained multiple variants of the model that ablate and modify different components which are detailed in FIGS. 37A-37B. These ablations were evaluated through the lenses of likelihood and sample quality to holistically evaluate their effects on model performance.

Figure 36:
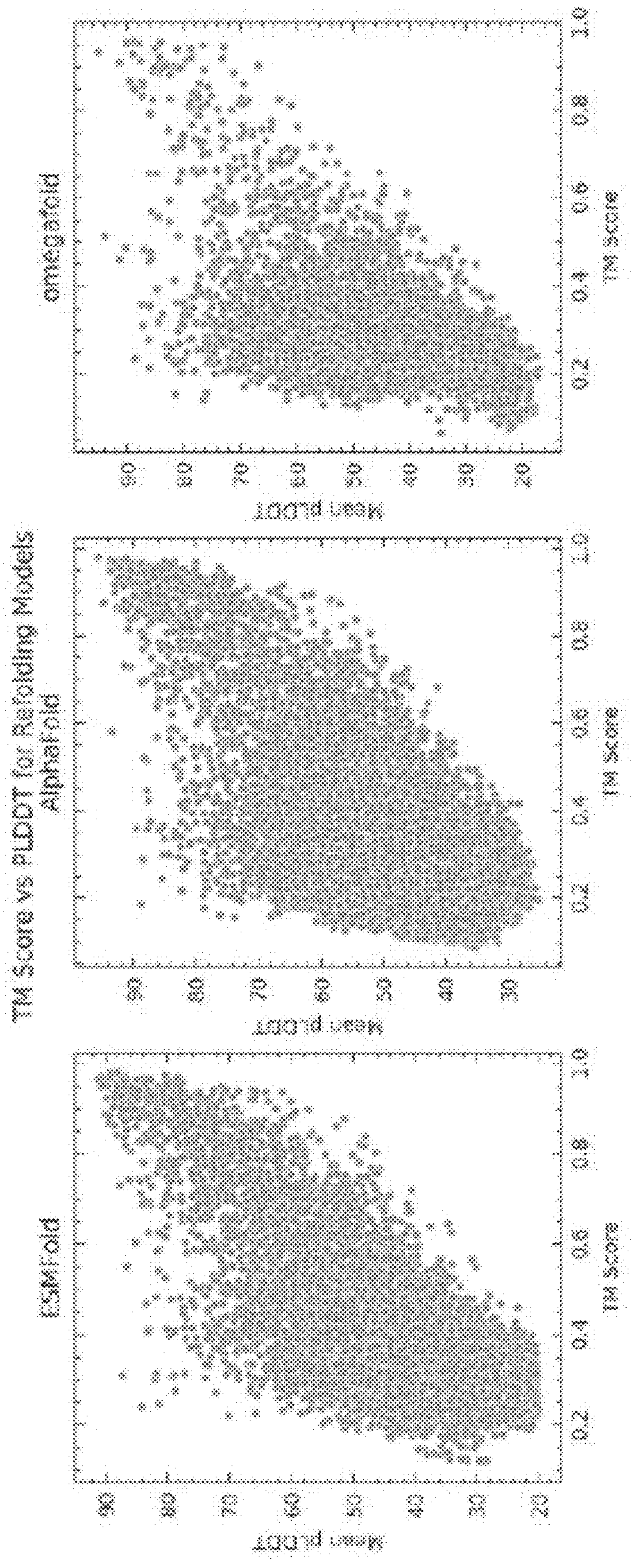
FIG. 36 shows that the agreement of predicted structures with designs (TM-score) is correlated to model confidence (pLDDT).

FIG. 36: The agreement of predicted structures with designs (TM-score) is correlated to model confidence (pLDDT). We evaluated ESMFold, AlphaFold, and OmegaFold models on the 35,000 unconditional samples generated in the ablation study, which represent model behaviors and biases across several different configurations. We see across these data that structure predictions with high correspondence between Chroma models and refolded predictions are also generally higher confidence predictions, suggesting a general self-consistency between the sequence structure relationships being modeled across these different systems.

K.1 Alternate Model Configurations and Training

In this section, we briefly review the components of the model that we modified as well as their respective variations.

Model component: Covariance. We consider two covariance models for defining the diffusion process, which are are visualized in FIG. 18 and described in Appendix C:

- Covariance variant: ResidueGas. In this model, the coordinates of each of each $C_\alpha$ are independently and identically normally distributed with standard deviation 10 Å (along each x, y, z dimension). The other coordinates of the N, C, and O atoms within the residue are then normally around $C_\alpha$ with 1 Å conditional standard deviation. This can be considered an off-frame relaxation of frame diffusion models [59] or an all-backbone-atom extension of IID $C_\alpha$ diffusion models. [83].
- Covariance variant: Globular. This covariance model captures spatial proximity constraints in the form of correlations within atoms in a residue and between residues in a chain, while also respecting global length-dependent $R_g$ scaling effects that arise from polymer collapse. This version includes Complex $R_g$ scaling.

FIGS. 37A-37B: Ablation study demonstrates utility of novel model components as measured by likelihood and sample quality. We trained seven models composing different configurations of proposed components and baselines, modifying the covariance model (Appendix A), graph neural network topology (Appendix D), atomic output parameterization (Appendix E), and losses (Appendix A) (top left). We indicate the two configurations corresponding to ChromaBackbone v0 and ChromaBackbone v1, where v0 has one additional change of using the globular monomer version of globular covariance scaling. Training for ~500, 000 steps on 8 V100 GPUs with a batch size of ~32,000 residues per step suggests that there is little generalization gap between the training and validation sets (top middle, windowed averaged training curves across 100 epochs). From the perspective of likelihood (top right), globular covariance is favorable to residue gas covariance (Appendix C), inter-residue geometry prediction layer is favorable to local frame updates if tuned appropriately (Appendix E), and auxiliary losses incur a cost to ELBO (Appendix A). When we applied these trained models to generate unconditional samples (bottom left), we observed significant fluctuations in secondary structure composition between adjacent checkpoints (bottom, middle left). When aggregating across these checkpoints, we observed that refolding by AlphaFold was highly dependent on the fraction of α-helices in the sampled structure (bottom, middle right). In spite of this, the refolding rate of samples based on a model with random graph topologies was higher than those of a model based on k-NN topologies (Appendix D) and losses weighted in x-space induced better refolding than losses weighted only in chain-whitened space (bottom right).

Model component: Graph We consider two kinds of graph structure, which are visualized in FIG. 19 and described in Appendix D:

- Graph variant: k-NN. This used a graph topology based on the 60 nearest neighbors in the current structure.
- Graph variant: Random Graph. This used a hybrid graph topology for which 20 of the edges are the nearest neighbors in the current structure and 40 of the edges are sampled according to the inverse cubic attachment model.

Model component: Output. We consider three kinds of output parameterization varying from the consensus update visualized in FIG. 20 and described in Appendix E:

Output variant: PairFrameA. This uses the inter-residue geometry parameterization with 3 equilibration steps, one uncertainty parameter per i, j that is coupled to both translation and rotation. The predicted transforms $T_{ij}$ are parameterized as linear projections from the final edge embeddings, and the coordinates are post-processed with time-dependent scaling method A.

Output variant: PairFrameB. This uses the inter-residue geometry parameterization with 10 equilibration steps, two uncertainty parameters per i, j, one for translation and one for rotation. The predicted transforms $T_{ij}$ are parameterized as residual updates to the transforms of the current structure based on the final edge embeddings and the coordinates are post-processed with time-dependent scaling method B.

Output variant: LocalFrame. This uses a local frame-transform update to the coordinates that is parameterized based on the final node embeddings. The coordinates are postprocessed with time-dependent scaling method A.

We consider three kinds of losses, described in Appendix A:

ELBO This is a pure likelihood loss, which is a weighted average squared error loss in whitened space together with additional additive terms to account for normalization and change of variables. It is measured in Nats per atom in Cartesian space and is comparable across different diffusion models.

+AuxLoss1 To the base ELBO loss, we add the ELBO-weighted unwhitened loss (Equation 1) that measures mean squared error in Cartesian space.

+AuxLoss2 To the base ELBO loss, we add the SSNR-weighted global MSE loss, the SSNRweighted 7 mer fragment MSE loss, the Distance MSE loss, and a the Inter-residue Transform MSE loss.

Training For each of the model configurations in the ablation study, we trained on batch sizes of 32,000 residues by leveraging data parallelism across 8 V100 GPUs for ~500,000 steps, which is approximately ~1500 epochs and ~28 days of wall clock time. Models were trained with the Adam optimizer [124] and a learning rate of $2\times10^{-4}$ with an initial linear warm-up phase of 10,000 steps. After each epoch, we evaluated one-sample estimates of ELBO and other losses across the full Training and evaluation sets.

K.2 Ablation Results

Likelihood analysis While it is clear that sample quality evaluations are very important for diffusion models generally [52] and also specifically in the case of protein generative models [83, 95], we first compare the different model variants from the point of view of likelihood. Likelihood measures have been broadly useful in deriving scoring functions for criticizing proteins and can, in certain instances, form a useful framework to make contact with free-energy quantities arising from statistical physics. We expect that models which behave well from the point of view of likelihood may also be useful as scoring functions to be used more broadly in protein design and modeling.

We visualizes the trajectories of ELBO (Appendix A) for the training and validation sets in FIGS. 37A-37B. While the trajectories are smoothed with a 100-epoch moving average because they are noisy one-sample estimates per datapoint, there is a clear and consistent separation. between the different model configurations. We make three observations:

First, there is a consistent improvement as measured by ELBO of the globular covariance models over the residue gas models. In some ways, this is to be expected from theory, because the information theoretic diffusion likelihood can be rewritten terms of the bits accounted for by the prior plus additional corrections to account for non-Gaussianity [56]. Therefore a prior that better fits the data distribution, such as our globular covariance model that is based on the empirical scaling of real proteins, should do better as measured by likelihood even if the learned denoisers can account for a similar number of bits.

Second, we see similar but modest improvements in likelihood across the three different output layer parameterizations, where PairFrameB is favorable to LocalFrame which is favorable to PairFrameA. Thus we see evidence suggestive of favorable performance for our inter-residue geometry prediction over purely local prediction, though this can depend on tuning and is potentially confounded by the fact that PairFrameB also changes the output scaling at the same time. Optimizing the output layer will likely warrant further investigation.

Finally, we observe that adding auxiliary non-ELBO losses to otherwise purely ELBO-based training reduces ELBO performance.

Sample quality analysis. To evaluate each of the model configurations from the point of view of sample quality, we performed a large scale sample-and-refolding analysis. For each of the seven model configurations, we took five checkpoints from consecutive epochs around epoch 1100, sampled 1000 backbones per checkpoint with lengths uniformly distributed between 100 and 500 amino acids. We note that this epoch corresponds to ~360,000 training steps, which is approximately one quarter of the total training time of the ChromaBackbone v0.4998 that was used in our broader refolding experiments. We expect that the total refolding rates reported in this section may be generally lower than our production model.

We observe significant epoch-to-epoch fluctuations in secondary structure biases of the samples (FIGS. 37A-37B). This is reminiscent of behaviors previously observed in other diffusion models [125], in which a batch of images may be all tinted one color, then another, even when the underlying denoising function is only changing slightly. These macroscopic fluctuations arising from microscopic changes may be intuitively understood as a tendency of the sampling process to amplify small per-time-step discrepancies. This phenomenon has previously been addressed by exponential moving averaging (EMA) of the checkpoints [55, 125], and we anticipate this is a worthwhile direction for future work.

Nevertheless, when we aggregate across checkpoints, we observe a few trends. All of the models trained with denoising losses that measure squared error in Cartesian space, which includes both the auxiliary loss models and the residue gas models, tend to have higher refolding rates than the models which were trained only with a chain whitened losses. This aligns with classical intuition on proteins in the sense that chained whitened coordinates emphasize local geometries in proteins while Cartesian coordinates much more directly measure absolute positioning of coordinates in space that underlie contacts and interatomic distances. We also observe that the random graph neural networks have considerably higher folding rates than a purely k-NN based model, and that the best performing model overall combined our new diffusion and output parameterizations together with several new auxiliary loss functions. Thus, as has been a common lesson in the diffusion modeling literature, nonlikelihood based losses or denoising weightings can be important to driving sample quality measures [52].

Low-temperature sampling remains essential All of the model configurations in this ablation study can generate samples which successfully refold and, in that sense, none of these changes qualitatively break model performance. We emphasize that the same cannot be said about lowtemperature sampling, as all of these experiments were sampled with λ=10. As shown in FIGS. 17A-17B, low temperature sampling is important to generate high likelihood samples which are sufficiently compact and structured to have a chance at refolding.

L Programmability: Conditioners Framework

Overview In principle, the set of proteins satisfying a given set of functional constraints can be described using Bayes' Theorem, $$p(\text{protein}|\text{function}) \propto p(\text{protein}) \times p(\text{function}|\text{protein})$$

where the posterior distribution of proteins p (protein|function) is proportional to the likelihood, i.e. the probability of satisfying the set of functional constraints p (function|protein) times the prior probability of the protein molecule being able to host function p(protein). This characterization has been appreciated for several decades [143], but leveraging it is challenging in practice for two reasons. First, developing tractable and accurate priors over the space of possible proteins has proven extremely difficult owing to the tremendous complexity in a single protein system (a complex can easily have $>10^4$ atoms) and the intractabilities of marginalizing out low level details. Secondly, even with an accurate prior, sampling from the space of polypeptide conformations is highly difficult as it will typically involve a rugged landscape for which global optimization is infeasible.

One potential way to simplify the difficult inverse problem posed by protein design is given by contemporary methods from machine learning. In particular, diffusion models simplify conventionally intractable inverse problems by learning a sequence of distributions that gradually transform from a complex data distribution turns into a simple and tractable distribution [51, 77]. This has enabled transformative applications in text-to-image modeling [74, 75].

L.1 Bayes' Theorem for Score Functions

Bayes' Theorem can be directly applied to Bayesian inversion with diffusion models where we can derive the time-dependent posterior score $\nabla_x \log p_t(x|y)$ as the sum of the original prior score $\nabla_x \log p_t(x)$ and the likelihood score $\nabla_x \log p_t(y|x)$ as $$\begin{aligned}\nabla_x \log p_t(x \mid y) &= \nabla_x \log \frac{p_t(x) p_t(y \mid x)}{p_t(y)} \\ &= \nabla_x \log p_t(x) + \nabla_x \log p_t(y \mid x) - \nabla_x \log p_t(y) \\ &= \nabla_x \log p_t(x) + \nabla_x \log p_t(y \mid x)\end{aligned}$$

This formulation can treat arbitrary combinations of conditions if we model the joint event y as factorizing into independent sub-events $y_1, \ldots, y_M$. Then we have the posterior score $$\nabla_x \log p_t(x \mid y_1, \ldots, y_M) = \nabla_x \log p_t(x) + \sum_{i=1}^{M} \nabla_x \log p_t(y_i \mid x)$$

These posterior scores can directly substitute the usual score function in the posterior SDE and ODE described in Appendix A.

Joint programmable sampling of sequence and structure While we focus on classifier conditioning of backbone structures throughout this work, it is also straightforward to extend the above picture to include joint gradient-based sequence and structure sampling by leveraging new discrete sampling methods based on locally gradient-adjusted MCMC proposals [117, 144]. It is an important distinction that joint sequence-structure sampling at inference time does not require joint sequence-structure diffusion at training time; all we require for joint sampling is access to a time-dependent joint likelihood $p_t(x, s)$. Our current Chroma model satisfies this as $p_t(x_t, s_t)=p_t(x_t)p_t(s|x_t)$, which may be leveraged as $$\nabla_{x,s} \log p_t(x, s \mid y_1, \ldots, y_M) = \nabla_{x,s} \log p_t(x, s) + \sum_{i=1}^{M} \nabla_{x,s} \log p_t(y_i \mid x, s)$$

L.2 Conditioners: Motivation

Motivation: Constraints versus Restraints Bayes' theorem can incorporate both soft restraints, which reweight the posterior but do not restrict its support, and hard constraints, which can completely eliminate certain regions of space. Hard constraints are just as useful and sometimes more natural than soft restraints in protein design, for example when conditioning on precise coordinates of a small molecule binding substructure or when exactly enforcing symmetries across large systems. Nevertheless, unconstrained gradient-based sampling algorithms such as Langevin dynamics or diffusion SDEs (Appendix A) do not directly apply to constrained posteriors without special modifications. Here, we seek a framework that can support both restraints and constraints in concert with fully general sampling algorithms.

Requirements We propose four *desiderata* for a programmable protein design framework:

Compositionality. Problems are expressed as design programs which are composed from "building blocks" encoding different required attributes.

Restraints. Building blocks should be able to express soft restraints (e.g. classifier guidance) as a special case.

Constraints. Building blocks should be able to express hard constraints, such as manifold constraints, as a special case.

Automatic sampling. It should be feasible to automatically synthesize a valid sampling algorithm for any design program without requiring additional logic to be implemented by the user.

Design specifications as energy functions The Bayesian picture, as well as classical protein design approaches [143], formulate protein design problems in terms of energy functions which express the (unnormalized) negative log-posterior probability density of a protein system given a set of conditions. We can similarly cast posterior diffusions in terms of a time-dependent total energy as $$\begin{aligned}U(x_t; y, t) &= -\log p_t(x_t) - \log p_t(y \mid x_t) + C_1 \\ &= \underbrace{\frac{1}{2}\left\|\sigma_t^{-1} R^{-1}(x_t - \alpha_t \hat{x}_t(x_t, t))\right\|_2^2}_{\text{Diffusion Energy}} + \underbrace{\log p_t(y \mid x_t)}_{\text{Restraint Energy}} + C_2,\end{aligned}$$

where the gradient of the total energy with respect to x will yield the negative posterior score function.[5]

[5] We may choose to stop gradient flow through the denoiser model, which saves compute cost and recovers the behavior of the score functions from training time. This will lead to a non-conservative vector field (as is standard practice for diffusion models), but allowing gradients to flow through the denoiser restores energy conservation [145.]

Constraints via linear transformations How can we encode constraints such as symmetry and substructure? Many constraints, including these, can be enforced via affine transformation functions of the form $f(\tilde{x})=A\hat{x}+b$ which map points in unconstrained Euclidean space $\hat{x}\in\mathbb{R}^N$ to points in a constrained space $f(\tilde{x})\in\Omega\subseteq\mathbb{R}^M$. We can then run Langevin dynamics (Appendix A) with the gradient of constrained energy $U(f(\tilde{x}_t); y, t)$ with respect to the unconstrained coordinate $\tilde{x}_t$ as $$d\tilde{x} = -\frac{\beta_t\psi}{2}\lambda_t RR^T\nabla_x U(f(\tilde{x}_t); y, t)dt + \sqrt{\beta_t\psi}\, R\ d\overline{w}.$$

Figure 38:
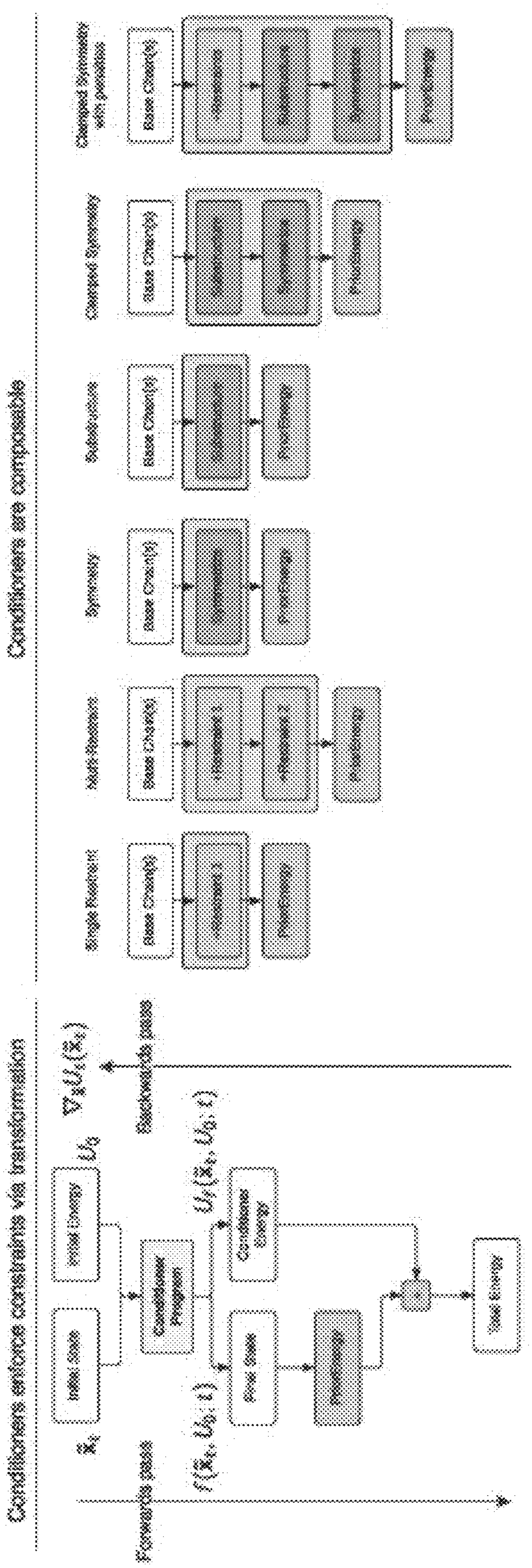
FIG. 38 shows that conditioners parameterize protein design problems, facilitate automatic sampling algorithms, and are composable.

FIG. 38: Conditioners parameterize protein design problems, facilitate automatic sampling algorithms, and are composable. (Left) Conditioners are functions which map an unconstrained system consisting of an initial state $\tilde{x}_t$ and energy $U_0=0$ to a transformed state $x_t=f(\tilde{x}_t, U_0; t)$ and an updated energy $U_f(\tilde{x}_t, U_0; t)$. Gradient-based sampling with respect to unconstrained $\tilde{x}_t$ on the Conditioner-adjusted Diffusion energy (left) will induce constrained dynamics on $x_t$. Many kinds of restraints and constraints can be realized in this framework (right), and because of matched input-output types, simple Conditioners can be composed into complex Conditioners to jointly satisfy multiple design objectives within a complex protein design problem.

The constrained dynamics of $x_t$ will then evolve according to the SDE [6]

[6] The first step can be justified by Ito's lemma.

$$\begin{aligned} dx &= Ad\tilde{x} \qquad (10) \\ &= A\left(-\frac{\beta_t\psi}{2}\lambda_t RR^T\nabla_{\tilde{x}} U(f(\tilde{x}_t); y, t)dt + \sqrt{\beta_t\psi}\, R\ d\overline{w}\right) \\ &= -\frac{\beta_t\psi}{2}\lambda_t ARR^T\nabla_{\tilde{x}} U(f(\tilde{x}_t); y, t)dt + \sqrt{\beta_t\psi}\, AR\ d\overline{w} \\ &= -\frac{\beta_t\psi}{2}\lambda_t ARR^T A^T\nabla_x U(x_t; y, t)dt + \sqrt{\beta_t\psi}\, AR\ d\overline{w}, \end{aligned}$$

which is precisely Langevin dynamics with a modified mass matrix $(ARR^TA^T)^{-1}$[146,147] which will sample from the constrained domain $\Omega$.

Nonlinear constraints: Exact sampling Many constraint sets cannot be expressed as the images of affine transformations [148]. One such example relevant to protein design is box constraints, where some subsets of atoms may be confined to contiguous finite regions of space. To enforce these constraints while still sampling from the intended energy function, we can simply design a nonlinear function $f$ that implements the constraint and then adjust the total energy for sampling with the log-volume adjustment factor given by the multivariate change of variables formula:

$$\log\left|\det\frac{\partial f}{\partial\tilde{x}}\right|.$$

This works so long as $f$ is continuously differentiable and bijective onto the constrained space and the constrained space has the same dimension as the domain of $f$. It is further possible to extend this to also consider non-dimension-preserving transforms, e.g. with certain embedded Riemannian manifolds, for which we refer the reader to [149].

This transformed MCMC approach may be useful even when the nonlinear transformation function is fully unconstrained, for example, if it is a learned normalizing flow model of a particular class of structures of interest, in which case it will induce a dynamics similar to latent diffusion models [67].

Nonlinear constraints: Beyond If we are willing to sacrifice exact sampling from the true energy function, we may also discard the log-determinant adjustment and absorb the bias induced by running Langevin dynamics in a transformed space. These dynamics will still be exactly confined to the range of $f$, but may potentially be biased by change-of-volume effects as well as nonbijectivity. However, this opens up a large number of possibilities which are simple to implement by the user, as they only require a differentiable function $f$ that implements the desired constraints which need not have an inverse and which can be differentiated by automatic differentiation. We have found this latter paradigm useful, as one can quickly realize more complex functionalities such as restricting sampling of subsets of a system to rigid body motions, to satisfying complex constraints such as optimal transport by differentiable inner optimization, and beyond.

L.3 Conditioners

The previously described restraints and constraints for Langevin dynamics share a common form of implementation: they modify the system coordinates x and/or the total energy U. This suggests a natural "building block" for a protein programming framework: transformation functions which input and output system states (x, U).

We define a conditioner as a function $\mathcal{F}: \mathbb{R}^N\times\mathbb{R}\rightarrow\Omega\subseteq\mathbb{R}^M\times\mathbb{R}$ which maps state-energy pairs in unconstrained input space $\mathbb{R}^N\times\mathbb{R}$ to potentially constrained state-energy pairs in $\Omega\subseteq\mathbb{R}^M\times\mathbb{R}$. For ease of notation, we further refer to Conditioners component-wise $\mathcal{F}=(f, U_f)$ in terms of a state update function $f: \mathbb{R}^N\times\mathbb{R}\rightarrow\Omega_f\subseteq\mathbb{R}^M$ and an energy update function $U_f: \mathbb{R}^N\times\mathbb{R}\rightarrow\Omega_U\subseteq\mathbb{R}$.

Conditioned Diffusion To sample from Conditioner-biased diffusion problems, we will use a gradient-based sampling algorithm, such as Langevin dynamics or Hamiltonian Monte Carlo, on the Conditioner-transformed instance of the energy $$U(\tilde{x}_t; U_f, f, t) = \underbrace{\frac{1}{2}\left\|\sigma_t^{-1}R^{-1}(f(\tilde{x}_t, U_0; t) - \alpha_t\tilde{x}_t(x_t, t))\right\|_2^2}_{\text{Diffusion Energy}} + \underbrace{U_f(\tilde{x}_t, U_0; t)}_{\text{Conditioner Energy}},$$

where the gradient $\nabla_{\tilde{x}}U(\tilde{x}_t; U_f, f, t)$ for sampling is computed with respect to the unconstrained coordinates $\tilde{x}_t$. These gradients and dynamics can be computed efficiently even for complex composed conditioners by leveraging modern automatic differentiation frameworks, as shown in FIG. 38.

Desiderata The Conditioner formulation satisfies all of our *desiderata:*

Compositionality. Let $\mathcal{F}_1: \mathbb{R}^{N_1}\times\mathbb{R}\rightarrow\Omega_1\subseteq\mathbb{R}^{M_1}\times\mathbb{R}$ and $\mathcal{F}_2: \mathbb{R}^{N_2}\times\mathbb{R}\rightarrow\Omega_2\subseteq\mathbb{R}^{M_2}\times\mathbb{R}$ be Conditioners and assume $N_1=M_2$.[7] Then $\mathcal{F}_3=\mathcal{F}_1\cdot\mathcal{F}_2$ is a Conditioner with $\mathcal{F}_3: R^{N_2}\times R\rightarrow\Omega_1\in\mathbb{R}^{M_1}\times\mathbb{R}$.

[7] Composition of blocks will require that their inputs and outputs can be shape compatible, just as in the case of composing differentiable blocks in neural networks. For example, two substructure constraints by definition must be expressed in a way that can be jointly realized with one set of protein light chains Restraints. Generalized restraints may be realized with state update $f(x, U)=x$ (Identity function) and energy update $U_f(U, \tilde{x}_t, t)=U-\log p(y|x,t)$.

Constraints: Linear Transforms. Distribution-preserving linear transform constraints may be realized with state update $f(x, U)=Ax+b$ and energy update $U_f(U, \tilde{x}_t, t)=U$ (Identity function).

time; all we require is a valid joint posterior for sequence and structure conditioned on function which may be realized, for example, with a conditional language model for sequence given structure together with a diffusion model for the backbone structure joint marginal.

L.4 Example Applications of Constraint Composition

We list a table of composable constraint models in Table 6. Some practical protein design problems that could be realized through composite constraints under this framework are

TABLE 6

Conditioners for Chroma.

| Conditioner | $f(\tilde{x}, U, t)$ | $U_f(\tilde{x}, U, t)$ | Examples and applications |
|---|---|---|---|
| Symmetry constraint | $G\tilde{x}$ | U | Large assemblies |
| Substructure constraint | $\tilde{R}R^{-1}\tilde{x} + \tilde{\mu}$ | $U + \|\hat{x}_\theta(f(\tilde{x}, U, t), t)^M - x_t^M\|_2^2$ | Substructure grafting |
| Substructure distances | $\tilde{x}$ | $U - \log p_t(d_{ij} \mid \tilde{x})$ | Interface and contact constraints |
| Substructure motif | $\tilde{x}$ | $U + \eta\log(1 + e^{\zeta[\rho(x_t)-\rho_{max}])})$ | Motif-conditioned scaffolds |
| Shape constraint | $\tilde{x}$ | $U + \mathrm{ShapeLoss}_t(x, r)$ | Molecular shape control |
| Sequence | $\tilde{x}$ | $U - \log p_t(\text{sequence} \mid \tilde{x})$ | Sequence constraints |
| Secondary structure | $\tilde{x}$ | $U - \log p_t(\text{ss} \mid \tilde{x})$ | Topological constraints |
| Domain classification | $\tilde{x}$ | $U - \log p_t(\text{domain}\mid\tilde{x})$ | Pfam, CATH, Taxonomy |
| Text caption | $\tilde{x}$ | $U - \log p_t(\text{caption} \mid \tilde{x})$ | Natural language prompting |
| Likelihood restraint | $\tilde{x}$ | $U - \log p_t(\cdot \mid \tilde{x})$ | Biasing towards specifications |
| Linear constraint | $A\tilde{x} + b$ | U | Exactly enforcing specifications |
| Nonlinear constraint | $f(\tilde{x})$ | $U + \log\det\frac{df}{d\tilde{\chi}}$ | Exactly enforcing specifications |

Constraints: Non-Linear Transforms. Distribution-preserving nonlinear domain constraints may be realized with bijective and differentiable state update $f\colon \mathbb{R}^N\times\mathbb{R}\to\Omega_f\subseteq\mathbb{R}^M$ and $$\text{energy update} = U_f(U, \tilde{x}_t, t) = U + \log\det\left|\frac{\partial f}{\partial x}\right|$$

(Change of volume adjustment).

Automated Sampling. Any gradient-based sampling algorithm may be used in concert with the Conditioner-adjusted energy and an annealing schedule on the diffusion time t.

Conditioners for sequence and structure As noted in the previous section, the Conditioner framework is also straightforwardly applied to joint sampling of sequence and structure, where we define the joint energy $$U(x_t; y, t) = \underbrace{\frac{1}{2}\left\|\sigma_t^{-1}R^{-1}(f(\tilde{x}_t, U_0; t) - \alpha_t\hat{x}_t(x_t, t))\right\|_2^2}_{\text{Diffusion Energy}} - \underbrace{\log p(f_s(\tilde{s}_t)) \mid f_x(x_t), t)}_{\text{Sequence Likelihood}} + \underbrace{U_f(\tilde{x}_t, \tilde{s}_t, U_0, t)}_{\text{Conditioner Energy}},$$

where gradient and dynamics are computed in unconstrained space $\tilde{x}_t$, $s_t$ and we can use approaches such as Discrete Langevin sampling [117, 144] to sample from sequence space while leveraging gradients for building locally-informed proposals. Sequence and structure gradients can be computed in one pass via automatic differentiation frameworks.

Thus, we can perform joint sequence and structure sampling conditioned on a target objective without needing to train a joint diffusion on sequence and structure at the same De-novo binders Combine (i) substructure conditioning on antigen, (ii) optional scaffold constraint on binder, and (iii) contact constraints on epitope/paratope Enzyme miniaturization Use substructure RMSD to graft an active site into a novel scaffold or known scaffold (via combining with substructure constraints Nanostructure control Use the shape constraint to sample novel designable folds or complexes satisfying arbitrary shape constraints Nanomaterial design Combine nanostructure control with interfacial binding constraints on periodic boundary conditions L.5 Related Work Energy functions for specifying multi-objective design problems have a long history in and out of protein design, which we do not attempt to review here. Concurrent with this work, [150] proposed a framework for programmatic design of proteins by introducing a grammar for problem specifications which can be compiled into deep energy functions that are sampled via annealed MCMC in sequence space. Some advantages of our Conditioners framework include that it admits efficient gradient-based sampling, that it can exactly enforce hard constraints on continuous degrees of freedom during sampling, and that it support the fast-convergence properties of diffusion annealing which "tunnels" from a unimodal t=1 base distribution into the multimodal t=0 target posterior. Beyond protein design, the idea of using MCMC with diffusion models to sample from complex composed energy functions was explored in [76], which also presents useful tools for negation and other primitive composition operations.

M Programmability: Substructure Constraints

M.1 Motivation

Many protein design tasks including imputation of missing structural data, redesign of an enzyme scaffold given an active site, and redesign of the CDRs of a known antibody framework require exact specification of the known structural coordinates. In this section, we describe a method that allows for such specification as a hard constraint on the reverse diffusion trajectories.

We began by exploring methods for substructural conditioning that bias sampling by adding a conditional score term $\nabla \log_x p_t(y|x)$ to the drift component in the reverse SDE (Appendices O N). In practice we found that these methods do not always result in samples that satisfy the condition y exactly. Often to enforce y in these regimes one must upweight the conditional score relative to the prior score function which can result in a reduction in the likelihood (or ELBO) of the samples drawn, or even in numerical instability.

The method presented below is motivated by the approach described in [146] where the equilibrium states of a system are sampled by simulating the dynamics of an auxiliary system with a modified mass matrix. If the mass matrix is chosen appropriately, the original system's configuration space can be sampled more efficiently.

The method works by initializing $x_1$ in a way that enforces condition y, so that $p_1(y|x_1)=1$, and then integrating a modified Annealed Langevin Dynamics SDE (see appendix B) backwards in time to sample from $p_0(x|x_1)$, where the dynamics are modified to be y preserving by using a mass matrix that assigns higher mass to particles closer (in chain distance) to known coordinates and assigning infinite mass to known atoms. Samples drawn using this method satisfy y with probability 1.

Let $\mathcal{S}$, $\mathcal{M} \subset [1, \ldots, N]$ denote the atoms comprising the unknown scaffold and known motif, respectively, throughout this section.

M.1.1 Related Work

Song et al. [52] present a replacement method for drawing approximate conditional samples from $p(x_0{}^{\mathcal{S}}|x_0{}^{\mathcal{M}})$ in which one samples a sequence of noised motifs $\bar{x}_{1:T}{}^{\mathcal{M}} \sim q(x_{1:T}{}^{\mathcal{M}}|x_{(0)}{}^{\mathcal{M}})$, then running diffusion backwards in time but at each time step replacing $x_t{}^{\mathcal{M}} \leftarrow x_t{}^{\mathcal{M}}$ before sampling $x_{t-1} \sim p(x_{t-1}|x_t)$. [83] demonstrated that this method introduces irreducible error that is exacerbated by the correlation introduced by q and propose a particle-filtering based approach which furnishes arbitrarily accurate conditional samples given sufficient computation. Informally, the error introduced by the replacement method arises from imputing noised motifs that are highly unlikely given the corresponding noised scaffold.

M.1.2 Method

It is known that for $x \sim \mathcal{N}(\mu, \Sigma)$, if we partition the coordinates as above into subsets $\mathcal{M}$, $\mathcal{S}$ and write $$x = \begin{bmatrix} x^{\mathcal{S}} \\ x^{\mathcal{M}} \end{bmatrix} \text{ with}$$

$$\mu = \begin{bmatrix} \mu^{\mathcal{S}} \\ \mu^{\mathcal{M}} \end{bmatrix} \text{ and } \sum = \begin{bmatrix} \sum_{\mathcal{SS}} & \sum_{\mathcal{SM}} \\ \sum_{\mathcal{MS}} & \sum_{\mathcal{MM}} \end{bmatrix} \text{ that } (x^{\mathcal{S}} \mid x^{\mathcal{M}} = a) \sim \mathcal{N}\left(\overline{\mu}, \overline{\sum}\right)$$

Figure 39:
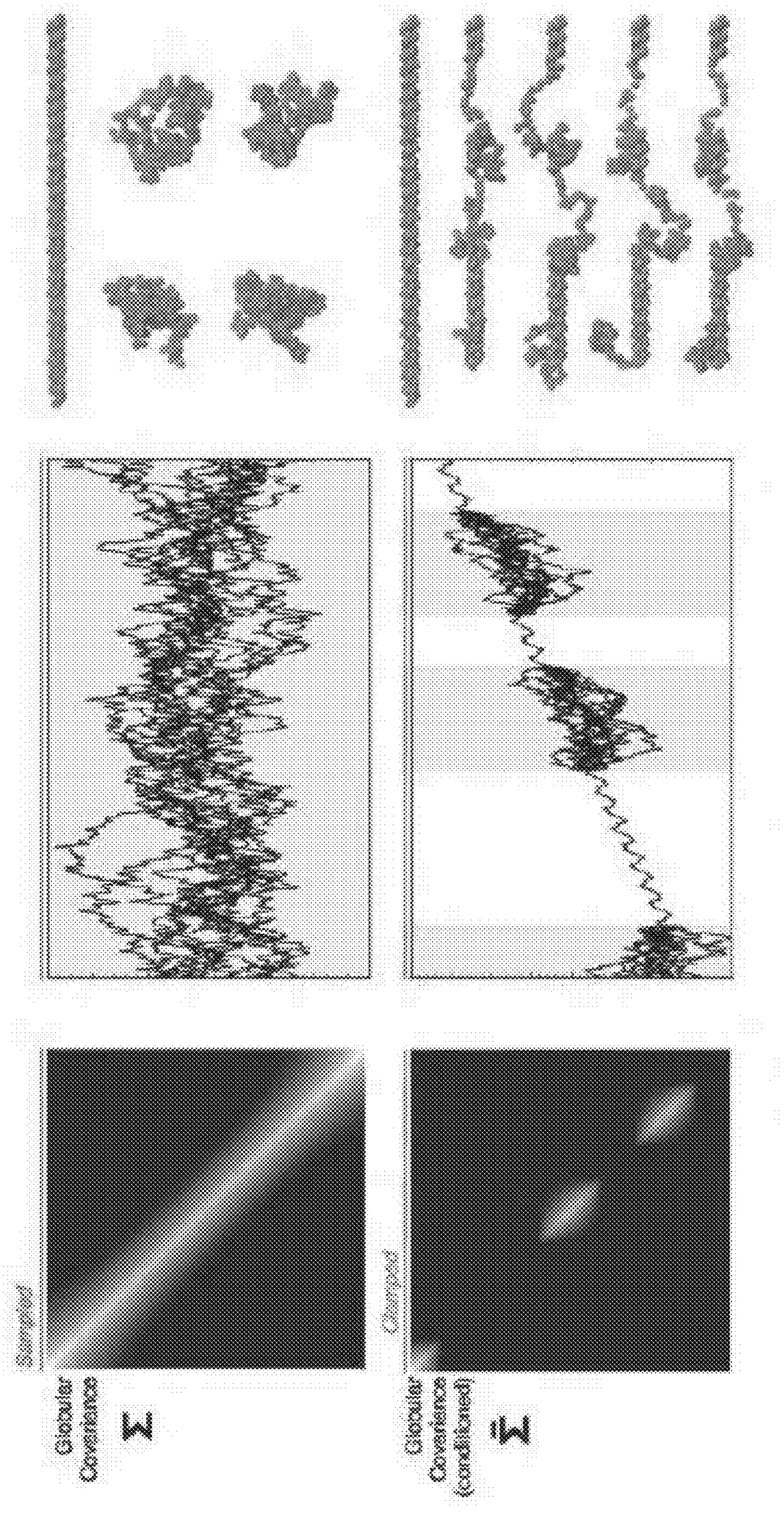
FIG. 39 shows that the globular covariance model admits analytic conditioning

FIG. 39: The globular covariance model admits analytic conditioning (Left) Heatmaps illustrating comparison of unconditional (top) globular covariance matrix $RR^T$ and conditioned (bottom) covariance matrix $\overline{RR}^T$. (Middle) X-coordinate plotted against residue index of samples drawn from unconditional (top) and conditional (bottom) prior. (Right) Initial samples $X_0$ and noised samples drawn from $p(X_1|X_0)$ for the unconditional (top) and conditional (bottom) priors. Conditioned-on structural residues are drawn in gray and correspond to the same residues that are conditioned in the covariance matrix and line plot.

where $$\mu = \mu^{\mathcal{S}} + \sum_{\mathcal{SM}} \sum_{\mathcal{M}}^{-1} (a - \mu^{\mathcal{M}})$$

and $$\sum = \sum_{\mathcal{SS}} - \sum_{\mathcal{SM}} \sum_{\mathcal{MM}}^{-1} \sum_{\mathcal{MS}}$$

where inverse matrices are understood to denote pseudo-inverses. We also compute the Cholesky factorization $\overline{RR}^T = \overline{\Sigma}$. To draw an approximate conditional sample from $p(x_0{}^{\mathcal{S}}|x_0{}^{\mathcal{M}}=a)$ we proceed as follows: we sample $x_1{}^{\mathcal{S}} \sim \mathcal{N}(\overline{\mu}, \overline{\Sigma})$ from the conditional prior, set $x_1{}^{\mathcal{M}}=a$, and integrate a modified Annealed Langevin Dynamics SDE (see section B.2)

$$dx = -\frac{\beta_t \psi}{2} \overline{R}\overline{R}^T \nabla_x \log p_t(x)^{\lambda_0} dt + \sqrt{\beta_t \psi}\, \overline{R}\, d\overline{w}$$

backwards in time, where the matrices $\overline{R}$, $\overline{R}^T$ are broadcast to the correct size with the conditioned on rows and columns filled by zeroes. FIG. 39 illustrates $\overline{R}$, $\overline{R}^T$ as well as samples from a conditional prior.

Additionally, we have found it helpful to incorporate a reconstruction-guidance based score term as in [151]. We have found that, while this can introduce some instability to the sampling, it can also improve sample quality.

Figure 40:
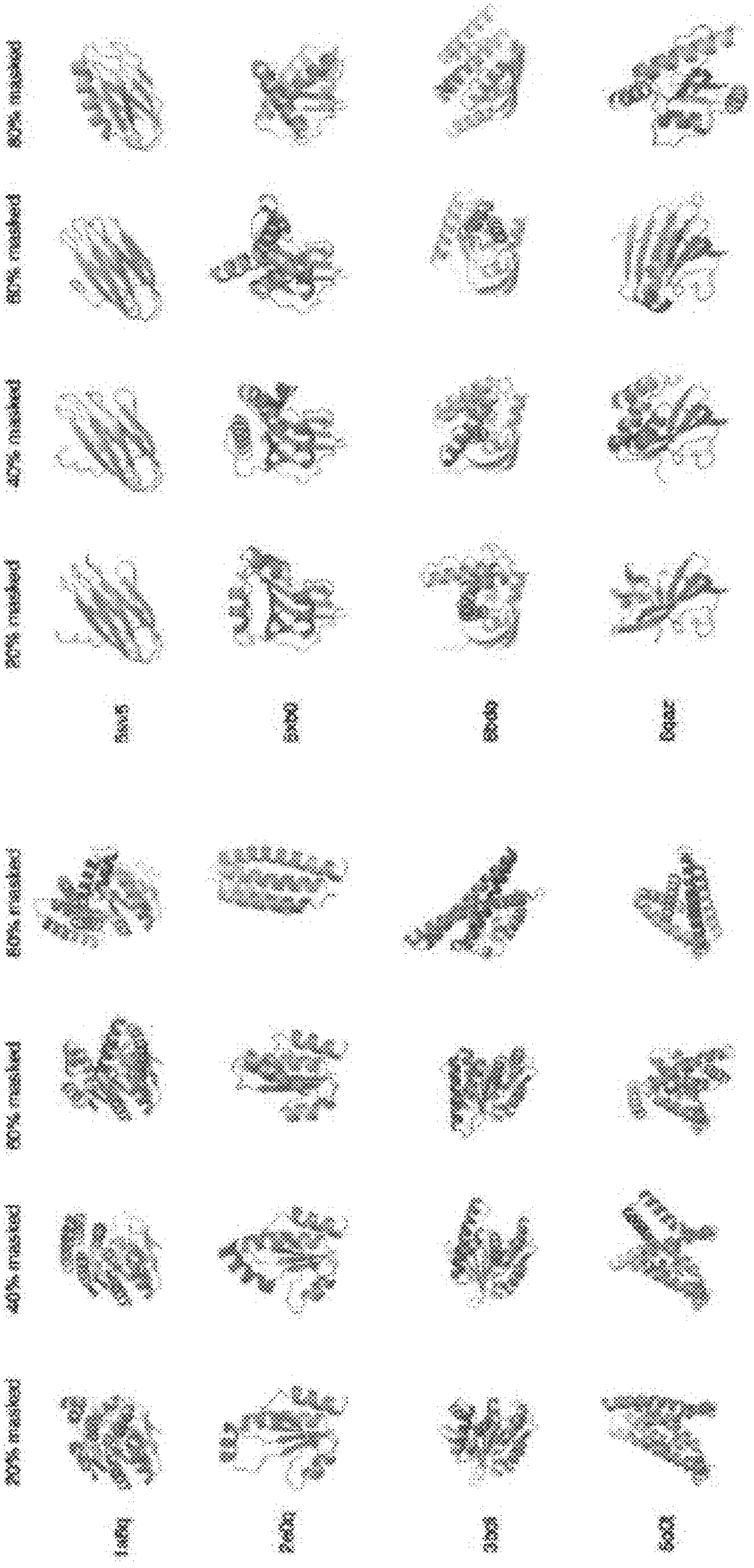
FIG. 40 shows examples of sub-structure conditioned Chroma samples

FIG. 40: Examples of sub-structure conditioned Chroma samples Example conditional samples drawn by conditioning on sub-structures of 8 PDBs sampled from the Chroma test split. Conditioned-on portions of the structure are defined by splitting the protein by a plane normal to the first principal component of the atom coordinates and are drawn in grey. The plane is shifted to condition on a specified fraction of the residues for each column.

To do so, in our conditioner formulation we define:

$$U_f(\tilde{x}_t, U, t) = U + \left\|\hat{x}_\theta(x_t, t)^{\mathcal{M}} - x_t^{\mathcal{M}}\right\|_2^2$$

where $$x_t = f(\tilde{x}_t) = \overline{R}R^{-1}\tilde{x}_t + \overline{\mu}$$

see section L.2 for a derivation that under this $f$, evolving $\tilde{x}$ according to the unmodified Annealed Langevin SDE induces dynamics on $x_t$ equivalent to the mass-modified dynamics presented above.

N Programmability: Substructure Distances

N.1 Motivation

In some instances, it may be useful to generate diverse protein chains or complex structures under the constraints that one or more specific residue pairs be in spatial proximity (i.e., form a "contact"). Such a conditioner could be used, for example, to design binders by ensuring that the desired binding site is being engaged. Or it could be used to enforce some desired topological properties i.e., the proximity of N- and C-termini (e.g., for ease of circular permutation). Assuming that we are interested in conditioning on a contact between atoms i and j within the diffusion conditioning framework, we wish to compute the probability that the distance between two atoms in the fully denoised structure $D_0^{ij}$ is below some desired cutoff c, i.e. $D_0^{ij}<c$, given a noised sample at time t and the corresponding distance $d_t^{ij}$.

N.2 Approach

The Bayesian approach to diffusion conditioning approach would be to build an estimate of the time-dependent likelihoid $p_t(y|x(t))$ to classify noisy inputs. In the case of a contact classifier, we can build an analytic approximation for $p_t(D_0^{ij}<c|x_t)$ as follows. First, we choose a prior $p(x_0)$ that will capture distance statistics in the PDB give rise to an tractable posterior denoising distribution $p(x_0|x_t)$. With a Gaussian prior for $x_0$, which we can use our globular covariance model for, we arrive at a Gaussian posterior for $p(x_0|x_t)$ and can further model the posterior distances $p(D_0^{ij}|x_t)$ with a non-central chi-squared distribution. This allows us to compute the desired $p(D_0^{ij}<c|x_t)$ using the CDF of the non-central chi-squared distribution.

N.2.1 Method

First, we can build a Gaussian approximation of a prior for protein chains $p(x_0)$ with our globular covariance model (Appendix C.3) as $$p(x_0) \sim \mathcal{N}(0, RR^T)$$

Then, according to our forward process we have a forwards transition kernel for the likelihood as $$p(x_t \mid x_0) \sim \mathcal{N}(\alpha_t x_0, \sigma_t^2 RR^T)$$

We can now apply Bayes' Theorem as $$\begin{aligned} p(x_0 \mid x_t) &\propto \mathcal{N}(x_0; 0, RR^T)\mathcal{N}(x_t; \alpha_t x_0, \sigma_t^2 RR^T) \\ &\propto \mathcal{N}(x_0; 0, RR^T)\mathcal{N}\left(x_0; \frac{x_t}{\alpha_t}, \frac{\sigma_t^2}{\alpha_t^2} RR^T\right) \\ p(x_0 \mid x_t) &= \mathcal{N}(x_0; \alpha_t x_t, \sigma_t^2 RR^T) \end{aligned}$$

We can therefore express a sample from the posterior $x_0 \sim p(x_0|x_t)$ as $$x_0 = \alpha_t x_t + \sigma_t Rz$$

where $z \sim \mathcal{N}(O, I)$. Assuming j>i, we have $$x_0^j - x_0^i = \alpha_t(x_t^j - x_t^i) + \sigma_t([Rz]_j - [Rz]_i).$$

From the $R_g$ scaling analysis of the globular covariance model (Appendix C.3) we have $$\begin{aligned} \sigma_{ij}^2 &\triangleq \mathrm{Var}([Rz]_j - [Rz]_i)) \\ &= \frac{2\alpha^2(1 - b^{j-i})}{1 - b^2}, \end{aligned}$$

and therefore the inter-atomic residual will be Gaussian distributed as $$\frac{x_0^j - x_0^i}{\sigma_t \sigma_{ij}} \sim \mathcal{N}\left(\frac{\alpha_t(x_t^j - x_t^i)}{\sigma_t \sigma_{ij}}, I\right).$$

The squared inter-atomic distance is a squared 2-norm of this residual, which will therefore follow a non-central Chi Squared distribution with 3 degrees of freedom as $$\left\| \frac{x_0^j - x_0^i}{\sigma_t \sigma_{ij}} \right\|_2^2 = \frac{(D_0^{ij})^2}{\sigma_t^2 \sigma_{ij}^2} \sim \mathrm{NonCentralChiSquared}\left(\frac{\alpha_t (d_t^{ij})^2}{\sigma_t^2 \sigma_{ij}^2}, k = 3\right).$$

We can therefore apply distance restraints by adjust the total energy by $$\log p(D_0^{ij} < C \mid x_t, t) = \log\left(1 - Q_{\frac{k}{2}}(AAA, BBB)\right),$$

where Q is the Marcum Q-function.

O Programmability: Substructure Motifs

O.1 Motivation

Figure 41:
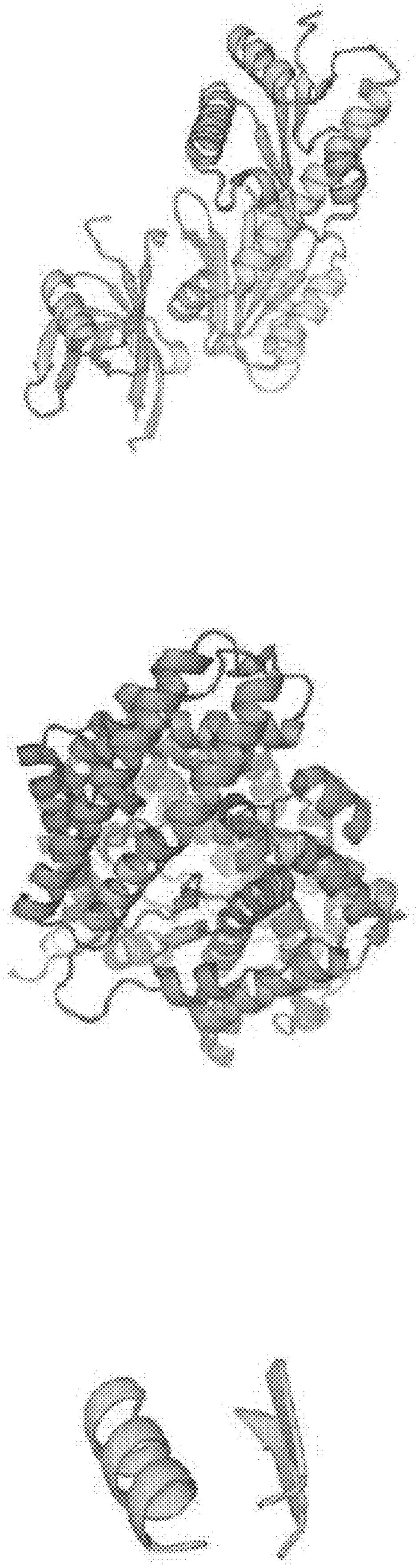
FIG. 41 shows that motifs can occur in entirely unrelated structural contexts.

It would be very useful for a variety of protein engineering applications to condition structure generation on the presence of a particular structural "motif." By this we mean an arbitrary substructure, composed of any number of disjoint backbone segments, that we would like to exist within our final generated structure. In practice, such a motif could represent a functional constellation of residues or a metal/small-molecule binding site—this could be useful for designing enzymes or other functional proteins, by exploring ideas around a core functional mechanism. In another example, the motif could correspond to a "scaffolding" part of the molecule that we would want to preserve—e.g., the binding scaffold that can admit different loop conformations. Or the motif could represent a desired epitope that we would like to faithfully present on the surface of a generated protein in the context of vaccine design. FIG. 41 shows an example motif and two unrelated native protein structures in which this motif is found with low RMSD.

O.2 Approach

To determine whether a pre-specified motif is present within a given structure S is simple-one can, for example, find the substructure of S with the lowest optimal superposition root-mean-squareddeviation (RMSD) to the motif and ask whether this RMSD value is below a desired cutoff; this can be done using previously published algorithms [152, 153]. To enable conditional generation based on the presence of a motif then, we employ a form of reconstruction guidance based on the best RMSD to the motif in the present de-noised structure. Specifically, at time t we define the best-match RMSD to the target motif with coordinates $x\mathcal{M}$ as:

$$\rho(x_t) = \min_{\pi \in \Pi} \min_{T \in SE(3)} \frac{\left\| x_t^{\mathcal{M}} - T \circ \hat{x}_\theta(x_t, t)^{\mathcal{M}_\pi} \right\|_2}{\sqrt{|\mathcal{M}_\pi|}} \quad (11)$$

where the outer minimization is over the combinatorial space $\Pi$ of alignment permutations $\pi$ of motif disjoint segments onto the current structure $x_t$ and the inner minimization is over the optimal superposition of the motif given a specific alignment $\pi$. The actual calculation is done using a branch-and-bound search similar to the one defined in Zhou et al. [152] rather than an explicit minimization over permutations. With this, we then modify the energy within our conditioner formulation (see section L) as:

$$U_f(x_t, U, t) = U + \eta\log\left(1 + e^{\zeta[\rho(x_t) - \rho_{max}]}\right)$$

where $\rho_{max}$ is the threshold RMSD below which we desire to find the motif in the final generated structure, and $\eta$ and $\zeta$ are parameters (we used $\eta$=50 and $\zeta$=4 in this work).

FIG. 41: Motifs can occur in entirely unrelated structural contexts. a, An example motif composed of three disjoint segments. b, PDB entry 3NXQ harbors the motif with a backbone RMSD of 0.45 Å. c, PDB entry 30 BW harbors the motif with a backbone RMSD of 0.64 Å.

With this modification, auto-differentiation of the resulting energy to obtain the score function creates gradients that pull the system towards containing the motif in question. Note that the location of the motif within the generated structure needs not be specified, as equation 11 optimizes over all possible alignments at each step of the reverse diffusion. On the other hand, it is also easy to introduce constraints to the possible matching alignments, such as either relative constraints on the mapping of individual segments of the motif (e.g., first and second segments must be separated by anywhere between 3 and 20 residues) or absolute constraints on the location of the motif (e.g., first segment must match in the first 100 residues of the generated structure). This can be easily accommodated by modifying the parameters of the search in equation 11 as shown previously [152].

P Programmability: Symmetry

P.1 Motivation

The functions of many proteins are often realized through self-assembly into large higher-order structures. One of the most powerful and widely employed tools for this in nature is symmetric assembly, observed in everything from large membrane pores that gate transfer of materials in and out of cells to icosahedral viral capsids which can encapsulate an entire genetic payload [154].

Similarly, incorporating symmetry into computational design of proteins holds great promise for building large functional complexes [155]. To realize this potential within our diffusion framework, we propose a method to directly constrain sampling to any prescribed discrete Euclidean symmetries.

Related work Incorporating group equivariance in machine learning has been an important topic in the machine learning community [156]. Incorporating symmetries is critical in molecular simulations [157, 158]. In this work, we proposed a method for incorporating symmetry for point set sampling with applications in the generation of large-scale protein complexes with arbitrary discrete symmetry groups.

P.2 Symmetry Breaking in Sampling

Group theory lays the foundation for describing symmetries in mathematics, physics, and biology. [159-161] Let $G=[g]_{i=0}^{M}$ be a collection of symmetry operations that form a group such as point groups and space groups. For point sets in $\mathbb{R}^3$, these symmetry operations can be represented as a set of orthogonal transformations, i.e. rotations and/or reflections.

To generate symmetric protein complexes, we want to sample structures $x \in \mathbb{R}^{M \times N \times 3}$ that are built from $M=|G|$ identical single chain proteins $x \in \mathbb{R}^{N \times 3}$ where N is the number of residues for each subunit. The SDE solving process produces final sample with:

$$x_0 = sde\text{solve}(x_T) \tag{12}$$

For sample generation to respect symmetries for an arbitrary group G, the SDE/ODE dynamics needs to be G-invariant up to a permutation of subunits. Let • represent the symmetric operations (rotation, reflection, and translation) performed on point sets in $\mathbb{R}^3$, we define the sampling procedure sdesolve: $\mathbb{R}^{M \times N \times 3} \to \mathbb{R}^{|G| \times n \times 3}$ with bfx $x_0$=sdesolve ($x_T$) being the desired samples. The sampling procedure should follow the following G-invariance condition:

$$sde\text{solve}(gx_T) = gsde\text{solve}(x_T) = \sigma(g)\ sde\text{solve}(x_T),\ \forall\ g \in G \tag{13}$$

where g indicates a group element in G and we impose an arbitrary order on G and our method is equivariant to the permutation of subunits. $\sigma(g)$ is the induced permutation operation that satisfies the relation: $gG=\sigma(g)\,G$, as computed from the group multiplication table (also called the Caley table).

The first equality in eq. (13) is trivially satisfied if $f(\cdot)$ or the underlying gradient update is E(3) equivariant, as G consists of only orthogonal transformations and translations. However, the second equality is generally not satisfied. For molecular simulations where Hamiltonian dynamics is used, the second equality can be satisfied if (i) the energy function is E(3) invariant, and (ii) the initial $$x_T \text{ and } \frac{dx_T}{dt}$$

are symmetric, i.e $$gx_T = \sigma(g)x_T,\ g\frac{dx_T}{dt} = \sigma(g)\frac{dx_T}{dt}.$$

At each successive time step, $x_t$ automatically satisfies the prescribed G-symmetry. This approach confines both the position and momentum update to ensure that the sampled configurations remain symmetric.

However, this is not the case for SDE/ODE sampling in our framework. We list three origins of the symmetry-breaking error if eq. (12) is used: (i) the denosing network uses distances as features and is automatically E(3) equivariant. However, because protein feature graphs are generated probabilistically, with each subunit protein having different geometric graphs, although they are symmetric. (ii) Our polymer structured noise is randomly sampled from $\mathcal{N}(x_T; \mu, \Sigma)$, so each subunit protein has different chain noises. (iii) The sampling procedure requires solving an ODE/SDE which is vulnerable to accumulated integration error. Integration error can induce unwanted geometric drifts such as rotation and translation [162], and be a substantial symmetry breaking force.

P.3 Symmetric Transformation as a Conditioner

Basic case. We propose the symmetric sampling approach as a constrained transformation formalism implemented as a conditioner block, as delineated in the referenced literature. Using the representations of G, we demonstrate the building of protein symmetric assemblies from an asymmetric unit (AU) chain $\tilde{x}$ through symmetrization. We commence with the mathematical formulation of the transformation, subsequently elucidating the induced linear transformation on the intrinsic gradient dynamics.

Representing G as M×3×3 rotation matrices G, we define the constrained transformation as $$x_t = f(\tilde{x}_t, t) = \text{symmetrize}(\tilde{x}_t) = G\tilde{x}_t \tag{14}$$

with the equivalent indexed tensor multiplication as:

$$[x_t]_{m,n,i} = \sum_j G_{m,i,j}[\tilde{x}_t]_{n,j} \tag{15}$$

where n is the index of the elements of the group, m is the index of atoms in AU, and i,j are Euclidean indices. The associated diffusion energy transformation is the following:

$$\frac{1}{|G|}U_f(x_t) = \frac{1}{2|G|}\left\|\sigma_t^{-1}R^{-1}(f(\tilde{x}_t, U_0; t) - \alpha_t\hat{x}_t(x_t, t))\right\|_2^2 = -\frac{1}{|G|}\log\, p_t(x_t) \tag{16}$$

The energy is averaged with |G| to account for the diffusion energy in individual AU with M atoms. we can compute the Jacobian of the transformation $f$: $\mathbb{R}^{M\times 3} \to \mathbb{R}^{N\times M\times 3}$:

$$\frac{df(x_t)}{d\tilde{x}_t} = G \to \frac{d[f(x_t)]_{m,n,i}}{d[\tilde{x}_t]_{n',j}} = G_{m,i,j}\delta_{n,n'} \tag{17}$$

To derive the transformed dynamics, we inspect one solver step for the reverse Langevin dynamics (identical analysis can be done for reverse diffusion):

$$\tilde{x}_{t+dt} = \tilde{x}_t - \frac{1}{2}RR^T\left[\frac{df(\tilde{x}_t)}{d\tilde{x}_t}\right]^T\frac{dU_f(x_t)}{dx_t}dt - Rd\overline{w} \tag{18}$$

We analyze the induced gradient transform with its associated indexed representation.

$$\frac{dU_f(x_t)}{d\tilde{x}_t} = \left[\frac{df(\tilde{x}_t)}{d\tilde{x}_t}\right]^T\frac{dU_f(x_t)}{dx_t} = G^T\frac{dU_f(x_t)}{dx_t} \tag{19}$$

$$\frac{dU_f(x_t)}{d[\tilde{x}_t]_{n,j}} = \sum_m\sum_i G_{m,i,j}\left[\frac{dU_f(x_t)}{dx_t}\right]_{m,n,i} \tag{20}$$

Observe that in the gradient transformation, the summation occurs over indices i, contrasting with the index j used in the forward transformation to account for the index transposition $[\cdot]^T$ between i and j. For orthogonal transformation, the transposition is also equivalent to the inverse of the individual rotation matrix in G. This method inherently pulls the gradients back to the AU. The computation of the transformed gradient can be adeptly handled using auto-differentiation, specifically as vector-Jacobian products. Furthermore, the gradients accumulated in AU are also averaged by the number of chains in the tessellated domain by dividing the gradient by |G|.

We then analyze the transformed solver step with the pull-back gradient transform.

$$\begin{aligned} f(\tilde{x}_t + d\tilde{x}_t) &= f\left(\tilde{x}_t - \frac{1}{2}RR^T\left[\frac{df(\tilde{x}_t)}{d\tilde{x}_t}\right]^T\frac{1}{|G|}\frac{dU(x_t)}{dx_t}dt + Rd\overline{w}\right) \\ &= \underbrace{G}_{symmetrize}\underbrace{\left(\tilde{x}_t - \frac{1}{2}RR^TG^{-1}\frac{1}{|G|}\frac{dU(x_t)}{dx_t}dt + Rd\overline{w}\right)}_{folding\ to\ AU} \end{aligned} \tag{21}$$

The constrained transformation has a nice interpretation: the solver step first folds the infinitesimal change back, followed by symmetrization. Note that this method is equivariant to permutations of group elements in G because the gradients are pulled back a AU and tessellate following the order of group elements in G.

Another option to pull the gradients is perform a "broadcasting" operation from a single AU (indexed with u) of x. This is also a valid gradient transformation that ensures G-invariance. This equation is an example of constrained transformations in eq. (10), and in practice we apply the temperature adjustment described in appendix B.

$$f(\tilde{x}_t + d\tilde{x}_t) = f\left(\tilde{x}_t - \frac{1}{2}RR^T[G]_u^{-1}\left[\frac{dU(x_t)}{dx_t}\right]_u dt + Rd\overline{w}\right) \tag{22}$$

Symmetry operation compositions. The conditioner formalism facilitates the composability of constrained transformations, paving the way for intricate protein geometrical designs. For instance, by strategically combining rotations and translations, we can craft periodic protein assemblies. This technique enables the design of both crystals and quasi-crystals through prescribed tiling operations. Moreover, by combining rotational symmetries with translations, one can engineer protein assemblies exhibiting hierarchical symmetries, producing in fractal-like assembly structures, as depicted in the bottom row of FIG. 43.

P.4 Practical implementation with additional transformation blocks subsampling. For efficient memory sampling of large symmetric assemblies, consider reducing the number of chains using chain subsampling techniques. This approach allows us to focus on updating a specific subset, denoted as $\mathcal{S} \subset [1, \ldots, |G|]$, of subunits in $x_T$, thereby conserving both memory and computational time.

Given a designated subunit i, the subset S is derived by selecting the k-nearest neighbor (k-NN) subunits. This selection is determined by the distances between the geometric centers of the subunits, ensuring the incorporation of short-range interactions between them. Through this method, K subunits are chosen, where K represents the count of neighbors the denoiser interacts with during each integration phase.

This randomized selection not only ensures that the gradient update remains globally consistent but also prevents potential structural clashes and suboptimal contact formations. For a visual illustration of the composed constrained transformation process, refer to FIG. 42 which provides an illustrative example of symmetric sampling in $C_4$.

Interestingly, this procedure, at its core an index selection mechanism, can also be depicted as a linear transformation using a sparse matrix comprised of 0 s and 1 s. By harnessing interchain distances, we are equipped to select K<|G| chains following an exhaustive symmetric tessellation. This method of subsampling aligns with established techniques in molecular simulations that employ periodic boundary conditions. To further understand the subsampling process, it is interesting to note that, much like the tessellation method, the subsampling can be described as:

$$x_t = f(\tilde{x}_t, t) = \tilde{x}_t^S = \text{subsample}(\tilde{x}_t) = S\tilde{x}_t \quad (23)$$

$$\frac{df(x_t)}{d\tilde{x}_t} = S \in [0, 1]^{MN \times KN} \quad (24)$$

where S is the chain selection matrix of size (KN×K) where K<M is the number of chains selected computation, efficient computation and this can be efficient.

$R_g$ energy restraints. The conditioner formalism provides the flexibility to seamlessly incorporate the restraint energy during energy updates. To ensure optimal contact and packing, we can integrate an $R_g$ penalty through a harmonic or flat-bottom potential. This serves to maintain both the interchain distance and the Asymmetric Unit (AU) Radius of Gyration within reasonable range:

$$U_f(x_t, U, t) = U + U_{R_g}(x_t) = U + \left\| R_g(x_t) - \langle R_g \rangle \right\|_2^2 \quad (25)$$

The proposed samplers can also be combined with other conditioners (substructure, natural language, shape, etc.) to realize symmetric assembly design with controllable functions.

Composed transformation. Putting this together, the composed transformation is as follows:

$$x = \text{subsample}(\text{symmetrize}(\tilde{x})) \quad (26)$$

$$U_f(x, U, t) = U + U_{R_g}(\tilde{x}) + U_{R_g}(\text{subsample}(\text{symmetrize}(\tilde{x})))$$

Figure 42:
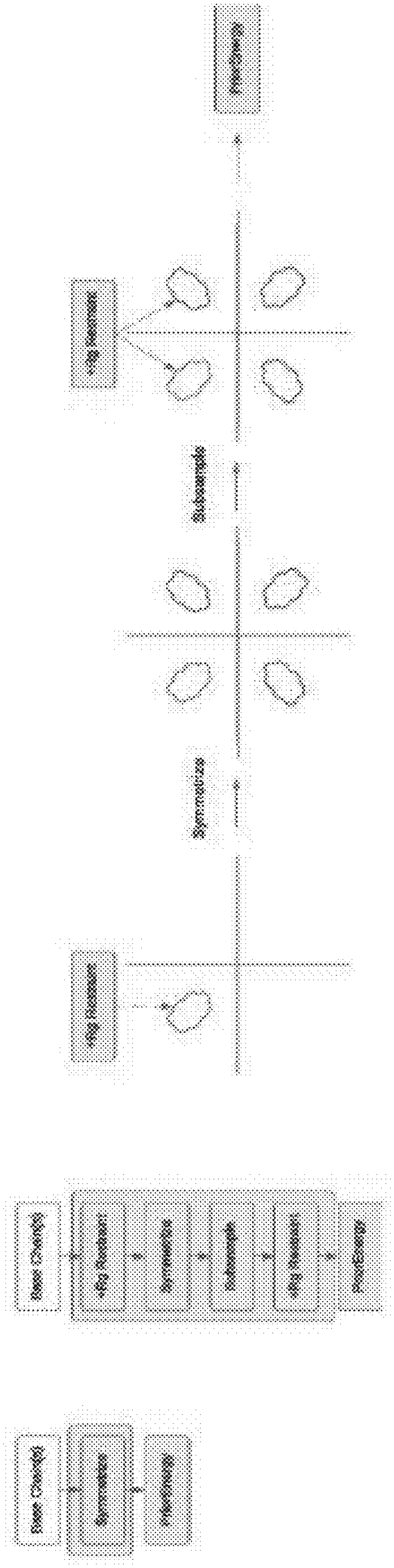
FIG. 42 shows constrained transformations for symmetry operations.

We include the schematic of the composed conditioner blocks in FIG. 42. For implementation, this can be easily implemented in a composable function.

P.5 Additional Symmetric Samples

We include more generated samples for selected point groups including $C_n$ (cyclic symmetry), $D_n$ (dihedral symmetry), T (tetrahedral symmetry), O (octahedral symmetry), I (icosahedral symmetry). For all the samples we use the reverse Langevin dynamics $\lambda_0=8$ with the Heun SDE solver that integrates from 1 to 0 for 500 steps. We used subunit k-NN sampling with K=5. When K>|G|, we set K=|G|−1. We provide additional samples categorized by the imposed symmetry group in FIG. 43 with a range of sequence lengths per subunit. Our method strictly imposes symmetries.

Q Programmability: Shape

Q.1 Motivation

Proteins often realize particular functions through particular shapes, and consequently being able to sample proteins subject to generic shape constraints would seem to be an important capability. Pores allow molecules to pass through biological membranes via a doughnut shape, scaffolding proteins spatially organize molecular events across the cell with precise spacing and interlocking assemblies, and receptors on the surfaces of cells interact with the surrounding world through precise geometries. Here, we aim to explore and test generalized tools for conditioning on volumetric shape specifications within the diffusion framework.

Q.2 Approach

Figure 43:
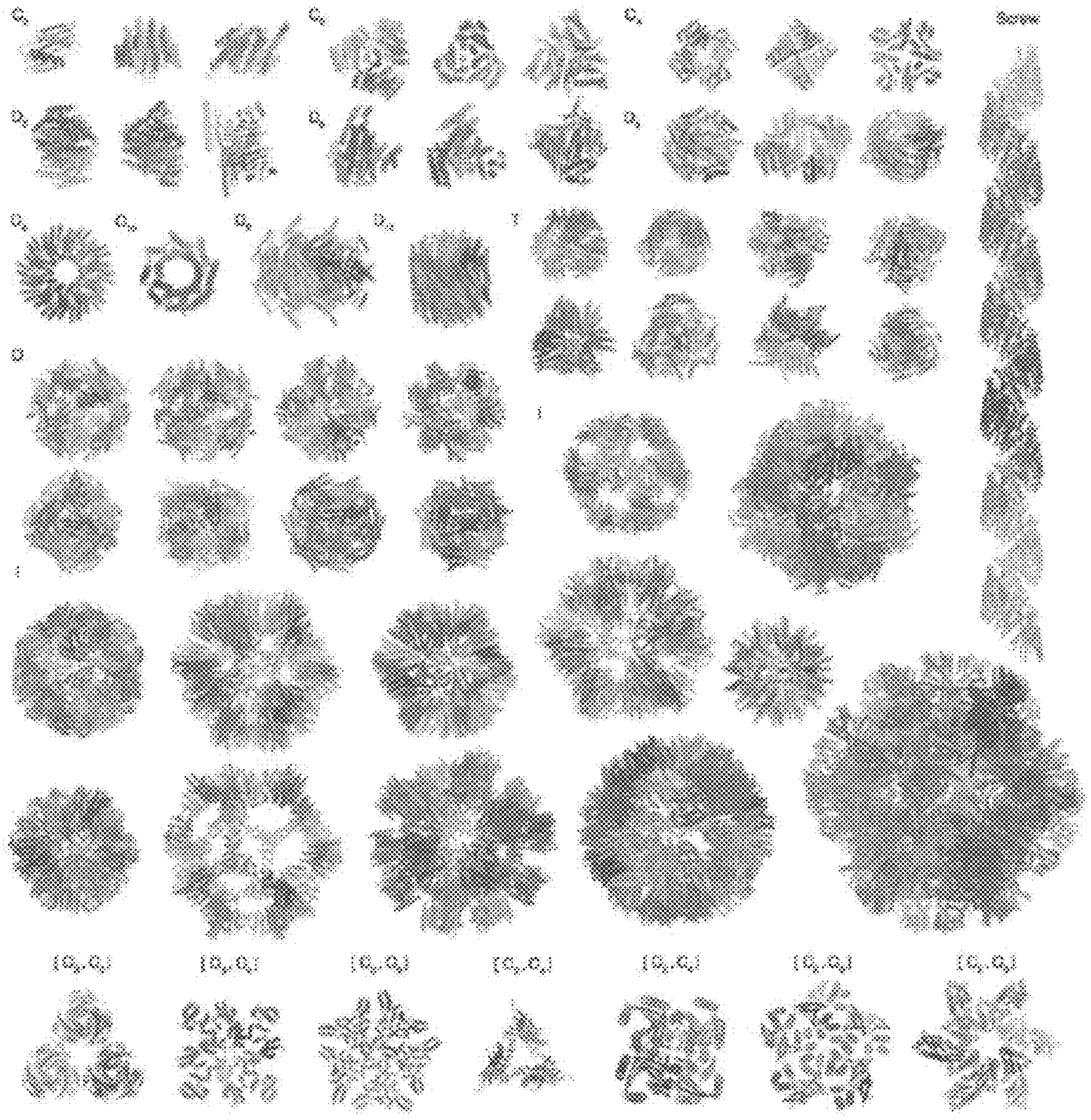
FIG. 43 shows additional generated complexes based on imposed symmetry groups.

FIG. 43: Additional generated complexes based on imposed symmetry groups.

Our shape conditioning approach is based on optimal transport [163], which provides tools for identifying correspondences and defining similarities between objects, such as the atoms in a protein backbone and a point cloud sampled from a target shape. We leverage two tools in particular: (i) the Wasserstein distance [163], which measures point cloud correspondences in Euclidean space and (ii) the Gromov-Wasserstein distance, which can measure the correspondences between objects in different domains by comparing their intra-domain distances or dissimilarities. Because Gromov-Wasserstein distance leverages relational comparisons, it can measure correspondences between unaligned objects of different structure and dimensionality such as a skeleton graph and a 3D surface [164] or unsupervised word embeddings in two different languages [165].

Figure 44:
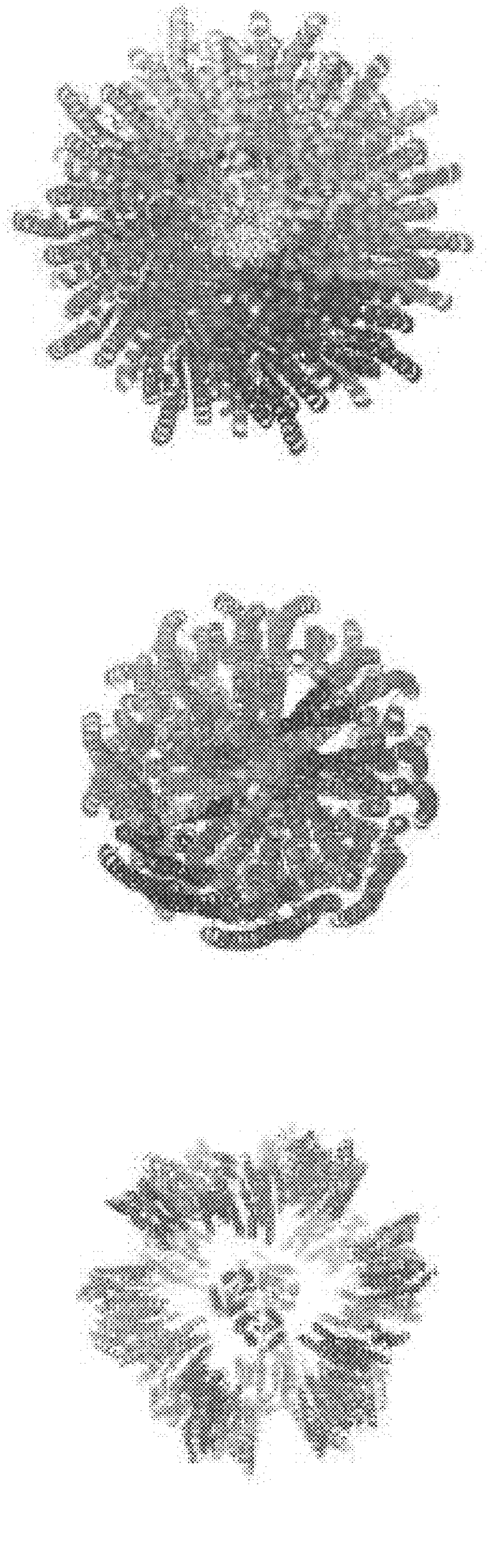
FIG. 44 shows examples of poor packing in sampled symmetric complexes.

FIG. 44: Examples of poor packing in sampled symmetric complexes. Underpacking or overpacking can occur occasionally, and may be partially addressed by density restraints.

Bounding degeneracy We initially experimented with restraints based purely on the Wasserstein distance and a target point cloud, which can estimated with the Sinkhorn algorithm [163], but found that the huge degeneracy in potential volume-filling conformations would often lead to jammed or high-contact-order solutions when using a modest amount of MCMC sampling. While long-run Langevin sampling or similar approaches could allow gentle annealing into a satisfactory configuration in principle, we sought to accelerate convergence by breaking this degeneracy with a very coarse "space-filling plan" for how the fold should map into the target point cloud, which the prior can then realize with a specific protein backbone.

Mapping 1D to 3D We can leverage Gromov-Wasserstein (GW) optimal transport to answer the question "How would an idealized protein fill a given space in a target 3D volume?". To do so, we (i) built an idealized distance matrix for a protein based on the 1D to 3D distance scaling law[8] of $D^{ideal}(|i-*j|)=7.21\times|i-j|^{0.32}$, (ii) computed the distance matrix for our target shape, and (iii) solved for the Gromov-Wasserstein optimal transport given these two distance matrices [163] yielding a coupling matrix $K_{GromovWasserstein}$ with dimensionality $N_{atoms}\times N_{points}$. This coupling map sums to unity and captures the correspondence between each point in the protein and in the shape. We use a small amount of entropy regularization to solve the optimal transport problem [163].

[8] This scaling law was fit on a large single-domain protein 6HYP

Optimal Transport loss In the inner loop of sampling, we can combine the Gromov-Wasserstein coupling with simple Wasserstein couplings as a form of regularization towards our fold "plan". Our final loss is then $$\text{ShapeLoss}(x, r) = \sum_{i,j} \left(K_{ij}^{GW} + K_{ij}^{W}(x, r)\right) \|x_i - r_j\|$$

where we compute the Wasserstein optimal couplings $K_{ij}^{W}$ with the Sinkhorn algorithm [163]. This yields a fast, differentiable loss that can be used directly for sampling.

Time-dependent scaling We weight the ShapeLoss (x, r) term with the scaling factor $$w_t^{(shape)} = \text{Clamp}\left(\sqrt{SNR_t}, [0.001, 3.0]\right)$$

and then add its gradient directly to the loss during sampling. So the weighted objective is $$\text{ShapeLoss}_t(x, r) = \text{Clamp}\left(\sqrt{SNR_t}, [0.001, 3.0]\right) \sum_{i,j} \left(K_{ij}^{GW} + K_{ij}^{W}(x, r)\right) \|x_i - r_j\|.$$

Scaling point clouds to protein sizes The Wasserstein and Gromov-Wasserstein losses are sensitive to the point cloud length scales, but our shapes will not in general be correctly sized to the protein that we wish to design them with. Of the methods that we explored to deal with this, two that demonstrated some success were

- Fixed volume scaling. We estimate an approximate volume of our point cloud via on a hard-sphere probe with radius set on typical nearest neighbor distance. We correct for sphere overlaps via second-order inclusion-exclusion formulas. We then resize the point cloud geometry to match ideal protein geometry scaling of approximately ≈128 Å$^3$ per residue and then adjust by a manually tuned factor (in practice anywhere from 0.3-1.0).
- Autoscaling We use the fixed scaling approach for GW distance calculation but also make our loss scale invariant during optimization by computing the loss with a version of the current structure that has been rescaled to have the same radius of gyration as the target point cloud.

Generating point clouds for characters We rendered Latin letters and Arabic numerals in the Liberation Sans font, extruded these 2D images into 3D volumes, and then sampled isotropic point clouds from these volumes.

R Programmability: Classification

R.1 Motivation

Protein databases provide a rich structured set of descriptions of various aspects of proteins. Proteins are classified in these databases in terms of various aspects of their sequence, structure, and functions. We can use any of these structured descriptors to generate proteins with structurally and semantically useful features. Some of these descriptors, particularly ones that correspond with protein function, may induce diffuse and complex structure changes that resist simple description. To this end, we explore using a multi-property protein classifier as a conditioner for generation, attempting to provide the ability to directly design proteins with desired categorical descriptions. We see this as an initial step towards programmability of protein function.

R.2 Approach

In order to create a conditioner

Figure 45:
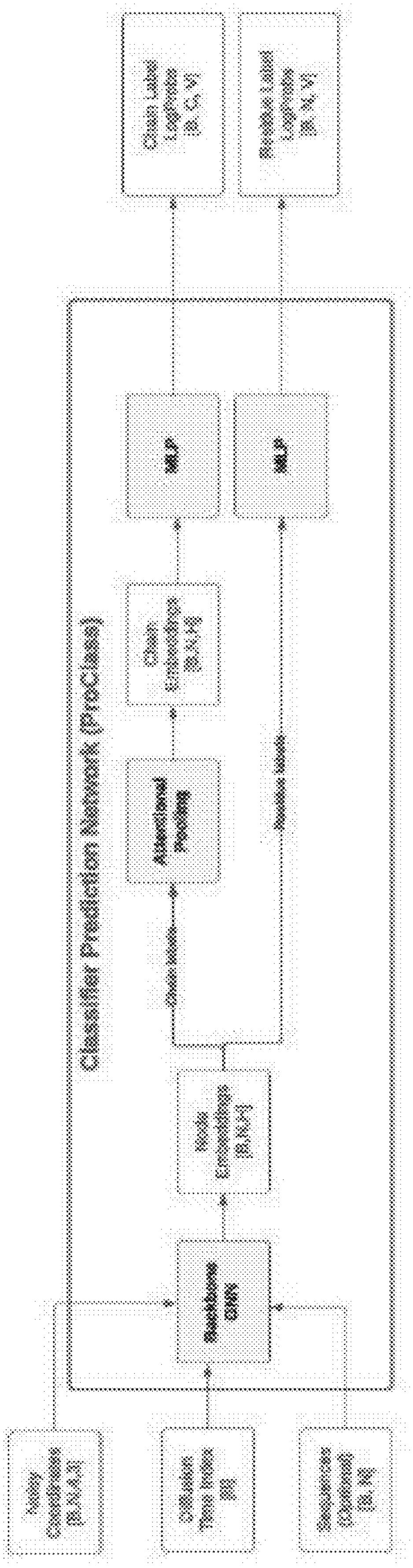
FIG. 45 shows ProClass model architecture.

FIG. 45: ProClass model architecture.

R.3 Model Inputs

We passed noised backbone coordinates obtained from the PDB as input to the model, along with a scalar $0<t<1$ denoting the time during diffusion (indexed between zero and one) that the noise was sampled at. The model can optionally consume sequence information if available.

R.4 Featurization

We encoded the diffusion time with a random Fourier featurization (e.g., see [166]). When providing a sequence, we encoded it with a learnable embedding layer of amino acid identity. Finally, we passed backbone coordinates to our ProteinFeatureGraph that extracts 2-mer and chain-based distances and orientations. We passed the sum of these components to the neural network.

R.5 Architecture

The encoder is a message-passing neural network. We formed the graph by taking K=20 nearest neighbors and sampling additional neighbors from a distribution according to a random exponential method.

We passed node and edge embeddings to each layer, with each node being updated by a scaled sum of messages passed from its neighbors. We obtained the message to pass from node i to node j by stacking the embeddings at node i, those at node j, and ε, and passing these to a multi-layer perceptron (1 hidden layer). We updated edges similarly. In each layer, we also applied layer normalization (along the channel dimension) and dropout (dropout probability=0.1).

After processing by the MPNN, we passed node embeddings to a different classification head for each label. For each head corresponding to a chain-level label, we pooled residues from each chain using an attentional pooling layer. We then passed the resulting embeddings to an MLP with 1 hidden layer to output logits for each label.

R.6 Labels and Loss Functions

We trained the model to predict the following labels: CATH, PFAM, Funfam, Organism, Secondary Structure, Interfacial Residue. We quantified the loss for each label prediction using cross entropy, and summed all components with equal weights.

R.7 Training

We trained the model for 50 epochs with an Adam optimizer with default momentum settings (betas=(0.9, 0.999)). We linearly annealed the learning rate from 0 up to 0.0001 over the first 10,000 steps and then kept it constant. During training, we first sampled a time stamp $0<t<1$ uniformly, then sampled noise from the globular covariance distribution, injected this noise into the backbone coordinates, and fed the result to the model. Next, we predicted labels, computed losses, and updated parameters with the Adam optimizer.

R.8 Hyperparameters

Our classification model has 4 layers, with node feature dimension 512 and edge feature dimension 192. Our node update MLP has hidden dimension 256 with 2 hidden layers, and our edge update MLP has hidden dimension 128 with 2 hidden layers.

S Programmability: Natural Language Annotations

S.1 Motivation

Recent advances in text-to-image diffusion models such as DALL-E 2 [75] and Imagen [74] have produced qualitatively impressive results using a natural language interface. Given the open availability of pre-trained language models and a corpus of protein captions form large scientific databases such as the PDB [118] and UniProt [167], we explore the possibility of creating a natural language interface to protein backbone generation. To do this, we build a protein captioning model (ProCap), which predicts $p(y|x_t)$, where y is a text description of a protein and $x_t$ is a noised protein backbone. This conditional model, when used in conjunction with the structural diffusion model presented in the main text, can be used as a text-to-protein backbone generative model.

S.2 Dataset Curation

To build a caption model, we begin by curating a paired dataset of protein structures and captions from both the PDB and UniProt databases. Caption information is collected for the structures used for the backbone diffusion model training, as well as the individual chains within these structures. For each structure, we use the PDB descriptive text as an overall caption. For each chain in a structure, we obtain a caption by concatenating all available functional comments from UniProt. Structures containing more than 1000 residues are not used, corresponding to a minority (10%) of all structures. The final set used to train and validate the caption model contains approximately 45 thousand captions, including those from both PDB and UniProt. Unlike the backbone model, the splits used for training are completely random. The small size of the dataset constrained architecture choices to those with relatively few free parameters.

Figure 46:
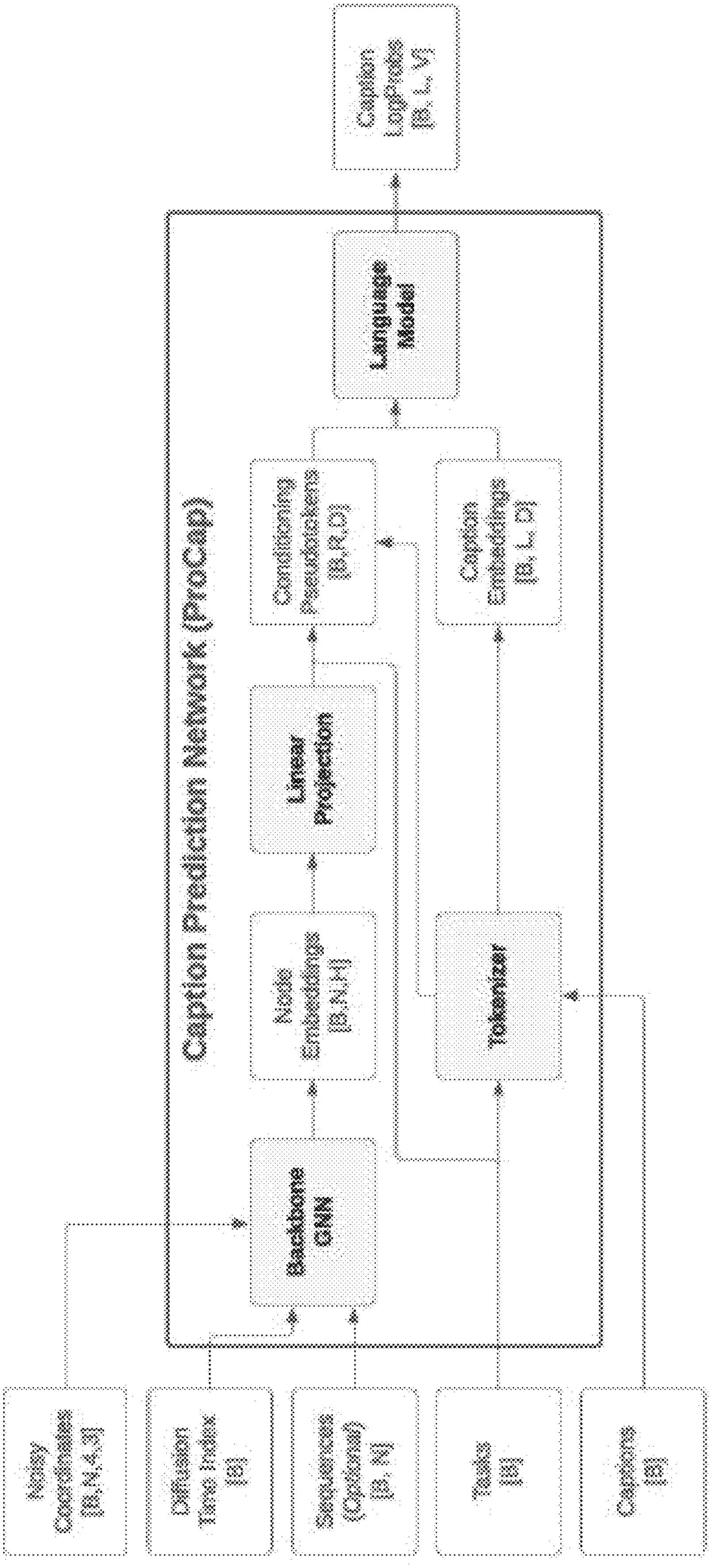
FIG. 46 shows ProClass model architecture.

FIG. 46: ProCap model architecture. ProCap connects a pretrained graph neural network encoder to an autoregressive language model trained on a large data corpus including scientific documents. We use the 125 M parameter GPT-Neo as the language model, with internal dimension D=768. Conditioning is achieved with pseudotokens generated from encodings of protein complex 3D backbone coordinates (batch size B, number of residues N, embedding dimension H) and a task token indicating whether a caption describes the whole complex or a single chain. The R relevant pseudotokens for each caption, consisting of the chain/structure residue tokens and the task token, are passed to the language model along with the caption. When used in the forward mode, ProCap can describe the protein backbone by outputting the probabilities of each word in the language model's vocabulary of size V for each of the L tokens of a caption. When used in conjunction with the prior model, it can be used for text to protein backbone synthesis. In training, ProCap uses a masked cross entropy loss applied only to the caption logits.

S.3 Model Architecture

S.3.1 Architecture Overview

To predict captions given noised structures, we construct ProCap using a pretrained language. model and a pretrained protein encoder. The pretrained language model is the GPT-Neo 125 million parameter model [168]. GPT-Neo was trained on the Pile [169] which contains articles from arXiv and PubMed. Its choice is motivated to maximize the chance that the model would begin training with some understanding of protein-related text. We also use the pretrained graph neural network encoder from ProClass, the protein structure classification model introduced above, to encode protein backbones. Analogously to the choice of the language model, the purpose of the structure encoder is to start ProCap with semantic knowledge of protein structure. To condition the autoregressive language model, GPT-Neo, pseudotokens are formed from structures using the ProClass encoder and prepended to the caption as context, similar to [170].

S.3.2 Data Embedding

Here, we describe the embedding of task, caption, and structure data into a shared tensor representation for input to the language model. We encode captions and task tokens using a modified version of the GPT-Neo tokenizer, whose vocabulary we augment with a special token to distinguish between prediction tasks involving single chains and those relating to entire structures. We convert structure inputs into pseudotokens with the same shape as text embeddings through the graph neural network encoder of the pre-trained ProClass model. We then concatenate the task, structure, and caption embeddings into a representation to pass to the language model to obtain logits representing the probabilities of caption tokens. We train our model on a standard masked cross entropy loss of the caption. FIG. 46 details the overall architectural flow. We proceed to discuss the details of the embedding procedure.

Structure encoding in ProCap relies on a pretrained ProClass model. This classifier model consists of a GNN with multiple heads to extract different class information, as described previously. We use the GNN portion of the classifier network to obtain embeddings of each residue in the latent space of the classifier, with the intent that the pretrained classifier weights should help ProCap learn the relationship between structures and captions. Besides the 3D information of the atoms in each structure, we input the diffusion timestep (noise level) to the GNN via a Fourier featurization layer which converts the diffusion time to a vector with the same dimension as the GNN node embedding space using randomly chosen frequencies between 0 and 16. To allow for ProCap to learn the optional use of sequence information, in 25% of the training data we pass sequences along with structures. In these cases, we convert the amino acid information for each residue through a single embedding layer with output size equal to that of the GNN node embedding space dimension, adding the result to the time step vector.

We add task tokens to the model to allow for captions of both single chain and full complex captions. For the prediction of UniProt captions describing single chains within structures, we pass only the embeddings of the residues in the relevant chain to the language model. For the prediction of the PDB captions related to entire structures, we pass all residue embeddings. In addition, we use a linear layer after the ProClass embeddings to go between the ProClass latent space and the embedding space of the language model, which are of different dimensionality. Finally, in order to help the model distinguish between PDB and UniProt prediction tasks, we prepend the encodings of entire structures with an embedding vector of a newly defined PDB marker token. We normalize the components of all structure vectors such that each one has zero mean and unit variance.

In summary, the ProCap architecture consists of a pretrained GNN model for structure embedding and a pretrained language model for caption embedding, with a learnable linear layer to interface between the two and a learnable language model head to convert the raw language model outputs to token probabilities.

S.4 Model Training

We train ProCap to be compatible with conditional generation using the structural diffusion prior model. Like the other conditional models in this paper, we noise each structure according to the schedule of the structural diffusion model. During ProCap training, we freeze the graph neural network encoder weights from the pre-trained ProClass model. As we add a <|PDB|> task token to the GPT-Neo vocabulary to cue the model to predict whole complex captions from the PDB, we allow the language model to learn in order to optimize the encoding of this new token and refine the embeddings of existing ones. Given the relatively small training data size, we also experimented with training ProCap with the language model frozen except for its head. As we found that the average perplexity achieved on the validation set was generally inferior when freezing language model weights, in our final training run we optimize all weights of the language model.

We conduct training on a single V100 with a constant learning rate of $5\times10^{-5}$ and the Adam optimizer with hyper-parameters $\beta_1=0.9$, $\beta_2=0.999$. We evaluate loss on our validation set after every 2000 training examples. Over 24 epochs, the validation cross entropy loss reaches a minimum of approximately 2.44, and the weights from this checkpoint are used to assess model performance.

S.5 Performance

In order to test ProCap as a generative model, we draw high-quality conditional and corresponding unconditional low-temperature samples from the model. To that end, we employ a structural denoising approach in a similar fashion to the method described in [52]. Specifically, we use the hybrid Langevin-reverse time SDE of Appendix B to evolve noisy random sample structures drawn from the diffusion model prior, with gradients of the ProCap loss with respect to structure added to the gradients of the structure diffusion model. When the size of the ProCap gradients is too small relative to those from the prior model, there is little appreciable difference between a caption-conditioned sample and an unconditional sample drawn from the same seed. We thus scale the ProCap gradients by a guidance scale of up to 100 and find that the resulting samples are better conditioned, analogously to previous work on classifier guidance [72]. At even larger guidance scales, the coherence of the samples breaks down as the base model's gradients are overwhelmed.

We present examples of our generated samples in the main text. To evaluate ProCap model performance, we measure the improvement in caption loss during the SDE evolution between the unconditioned and conditioned samples. As an independent check, we also examine the gain in the TM-score between our sample (conditioned over unconditioned) and a target PDB structure which exemplifies the caption being used for conditioning. Finally, we analyze the generated structures visually for structural coherence. Qualitatively, starting from the same noisy random structure, the diffusion model yields denoised structures which demonstrate desirable characteristics including secondary structure elements, both with and without guidance from the caption model.

Figure 47:
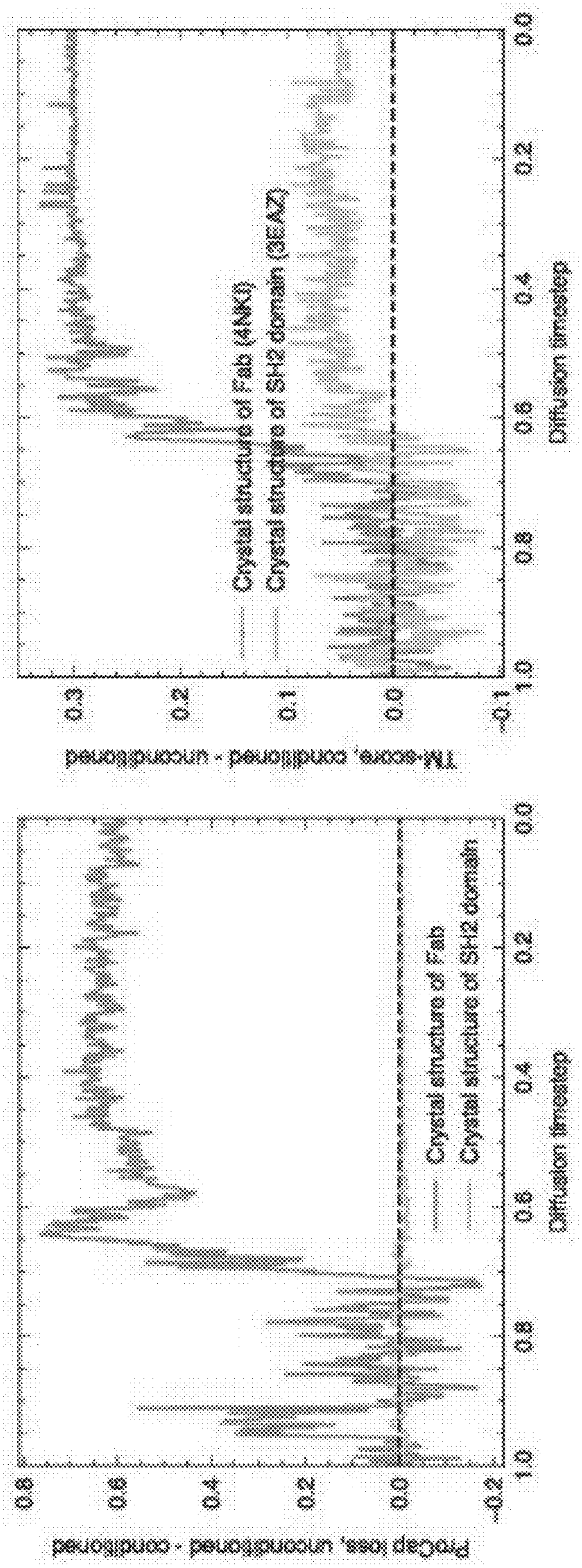
FIG. 47 shows that ProCap evaluation metrics show effect of natural language conditioning compared to unconditioned samples from the same noised seed structure.

The caption loss and TM-score metrics for example sampling trajectories are shown in FIG. 47. Both are initially quite noisy, and the conditioned and unconditioned samples are equally likely at high t to have lower ProCap loss and/or better alignment with the target structure. However, over the course of the reverse diffusion, the effect of the conditioning is demonstrated. It is particularly notable that the TM-score is relatively stable at low t, indicating a regime where the SDE evolution is fine-tuning structural details rather than making large-scale changes. In addition, we see that the impact of the classifier guidance can vary significantly, possibly owing to the balance required between the gradients over the diffusion trajectory. It remains challenging to robustly generate samples with natural language conditioning in a systematic fashion; nevertheless, our results serve as a proof of concept of guided diffusion using text input.

FIG. 47: ProCap evaluation metrics show effect of natural language conditioning compared to unconditioned samples from the same noised seed structure. (Left) The caption model cross-entropy loss as a function of diffusion timestep, for two sample trajectories with and without the use of caption gradients. (Right) The TM-score between sampled structures and example structures from the PDB corresponding to the captions used for conditioning.

Figure 48:
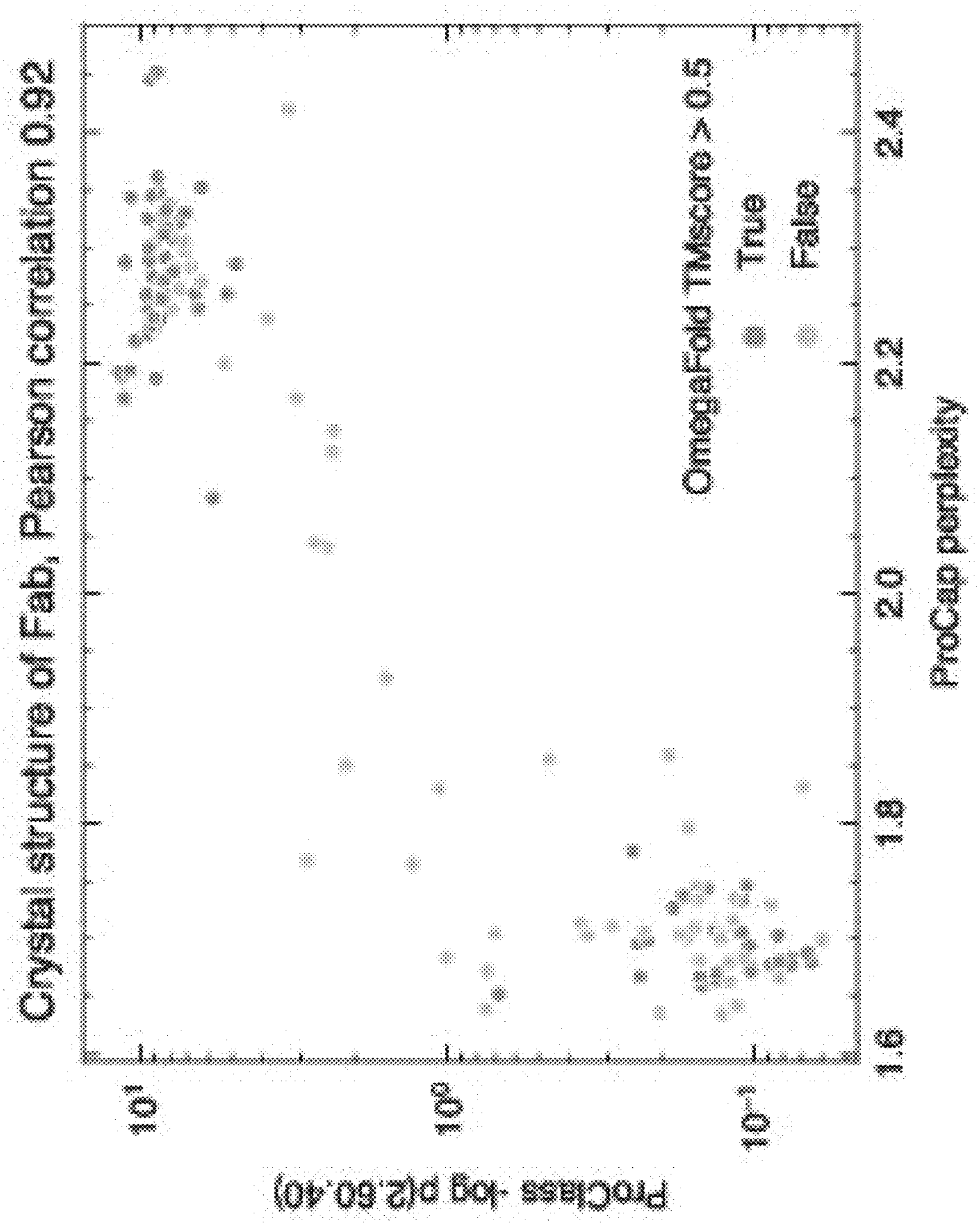
FIG. 48 shows that ProCap perplexity shows correlation with ProClass loss.

FIG. 48: ProCap perplexity shows correlation with ProClass loss. From a group of samples generated with classifier guidance from ProCap using an antibody-related caption, we plot the resulting perplexity of each backbone against its probability of an immunoglobulin fold (CATH 2.60.40). We estimate the fold probability of a backbone using the classification model described in appendix R, after the backbone is generated. Successful refolding can take place regardless of perplexity, as described further in appendix J.5.

As a final check of the ProCap model, we ask whether samples generated guided by natural language suggestive of a particular CATH topology are seen as being representative of that topology, as measured by the model of appendix R. In FIG. 48, we compare the ProCap perplexity and ProClass probability of an immunoglobulin fold (CATH 2.60.40) for backbones generated using the caption "Crystal structure of Fab". We see a strong correlation between the negative log probability of the relevant topology and the ProCap loss, suggesting that ProCap shows signs of understanding the meaning of natural language captions at the level of CATH topologies.

TABLE 7

Design protocol details

| | Unconditional I | Unconditional II | Conditioned I | Conditioned II |
|---|---|---|---|---|
| Length | [100; 450], uniform | [100; 950], uniform | 100 or 200, uniform | 150 |
| Model | ChromaBackbone v0.4999 | ChromaBackbone v0.4998 | ChromaBackbone v0.4999 | ChromaBackbone v0.4999 |
| Integration Parameters | 1000 steps of SDE, $\lambda_0 = 10$, $\psi = 2$ | 1000 steps of SDE, $\lambda_0 = 10$, $\psi = 0.1$ | 200, 600, or 2000 steps of SDE, $\lambda_0 = 10$, $\psi = 2$ | 2000 steps of HMC, $\lambda_0 = 10$, $\psi = 0.9$ |
| Conditioning | N/A | N/A | CATH class: $\alpha$, $\beta$, or mixed $\alpha/\beta$ | CATH topo 2.40.155 |
| Backbones generated | 500 | 2000 | 335 per class | 54 |
| Filter [1] | log p(s) | $R'_g$ | $\mathcal{L}$(x), log p(s), log p($\chi$) | $\mathcal{L}$(x), log p(s), log p($\chi$) |
| Final designs | 172 | 96 | 36 | 6 |

[1] $\mathcal{L}$(x)-Chroma ELBO; log p(s)-Chroma Design A sequence log-likelihood; log p($\chi$)-Chroma Design B chi-angle log-likelihood; $R'_g$-ratio of observed over expected radius of gyration, for given sequence length.

T Experimental Validation

T.1 Protein Design

Four sets of designs were generated for experimental validation: two unconditional sets (Unconditional I and II) and two sets conditioned on CATH class or topology (Conditioned I and II, respectively). The full protocol for each of these involved generating a set of Chroma backbones (either unconditionally or conditioned), designing sequences for each backbone (10 per backbone for Unconditional I and 1 per backbone for the rest), and sub-selecting a smaller set of designs to be experimentally characterized (see Supplementary Table 7 for details). Importantly, no sub-selection based on refolding or structural energy calculations was performed. Further, protocols were run in an automated fashion with no manual intervention or selection of designs. All experimentally addressed protein sequences are included in Extended Data Table 1.

T.2 Experimental Methods

T.2.1 DNA Design

Chroma protein sequences were backtranslated and codon optimized for mammalian expression, but omitting *E. coli* rare codons AGA and AGG to enable flexibility in the choice of expression host. DNA sequences were ordered as eBlocks from Integrated DNA Technologies, Inc. and cloned into either mammalian or bacterial expression plasmids using Golden Gate Assembly (NEB E1601L), with recipient vector information detailed in corresponding subsequent sections. All DNA sequences are included in Extended Data Table 1.

T.2.2 Pooled Split-GFP Solubility Assay

Split-GFP components GFP1-10 and GFP11 were codon optimized for expression in *E. coli* and cloned into the pNAS1b vector [171] under araBAD and pLtetO promoters, respectively. Chroma protein-encoding eBlocks were introduced into the split-GFP vector using pooled Golden Gate Assembly, resulting in gene cassettes under the pLtetO promoter with a C-terminal GFP11 fusion tag. The final encoded library protein sequences were as follows: MGSSHHHHHHSSGLVP RGS-[Chroma protein]-GSDGGSGGGS-[GFP11]. Pooled plasmid libraries were cloned using ElectroMAX DH10B cells (Invitrogen 11635018), and subsequently transformed into BL21 strain T7 Express Competent *E. coli* (NEB C2566I).

BL21 cells electroporated with the split-GFP plasmid library were recovered for 1 h in SOC medium (NEB B9020S) and inoculated directly into 50 mL terrific broth (TB, Gibco A1374301)+100 ng/μL carbenicillin and grown at 37° C., 230 rpm for 16 h. Cells were then diluted to $OD_{600}$=0.2 and grown at 37° C., 230 rpm until $OD_{600}$=0.8. Split-GFP system components were then induced using 0.1% w/vL(+)-arabinose (Thermo Scientific TS36518-0250) and 100 ng/μL anhydrotetracycline (Sigma Aldrich 37919-100 MG-R) and cells were grown for an additional 3 h. In parallel, cultures of BL21 cells expressing either dihydrofolate reductase (DHFR, a positive control) or human beta-3 adrenergic receptor (ADRB3, a negative control GPCR https://www.uniprot.org/uniprotkb/P13945) in the split-GFP vector were grown and induced under the same conditions as the library (Table 8). These control cells were then spiked into the library population at a 1:1000 ratio. 5 mL of the library with control spike-in cell mixture were set aside for miniprep and sequencing analysis of pre-FACS populations. 5 μL of the cell mixture was then washed twice with 1 mL cold PBS and then sorted into 4 different gated populations representing a range of GFP fluorescence values on a BD FACSAria. Gating parameters were determined empirically based on clonal positive and negative control cells, as shown in FIG. 53. At least 50,000 cells were collected per gate and recovered for 1 h in 1 mL SOC at 37° C., 230 rpm. Recovered cells were inoculated in 5 mL TB+100 ng/μL carbenicillin and grown for an additional 16 h. Plasmid populations were then isolated by miniprep (MacheryNagel 740588.50). For the fluorescence stability experiment shown in FIG. 53, cells recovered after FACS and regrown overnight were then subjected to a second round of identical experimentation in which split-GFP components were induced and cells were re-examined on the BD FACSAria.

T.2.3 Nanopore Sequencing and Analysis

Plasmid libraries from each population (i.e. the cells harboring the split-GFP Chroma library+spike-in controls prior to sorting and each of the 4 bin-sorted populations) were digested using HindIII and desalted using 0.7×v/v AMPure XP beads (Beckman Coulter A63880). 200 fmol of each library (assuming an average length of 6 kb) underwent DNA repair and end prep using manufacturer guidelines for R9 MinION flow cells (Oxford Nanopore FLO-MIN106D). The DNA was then purified with AMPure XP beads at a 1:1 ratio then quantified by Qubit 4 Fluorometer (ThermoFisher). 500 ng of DNA from each library underwent barcode ligation (Oxford Nanopore barcoding kit EXP-NBD104), followed by another 1:1 AMPure XP bead purification. Each library was then pooled in equimolar ratios and loaded onto the MinION flow cell. One experiment was performed using only proteins UNC_001 through UNC_172 (unconditional designs, 13.68 million reads) and two additional experiments were performed using all Chroma proteins pooled together (unconditional and conditional designs, 18.28 million reads total).

Sequencing reads were basecalled using Bonito Basecaller v0.6.1 (https://github. com/nanoporetech/bonito) with ONT Chemistry r9.4.1 and accuracy mode 'high'. Raw fastq files were generated and demultiplexed using a custom script. Demultiplexed reads were filtered for reads more than 400 bp using SeqKit v2.3.1 (https://bioinf.shenwei.me/seqkit/) [172] and aligned to reference Chroma sequences using Minimap2 v2.23 (https://github.com/lh3/minimap2) [173] to generate BAM alignment files. BAMs were sorted and indexed using samtools v1.16.1 (https://github.com/samtools/samtools). For each BAM file, pysam v0.20.0 (https://github.com/pysam-developers/pysam) was used to count reads aligned with each reference sequence. For sequence enrichment analysis, enrichment scores were assigned to each protein in each sorting bin by dividing normalized read counts for a given protein in a given bin by normalized read counts of that protein in the pre-FACS library. Split-GFP scores were assigned to each protein, j, as follows:

$$\text{score}_j = \sum_{i=0}^{n=3} \frac{\text{enrichment score}_i}{\text{sum of enrichment scores}_j} \times \text{bin}_i$$

For pooled assay score calculations, proteins in the set containing UNC_001 through UNC_172 (smaller unconditional designs) were analyzed alone (i.e. not considering read counts for other protein sequences) to enable triplicate data analysis between all three experiments. The set: containing UNC_173 through UNC 268 (larger unconditional designs) were also analyzed alone for the duplicate experiments performed. Given the small number of conditional designs, these proteins were analyzed with all other proteins. Raw and processed read counts are included in Extended Data Table 1.

T.2.4 Soluble Protein Expression Confirmation Via Western Blot

The top and bottom 20 scoring unconditional proteins from set UNC_001 through UNC_172 (smaller unconditional designs) and the top 10 proteins from set UNC_173 through UNC 268 (larger unconditional designs) were cloned into an *E. coli*-based overexpression vector based on pET (kanR, pBR22 origin, T7 promoter for Chroma protein expression) by Golden Gate Assembly, resulting in the following protein expression format: MGS-[Chroma protein]-GSENLYFQG SAWSHPQFEK, which includes a C-terminal TEV cleavage site and Strep-tag. Plasmids were transformed into the BL21 derivative T7 Express Competent *E. coli* (NEB C25661). Recovered cells were inoculated into 1 mL TB+50 ng/μL kanamycin and cells were grown in a 96-well deep well plate at 37° C., 230 rpm for 16 h. Cells were then diluted to $OD_{600}$=0.15 in1 mL TB and grown to $OD_{600}$=0.8. Protein expression was induced with 400 μM isopropyl B-D-1thiogalactopyranoside (Teknova NC1601425) and cells were grown for an additional 3 h. Cells were spun down at 500×g, media was discarded, and cell pellets were stored at −80° C. for 1 day. Cell pellets were then thawed on ice for 5 min and pellets were resuspended in 40 μL lysis buffer consisting of 50 mM NaCl (Invitrogen AM9760G), 50 mM Tris pH 7.4 (Invitrogen 15567027), 1× BugBuster (Millipore 70584-3), 5% glycerol (Fisher G331), 1× complete protease inhibitor cocktail (Roche 11873580001), and 1 mM dithiothreitol (Sigma 10197777001). Cells were allowed to lyse on ice for 10 min, then spun at 500×g for 15 minutes to clear lysates.

1 μL of each lysate was run on a NuPAGE 12% or 4-12% Bis-Tris mini protein gel (ThermoFisher NP0341 or NP0322) in MES buffer (Novex NP0002) and transferred to a PDVF membrane (iBlot, ThermoFisher IB401002). Membranes were blocked in 5% milk powder in TBST for 1 h at 23° C., shaking. Membranes were then treated with either 1:5000 Streptactin-HRP (IBA-Lifesciences 2-1502-001) or anti-Strep-tag-HRP (StrepMAB-Classic HRP conjugate, IBA-Lifesciences 2-1509001) in 5% milk in TBST for 1 h at 23° C., shaking. Membranes were then treated with ECL western blotting substrate (SuperSignal West Dura, ThermoFisher 34075) and visualized on an iBright FL1500 imaging system (ThermoFisher). As some proteins expressed at much higher levels than others, some blots were rerun with 10- to 100-fold lysate dilutions to enable qualitative visualization of proteins at various expression levels on the same blot. Proteins were considered to be detected if a band was visible at approximately the anticipated molecular weight.

T.2.5 Protein Purification

For *E. coli*-based protein expression (for all tested proteins except SEM_011), 1 L of Gibco Terrific Broth (ThermoFisher A1374301)+50 ng/μL kanamycin was inoculated with *E. coli* BL21 (NEB C3010I) containing the bacterial expression vector of the desired protein with C-terminal Strep-tag (plasmid information in previous section). Cells were allowed to grow to log phase at 37° C. with shaking before induction with 400 μM IPTG (Teknova 13502) and further incubation for 3 hours at 37° C.

Cells were harvested by centrifugation at 4,000×g for 30 minutes, resuspended in lysis buffer (20 mM Tris pH8,150 mMNaCl, 1× Halt protease inhibitor cocktail ThermoFisher 1861279, 1× Benzonase Nuclease Sigma-Aldrich E1014) and lysed by sonication. Lysates were cleared with centrifugation at 15,000×g for 30 min, passed through a 0.2 μm filter, and incubated overnight at 4° C., with shaking, with 5 mL Strep-Tactin XT 4Flow High-capacity resin (IBA Lifesciences 2-5030).

After incubation, resin was loaded on gravity column and allowed to flow through, then washed with 2×10 CV Strep-Tactin XT wash buffer W (IBA Lifesciences 2-1003) and eluted with 2×1CV Strep-Tactin XT elution buffer BXT (IBA Lifesciences 2-1042). Elution fractions were pooled and incubated with TEV (Sigma Aldrich T4455) at a 1:100v/v concentration ratio to protein, overnight at room temperature.

The sample was then buffer exchanged back into Strep-Tactin XT wash buffer W using a Zeba desalting column (Thermo Scientific 89893) and incubated with 5 ml Strep-Tactin XT resin and 1 ml cOmplete His-Tag Purification Resin (Millipore Sigma 5893801001) for 1 hr at 4° C. before flowing through a gravity column to remove TEV and uncleaved protein.

Samples were then concentrated to a volume of approximately 5 mL and purified via size exclusion chromatography (SEC) on a HiLoad 16/600 Superdex 75 Column (Cytiva GE28-9893-33) into a final buffer of 20 mM Tris pH 7.5100 mM NaCl. Fractions were collected, purity was assessed by SDS-PAGE, and appropriate fractions were pooled.

For mammalian-based protein expression of SEM_011, a gBlock encoding the protein was introduced into a plasmid for transient transfection via Golden Gate Assembly under the CMV promoter with an N-terminal signal peptide, based on vector pcDNA3.4 (ThermoFisher, A14697). The pro-tein also had a C-terminal TEV cleavage site and Strep-tag identical to the configuration used for bacterial expression described above. 100 mL of Expi293F cells (ThermoFisher A14635) in Expi293 expression medium was transfected with the construct containing C-terminal Strep tag following manufacturer's guidelines. Cells were transfected on Day 0 at a density of $3\times10^6$ viable cells/mL with 100 μg of plasmid DNA and placed in shaker at 37° C., 8% CO2. At 24 h post-transfection, cells were fed with transfection enhancers and returned to shaker for expression until day 5.

Expression supernatant was harvested at 70% cell viability by centrifugation at 4,000×g for 30 min. Supernatant was clarified further through a 0.22 μM filter for immediate purification. 2 ml of Strep-Tactin XT 4Flow High-capacity resin (IBA Lifesciences 2-5030) was added to the supernatant and placed on a roller for 24 h at 4° C. for batch binding.

After incubation, resin was loaded on gravity column and allowed to flow through, then washed with 7.5 CV Strep-Tactin XT wash buffer W (IBA Lifesciences 2-1003) and eluted with 2×2.5CV Strep-Tactin XT elution buffer BXT (IBA Lifesciences 2-1042). Eluted protein was concentrated to 2.5 mL using Amicon Ultra-15 3 kDa spin concentrators (Millipore UFC900324) followed by buffer exchange into PBS pH 7.4 using PD-10 desalting columns packed with Sephadex G-25 resin (Cytiva 17085101). Desalted protein was incubated overnight with TEV protease (Sigma Aldrich T4455) at a 1:100v/v concentration ratio to protein, overnight at 4° C.

The sample was then incubated with 1 mL Strep-Tactin XT resin and 1 mL complete His-Tag Purification Resin (Millipore Sigma 5893801001) for 1 h at 4° C. before flowing through a gravity column to remove TEV and uncleaved protein.

Cleaved protein was then concentrated to a volume of approximately 1 mL and purified via size exclusion chromatography (SEC) on a 10/300 Superdex 75 Increase Column (Cytiva 29148721) into a final buffer of 20 mM Tris pH 7.5100 mM NaCl. Fractions were collected, purity was assessed by SDS-PAGE, and appropriate fractions were pooled.

T.2.6 Circular Dichroism

CD spectra to capture protein secondary structure were acquired using a 1 mm pathlength cuvette (JASCO Part #0556) on a JASCO CD-1500 spectropolarimeter at 20° C. To capture far-UV CD, proteins were buffer exchanged into 10 mM NaPO 44 pH 8.5 (Thermo Scientific), concentrated to 0.3-0.5 mg/mL using 10 kDa molecular weight cutoff Amicon Ultra-4 Centrifugal filters (Millipore UFC801024), and read in the UV spectral range of 190-250 nm. The CD scale used was 200 mdeg/1.0 dOD with a DIT of 4 s, a bandwidth of 1 nm, a data pitch of 0.5 nm, and a scanning speed of 50 nm/min with 1 accumulation. Background spectra were acquired across this same spectral range for 10 mM NaPO 4 pH 8.5 (J61151.AP) without protein added and was manually subtracted after conversion. To estimate secondary structure content, deconvolution of far-UV spectra was performed using the Beta Structure Selection (BestSel, https://bestsel.elte.hu/index.php) Internet server [174]. Percent beta sheets predicted as shown in FIGS. 15E-1-15E-3 were the sum of predictions for parallel, antiparallel, and turn content of each protein.

T.2.7 Differential Scanning Calorimetry

Protein thermal stability was assessed using a MicroCal PEAQ-DSC Automated calorimeter (Malvern Panalytical). For sample analysis, 325 μL of each sample and matching buffer was loaded into a 96-well deep well plate (Malvern Panalytical WEL190010-010), sealed with a silicone plate seal (Malvern Panalytical WEL190020-010), and loaded into the PEAQ-DSC Peltier stack with the thermostat held at 4° C.

Thermal scans were performed from 20-110° C. using a scan rate of 210° C./h. At the beginning and end of the run, the sample and reference cells of the calorimeter were cleaned with a 20% w/v Contrad 70 (Decon Labs #1002) using a standard SCAN procedure at the same scan rate. Additionally, every third sample injection a buffer-buffer injection at the same scan rate was performed.

Data analysis was conducted using the dedicated PEAQ DSC Analysis tab (Malvern Panalytical). Baseline correction was performed by subtraction of the corresponding buffer-buffer scan and sample thermograms were further baseline corrected using the spline function to assess pre- and post-dissociation baselines. Peak integration was then performed using a non-two-state model to identify $T_{onset}$, $T_m$, and $\Delta H_{cal}/\Delta H_{VH}$.

T.2.8 Protein Crystallization and X-Ray Crystallography

Diffraction quality crystals of UNC_079 were obtained by hanging drop diffusion at 4° C. by mixing 750 nL protein (15 mg/ml in 20 mM Tris pH8,100 mMNaCl) with 750 nL reservoir solution (2.1 M DL-malic acid, pH 7.0) over 500 μL reservoir. The drop containing crystals was mixed with glycerol to 20% before flash freezing. X-ray diffraction data was collected at 100 K at a wavelength of 0.97624 Å at the PETRA3 synchrotron on the P13 beamline [175]. The data were processed using DIALS [176] and Aimless [177] in $P4_32_12$ space group with 1 molecule in the ASU. A structure was able to be phased using the Chroma-generated model using PhaserMR [178] and was fully refined using phenix.refine [179] to a resolution of 1.1 Å. Data collection and refinement statistics are listed in Extended Data Table 2.

Diffraction quality crystals of UNC 239 were obtained by hanging drop diffusion at 4° C. by mixing 750 nL protein (27 mg/ml in 20 mM Tris pH8,100 mMNaCl) with 750 nL reservoir solution (0.2 M ammonium acetate, 0.1 M Tris pH8.5,25% w/v polyethylene glycol) over 500 μL reservoir. The drop containing crystals was mixed with ethylene glycol to 20% before flash freezing. X-ray diffraction data was collected at 100 K at a wavelength of 0.97624 Å at the PETRA3 synchrotron on the P13 beamline [175]. The data was processed using DIALS [176] and Aimless [177] in $P2_12_12_1$ space group with 2 molecules in the ASU. A structure was able to be phased using the Chroma-generated model using PhaserMR [178] and was fully refined using phenix.refine [179] to a resolution of 2.36 Å. Data collection and refinement statistics are listed in Extended Data Table 2.

T.2.9 In-Silico Score Comparison to Split-GFP

Split-GFP values from both unconditional design sets were compared to ChromaDesign PurePotts/Multi potts and autoregressive negative log-likelihood, ChromaBackbone v0/v1 ELBO, TMscore to predicted AlphaFold, ESMFold and OmegaFold structures, AlphaFold mean pLDDT and FoldSeek highest TM-score to the training set. ESMFold and OmegaFold structure prediction failed for design with lengths above 848 and 631 in the second unconditional set. Experimental values and most of the in silico scores have a strong dependency to design length (FIG. 49). Scores for the first unconditional set were length normalized by fitting them to design length with LOWESS smoothing and evaluating the Pearson correlation between scores residuals to split-GFP values (FIG. 49). Moreover, 95% confidence intervals of partial Spearman correlation against each unconditional set were evaluated using the pingouin python package [180] with design length being the covariate (FIG. 50).

FIG. 49: In silico scores compared to Unconditional I split-GFP and sequence length. Top) Scatter plot of each score compared to design length Bottom) Score residuals after lowess smoothing compared to split GFP values. Pearson correlation is written in each plot. LOWESS fit shown in black FIG. 50: In silico scores partial Spearman correlation to split GFP controlling for sequence length Horizontal bar is the median partial Spearman correlation of each score and the vertical bar their 95% confidence interval.

T.2.10 Novelty Assessment of Crystallized Proteins

Both crystal structures were queried against the PDB (May 2023) for structural homologs with FoldSeek. TM-scores were recomputed for both the query and target using FoldSeek-provided translation and rotation matrices. Internal benchmarking to replicate the CATH coverage analysis with FoldSeek instead of all-vs-all TMalign revealed that the following parameters--alignment-type 1--min-seq-id 0-s 20-e inf--max-seqs 20000-k 5--num-iterations 2 provide the best tradeoff between compute time and retrieval.

T.3 Experimental Figures

FIG. 51: Unconditional protein designs. 172 unconditional Chroma proteins (UNC_001 through UNC_172) constructed for experimental validation between 100 and 450 amino acids in length.

FIG. 52: Secondary structure conditional designs. a, 42 proteins were designed based on secondary structure composition (SEM_001 through SEM_042). b, Split-GFP rank-ordered bin scores for designed proteins conditioned on secondary structure content. Individual data points for two independent biological replicates shown. c, Differential scanning calorimetry data for one protein from each of various secondary structure design classes. Split-GFP data shown for reference.

FIG. 53: Split-GFP protein solubility assay. a, Schematic of split-GFP reporter concept. Co-expression of soluble protein fused to the GFP11 tag with the GFP1-10 protein results in restoration of GFP fluorescence. b, Split-GFP experimental workflow to determine protein solubility. FACS=fluorescence-activated cell sorting; NGS=next-generation sequencing. c, FACS gating strategy informed by positive and negative control cells. Chroma library was sorted into 4 different gates based on GFP fluorescence for subsequent sequencing enrichment analysis. d, Flow cytometry of sorted cell populations that were regrown and split-GFP components were re-induced to evaluate signal stability within sorted populations.

FIGS. 54A-54D: Soluble protein expression confirmation via western blot. The top 20 and bottom 20 hits from the split-GFP solubility screen on proteins UNC_001 through UNC_172 were reformatted to contain a C-terminal Strep-tag. Protein expression from *E. coli* lysates was detected by western blot using Streptactin or anti-Strep-tag antibody. Lane designations: L=ladder; C=control protein (same on each blot)

FIGS. 55A-55D: Evaluation of additional set of unconditional protein designs. a, 96 additional unconditional designs (UNC_173 through UNC.268) were evaluated experimentally up to 950 amino acids in length. b, Rank-ordered split-GFP bin scores for additional unconditional proteins. Individual data points for two biological replicates shown. c, Reproducibility of splitGFP bin scores between two independent biological replicates. d, Western blot-based confirmation of soluble protein expression from *E. coli* lysates for the top 10 scoring proteins in this set using either Streptactin or anti-Strep-tag antibody for detection. Lane designations: L=ladder FIGS. 56A-56B: Differential scanning calorimetry experiments. Evaluation of 7 SECpurified unconditional proteins by differential scanning calorimetry. Split-GFP solubility score shown for reference.

REFERENCES (OMITTED)

What is claimed is:

1. A method for generating a protein or a protein complex using a trained diffusion model, the method comprising:
- using one or more computer processors to perform:
  - determining an initial state representing a protein backbone, the initial state specifying three-dimensional (3D) coordinates of heavy atoms in amino acid residues of the protein backbone;
  - transforming the initial state representing the protein backbone, through a series of states representing a respective series of protein backbones, to a final state representing a denoised protein backbone, the transforming performed by sampling using the trained diffusion model, the trained diffusion model comprising a graph neural network (GNN) that comprises nodes for amino acid residues of the protein backbone and has a sparse edge structure, wherein the sampling is performed using a reverse-time stochastic differential equation (SDE), a Langevin dynamics SDE, or a hybrid SDE combining both the reverse-time SDE and the Langevin dynamics SDE; and
  - applying a trained sequence generation model to the denoised protein backbone to generate an amino acid sequence for the protein; and
- manufacturing the protein having the amino acid sequence,
- wherein the sampling is performed using a stochastic differential equation with a structured covariance enforcing protein chain and radius of gyration statistics.

2. The method of claim 1, wherein the GNN is a random graph neural network (RGNN).

3. The method of claim 1, wherein the GNN is not fully connected.

4. The method of claim 1, wherein the sampling is performed using the trained diffusion model, a diffusion energy component, and one or more energy components corresponding to respective one or more protein property conditions.

5. The method of claim 4,
- wherein the one or more protein property conditions include one or more constraints or restraints selected from among: a domain classifier constraint, a secondary structure constraint, a distance constraint, a substructure root mean squared deviation (RMSD) constraint, a substructure infilling restraint, a shape constraint, a symmetry constraint, and a text caption restraint, and
- wherein the one or more energy components includes an energy components for each of the one or more constraints or restraints.

6. A method for generating a protein or a protein complex using a trained diffusion model, the method comprising:
- using one or more computer processors to perform:
  - determining an initial state representing a protein backbone, the initial state specifying three-dimensional (3D) coordinates of heavy atoms in amino acid residues of the protein backbone;
  - transforming the initial state representing the protein backbone, through a series of states representing a respective series of protein backbones, to a final state representing a denoised protein backbone, the transforming performed by sampling the trained diffusion model, the trained diffusion model comprising a first graph neural network (GNN) that comprises nodes for the amino acid residues of the protein backbone; and
  - applying a trained sequence generation model to the denoised protein backbone to generate an amino acid sequence for the protein, the trained sequence generation model comprising a second GNN, wherein the first GNN and the second GNN are the same; and
- manufacturing the protein having the amino acid sequence,
- wherein the sampling is performed using a stochastic differential equation with a structured covariance enforcing protein chain and radius of gyration statistics.

7. The method of claim 6,
- wherein the trained diffusion model further comprises an inter-residue geometry predictor and a backbone solver,
- wherein the inter-residue geometry predictor is configured to process node and edge embeddings generated by the first graph neural network and provide outputs to the backbone solver.

8. The method of claim 6, wherein the first GNN is a sparse GNN.

9. The method of claim 6,
- wherein the sampling is performed using the trained diffusion model, a diffusion energy component, and one or more energy components corresponding to respective one or more protein property conditions, and
- wherein the one or more protein property conditions include one or more constraints or restraints selected from among: a domain classifier constraint, a secondary structure constraint, a distance constraint, a substructure root mean squared deviation (RMSD) constraint, a substructure infilling restraint, a shape constraint, a symmetry constraint, and a text caption restraint, and wherein the one or more energy components includes an energy component for each of the one or more constraints or restraints.

10. A method for generating a protein or a protein complex using a trained diffusion model, the method comprising:

using one or more computer processors to perform:

determining an initial state representing a protein backbone, the initial state specifying three-dimensional (3D) coordinates of heavy atoms in amino acid residues of the protein backbone;

transforming the initial state representing the protein backbone, through a series of states representing a respective series of protein backbones, to a final state representing a denoised protein backbone, the transforming performed by sampling the trained diffusion model, the trained diffusion model comprising a graph neural network (GNN) that comprises nodes for the amino acid residues of the protein backbone, wherein the sampling is performed using a stochastic differential equation with a structured covariance enforcing protein chain and radius of gyration statistics; and applying a trained sequence generation model to the denoised protein backbone to generate an amino acid sequence for the protein; and manufacturing the protein having the amino acid sequence.

11. The method of claim 10, wherein the sampling is performed using the trained diffusion model, a diffusion energy component, and one or more energy components corresponding to respective one or more protein property conditions, and wherein the one or more protein property conditions include one or more constraints or restraints selected from among: a domain classifier constraint, a secondary structure constraint, a distance constraint, a substructure root mean squared deviation (RMSD) constraint, a substructure infilling restraint, a shape constraint, a symmetry constraint, and a text caption restraint, and wherein the one or more energy components includes an energy component for each of the one or more constraints or restraints.

* * * * *